(12) United States Patent
Blumenfeld et al.

(10) Patent No.: US 6,825,004 B1
(45) Date of Patent: Nov. 30, 2004

(54) NUCLEIC ACIDS ENCODING HUMAN TBC-1 PROTEIN AND POLYMORPHIC MARKERS THEREOF

(75) Inventors: Marta Blumenfeld, Paris (FR); Lydie Bougueleret, Petit Lancy (CH); Ilya Chumakov, Vaux-le-Penil (FR)

(73) Assignee: Genset S.A. (FR)

( * ) Notice: Subject to any disclaimer, the term of this patent is extended or adjusted under 35 U.S.C. 154(b) by 0 days.

(21) Appl. No.: 09/762,311

(22) PCT Filed: Jun. 8, 1999

(86) PCT No.: PCT/IB99/01444

§ 371 (c)(1),
(2), (4) Date: Jun. 25, 2001

(87) PCT Pub. No.: WO00/08209

PCT Pub. Date: Feb. 17, 2000

Related U.S. Application Data

(60) Provisional application No. 60/095,653, filed on Aug. 7, 1998.

(51) Int. Cl.[7] .................. C07H 21/04; C07H 21/02; C12N 15/63; C12N 1/21
(52) U.S. Cl. .................. 435/69.1; 435/71.1; 435/252.3; 435/320.1; 536/23.5; 536/24.31; 536/24.33
(58) Field of Search .................. 536/23.5, 24.31, 536/24.33, 23.1; 435/69.1, 71.1, 252.3, 320.1

(56) References Cited

U.S. PATENT DOCUMENTS 5,700,927 A * 12/1997 Zon et al. .................. 536/23.5

FOREIGN PATENT DOCUMENTS

| WO | WO 98/20165 A2 | 5/1998 |
|----|---------------|--------|
| WO | WO 99/32644 A3 | 7/1999 |

OTHER PUBLICATIONS

Philippe Berthon, et al.; "Predisposing Gene for Early-Onset Prostate Cancer, Localized on Chromosome 1q42.2–43"; Am. J. Hum. Genet. 62:1416–1424, 1998.

David G. Wang, et al.; "Large-Scale Identification, Mapping, and Genotyping of Single-Nucleotide Polymorphisms in the Human Genome"; Science; vol. 280, pp. 1077–1082, May 15, 1998.

J. Fan, et al.; "Genetic mapping: Finding and analyzing single-nucleotide polymorphisms with high-density DNA arrays"; XP–002089397.

EMBL Genbank AC X40323—WO-A-9 906 439.
EMBL Genbank ACZ41904.
EMBL Genbank AC AA346082.
EMBL Genbank Z78359.
EMBL Genbank H62992.
EMBL Genbank AA804534.

* cited by examiner

*Primary Examiner*—Carla J. Myers
(74) *Attorney, Agent, or Firm*—Saliwanchik, Lloyd & Saliwanchik

(57) ABSTRACT

The invention concerns genomic and cDNA sequences of the human TBC-1 Gene. The invention also concerns polypeptides encoded by the TBC-1 gene. The invention also deals with antibodies directed specifically against such polypeptides that are useful as diagnostic reagents. The invention further encompasses biallelic markers of the TBC-1 gene useful in genetic analysis.

30 Claims, 5 Drawing Sheets

Figure 1

```
              1                                                          50
Mur. tbc1    MPMLPWVVAE  VRRLSGQCSK  KEPRTKQVRL  WVSPSGLRCE  PDLEKSQPWD
    TBC-1    mpmlpwvvae  vrrlsrqstr  kepvtkqvrl  cvspsglrce  pepgrsqqwd
 dmu50542    ----------  ----------  ----------  ----------  ----------
 celf35h12   ----------  ----------  ----------  ----------  ----------
Consensus    ----------  ----------  ----------  ----------  ----------

51                                                         100
Mur. tbc1    PLICSSIFEC  KPQRVHKLIH  NSHDPSYFAC  LIKEDAAHRQ  SLCYVFKADD
    TBC-1    pliyssifec  kpqrvhklih  nshdpsyfac  likedavhrq  sicyvfkadd
 dmu50542    ----------  ----------  ----------  ----------  ----------
 celf35h12   ----------  ----------  ----------  ----------  ----------
Consensus    ----------  ----------  ----------  ----------  ----------

101                                                        150
Mur. tbc1    QTKVPEIISS  IRQAGKIARQ  EELRCPSEFD  DTFAKKFEVL  FCGRVTVAHK
    TBC-1    qtkvpeiiss  irqagkiarq  eelhcpsefd  dtfskkfevl  fcgrvtvahk
 dmu50542    ----------  ----------  ----------  ----------  ----------
 celf35h12   ----------  ----------  ----------  ----------  ----------
Consensus    ----------  ----------  ----------  ----------  ----------

151                                                        200
Mur. tbc1    KAPPALIDEC  IEKFNHVSCG  RRTDWEAPTG  Q......PSA  PGPRPMRKSF
    TBC-1    kappalidec  iekfnhvsgt  ggprapaptr  pmprpqwsqe  pvrrpmrksf
 dmu50542    ----------  ----------  ----------  ----------  ----------
 celf35h12   ----------  ----------  ----------  ----------  ----------
Consensus    ----------  ----------  ----------  ----------  ----------

201                                                        250
Mur. tbc1    SQPGLRSLAF  RKEFQDASLR  SS.TFSSF.D  NDIENHLIGG  HNVVQPTDME
    TBC-1    sqpglrslaf  rkelqdgglr  ssgffssfee  sdienhlisg  hnivqptdie
 dmu50542    ----------  ----------  ----------  ----------  ----------
 celf35h12   ----------  ----------  ----------  ----------  ----------
Consensus    ----------  ----------  ----------  ----------  ----------

251                                                        300
Mur. tbc1    ENRTMLFTIG  PSEVYLISPD  TKKIALEKNF  KEISFCSQGI  RHVDHFGFIC
    TBC-1    enrtmlftig  qsevylispd  tkkialeknf  keisfcsqgi  rhvdhfgfic
 dmu50542    ----------  ----------  ----------  ----------  ----------
 celf35h12   ----------  ----------  ----------  ----------  ----------
Consensus    ----------  ----------  ----------  ----------  ----------

301                                                        350
Mur. tbc1    RECSGGGSGG  FHFVCYVFQC  TNEALVDEIM  MTLKQAFTVA  AVQQTAKA.P
    TBC-1    ressgg..gg  fhfvcyvfqc  tnealvdeim  mtlkqaftva  avqqtaka.p
 dmu50542    ----------  ----------  ----------  ----------  ----------
 celf35h12   MEDFKDFTEV  TQFTNVQYLG  CSQLVNNDND  NEMKALMKVL  DEQKGAQTIN
Consensus    -E--------  --F-------  ----------  ---K----V-  --Q--A----
```

Figure 1 (Continued I)

```
               351                                                              400
Mur. tbc1      AQLCEGCPLQ GLHKLCERIE GMNSSKTKLE LQKHLTTLTN QEQATIFEEV
    TBC-1      aqlcegcplq slhklcerie gmnssktkle lqkhlttltn qeqatifeev
 dmu50542      ---------- ---------- ---------- ---------- ----------
 celf35h12     VTLVVPHNIS GTVKLIDAQG KVLSSFSLVN IRFCIRGESS TSQNNCF.GI
 Consensus     --L------- ---KL----- ---SS----- ---------- --Q---F---

401                                                              450
Mur. tbc1      QKLRPRNEQR ENELIISFLR CLYEEKQKEH SHTGAPKQTL QVAAENIGSD
    TBC-1      qklrprneqr eneliisflr clyeekqkeh ihigemkqts qmaaenigse
 dmu50542      ---------- ---------- ---------- ---------- ----------
 celf35h12     SFTHKISVGE HNSSDILHQC HVFRTSKAET AAKALYSFSY AFSNKNVSSE
 Consensus     ---------- -N---I---- --------E- ---------- -----N--S-

451                                                              500
Mur. tbc1      LPPSASRFRL DSLKNRAKRS LTESLESILS RGNKARGLQD HSASVDLDSS
    TBC-1      lppsatrfrl dmlknkakrs lteslesils rgnkarrlqe hsisvdldss
 dmu50542      ---------- ---------- ---------- ---------- ----------
 celf35h12     SNRLEFQFES ILEVKENDGT VEKPSWKLCP QHNGVFKVRR DREKKIVVQL
 Consensus     ------F--- ---------- ---------- --N------- ----------

501                                                              550
Mur. tbc1      TSSTLSNTSK ELSMGDKEAF PVSETSFKLL GSSDDLSSDS EGHIAEESAL
    TBC-1      lsstlsntsk epsvcekeaf pisessfkll gssedlssds eshlpeepap
 dmu50542      ---------- ---------- ---------- ---------- ----------
 celf35h12     RQVARKKTID GFLLNIKKCF GMLLAAGRNL RHSDLQLLEM DRNATGTDSA
 Consensus     -------T-- ------K--F ---------L --S------- ----------

551                                                              600
Mur. tbc1      LSPQQAFRRR ANTLSHFPVE CPAPPEPAQS SPGVSQRKLM RYHSVSTETP
    TBC-1      lspqqafrrr antlshfpie cqeppqparg spgvsqrklm ryhsvstetp
 dmu50542      ---------- ---------- ---------- ---------- ----------
 celf35h12     VFVIEA..NW DPRVHMFEVL NTETPRDTRV FMTVAIDVIV SEISEPIRFS
 Consensus     -----A---- ------F--- ----P----- ---V------ ---S------

601                                                              650
Mur. tbc1      HERKDFESKA NHLGDTDGTP VKTRRHSWRQ QIFLRVATPQ KACDSPSRYE
    TBC-1      herkdfeska nhlgdsggtp vktrshswrq qiflrvatpq kacdsssrye
 dmu50542      ---------- ---------- ---------- ---------- ----------
 celf35h12     MEAMSRVFHE HERFYKTPQT VVSEEFTLVL EVRIRTEKLL ETHGNMLLKS
 Consensus-E-- ------- ---------- V--------- ----R----- ----------

651                                                              700
Mur. tbc1      DYSELGELPP RSPLEPVCED GPFGQYRKKR GRRHASFESC GKRPSCSRSC
    TBC-1      dyselgelpp rsplepvced gpfaphqrkr kghlvssesc akrlffnryc
 dmu50542      ---------- ---------- --MRKPAKRG KRDAAELREL WRTAIRQTIM
 celf35h12     VPIDFAWQLE GVYFLPTPSK SCDQSDPNDR KLTFISLESD SDRKRSKQNL
 Consensus     ---------- -----P---- ---------R K----S-ES- --R-------
```

Figure 1 (Continued II)

```
            701                                                         750
Mur. tbc1   ...LVRMEKE NQKLQASEND LLNKRLKLDY .EEITPCLKE VTTVWEKMLS
    TBC-1   ...clgmeke nqklqasend llnkrlklrf mkeitpclke vttvwekmls
 dmu50542   ...LNRMETE NAMLQARQNE NELKRIKLDY .EEIVPCDKQ LIERWEQIIE
 celf35h12  GKSPSRMPTQ LLHPTGDDES DCDEPLLSGS GKVSQECKEE HLEMWDQLIE
 Consensus  -----RME-E N--LQA--N- ---KRLKL-- --EI-PC-KE ----WE----

751                                                         800
Mur. tbc1   .TPGRSKIKF DMEKVHSAVG QGVPRHHRGE IWKFLAEQFH LK.HPFPSKQ
    TBC-1   .tpgrskikf dmekmhsavg qgvprhhrge iwkflaeqfh lk.hqfpskq
 dmu50542   RNSTQIGNKK DPKVLGHAIF TGVPRSKRGD VWTRLAEQHS MNTAPVDTKR
 celf35h12  NWDQQSD... RPQKISELVL DGIPDKLRGR VWQLLSNAL.........D
 Consensus  -----S--K- D--K---AV- -GVPR--RG- -W-FLAEQ-- --------K-

801                                                         850
Mur. tbc1   QPK DVPYKE LLKHLTSQQH AILIDLGRTF PTHPYFSAQL GAGQLSLYNI
    TBC-1   qpk dvpyke llkqltsqqh ailidlgrtf pthpyfeaql gagqlslyni
 dmu50542   FPNFNIPTHM LLKHLTEHQH AIFIDLGRTF PNHQFIKDPL GLGQLSLFNL
 celf35h12  QPDLVEKYHI PISQPCPSEQ VIMRDIHRTF PAHDYFKESQ GKGQQSLYKI
 Consensus  QP-----PY-- LLK-LT--QH AI-IDLGRTF P-H-YF---L G-GQLSLYNI 851                                                         900
Mur. tbc1   LKAYS LLDQ EVGYCQGLSF VAGILLLHMS REEAFKMLKF LMPDMGLRKQ
    TBC-1   lkayc lldq evgycqglsf vagilrlhms eeeackmlkf llvdmglwrq
 dmu50542   LKAYS ILDP ELGYCQGLGF ICGVLLLHCD EANSPQLLKH LMFRRNMRTK
 celf35h12  SKVYS LYDE EVGYCQGLSF LAASLLLHMP REQAFCTLVK IMPNYGLRDL
 Consensus  LKAYS-LLD- EVGYCQGLSF -AG-LLLHM- EE-AF--LK- LMF---GLR--

901                                                         950
Mur. tbc1   YPDMIILGI QMYQLSRILL DYHRDLYNHL EEHRTGPPLY AAPWFLTVFA
    TBC-1   ypdmiilqi qmvqlsrilh dyhrdlnnhl eeheigpsly aapwfltmfa
 dmu50542   KLPDMKKEQL QLYQLSRLVK DHLPDLYVWL DQNDVSPILY AAPWILTVES
 celf35h12  FKLGFDNHL RFFQLTALLK DYLPDLSHHL EHIGLETHMY ASQWFLTLET
 Consensus  Y-PDM--LQ- Q-YQLSRLL- DY--DL--HL E-----P--Y AAPWFLT-F-

951                                                        1000
Mur. tbc1   SQFPLGFVAR VFDMIFLQGS EVIFKVALSL LGSHKPLILQ HENLETIVDF
    TBC-1   sqfplgfvar vfdmiflqgt evifkvavsl lgshkplilq henletivdf
 dmu50542   SQFPLGFVAR VFDLLFLESS DVIFKFAIAL LSVHKQQLLA KDNFEEIMDY
 celf35h12  AKFPLQMVFF ILDLFLSQGM NTIFHISLAL LDDAKTDLLQ LD.FEGTLKY
 Consensus  SQFPLGFVAR VFD--FLQG- -VIFK-A--L L--HK---LQ --N-E-I-D-

1001                                                       1050
Mur. tbc1   IKNTLPNLGL VQMEKTISQV FEMDIAKQLQ AYEVEYHVVQ EELIESSPLS
    TBC-1   ikstlpnlgl vqmektinqv femdiakqlq ayevehhvlq eelidsspls
 dmu50542   LKTVVPKMEH TCMEQIMKLV FSMDIGKQLA EYNVEYNVLQ EEI.....TT
 celf35h12  FRVSLPRKYR T..EASTKCL IHKAVKFRLN HSKLEVYENE YKRIKELERE
 Consensus  -K--LP---- --ME-----V F-MDI-KQL- -Y-VE--V-Q EE-I------
```

Figure 1 (Continued III)

```
             1051                                                          1100
Mur. tbc1    DNQRMEKLEK  TNSTLRKQNL  DLL.EQLQVA  NARIQSLEAT  VEKLLTSESK
   TBC-1     dnqrmdklek  tnsslrkqnl  dll.eqlqva  ngriqsleat  iekllssesk
 dmu50542    TNHHLEMLNR  E....KTQNQ  HLE.QQLQFA  QSSIAQLETT  RSSQQAQITT
celf35h12    NEDPVLRMEK  EIGRHQANTL  RLERENDDLA  HELVTSKIEL  RRKLDVAEDQ
Consensus    -N-----LEK  -------QNL  -L--EQLQ-A  ---I-SLE-T  --KL---E--

1101                                                          1150
Mur. tbc1    LKQRALTLEV  ERRPAADGGG  AAEAKRPAQH  SR.ARLHPAG  AHRRLTAAR.
   TBC-1     lkqamltlel  ersallqtve  elrrrsaeps  drepectqpe  ptgd------
 dmu50542    LQSQVQSLEL  TIQTLGRYVG  QLVEHNP...  DLELPNEVRR  MLQQLDDLDR
celf35h12    IETSANAIER  LTRQNMDILE  E..NKNLMRE  YEQIKEMYRR  DVLRLEENGS
Consensus    L------LE-  ----------  ----------  ----------  ---RL-----

1151                                                          1200
Mur. tbc1    RDCAPLTLSK  P---------  ----------  ----------  ----------
   TBC-1     ----------  ----------  ----------  ----------  ----------
 dmu50542    QRRKPIFTER  KIGKSVSVNS  HLGFPLKVLE  ELTERDELGS  PQKQKKEKTP
celf35h12    RAEKLLAEYK  KLFSERSKRA  ENEREHFEVQ  KKAIIARISD  CDKCWPAVCE
Consensus    R---------  ----------  ----------  ----------  ----------

1201                                                          1250
Mur. tbc1    ----------  ----------  ----------  ----------  ----------
   TBC-1     ----------  ----------  ----------  ----------  ----------
 dmu50542    FFEQLRQQQQ  QHRLNGGGQS  SNVGESGSPT  PPSRPNRLLD  NASARTVMQV
celf35h12    .WEKNRSPVH  SASTPTGPDL  LTKLEEREDH  IKNLEIDLAQ  TKLSLVEAEC
Consensus    ----------  ----------  ----------  ----------  ----------

1251                                                          1300
Mur. tbc1    ----------  ----------  ----------  ----------  ----------
   TBC-1     ----------  ----------  ----------  ----------  ----------
 dmu50542    KLDELKLPEH  VDKFVANIKS  PLEVDSGVGT  PLSPPSTASN  SSGGSIFSRM
celf35h12    RNQDLTHQLM  AQSESDGKKW  FKKTITQLKE  VGSSLKHHER  SNSSVTPHFS
Consensus    ----------  ----------  ----------  ----------  ----------

1301                                                          1350
Mur. tbc1    ----------  ----------  ----------  ----------  ----------
   TBC-1     ----------  ----------  ----------  ----------  ----------
 dmu50542    GYRTTPPALS  PLAQRQSYGV  AITTAPCPQH  MEEVAPATTM  AVMPQEDVEE
celf35h12    STFQLQMDHT  ETTTSNNIGY  NSSSESFAVR  FMQTPSAVLK  ITNGEMTEDN
Consensus    ----------  ----------  ----------  ----------  ----------

1351                                                          1400
Mur. tbc1    ----------  ----------  ----------  ----------  ----------
   TBC-1     ----------  ----------  ----------  ----------  ----------
 dmu50542    PQPMHPLSMV  GGDVNVRFKG  TTQLKSIRPV  HHMRAIPLGG  VQHPSSTEPA
celf35h12    NNMLHGINGV  DLLDLQSTDN  DDQYSNSSSL  ESRNSLTNHQ  GKAEDSTMVT
Consensus    ----------  ----------  ----------  ----------  ----------
```

Figure 1 (Continued IV)

```
              1401                                                              1450
Mur. tbc1     ----------  ----------  ----------  ----------  ----------
     TBC-1    ----------  ----------  ----------  ----------  ----------
  dmu50542    VRVAPVPVEL  APPAATATTG  RS--------  ----------  ----------
  celf35h12   VNLDQLPARR  TLLKCLVLVV  FGKSYTKVIF  QMLRFSGFLM  RRGVYPGTLY
Consensus     ----------  ----------  ----------  ----------  ----------

1451        1465
Mur. tbc1     ----------  -----
     TBC-1    ----------  -----
  dmu50542    ----------  -----
  celf35h12   FRRCSKILLK  KYDRI
Consensus     ----------  -----
```

NUCLEIC ACIDS ENCODING HUMAN TBC-1 PROTEIN AND POLYMORPHIC MARKERS THEREOF This application is a national stage application of International Application No. PCT/IB99/01444, filed Aug. 6, 1999, which claims the benefit of U.S. Provisional Application Ser. No. 60/095,653, filed Aug. 7, 1998, both of which are incorporated by reference herein in their entireties.

FIELD OF THE INVENTION

The invention concerns genomic and cDNA sequences of the human TBC-1 gene. The invention also concerns polypeptides encoded by the TBC-1 gene. The invention also deals with antibodies directed specifically against such polypeptides that are useful as diagnostic reagents. The invention further encompasses biallelic markers of the TBC-1 gene useful in genetic analysis.

BACKGROUND OF THE INVENTION

The incidence of prostate cancer has dramatically increased over the last decades. It averages 30–50/100,000 males in Western European countries as well as within the US White male population. In these countries, it has recently become the most commonly diagnosed malignancy, being one of every four cancers diagnosed in American males. Prostate cancer's incidence is very much population specific, since it varies from 2/100,000 in China, to over 80/100,000 among African-American males.

In France, the incidence of prostate cancer is 35/100,000 males and it is increasing by 10/100,000 per decade. Mortality due to prostate cancer is also growing accordingly. It is the second cause of cancer death among French males, and the first one among French males aged over 70. This makes prostate cancer a serious burden in terms of public health.

Prostate cancer is a latent disease. Many men carry prostate cancer cells without overt signs of disease. Autopsies of individuals dying of other causes show prostate cancer cells in 30% of men at age 50 and in 60% of men at age 80. Furthermore, prostate cancer can take up to 10 years to kill a patient after the initial diagnosis.

The progression of the disease usually goes from a well-defined mass within the prostate to a breakdown and invasion of the lateral margins of the prostate, followed by metastasis to regional lymph nodes, and metastasis to the bone marrow. Cancer metastasis to bone is common and often associated with uncontrollable pain.

Unfortunately, in 80% of cases, diagnosis of prostate cancer is established when the disease has already metastasized to the bones. Of special interest is the observation that prostate cancers frequently grow more rapidly in sites of metastasis than within the prostate itself.

Early-stage diagnosis of prostate cancer mainly relies today on Prostate Specific Antigen (PSA) dosage, and allows the detection of prostate cancer seven years before clinical symptoms become apparent. The effectiveness of PSA dosage diagnosis is however limited, due to its inability to discriminate between malignant and non-malignant affections of the organ and because not all prostate cancers give rise to an elevated serum PSA concentration. Furthermore, PSA dosage and other currently available approaches such as physical examination, tissue biopsy and bone scans are of limited value in predicting disease progression.

Therefore, there is a strong need for a reliable diagnostic procedure which would enable a more systematic early-stage prostate cancer prognosis.

Although an early-stage prostate cancer prognosis is important, the possibility of measuring the period of time during which treatment can be deferred is also interesting as currently available medicaments are expensive and generate important adverse effects. However, the aggressiveness of prostate tumors varies widely. Some tumors are relatively aggressive, doubling every six months whereas others are slow-growing, doubling once every five years. In fact, the majority of prostate cancers grows relatively slowly and never becomes clinically manifest. Very often, affected patients are among the elderly and die from another disease before prostate cancer actually develops. Thus, a significant question in treating prostate carcinoma is how to discriminate between tumors that will progress and those that will not progress during the expected lifetime of the patient.

Hence, there is also a strong need for detection means which may be used to evaluate the aggressiveness or the development potential of prostate cancer tumors once diagnosed.

Furthermore, at the present time, there is no means to predict prostate cancer susceptibility. It would also be very beneficial to detect individual susceptibility to prostate cancer. This could allow preventive treatment and a careful follow up of the development of the tumor.

A further consequence of the slow growth rate of prostate cancer is that few cancer cells are actively dividing at any one time, rendering prostate cancer generally resistant to radiation and chemotherapy. Surgery is the mainstay of treatment but it is largely ineffective and removes the ejaculatory ducts, resulting in impotence. Oral oestrogens and luteinizing releasing hormone analogs are also used for treatment of prostate cancer. These hormonal treatments provide marked improvement for many patients, but they only provide temporary relief. Indeed, most of these cancers soon relapse with the development of hormone-resistant tumor cells and the oestrogen treatment can lead to serious cardiovascular complications. Consequently, there is a strong need for preventive and curative treatment of prostate cancer.

Efficacy/tolerance prognosis could be precious in prostate cancer therapy. Indeed, hormonal therapy, the main treatment currently available, presents important side effects. The use of chemotherapy is limited because of the small number of patients with chemosensitive tumors. Furthermore the age profile of the prostate cancer patient and intolerance to chemotherapy make the systematic use of this treatment very difficult.

Therefore, a valuable assessment of the eventual efficacy of a medicament to be administered to a prostate cancer patent as well as the patent's eventual tolerance to it may permit to enhance the benefit/risk ratio of prostate cancer treatment.

It is known today that there is a familial risk of prostate cancer. Clinical studies in the 1950s had already demonstrated a familial aggregation in prostate cancer. Control-case clinical studies have been conducted more recently to attempt to evaluate the incidence of the genetic risk factors in the disease. Thus Steinberg et al., 1990, and McWhorter et al., 1992 confirm that the risk of prostate cancer is increased in subjects having one or more relatives already affected by the disease and when forms of early diagnosis in the relatives exist.

It is now well established that cancer is a disease caused by the deregulation of the expression of certain genes. In fact, the development of a tumor necessitates an important succession of steps. Each of these steps comprises the deregulation of an important gene intervening in the normal metabolism of the cell and the emergence of an abnormal cellular sub-clone which overwhelms the other cell types because of a proliferative advantage. The genetic origin of this concept has found confirmation in the isolation and the characterization of genes which could be responsible. These genes, commonly called "cancer genes", have an important role in the normal metabolism of the cell and are capable of intervening in carcinogenesis following a change.

Recent studies have identified three groups of genes which are frequently mutated in cancer. The first group of genes, called oncogenes, are genes whose products activate cell proliferation. The normal non-mutant versions are called protooncogenes. The mutated forms are excessively or inappropriately active in promoting cell proliferation, and act in the cell in a dominant way in that a single mutant allele is enough to affect the cell phenotype. Activated oncogenes are rarely transmitted as germline mutations since they may probably be lethal when expressed in all the cells. Therefore oncogenes can only be investigated in tumor tissues.

The second group of genes which are frequently mutated in cancer, called tumor suppressor genes, are genes whose products inhibit cell growth. Mutant versions in cancer cells have lost their normal function, and act in the cell in a recessive way in that both copies of the gene must be inactivated in order to change the cell phenotype. Most importantly, the tumor phenotype can be rescued by the wild type allele, as shown by cell fusion experiments first described by Harris and colleagues (1969). Germline mutations of tumor suppressor genes may be transmitted and thus studied in both constitutional and tumor DNA from familial or sporadic cases. The current family of tumor suppressors includes DNA-binding transcription factors (i.e., p53, WT1), transcription regulators (i.e., RB, APC, probably BRCA1), protein kinase inhibitors (i.e., p16), among others (for review, see Haber D & Harlow E, 1997).

The third group of genes which are frequently mutated in cancer, called mutator genes, are responsible for maintaining genome integrity and/or low mutation rates. Loss of function of both alleles increases cell mutation rates, and as a consequence, proto-oncogenes and tumor suppressor genes may be mutated. Mutator genes can also be classified as tumor suppressor genes, except for the fact that tumorigenesis caused by this class of genes cannot be suppressed simply by restoration of a wild-type allele, as described above. Genes whose inactivation may lead to a mutator phenotype include mismatch repair genes (i.e., MLH1, MSH2), DNA helicases (i.e., BLM, WRN) or other genes involved in DNA repair and genomic stability (i.e., p53, possibly BRCA1 and BRCA2) (For review see Haber D & Harlow E, 1997; Fishel R & Wilson T. 1997; Ellis N A, 1997).

There is growing evidence that a critical event in the progression of a tumor cell from a non-metastatic to metastatic phenotype is the loss of function of metastasis-suppressor genes. These genes specifically suppress the ability of a cell to metastasize. Work from several groups has demonstrated that human chromosomes 8, 10, 11 and 17 encode prostate cancer metastasis suppressor activities. However, other human chromosomes such as chromosomes 1, 7, 13, 16, and 18 may also be associated to prostate cancer.

It thus remains to localize and to identify the genes specifically involved in the development and the progression of prostate cancers starting from the genetic analysis of the hereditary and the non-hereditary forms and to define their clinical implications in terns of prognosis and therapeutic innovations.

SUMMARY OF THE INVENTION

The present invention pertains to nucleic acid molecules comprising the genomic sequence of a novel human gene which encodes a TBC-1 protein. The TBC-1 genomic sequences comprise regulatory sequence located upstream (5'-end) and downstream (3'-end) of the transcribed portion of said gene, these regulatory sequences being also part of the invention. The human TBC-1 genomic sequence is included in a previously unknown candidate region of prostate cancer located on chromosome 4.

The invention also deals with the two complete cDNA sequences encoding the TBC-1 protein, as well as with the corresponding translation product.

Oligonucleotide probes or primers hybridizing specifically with a TBC-1 genomic or cDNA sequence are also part of the present invention, as well as DNA amplification and detection methods using said primers and probes.

A further object of the invention consists of recombinant vectors comprising any of the nucleic acid sequences described above, and in particular of recombinant vectors comprising a TBC-1 regulatory sequence or a sequence encoding a TBC-1 protein, as well as of cell hosts and transgenic non human animals comprising said nucleic acid sequences or recombinant vectors.

The invention also concerns a TBC-1-related biallelic marker and the use thereof.

Finally, the invention is directed to methods for the screening of substances or molecules that inhibit the expression of TBC-1, as well as with methods for the screening of substances or molecules that interact with a TBC-1 polypeptide.

BRIEF DESCRIPTION OF THE DRAWINGS

FIG. 1: An amino acid alignment of a portion of the amino acid sequence of the TBC-1 protein of SEQ ID No 5 with other proteins sharing amino acid homology with TBC-1. The amino acid numbering refers to the murine TBC-1.

BRIEF DESCRIPTION OF THE SEQUENCES PROVIDED IN THE SEQUENCE LISTING

SEQ ID No 1 contains a first part of the TBC-1 genomic sequence comprising the 5' regulatory sequence and the exons 1,1bis, and 2.

SEQ ID No 2 contains a second part of the TBC-1 genomic sequence comprising the 12 last exons of the TBC-1 gene and the 3'regulatory sequence.

SEQ ID No 3 contains a first cDNA sequence of the TBC-1 gene.

SEQ ID No 4 contains a second cDNA sequence of the TBC-1 gene.

SEQ ID No 5 contains the amino acid sequence encoded by the cDNAs of SEQ ID Nos 3 and 4.

SEQ ID No 6 contains a primer containing the additional PU 5' sequence described further in Example 3.

SEQ ID No 7 contains a primer containing the additional RP5' sequence described further in Example 3.

In accordance with the regulations relating to Sequence Listings, the following codes have been used in the Sequence Listing to indicate the locations of biallelic markers within the sequences and to identify each of the alleles present at the polymorphic base. The code "r" in the sequences indicates that one allele of the polymorphic base is a guanine, while the other allele is an adenine. The code "y" in the sequences,indicates that one allele of the polymorphic base is a thymine, while the other allele is a cytosine. The code "m" in the sequences indicates that one allele of the polymorphic base is an adenine, while the other allele is an cytosine. The code "k" in the sequences indicates that one allele of the polymorphic base is a guanine, while the other allele is a thymine. The code "s" in the sequences indicates that one allele of the polymorphic base is a guanine, while the other allele is a cytosine. The code "w" in the sequences indicates that one allele of the polymorphic base is an adenine, while the other allele is an thymine. The nucleotide code of the original allele for each biallelic marker is the following:

| Biallelic marker | Original allele |
| --- | --- |
| 99-430-352 | G |
| 99-20508-456 | C |
| 99-20469-213 | C |
| 5-254-227 | A |
| 5-257-353 | C |
| 99-20511-32 | T |
| 99-20511-221 | A |
| 99-20504-90 | G |
| 99-20493-238 | A |
| 99-20499-221 | G |
| 99-20499-364 | A |
| 99-20499-399 | A |
| 5-249-304 | G |
| 99-20485-269 | A |
| 99-20481-131 | G |
| 99-20481-419 | T |
| 99-20480-233 | A |

DETAILED DESCRIPTION OF THE INVENTION

The present invention concerns polynucleotides and polypeptides related to the human TBC-1 gene (also termed "TBC-1 gene" throughout the present specification), which is potentially involved in the regulation of the differentiation of various cell types in mammals. A deregulation or an alteration of TBC-1 expression, or alternatively an alteration in the amino acid sequence of the TBC-1 protein may be involved in the generation of a pathological state related to cell differentiation in a patient, more particularly to abnormal cell proliferation leading to cancer states, such as prostate cancer.

Definitions

Before describing the invention in greater detail, the following definitions are set forth to illustrate and define the meaning and scope of the terms used to describe the invention herein.

The term "TBC-1 gene", when used herein, encompasses mRNA and cDNA sequences encoding the TBC-1 protein. In the case of a genomic sequence, the TBC-1 gene also includes native regulatory regions which control the expression of the coding sequence of the TBC-1 gene.

The term "functionally active fragment" of the TBC-1 protein is intended to designate a polypeptide carrying at least one of the structural features of the TBC-1 protein involved in at least one of the biological functions and/or activity of the TBC-1 protein.

A "heterologous" or "exogenous" polynucleotide designates a purified or isolated nucleic acid that has been placed, by genetic engineering techniques, in the environment of unrelated nucleotide sequences, such as the final polynucleotide construct does not occur naturally. An illustrative, but not limitative, embodiment of such a polynucleotide construct may be represented by a polynucleotide comprising (1) a regulatory polynucleotide derived from the TBC-1 gene sequence and (2) a polynucleotide encoding a cytokine, for example GM-CSF. The polypeptide encoded by the heterologous polynucleotide will be termed an heterologous polypeptide for the purpose of the present invention.

By a "biologically active fragment or variant" of a regulatory polynucleotide according to the present invention is intended a polynucleotide comprising or alternatively consisting in a fragment of said polynucleotide which is functional as a regulatory region for expressing a recombinant polypeptide or a recombinant polynucleotide in a recombinant cell host.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operatively linked" to nucleotide sequences which encode the desired polypeptide or the desired polynucleotide. An operable linkage is a linkage in which the regulatory nucleic acid and the DNA sequence sought to be expressed are linked in such a way as to permit gene expression.

A "promoter" refers to a DNA sequence recognized by the synthetic machinery of the cell required to initiate the specific transcription of a gene.

A sequence which is "operably linked" to a regulatory sequence such as a promoter means that said regulatory element is in the correct location and orientation in relation to the nucleic acid to control RNA polymerase initiation and expression of the nucleic acid of interest.

As used herein, the term "operably linked" refers to a linkage of polynucleotide elements in a functional relationship. For instance, a promoter or enhancer is operably linked to a coding sequence if it affects the transcription of the coding sequence. More precisely, two DNA molecules (such as a polynucleotide containing a promoter region and a polynucleotide encoding a desired polypeptide or polynucleotide) are said to be "operably linked" if the nature of the linkage between the two polynucleotides does not (1) result in the introduction of a frame-shift mutation or (2) interfere with the ability of the polynucleotide containing the promoter to direct the transcription of the coding polynucleotide. The promoter polynucleotide would be operably linked to a polynucleotide encoding a desired polypeptide or a desired polynucleotide if the promoter is capable of effecting transcription of the polynucleotide of interest.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., polynucleotide as defined hereinbelow) which can be used to identify a specific polynucleotide sequence present in samples, said nucleic acid segment comprising a nucleotide sequence complementary of the specific polynucleotide sequence to be identified.

The terms "sample" or "material sample" are used herein to designate a solid or a liquid material suspected to contain a polynucleotide or a polypeptide of the invention. A solid material may be, for example, a tissue slice or biopsy within which is searched the presence of a polynucleotide encoding a TBC-1 protein, either a DNA or RNA molecule or within which is searched the presence of a native or a mutated TBC-1 protein, or alternatively the presence of a desired protein of interest the expression of which has been placed under the control of a TBC-1 regulatory polynucleotide. A liquid material may be, for example, any body fluid like serum, urine etc., or a liquid solution resulting from the extraction of nucleic acid or protein material of interest from a cell suspension or from cells in a tissue slice or biopsy. The term "biological sample" is also used and is more precisely defined within the Section dealing with DNA extraction.

As used herein, the term "purified" does not require absolute purity; rather, it is intended as a relative definition. Purification if starting material or natural material to at least one order of magnitude, preferably two or three orders, and more preferably four or five orders of magnitude is expressly contemplated. As an example, purification from 0.1% concentration to 10% concentration is two orders of magnitude.

The term "isolated" requires that the material be removed from its original environment (e.g. the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition and still be isolated in that the vector or composition is not part of its natural environment.

The term "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

The term "purified" is used herein to describe a polypeptide of the invention which has been separated from other compounds including, but not limited to nucleic acids, lipids, carbohydrates and other proteins. A polypeptide is substantially pure when at least about 50%, preferably 60 to 75% of a sample exhibits a single polypeptide sequence. A substantially pure polypeptide typically comprises about 50%, preferably 60 to 90% weight/weight of a protein sample, more usually about 95%, and preferably is over about 99% pure. Polypeptide purity or homogeneity is indicated by a number of means well known in the art, such as polyacrylamide gel electrophoresis of a sample, followed by visualizing a single polypeptide band upon staining the gel. For certain purposes higher resolution can be provided by using HPLC or other means well known in the art.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, in Fab', F(ab)$_2$, and F(ab')$_2$ fragments.

As used herein, an "antigenic determinant" is the portion of an antigen molecule, in this case a TBC-1 polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8–10 such amino acids. Methods for determining the amino acids which make up an epitope include x-ray crystallography, 2-dimensional nuclear magnetic resonance, and epitope mapping e.g. the Pepscan method described by Geysen et al. 1984; PCT Publication No. WO 84/03564; and PCT Publication No. WO 84/03506.

Throughout the present specification, the expression "nucleotide sequence" may be employed to designate indifferently a polynucleotide or an oligonucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

As used interchangeably herein, the term "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modification (a) an alternative linking group, (b) an analogous form of purine, (c) an analogous form of pyrimidine, or (d) an analogous sugar, for examples of analogous linking groups, purine, pyrimidines, and sugars see for example PCT publication No WO 95/04064. However, the polynucleotides of the invention are preferably comprised of greater than 50% conventional deoxyribose nucleotides, and most preferably greater than 90% conventional deoxyribose nucleotides. The polynucleotide sequences of the invention may be prepared by any known method, including synthetic, recombinant, ex vivo generation, or a combination thereof, as well as utilizing any purification methods known in the art.

The term "heterozygosity rate" is used herein to refer to the incidence of individuals in a population which are heterozygous at a particular allele. In a biallelic system, the heterozygosity rate is on average equal to $2P_a(1-P_a)$, where $P_a$ is the frequency of the least common allele. In order to be useful in genetic studies, a genetic marker should have an adequate level of heterozygosity to allow a reasonable probability that a randomly selected person will be heterozygous.

The term "genotype" as used herein refers the identity of the alleles present in an individual or a sample. In the context of the present invention a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is a single base pair change. Typically a single nucleotide polymorphism is the replacement of one nucleotide by another nucleotide at the polymorphic site. Deletion of a single nucleotide or insertion of a single nucleotide, also give rise to single nucleotide polymorphisms. In the context of the present invention "single nucleotide polymorphism" preferably refers to a single nucleotide substitution. However, the polymorphism can also involve an insertion or a deletion of at least one nucleotide, preferably between 1 and 5 nucleotides. Typically, between different genomes or between different individuals, the polymorphic site may be occupied by two different nucleotides.

The term "biallelic polymorphism" and "biallelic marker" are used interchangeably herein to refer to a single nucleotide polymorphism having two alleles at a fairly high frequency in the population. A "biallelic marker allele" refers to the nucleotide variants present at a biallelic marker site. Typically, the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker".

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

As used herein the terminology "defining a biallelic marker" means that a sequence includes a polymorphic base from a biallelic marker. The sequences defining a biallelic marker may be of any length consistent with their intended use, provided that they contain a polymorphic base from a biallelic marker. The sequence has between 1 and 500 nucleotides in length, preferably between 5, 10, 15, 20, 25, or 40 and 200 nucleotides and more preferably between 30 and 50 nucleotides in length. Each biallelic marker therefore corresponds to two forms of a polynucleotide sequence included in a gene, which, when compared with one another, present a nucleotide modification at one position. Preferably, the sequences defining a biallelic marker include a polymorphic base selected from the group consisting of the biallelic markers A1 to A19 and the complements thereof. In some embodiments the sequences defining a biallelic marker comprise one of the sequences selected from the group consisting of P1 to P7, P9 to P13, P15 to P19 and the complementary sequences thereto. Likewise, the term "marker" or "biallelic marker" requires that the sequence is of sufficient length to practically (although not necessarily unambiguously) identify the polymorphic allele, which usually implies a length of at least 4, 5, 6, 10, 15, 20, 25, or 40 nucleotides.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another be virtue of their sequence identities in a manner like that found in double-helical DNA with thymine or uracil residues linked to adenine residues by two hydrogen bonds and cytosine and guanine residues linked by three hydrogen bonds (See Stryer, L., *Biochemistry*, $4^{th}$ edition, 1995).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences ad not any particular set of conditions-under which the two polynucleotides would actually bind.

Variants and Fragments

1. Polynucleotides

The invention also relates to variants and fragments of the polynucleotides described herein, particularly of a TBC-1 gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the invention include, without being limited to, nucleotide sequences that are at least 95% identical to any of SEQ ID Nos 1–4 or the sequences complementary thereto or to any polynucleotide fragment of at least 8 consecutive nucleotides of any of SEQ ID Nos 1–4 or the sequences complementary thereto, and preferably at least 98% identical, more particularly at least 99.5% identical, and most preferably at least 99.9% identical to any of SEQ ID Nos 1–4 or the sequences complementary thereto or to any polynucleotide fragment of at least 8 consecutive nucleotides of any of SEQ ID Nos 1–4 or the sequences complementary thereto.

Changes in the nucleotide of a variant may be silent, which means that they do not alter the amino acids encoded by the polynucleotide.

However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as the mature TBC-1 protein.

A polynucleotide fragment is a polynucleotide having a sequence that entirely is the same as part but not all of a given nucleotide sequence, preferably the nucleotide sequence of a TBC-1 gene, and variants thereof. The fragment can be a portion of an exon or of an intron of a TBC-1 gene. It can also be a portion of the regulatory sequences of the TBC-1 gene. Preferably, such fragments comprise the polymorphic base of a biallelic marker selected from the group consisting of the biallelic markers A1 to A19 and the complements thereof.

Such fragments may be "free-standing", i.e. not part of or fused to other polynucleotides, or they may be comprised within a single larger polynucleotide of which they form a part or region. However, several fragments may be comprised within a single larger polynucleotide.

As representative examples of polynucleotide fragments of the invention, there may be mentioned those which have from about 4, 6, 8, 15, 20, 25, 40, 10 to 20, 10 to 30, 30 to 55, 50 to 100, 75 to 100 or 100 to 200 nucleotides in length. Preferred are those fragments having about 49 nucleotides in length, such as those of P1 to P7, P9 to P13, P15 to P19 or the sequences complementary thereto and containing at least one of the biallelic markers of a TBC-1 gene which are described herein.

2. Polypeptides

The invention also relates to variants, fragments, analogs and derivatives of the polypeptides described herein, including mutated TBC-1 proteins.

The variant may be 1) one in which one or more of the amino acid residues are substituted with a conserved or non-conserved amino acid residue (preferably a conserved amino acid residue) and such substituted amino acid residue may or may not be one encoded by the genetic code, or 2) one in which one or more of the amino acid residues includes a substituent group, or 3) one in which the mutated TBC-1 is fused with another compound, such as a compound to increase the half-life of the polypeptide (for example, polyethylene glycol), or 4) one in which the additional amino acids are fused to the mutated TBC-1, such as a leader or secretory sequence or a sequence which is employed for purification of the mutated TBC-1 or a preprotein sequence. Such variants are deemed to be within the scope of those skilled in the art.

More particularly, a variant TBC-1 polypeptide comprises amino acid changes ranging from 1, 2, 3, 4, 5, 10 to 20 substitutions, additions or deletions of one amino acid, preferably from 1 to 10, more preferably from 1 to 5 and most preferably from 1 to 3 substitutions, additions or deletions of one amino acid. The preferred amino acid changes are those which have little or no influence on the biological activity or the capacity of the variant TBC-1 polypeptide to be recognized by antibodies raised against a native TBC-1 protein.

By homologous peptide according to the present invention is meant a polypeptide containing one or several aminoacid additions, deletions and/or substitutions in the amino acid sequence of a TBC-1 polypeptide. In the case of an aminoacid substitution, one or several—consecutive or non-consecutive—aminoacids are replaced by <<equivalent>> aminoacids.

The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged. Generally, the following groups of amino acids represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His.

By an equivalent aminoacid according to the present invention is also meant the replacement of a residue in the L-form by a residue in the D form or the replacement of a Glutamic acid (E) residue by a Pyro-glutamic acid compound. The synthesis of peptides containing at least one residue in the D-form is, for example, described by Koch (1977).

A specific, but not restrictive, embodiment of a modified peptide molecule of interest according to the present invention, which consists in a peptide molecule which is resistant to proteolysis, is a peptide in which the —CONH— peptide bond is modified and replaced by a ($CH_2NH$) reduced bond, a (NHCO) retro inverso bond, a ($CH_2$—O) methylene-oxy bond, a ($CH_2$—S) thiomethylene bond, a ($CH_2CH_3$) carba bond, a (CO—$CH_2$) cetomethylene bond, a (CHOH—$CH_2$) hydroxyethylene bond), a (N—N) bound, a E-alcene bond or also a CH=CH— bond.

The polypeptide accoding to the invention could have post-translational modifications. For example, it can present the following modifications: acylation, disulfide bond formation, prenylation, carboxymethylation and phosphorylation.

A polypeptide fragment is a polypeptide having a sequence that entirely is the same as part but not all of a given polypeptide sequence, preferably a polypeptide encoded by a TBC-1 gene and variants thereof. Preferred fragments include those regions possessing antigenic properties and which can be used to raise antibodies against the TBC-1 protein.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which comprise at least about 5, 6, 7, 8, 9 or 10 to 15, 10 to 20, 15 to 40, or 30 to 55 amino acids of the TBC-1. In some embodiments, the fragments contain at least one amino acid mutation in the TBC-1 protein.

Identity between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e, gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art Preferably, the scoring matrix used is the BLOSUM62 matrix (Gonnet et al., 1992; Henikoff and Henikoff, 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990).

Stringent Hybridization Conditions

By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 $\mu$/ml denatured salmon sperm DNA. Filters are hybridized for 48 h at 65° C., the preferred hybridization temperature, in prehybridization mixture containing 100 $\mu$g/ml denatured salmon sperm DNA and 5–20× $10^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0. 1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989; and Ausubel et al., 1989, are incorporated herein in their entirety. These hybridization conditions are suitable for a nucleic acid molecule of about 20 nucleotides in length. There is no need to say that the hybridization conditions described above are to be adapted according to the length of the desired nucleic acid, following techniques well known to the one skilled in the art. The suitable hybridization conditions may for example be adapted according to the teachings disclosed in the book of Hames and Higgins (1985) or in Sambrook et al.(1989).

Candidate Region on the Chromosome 4 (Linkage Analysis)

In order to localize the prostate cancer gene(s) starting from families, a systematic familial study of genetic link research is carried out using markers of the microsatellite type described at the Genethon laboratory by the Jean Weissenbach team (Dib et al., 1996).

The studies of genetic link or of "linkage" are based on the principle according to which two neighboring sequences on a chromosome do not present (or very rarely present) recombinations by crossing-over during meiosis. To do this, microsatellite DNA sequences (chromosomal markers) constantly co-inherited with the disease studied are searched for in a family having a predisposition for this disease. These DNA sequences organized in the form of a repetition of di-, tri- or tetranucleotides are systematically present along the genome, and thus allow the identification of chromosomal fragments harboring them. More than 5000 microsatellite markers, have been localized with precision on the genome as a result of the first studies on the genetic map carried out at Genethon under the supervision of Jean Weissenbach, and on the physical map (using the "Yeast Artificial Chromosomes"), work conducted by Daniel Cohen at C.E.P.H. and at Genethon (Chumakov et al, 1995). Genetic link analysis calculates the probabilities of recombinations of the target gene with the chromosomal markers used, according to the genealogical tree, the transmission of the disease, and the transmission of the markers. Thus if a particular allele of a given marker is transmitted with the disease more often than chance would have it (recombination level of between 0 and 0.5), it is possible to deduce that the target gene in question is found in the neighborhood of the marker. Using this technique, it has been possible to localize several genes of genetic predisposition to familial cancers. In order to be able to be included in a genetic link study, the families affected by a hereditary form of the disease must satisfy the "informativeness" criteria: several affected subjects (and whose constitutional DNA is available) per generation, and at best having a large number of siblings.

By linkage analysis, the inventors have identified a candidate region for prostate cancer on chromosome 4. Indeed, the LOD scores at 2 points between the disease and the markers on a total population of approximately fifty families present a value of 2.49 for marker D4S398 which indicates a probable genetic link with this marker. The curve of the variation of the LOD score on a map of 5 markers is centered on D4S398 and the value higher than 3.3 indicates that a gene involved in familial prostate cancer is probably found in the region located between markers D4S2978 and D4S3018, or a space of approximately 9.7 cM.

Homologies of the Novel Human Gene Translation Product with a Known Murine Protein A novel human gene was found in this candidate region. It presents a good probability to be involved in cancer. Database homology searches have allowed the inventors to determine that the translation product of this novel human gene has significant identity with a murine protein called tbc1. Therefore, the novel human gene of the invention has thus been called TBC-1 throughout the present specification. TBC-1 comprises an open Reading frame that encodes a novel protein, the TBC-1 protein. Based on sequence similarity, an alignment of a portion of the TBC-1 amino acid sequence with the known tbc-1 murine protein, it is expected that TBC1 protein may play a role in the cell cycle and in differentiation of various tissues. Indeed, the TBC1 protein contains a 200 amino acid domain called the TBC domain that is homologous to regions in the tre2-oncogene and in the yeast regulators of mitosis BUB2 and cdc16.

The cDNA of the murine tbc1 gene has been described in U.S. Pat. No. 5,700,927 and it encodes a putative protein product of 1141 amino acids. The N-terminus of the murine tbc1 protein contains stretches of cysteines and histidines which may form zinc finger structures in the mature polypeptides. The N-terminus also comprises short stretches of basic amino acids which may be involved in a nuclear localization signal. The TBC domain of the murine tbc1 protein contains several tyrosine residues which are conserved in BUB2 and cdc16. The C-terminus of the murine tbc1 protein contains a long stretch of evenly spaced leucine residues which are susceptible to form a leucine zipper motif.

The murine tbc1 gene has been shown to be highly expressed in testis and kidney. However, lower levels of expression have also be identified in lung, spleen, brain, and heart. Moreover, murine tbc1 is a nuclear protein which is expressed in a cell-and stage-specific manner.

Studies of murine bone marrow have demonstrated that erythroid cells and megakaryocytes expressed substantial levels of the murine tbc1 protein, but none was detected in mature neutrophils. Similarly, spermatogonia do not express murine tbc1, but primary and secondary spermatocytes express abundant tbc1. Later in the differentiation of the germ cells, the tbc1 levels appear to decrease in spermatids and active sperm. The differentiation program of spermatogonia to spermatocytes therefore involves a significant upregulation of murine tbc1 expression.

The general distribution of murine tbc is not tissue-specific, but is cell-specific within individual tissues and intimately linked to tissue differentiation. The developmental expression of murine tbc1, particularly in hematopoictic and germ cells, suggests that this gene plays a role in the terminal differentiation program of several tissues.

Consequently, an alteration in the expression of the TBC-1 gene or in the amino acid sequence of the TBC-1 protein leading to an altered biological activity of the latter is likely to cause, directly or indirectly, cell proliferation disorders and thus diseases related to an abnormal cell proliferation such as cancer, particularly prostate cancer.

Genomic Sequence of TBC-1

The present invention concerns the genomic sequence of TBC-1. The present invention encompasses the TBC-1 gene, or TBC-1 genomic sequences consisting of, consisting essentially of, or comprising a sequence selected from the group consisting of SEQ ID Nos 1 and 2, a sequence complementary thereto, as well as fragments and variants thereof. These polynucleotides may be purified, isolated, or recombinant.

The inventors have sequenced two portions of the TBC-1 genomic sequence. The first portion of the TBC-1 gene sequence contains the three first exons of the TBC-1 gene, designated as Exon 1, Exon 1bis and Exon 2, and the 5' regulatory sequence located upstream of the transcribed sequences. The sequence of the first portion of the genomic sequence is disclosed in SEQ ID No 1. The second portion contains the twelve last exons of the TBC-1 gene, designated as exons A, B, C, D, E, F, G, H, I, J, K, and L, and the 3' regulatory sequence which is located downstream of the transcribed sequences.

The exon positions in SEQ ID Nos 1 and 2 are detailed below in Table A.

TABLE A

| Exon | Begin-ning | End | Intron | Begin-ning | End |
|---|---|---|---|---|---|
| | Position in SEQ ID No 1 | | | Position in SEQ ID No 1 | |
| 1 | 2001 | 2077 | 1 | 2078 | 12739 |
| 1bis | 12292 | 12373 | 1bis | 12374 | 12739 |
| 2 | 12740 | 13249 | 2 | 13250 | at least 17590 |
| | Position in SEQ ID No 2 | | | Position in SEQ ID No 2 | |
| A | 4661 | 4789 | A | 4790 | 6115 |
| B | 6116 | 6202 | B | 6203 | 9918 |
| C | 9919 | 10199 | C | 10200 | 14520 |
| D | 14521 | 14660 | D | 14661 | 50256 |
| E | 50257 | 50442 | E | 50443 | 56255 |
| F | 56256 | 56417 | F | 56418 | 63325 |
| G | 63326 | 63484 | G | 63485 | 76035 |
| H | 76036 | 76280 | H | 76281 | 78363 |

TABLE A-continued

| Exon | Beginning | End | Intron | Beginning | End |
|---|---|---|---|---|---|
| I | 78364 | 78523 | I | 78524 | 85294 |
| J | 85295 | 85464 | J | 85465 | 93416 |
| K | 93417 | 93590 | K | 93591 | 97475 |
| L | 97476 | 97960 | | | |

Intron 1 refers to the nucleotide sequence located between Exon 1 and Exon 2; Intron 1bis refers to the nucleotide sequence located between Exon 1bis and Exon 2; Intron A refers to the nucleotide sequence located between Exon A and Exon B; and so on. The position of the introns is detailed in Table A.

The TBC-1 introns defined hereinafter for the purpose of the present invention are not exactly what is generally understood as "introns" by the one skilled in the art and will consequently be further defined below.

Generally, an intron is defined as a nucleotide sequence that is present both in the genomic DNA and in the unspliced mRNA molecule, and which is absent from the mRNA molecule which has already gone through splicing events. In the case of the TBC-1 gene, the inventors have found that at least two different spliced mRNA molecules are produced when this gene is transcribed, as it will be described in detail in a further section of the specification. The first spliced mRNA molecule comprises Exons 1 and 2. Thus, the genomic nucleotide sequence comprised between Exon 1 and Exon 2 is an intronic sequence as regards to this fist mRNA molecule, despite the fact that this intronic sequence contains Exon 1bis. In contrast, Exon 1bis is of course an exonic nucleotide sequence as regards to the second TBC-1 mRNA molecule.

For the purpose of the present invention and in order to make a clear and unambiguous designation of the different nucleic acids encompassed, it has been postulated that the polynucleotides contained both in any of the nucleotide sequences of SEQ ID Nos 1 or 2 and in any of the nucleotide sequences of SEQ ID Nos 3 or 4 are considered as exonic sequences. Conversely, the polynucleotides contained in any of the nucleotide sequences of SEQ ID Nos 1 or 2 but which are absent both from the nucleotide sequence of SEQ ID No 3 and from the nucleotide sequence of SEQ ID No 4 are considered as intronic sequences.

The nucleic acids defining the TBC-1 introns described above, as well as their fragments and variants, may be used as oligonucleotide primers or probes in order to detect the presence of a copy of the TBC-1 gene in a test sample, or alternatively in order to amplify a target nucleotide sequence within the TBC-1 intronic sequences.

Thus, the invention embodies purified, isolated, or recombinant polynucleotides comprising a nucleotide sequence selected from the group consisting of the 15 exons of the TBC-1 gene which are described in the present invention, or a sequence complementary thereto. The invention also deals with purified, isolated, or recombinant nucleic acids comprising a combination of at least two exons of the TBC-1 gene, wherein the polynucleotides are arranged within the nucleic acid, from the 5'-end to the 3'-end of said nucleic acid, in the same order as in SEQ ID Nos 1 and 2.

Thus, the invention embodies purified, isolated, or recombinant polynucleotides comprising a nucleotide sequence selected from the group consisting of the introns of the TBC-1 gene, or a sequence complementary thereto.

The invention also encompasses a purified, isolated, or recombinant polynucleotide comprising a nucleotide sequence having at least 70, 75, 80, 85, 90, or 95% nucleotide identity with a sequence selected from the group consisting of SEQ ID Nos 1 and 2 or a complementary sequence thereto or a fragment thereof. The nucleotide differences as regards to the nucleotide sequence of SEQ ID Nos 1 or 2 may be generally randomly distributed throughout the entire nucleic acid. Nevertheless, preferred nucleic acids are those wherein the nucleotide differences as regards to the nucleotide sequence of SEQ ID Nos 1 or 2 are predominantly located outside the coding sequences contained in the exons. These nucleic acids, as well as their fragments and variants, may be used as oligonucleotide primers or probes in order to detect the presence of a copy of the TBC-1 gene in a test sample, or alternatively in order to amplify a target nucleotide sequence within the TBC-1 sequences.

Another object of the invention consists of a purified, isolated, or recombinant nucleic acid that hybridizes with a sequence selected from the group consisting of SEQ ID Nos 1 and 2 or a complementary sequence thereto or a variant thereof, under the stringent hybridization conditions as defined above.

Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of a nucleotide sequence selected from the group consisting of SEQ ID Nos 1 and 2, or the complements thereof. Additionally preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least 1, 2, 3, 5, or 10 of the following nucleotide positions of SEQ ID No 1: 1–1000, 1001–2000, 2001–3000, 3001–4000, 4001–5000, 5001–6000, 6001–7000, 7001–8000, 8001–9000, 9001–10000, 10001–11000, 11001–12000, 12001–13000, 13001–14000, 14001–15000, 15001–16000, 16001–17000, and 17001–17590. Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least 1, 2, 3, 5, or 10 of the following nucleotide positions of SEQ ID No 2: 1–5000, 5001–10000, 10001–15000, 15001–20000, 20001–25000, 25001–30000, 30001–35000, 35001–40000, 40001–45000, 45001–50000, 50001–55000, 55001–60000, 60001–65000, 65001–70000, 70001–75000, 75001–80000, 80001–85000, 85001–90000, 90001–95000, and 95001–99960.

While this section is entitled "Genomic Sequences of TBC-1," it should be noted that nucleic acid fragments of any size and sequence may also be comprised by the polynucleotides described in this section, flanking the genomic sequences of TBC-1 on either side or between two or more such genomic sequences.

TBC-1 cDNA Sequences

The inventors have discovered that the expression of the TBC-1 gene leads to the production of at least two mRNA molecules, respectively a first and a second TBC-1 transcription product, as the results of alternative splicing events. They result from two distinct first exons, namely Exon 1 and Exon 1bis.

The first transcription product comprises Exons 1, 2, A, B, C, D, E, F, G, H, I, J, K, and L. This cDNA of SEQ ID No 3 includes a 5'-UTR region, spanning the whole Exon 1 and part of Exon 2. This 5'-UTR region starts from the nucleotide at position 1 and ends at the nucleotide at position 170 of the nucleotide sequence of SEQ ID No 3. The cDNA of SEQ ID No 3 includes a 3'-UTR region starting from the nucleotide at position 3726 and ending at the nucleotide at position 3983 of the nucleotide sequence of SEQ ID No 3. This first transcription product harbors a polyadenylation signal located between the nucleotide at position 3942 and the nucleotide at position 3947 of the nucleotide sequence of SEQ ID No 3.

The second TBC-1 transcription product comprises Exons 1bis, 2, A, B, C, D, E, F, G, H, I, J, K, and L. This cDNA of SEQ ID No 4 includes a 5'-UTR region starting from the nucleotide at position 1 and ending at the nucleotide at position 175 of the nucleotide sequence of SEQ ID No 4. This second cDNA also includes a 3'-UTR region starting from the nucleotide at position 3731 and ending at the nucleotide at position 3988 of the nucleotide sequence of SEQ ID No 4. This second transcription product harbors a polyadenylation signal located between the nucleotide at position 3947 and the nucleotide at position 3952 of the nucleotide sequence of SEQ ID No 4.

The 5'-end sequence of this second TBC-1 mRNA, more particularly the nucleotide sequence comprised between the nucleotide in position 1 and the nucleotide in position 458 of the nucleic acid of SEQ ID No 4 molecule corresponds to the nucleotide sequence of a 5'-EST that has been obtained from a human pancreas cDNA library and characterized following the teachings of the PCT Application No WO 96/34981. This 5'-EST is also part of the invention.

Another object of the invention consists of a purified or isolated nucleic acid comprising a polynucleotide selected from,the group consisting of the nucleotide sequences of SEQ ID Nos 3 and 4 and to nucleic acid fragments thereof.

Preferred nucleic acid fragments of the nucleotide sequences of SEQ ID Nos 3 and 4 consist in polynucleotides comprising their respective Open Reading Frames encoding the TBC-1 protein.

Other preferred nucleic acid fragments of the nucleotide sequences of SEQ ID Nos 3 and 4 consist in polynucleotides comprising at least a part of their respective 5'-UTR or 3'-UTR regions.

The invention also pertains to a purified or isolated nucleic acid having at least a 95% of nucleotide identity with any one of the nucleotide sequences of SEQ ID Nos 3 and 4, or a fragment thereof.

Another object of the invention consists of purified, isolated or recombinant nucleic acids comprising a polynucleotide that hybridizes, under the stringent hybridization conditions defined herein, with any one of the nucleotide sequences of SEQ ID Nos 3 and 4, or a sequence complementary thereto or a fragment thereof.

The invention also relates to isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of a nucleotide sequence selected from the group consisting of SEQ ID Nos 3 and 4, or the complements thereof. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, or 10 of the following nucleotide positions of SEQ ID No 3: 1–500, 501–1000, 1001–1500, 1501–2000, 2001–2500, 2501–3000, 3001–3500, and 3501–3983. Additionally preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least 1, 2, 3, 5, or 10 of the following nucleotide positions of SEQ ID No 4: 1–500, 501–1000, 1001–1500, 1501–2000, 2001–2500, 2501–3000, 3001–3500, and 3501–3988. Such a nucleic acid is notably useful as polynucleotide probe or primer specific for the TBC-1 gene or the TBC-1 mRNAs and cDNAs.

While this section is entitled "TBC-1 cDNA Sequences," it should be noted that nucleic acid fragments of any size and sequence may also be comprised by the polynucleotides described in this section, flanking the genomic sequences of TBC-1 on either side or between two or more such genomic sequences.

Coding Regions

The TBC-1 open reading frame is contained in the two TBC-1 mRNA molecules of about 4 kilobases isolated by the inventors.

More precisely, the effective TBC-1 coding sequence is comprised between the nucleotide at position 171 and the nucleotide at position 3725 of SEQ ID No 3, and between the nucleotide at position 176 and the nucleotide at position 3730 of the nucleotide sequence of SEQ ID No 4.

The invention further provides a purified or isolated nucleic acid comprising a polynucleotide selected from the group consisting of a polynucleotide comprising a nucleic acid sequence located between the nucleotide at position 171 and the nucleotide at position 3725 of SEQ ID No 3, and a polynucleotide comprising a nucleic acid sequence located between the nucleotide at position 176 and the nucleotide at position 3730 of SEQ ID No 4 or a variant or fragment thereof or a sequence complementary thereto.

The present invention concerns a purified or isolated nucleic acid encoding a human TBC-1 protein, wherein said TBC-1 protein comprises an amino acid sequence of SEQ ID No 5, a nucleotide sequence complementary thereto, a fragment or a variant thereof. The present invention also embodies isolated, purified, and recombinant polynucleotides which encode a polypeptides comprising a contiguous span of at least 6 amino acids, preferably at least 8 or 10 amino acids, more preferably at least 12, 15, 20, 25, 30, 40, 50, or 100 amino acids of SEQ ID No 5. In a preferred embodiment, the present invention embodies isolated, purified, and recombinant polynucleotides which encode a polypeptides comprising a contiguous span of at least 6 amino acids, preferably at least 8 or 10 amino acids, more preferably at least 12, 15, 20, 25, 30, 40, 50, or 100 amino acids of SEQ ID No 5 wherein said contiguous span includes at least 1, 2, 3, 5 or 10 of the following amino acid positions in SEQ ID No 5: 1–300, 301–600, 601–900, and 901–1168.

The above disclosed polynucleotide that contains only coding sequences derived from the TBC-1 ORF may be expressed in a desired host cell or a desired host organism, when said polynucleotide is placed under the control of suitable expression signals. Such a polynucleotide, when placed under the suitable expression signals, may be inserted in a vector for its expression.

Regulatory Sequences of TBC-1

The invention further deals with a purified or isolated nucleic acid comprising the nucleotide sequence of a regulatory region which is located either upstream of the first exon of the TBC-1 gene and which is contained in the TBC-1 genomic sequence of SEQ ID No 1, or downstream of the last exon of the TBC-1 gene and which is contained in the TBC-1 genomic sequence of SEQ ID No 2.

The 5'-regulatory sequence of the TBC-1 gene is localized between the nucleotide in position 1 and the nucleotide in position 2000 of the nucleotide sequence of SEQ ID No 1. The 3'-regulatory sequence of the TBC-1 gene is localized between nucleotide position 97961 and nucleotide position 99960 of SEQ ID No 2.

Polynucleotides derived from the 5' and 3' regulatory regions are useful in order to detect the presence of at least a copy of a nucleotide sequence of SEQ ID Nos 1 or 2 or a fragment thereof in a test sample.

The promoter activity of the 5' regulatory regions contained in TBC-1 can be assessed as described below.

Genomic sequences lying upstream of the TBC-1 Exons are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, beta galactosidase, or green fluorescent protein. The sequences upstream of the TBC-1 coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

Promoter sequences within the upstream genomic DNA may be further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter, individually or in combination. The effects of these mutations on transcription levels may be determined by inserting the mutations into the cloning sites in the promoter reporter vectors.

Thus, the minimal size of the promoter of the TBC-1 gene can be determined through the measurement of TBC-1 expression levels. For this assay, an expression vector comprising decreasing sizes from the promoter generally ranging from 2 kb to 100 bp, with a 3' end which is constant, operably linked to TBC-1 coding sequence or to a reporter gene is used. Cells, which are preferably prostate cells and more preferably prostate cancer cells, are transfected with this vector and the expression level of the gene is assessed.

The strength and the specificity of the promoter of the TBC-1 gene can be assessed through the expression levels of the gene operably linked to this promoter in different types of cells and tissues. In one embodiment, the efficacy of the promoter of the TBC-1 gene is assessed in normal and cancer cells. In a preferred embodiment, the efficacy of the promoter of the TBC-1 gene is assessed in normal prostate cells and in prostate cancer cells which can present different degrees of malignancy.

Polynucleotides carrying the regulatory elements located both at the 5' end and at the 3' end of the TBC-1 cDNAs may be advantageously used to control the transcriptional and translational activity of an heterologous polynucleotide of interest.

Thus, the present invention also concerns a purified or isolated nucleic acid comprising a polynucleotide which is selected from the group consisting of the 5' and 3' regulatory regions, or a sequence complementary thereto or a biologically active fragment or variant thereof. "5' regulatory region" refers to the nucleotide sequence located between positions 1 and 2000 of SEQ ID No 1. "3' regulatory region" refers to the nucleotide sequence located between positions 97961 and 99960 of SEQ ID No 2.

The invention also pertains to a purified or isolated nucleic acid comprising a polynucleotide having at least 95% nucleotide identity with a polynucleotide selected from the group consisting of the 5' and 3' regulatory regions, advantageously 99% nucleotide identity, preferably 99.5% nucleotide identity and most preferably 99.8% nucleotide identity with a polynucleotide selected from the group consisting of the 5' and 3' regulatory regions, or a sequence complementary thereto or a variant thereof or a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of the 5'- and 3' regulatory regions, or a sequence complementary thereto or a variant thereof or a biologically active fragment thereof.

The 5'UTR and 3'UTR regions of a gene are of particular importance in that they often comprise regulatory elements which can play a role in providing appropriate expression levels, particularly through the control of mRNA stability.

A 5' regulatory polynucleotide of the invention may include the 5'-UTR located between the nucleotide at position I and the nucleotide at position 170 of SEQ ID No 3, or a biologically active fragment or variant thereof.

Alternatively, a 5'-regulatory polynucleotide of the invention may include the 5'-UTR located between the nucleotide at position 1 and the nucleotide at position 175 of SEQ ED No 4, or a biologically active fragment or variant thereof.

A 3' regulatory polynucleotide of the invention may include the 3'-UTR located between the nucleotide at position 3726 and the nucleotide at position 3983 of SEQ ID No 4, or a biologically active fragment or variant thereof.

Thus, the invention also pertains to a purified or isolated nucleic acid which is selected from the group consisting of:

a) a nucleic acid comprising the nucleotide sequence of the 5' regulatory region;

b) a nucleic acid comprising a biologically active fragment or variant of the nucleic acid of the 5' regulatory region.

Preferred fragments of the nucleic acid of the 5' regulatory region have a length of about 1000 nucleotides, more particularly of about 400 nucleotides, more preferably of about 200 nucleotides and most preferably about 100 nucleotides. More particularly, the invention further includes specific elements within this regulatory region, these elements preferably including the promoter region.

Preferred fragments of the 3' regulatory region are at least 50, 100, 150, 200, 300 or 400 bases in length.

By a "biologically active fragment or variant" of a TBC-1 regulatory polynucleotide according to the present invention is intended a polynucleotide comprising or alternatively consisting in a fragment of said polynucleotide which is functional as a regulatory region for expressing a recombinant polypeptide or a recombinant polynucleotide in a recombinant cell host.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and if such sequences are "operatively linked" to nucleotide sequences which encode the desired polypeptide or the desired polynucleotide. An operable linkage is a linkage in which the regulatory nucleic acid and the DNA sequence sought to be expressed are linked in such a way as to permit gene expression.

In order, to identify the relevant biologically active polynucleotide derivatives of the 5' or 3' regulatory region, the one skill in the art will refer to the book of Sambrook et al. (Sambrook, 1989) in order to use a recombinant vector carrying a marker gene (i.e. beta galactosidase, chloramphenicol acetyl transferase, etc.) the expression of which will be detected when placed under the control of a biologically active derivative polynucleotide of the 5' or 3' regulatory region.

Regulatory polynucleotides of the invention may be prepared from any of the nucleotide sequences of SEQ ID Nos 1 or 2 by cleavage using the suitable restriction enzymes, the one skill in the art being guided by the book of Sambrook et al. (1989). Regulatory polynucleotides may also be prepared by digestion of any of the nucleotide sequences of SEQ ID Nos 1 or 2 by an exonuclease enzyme, such as Ba131 (Wabiko et al., 1986). These regulatory polynucleotides can also be prepared by chemical synthesis, as described elsewhere in the specification, when the synthesis of oligonucleotide probes or primers is disclosed.

The regulatory polynucleotides according to the invention may be advantageously part of a recombinant expression vector that may be used to express a coding sequence in a desired host cell or host organism. The recombinant expression vectors according to the invention are described elsewhere in the specification.

The invention also encompasses a polynucleotide comprising:

a) a nucleic acid comprising a regulatory nucleotide sequence of the 5' regulatory region, or a biologically active fragment or variant thereof;

b) a polynucleotide encoding a desired polypeptide or nucleic acid, operably linked to the nucleic acid comprising a regulatory nucleotide sequence of the 5' regulatory region, or its biologically active fragment or variant.

c) Optionally, a nucleic acid comprising a 3' regulatory polynucleotide, preferably a 3'regulatory polynucleotide of the invention.

The desired polypeptide encoded by the above described nucleic acid may be of various nature or origin, encompassing proteins of prokaryotic or eukaryotic origin. Among the polypeptides expressed under the control of a TBC-1 regulatory region, it may be cited bacterial, fungal or viral antigens. Are also encompassed eukaryotic proteins such as intracellular proteins, such as "house keeping" proteins, membrane-bound proteins, like receptors, and secreted proteins like the numerous endogenous mediators such as cytokines.

The desired nucleic acid encoded by the above described polynucleotide, usually a RNA molecule, may be complementary to a TBC-1 coding sequence and thus useful as an antisense polynucleotide.

Such a polynucleotide may be included in a recombinant expression vector in order to express a desired polypeptide or a desired polynucleotide in host cell or in a host organism. Suitable recombinant vectors that contain a polynucleotide such as described hereinbefore are disclosed elsewhere in the specification.

TBC-1 Polypeptide and Peptide Fragments thereof

It is now easy to produce proteins in high amounts by genetic engineering techniques through expression vectors such as plasmids, phages or phagemids. The polynucleotide that code for one the polypeptides of the present invention is inserted in an appropriate expression vector in order to produce the polypeptide of interest in vitro.

Thus, the present invention also concerns a method for producing one of the polypeptides described herein, and especially a polypeptide of SEQ ID No 5 or a fragment or a variant thereof, wherein said method comprises the steps of:

a) culturing, in an appropriate culture medium, a cell host previously transformed or transfected with the recombinant vector comprising a nucleic acid encoding a TBC-1 polypeptide, or a fragment or a variant thereof;

b) harvesting the culture medium thus conditioned or lyse the cell host, for example by sonication or by an osmotic shock;

c) separating or purifying, from the said culture medium, or from the pellet of the resultant host cell lysate the thus produced polypeptide of interest.

d) Optionally characterizing the produced polypeptide of interest.

In a specific embodiment of the above method, step a) is preceded by a step wherein the nucleic acid coding for a TBC-1 polypeptide, or a fragment or a variant thereof, is inserted in an appropriate vector, optionally after an appropriate cleavage of this amplified nucleic acid with one or several restriction endonucleases. The nucleic acid coding for a TBC-1 polypeptide or a fragment or a variant thereof may be the resulting product of an amplification reaction using a pair of primers according to the invention (by SDA, TAS, 3SR NASBA, TMA etc.).

The polypeptides according to the invention may be characterized by binding onto an immunoaffinity chromatography column on which polyclonal or monoclonal antibodies directed to a polypeptide of SEQ ID No 5, or a fragment or a variant thereof, have previously been immobilized.

Purification of the recombinant proteins or peptides according to the present invention may be carried out by passage onto a Nickel or Cupper affinity chromatography column. The Nickel chromatography column may contain the Ni-NTA resin (Porath et al., 1975).

The polypeptides or peptides thus obtained may be purified, for example by high performance liquid chromatography, such as reverse phase and/or cationic exchange HPLC, as described by Rougeot et al. (1994). The reason to prefer this kind of peptide or protein purification is the lack of byproducts found in the elution samples which renders the resultant purified protein or peptide more suitable for a therapeutic use.

Another object of the present invention consists in a purified or isolated TBC-1 polypeptide or a fragment or a variant thereof.

In a preferred embodiment, the TBC-1 polypeptide comprises an amino acid sequence of SEQ ID No 5 or a fragment or a variant thereof. The present invention also embodies isolated, purified, and recombinant polypeptides comprising a contiguous span of at least 6 amino acids, preferably at least 8 to 10 amino acids, more preferably at least 12, 15, 20, 25, 30, 40, 50, 100, 150 or 200 amino acids of SEQ ID No 5. The present invention also embodies isolated, purified, and recombinant polypeptides comprising a contiguous span of at least 6 amino acids, preferably at least 8 to 10 amino acids, more preferably at least 12, 15, 20, 25, 30, 40, 50, 100, 150 or 200 amino acids of SEQ ID No 5, wherein said contiguous span includes at least 1, 2, 3, 5 or 10 of the following amino acid positions: 1–200, 201–400, 401–400, 601–800, 801–1000, 1001–1168.

The invention also encompasses a purified, isolated, or recombinant polypeptides comprising an amino acid sequence having at least 90, 95, 98 or 99% amino acid identity with the amino acid sequence of SEQ ID No 5 or a fragment thereof.

The TBC-1 polypeptide of the invention possesses amino acid homologies as regards to the murine TBC-1 protein of 1141 amino acids in length which is described in U.S. Pat. No. 5,700,927. The TBC-1 protein of the invention also possesses some homologies with two other proteins: the Pollux drosophila protein (Zhang et al., 1996) and the CDC16 protein from *Caenorhabditis elegans* (Wilson et al., 1994). FIG. 1 represents an amino acid alignment of a portion of the amino acid sequence of the TBC-1 protein of SEQ ID No 5 with other proteins sharing amino acid homology with TBC-1. The upper line shows the whole amino acid sequence of the murine tbc-1 protein described in U.S. Pat. No. 5,700,927; the second line represents part of the amino acid sequence of the TBC-1 protein of SEQ ID No 5; the third line (Genbank access No: dmu50542) depicts the amino acid sequence of the Pollux protein mentioned above; the fourth line (Genbank access No: celf35h12) shows the amino acid sequence of the *C. elegans* protein mentioned above; the fifth line presents positions in which consensus amino acids are identified, i.e. amino acids shared by the sequences presented in the four upper lines, when present.

The TBC-1 polypeptide of the amino acid sequence of SEQ ID No 5 has 1168 amino acids in length. The TBC-1 polypeptide includes a "TBC domain" which is spanning from the amino acid in position 786 to the amino acid in position 974 of the amino acid sequence of SEQ ID No 5. This TBC domain is represented in FIG. 1 as a grey area spanning from the amino acid numbered 758 to the amino acid numbered 949. This TBC domain is likely to regulate protein-protein interactions. Moreover, the TBC-1 TBC domain includes the amino acid sequence EVGYCQGL, spanning from the amino acid in position 886 to the amino acid in position 893 of the amino acid sequence of SEQ ID No 5. The EVGYCQGL amino acid sequence spans from the amino acid numbered 861 to the amino acid numbered 868 of FIG. 1. This site may interact with a kinase. Based on the structural similarity to cdc16, a yeast regulator of mitosis, TBC-1 is likely to regulate mitosis and cytokinesis by interacting with other proteins which also participate with the regulation of mitosis, cytokinesis and septum formation.

Preferred polypeptides of the invention comprise the TBC domain of TBC-1, or alternatively at least the EVGYCQGL amino acid sequence motif.

A further object of the present invention concerns a purified or isolated polypeptide which is encoded by a nucleic acid comprising a nucleotide sequence selected from the group consisting of SEQ ID Nos 1, 2, 3, and 4 or fragments or variants thereof.

A single variant molecule of the TBC-1 protein is explicitly excluded from the scope of the present invention, which is a polypeptide having the same amino acid sequence than the murine tbc1 protein described in the U.S. Pat. No 5,700,927.

Amino acid deletions, additions or substitutions in the TBC-1 protein are preferably located outside of the TBC domain as defined above. Most preferably, a mutated TBC-1 protein has an intact "EVGYCQGL" amino acid motif.

Such a mutated TBC-1 protein may be the target of diagnostic tools, such as specific monoclonal or polyclonal antibodies, useful for detecting the mutated TBC-1 protein in a sample.

The invention also encompasses a TBC-1 polypeptide or a fragment or a variant thereof in which at least one peptide bound has been modified as described in the "Definitions" section.

Antibodies that Bind TBC-1 Polypeptides of the Invention

Any TBC-1 polypeptide or whole protein may be used to generate antibodies capable of specifically binding to an expressed TBC-1 protein or fragments thereof as described.

One antibody composition of the invention is capable of specifically binding or specifically bind to the variant of the TBC-1 protein of SEQ ID No 5. For an antibody composition to specifically bind to TBC-1, it must demonstrate at least a 5%, 10%, 15%, 20%, 25%, 50%, or 100% greater binding affinity for TBC-1 protein than for another protein in an ELISA, RIA, or other antibody-based binding assay.

In a preferred embodiment, the invention concerns antibody compositions, either polygonal or monoclonal, capable of selectively binding, or selectively bind to an epitope-containing a polypeptide comprising a contiguous span of at least 6 amino acids, preferably at least 8 to 10 amino acids, more preferably at least 12, 15, 20, 25, 30, 40, 50, 100, 150 or 200 amino acids of SEQ ID No 5; Optionally said epitope comprises at least 1, 2, 3, 5 or 10 of the following amino acid positions: 1–200, 201–400, 401–600, 601–800, 801–1000, 1001–1168.

The invention also concerns a purified or isolated antibody capable of specifically binding to a mutated TBC-1 protein or to a fragment or variant thereof comprising an epitope of the mutated TBC-1 protein. In another preferred embodiment, the present invention concerns an antibody capable of binding to a polypeptide comprising at least 10 consecutive amino acids of a TBC-1 protein and including at least one of the amino acids which can be encoded by the trait causing mutations.

In a preferred embodiment, the invention concerns the use in the manufacture of antibodies of a polypeptide comprising a contiguous span of at least 6 amino acids, preferably at least 8 to 10 amino acids, more preferably at least 12, 15, 20, 25, 30, 40, 50, 100, 150 or 200 amino acids of SEQ ID No 5; Optionally said polypeptide comprises at least 1, 2, 3, 5 or 10 of the following amino acid positions: 1–200, 201–400, 401–600, 601–800, 801–1000, 1001–1168.

The antibodies of the invention may be labeled by any one of the radioactive, fluorescent or enzymatic labels known in the art.

The TBC-1 polypeptide of SEQ ID No 5 or a fragment thereof can be used for the preparation of polyclonal or monoclonal antibodies.

The TBC-1 polypeptide expressed from a DNA sequence comprising at least one of the nucleic acid sequences of SEQ ID Nos 1, 2, 3 and 4 may also be used to generate antibodies capable of specifically binding to the TBC-1 polypeptide of SEQ ID No 5or a fragment thereof.

Preferred antibodies according to the invention are prepared using TBC-1 peptide fragments that do not comprise the EVGYCQGL amino acid motif.

Other preferred antibodies of the invention are prepared using TBC-1 peptide fragments that do not comprise the TBC domain defined elsewhere in the specification.

The antibodies may be prepared from hybridomas according to the technique described by Kobler and Milstein in 1975. The polyclonal antibodies may be prepared by immunization of a mammal, especially a mouse or a rabbit, with a polypeptide according to the invention that is combined with an adjuvant of immunity, and then by purifying of the specific antibodies contained in the serum of the immunized animal on a affinity chromatography column on which has previously been immobilized the polypeptide that has been used as the antigen.

The present invention also includes, chimeric single chain Fv antibody fragments (Martineau et al., 1998), antibody fragments obtained through phage display libraries (Ridder et al., 1995; Vaughan et al., 1995) and humanized antibodies (Reinmann et al., 1997; Leger et al., 1997).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Consequently, the invention is also directed to a method for detecting specifically the presence of a TBC-1 polypeptide according to the invention in a biological sample, said method comprising the following steps:

a) bringing into contact the biological sample with a polyclonal or monoclonal antibody that specifically binds a TBC-1 polypeptide comprising an amino acid sequence of SEQ ID No 5, or to a peptide fragment or variant thereof; and b) detecting the antigen-antibody complex formed.

The invention also concerns a diagnostic kit for detecting in vitro the presence of a TBC-1 polypeptide according to the present invention in a biological sample, wherein said kit comprises:

a) a polyclonal or monoclonal antibody that specifically binds a TBC-1 polypeptide comprising an amino acid sequence of SEQ ID No 5, or to a peptide fragment or variant thereof, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

TBC-1-Related Biallelic Markers

The inventors have discovered nucleotide polymorphisms located within the genomic DNA containing the TBC-1 gene, and among them SNP that are also termed biallelic markers. The biallelic markers of the invention can be used for example for the generation of genetic map, the linkage analysis, the association studies.

A—Identification of TBC-1-related Biallelic Markers

There are two preferred methods through which the biallelic markers of the present invention can be generated. In a first method, DNA samples from unrelated individuals are pooled together, following which the genomic DNA of interest is amplified and sequenced. The nucleotide sequences thus obtained are then analyzed to identify significant polymorphisms.

One of the major advantages of this method resides in the fact that the pooling of the DNA samples substantially reduces the number of DNA amplification reactions and sequencing which must be carried out. Moreover, this method is sufficiently sensitive so that a biallelic marker obtained therewith usually shows a sufficient degree of informativeness for conducting association studies.

In a second method for generating biallelic markers, the DNA samples are not pooled and are therefore amplified and sequenced individually. The resulting nucleotide sequences obtained are then also analyzed to identify significant polymorphisms.

It will readily be appreciated that when this second method is used, a substantially higher number of DNA amplification reactions must be carried out. It will further be appreciated that including such potentially less informative biallelic markers in association studies to identify potential genetic associations with a trait may allow in some cases the direct identification of causal mutations, which may, depending on their penetrance, be rare mutations. This method is usually preferred when biallelic markers need to be identified in order to perform association studies within candidate genes.

In both methods, the genomic DNA samples from which the biallelic markers of the present invention are generated are preferably obtained from unrelated individuals corresponding to a heterogeneous population of known ethnic background, or from familial cases.

The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to generate as many markers as possible and to generate statistically significant results.

As for the source of the genomic DNA to be subjected to analysis, any test sample can be foreseen without any particular limitation. The preferred source of genomic DNA used in the context of the present invention is the peripheral venous blood of each donor.

The techniques of DNA extraction are well-known to the skilled technician. Details of a preferred embodiment are provided in Example 2.

DNA samples can be pooled or unpooled for the amplification step. DNA amplification techniques are well-known to those skilled in the art.

Amplification techniques that can be used in the context of the present invention include, but are not limited to, the ligase chain reaction (LCR) described in EP-A-320 308, WO 9320227 and EP-A439 182, the polymerase chain reaction (PCR, RT-PCR) and techniques such as the nucleic acid sequence based amplification (NASBA) described in Guatelli J. C., et al.(1990) and in Compton J.(1991), Q-beta amplification as described in European Patent Application No 4544610, strand displacement amplification as described in Walker et al.(1996) and EP A 684 315 and, target mediated amplification as described in PCT Publication WO 9322461.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes, which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227). Gap LCR (GLCR) is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770 or, to use Asymmetric Gap LCR (RT-AGLCR) as described by Marshall et al.(1994). AGLCR is a modification of GLCR that allows the amplification of RNA.

The PCR technology is the preferred amplification technique used in the present invention. A variety of PCR techniques are familiar to those skilled in the art. For a review of PCR technology, see White (1991) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195; 4,683,202; and 4,965,188.

The PCR technology is the preferred amplification technique used to identify new biallelic markers. A typical example of a PCR reaction suitable for the purposes of the present invention is provided in Example 3.

One of the aspects of the present invention is a method for the amplification of a TBC-1 gene, particularly the genomic sequences of SEQ ID Nos 1 and 2 or of the cDNA sequence of SEQ ID Nos 3 or 4 or a fragment or variant thereof in a test sample, preferably using the PCR technology. The method comprises the steps of contacting a test sample suspected of containing the target TBC-1 sequence or portion thereof with amplification reaction reagents comprising a pair of amplification primers.

Thus, the present invention also relates to a method for the amplification of a TBC-1 gene sequence, particularly of a fragment of the genomic sequence of SEQ ID No 1 or of the cDNA sequence of SEQ ID No 2 or 3, or a fragment or a variant thereof in a test sample, said method comprising the steps of:

a) contacting a test sample suspected of containing the targeted TBC-1 gene sequence or portion thereof with amplification reaction reagents comprising a pair of amplification primers located on either side of the TBC-1 region to be amplified, and b) optionally, detecting the amplification products.

The invention also concerns a kit for the amplification of a TBC-1 gene sequence, particularly of a portion of the genomic sequence of SEQ ID Nos 1 or 2, or of the cDNA sequence of SEQ ID Nos 3 or 4, or a variant thereof in a test sample, wherein said kit comprises:

a) a pair of oligonucleotide primers located on either side of the TBC-1 region to be amplified;

b) optionally, the reagents necessary for performing the amplification reaction.

In one embodiment of the above amplification method and kit, the amplification product is detected by hybridization with a labeled probe having a sequence which is complementary to the amplified region. In another embodiment of the above amplification method and kit, primers comprise a sequence which is selected from the group consisting of B1 to B15, C1 to C15, D1 to D19, and E1 to E19.

In a first embodiment of the present invention, biallelic markers are identified using genomic sequence information generated by the inventors. Sequenced genomic DNA fragments are used to design primers for the amplification of 500 bp fragments. These 500 bp fragments are amplified from genomic DNA and are scanned for biallelic markers. Primers may be designed using the OSP software (Hillier L. and Green P., 1991). All primers may contain, upstream of the specific target bases, a common oligonucleotide tail that serves as a sequencing primer. Those skilled in the art are familiar with primer extensions, which can be used for these purposes.

Preferred primers, useful for the amplification of genomic sequences encoding the candidate genes, focus on promoters, exons and splice sites of the genes. A biallelic marker presents a higher probability to be an eventual causal mutation if it is located in these functional regions of the gene. Preferred amplification primers of the invention include the nucleotide sequences of B1 to B15 and C1 to C15 further detailed in Example 3.

The amplification products generated as described above with the primers of the invention are then sequenced using methods known and available to the skilled technician. Preferably, the amplified DNA is subjected to automated dideoxy terminator sequencing reactions using a dye-primer cycle sequencing protocol. Following gel image analysis and DNA sequence extraction, sequence data are automatically processed with adequate software to assess sequence quality.

A polymorphism analysis software is used that detects the presence of biallelic sites among individual or pooled amplified fragment sequences. Polymorphism search is based on the presence of superimposed peaks in the electrophoresis pattern These peaks which present distinct colors correspond to two different nucleotides at the same position on the sequence. The polymorphism has to be detected on both strands for validation.

19 biallelic markers were found in the TBC-1 gene. They are detailed in the Table 2. They are located in intronic regions.

K Genotyping of TBC-1-Related Biallelic Markers

The polymorphisms identified above can be further confirmed and their respective frequencies can be determined through various methods using the previously described primers and probes. These methods can also be useful for genotyping either new populations in association studies or linkage analysis or individuals in the context of detection of alleles of biallelic markers which are known to be associated with a given trait. The genotyping of the biallelic markers is also important for the mapping. Those skilled in the art should note that the methods described below can be equally performed on individual or pooled DNA samples.

Once a given polymorphic site has been found and characterized as a biallelic marker as described above, several methods can be used in order to determine the specific allele carried by an individual at the given polymorphic base.

The identification of biallelic markers described previously allows the design of appropriate oligonucleotides, which can be used as probes and primers, to amplify a TBC-1 gene containing the polymorphic site of interest and for the detection of such polymorphisms.

The biallelic markers according to the present invention may be used in methods for the identification and characterization of an association between alleles for one or several biallelic markers of the sequence of the TBC-1 gene and a trait.

The identified polymorphisms, and consequently the biallelic markers of the invention, may be used in methods for the detection in an individual of TBC-1 alleles associated with a trait, more particularly a trait related to a cell differentiation or abnormal cell proliferation disorders, and most particularly a trait related to cancer diseases, specifically prostate cancer.

In one embodiment the invention encompasses methods of genotyping comprising determining the identity of a nucleotide at a TBC-1-related biallelic marker or the complement thereof in a biological sample; optionally, wherein said TBC-1-related biallelic marker is selected from the group consisting of A1 to A19, and the complements thereof, or optionally the biallelic markers in linkage disequilibrium therewith; optionally, wherein said biological sample is derived from a single subject; optionally, wherein the identity of the nucleotides at said biallelic marker is determined for both copies of said biallelic marker present in said individual's genome; optionally, wherein said biological sample is derived from multiple subjects; Optionally, the genotyping methods of the invention encompass methods with any further limitation described in this disclosure, or those following, specified alone or in any combination; Optionally, said method is performed in vitro; optionally, further comprising amplifying a portion of said sequence comprising the biallelic marker prior to said determining step; Optionally, wherein said amplifying is performed by PCR, LCR, or replication of a recombinant vector comprising an origin of replication and said fragment in a host cell; optionally, wherein said determining is performed by a hybridization assay, a sequencing assay, a microsequencing assay, or an enzyme-based mismatch detection assay.

Source of Nucleic Acids for genotyping

Any source of nucleic acids, in purified or non-purified forth, can be utilized as the starting nucleic acid, provided it contains or is suspected of containing the specific nucleic acid sequence desired. DNA or RNA may be extracted from cells, tissues, body fluids and the like as described above. While nucleic acids for use in the genotyping methods of the invention can be derived from any mammalian source, the test subjects and individuals from which nucleic acid samples are taken are generally understood to be human.

Amplification of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers may be used in various methods and for various purposes and is not restricted to genotyping. Nevertheless, many genotyping methods although not all, require the previous amplification of the DNA region carrying the biallelic marker of interest Such methods specifically increase the concentration or total number of sequences that span the biallelic marker or include that site and sequences located either distal or proximal to it. Diagnostic assays may also rely on amplification of DNA segments carrying a biallelic marker of the present invention. Amplification of DNA may be achieved by any method known in the art. Amplification techniques are described above in the section entitled, "Identification of TBC-1-related biallelic markers."

Some of these amplification methods are particularly suited for the detection of single nucleotide polymorphisms and allow the simultaneous amplification of a target sequence and the identification of the polymorphic nucleotide as it is further described below.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention.

In some embodiments the present invention provides primers for amplifying a DNA fragment containing one or more biallelic markers of the present invention. Preferred amplification primers are listed in Example 2. It will be appreciated that the primers listed are merely exemplary and that any other set of primers which produce amplification products containing one or more biallelic markers of the present invention are also of use.

The spacing of the primers determines the length of the segment to be amplified. In the context of the present invention, amplified segments carrying biallelic markers can range in size from at least about 25 bp to 35 kbp. Amplification fragments from 25–3000 bp are typical, fragments from 50–1000 bp are preferred and fragments from 100–600 bp are highly preferred. It will be appreciated that amplification primers for the biallelic markers may be any sequence which allow the specific amplification of any DNA fragment carrying the markers. Amplification primers may be labeled or immobilized on a solid support as described in "Oligonucleotide probes and primers".

Methods of Genotyping DNA Samples for Biallelic Markers

Any method known in the art can be used to identify the nucleotide present at a biallelic marker site. Since the biallelic marker allele to be detected has been identified and specified in the present invention, detection will prove simple for one of ordinary skill in die art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as, conventional dot blot analyzes, single strand conformational polymorphism analysis (SSCP) described by Orita et al.(1989), denaturing gradient gel electrophoresis (DGGE), heteroduplex analysis, mismatch cleavage detection, and other conventional techniques as described in Sheffield et al.(1991), White et al.(1992), Grompe et al.(1989 and 1993). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by sequencing assay, enzyme-based mismatch detection assay, or hybridization assay. The following is a description of some preferred methods. A highly preferred method is the microsequencing technique/The term "sequencing" is generally used herein to refer to polymerase extension of duplex primer/template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing as described above. DNA sequencing methods are described in "Sequencing Of Amplified Genomic DNA And Identification Of Single Nucleotide Polymorphisms".

Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, the nucleotide at a polymorphic site in a target DNA is detected by a single nucleotide primer extension reaction. This method involves appropriate microsequencing primers which, hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883, the disclosure of which is incorporated herein by reference in its entirety. Alternatively capillary electrophoresis can be used in order to process a higher number of assays simultaneously. An example of a typical microsequencing procedure that can be used in the context of the present invention is provided in Example 4.

Different approaches can be used for the labeling and detection of ddNTPs. A homogeneous phase detection method based on fluorescence resonance energy transfer has been described by Chen and Kwok (1997) and Chen et al.(1997). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, 1997).

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner, oligonucleotides or templates may be attached to a solid support in a high-density format. In such solid phase microsequencing reactions, incorporated ddNTPs can be radiolabelled (Syvänen, 1994) or linked to fluorescein (Livak and Hainer, 1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosphatase conjugate (Haiju el al., 1993) or biotinylated ddNTP and horseradish peroxidase-conjugated streptavidin with o-phenylenediamine as a substrate (WO 92/15712). As yet another alternative solid-phase microsequencing procedure, Nyren et al.(1993) described a method relying on the detection of DNA polymerase activity by an enzymatic luminometric inorganic pyrophosphate detection assay (ELIDA).

Pastinen et al.(1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferred microsequencing primers include the nucleotide sequences D1 to D15 and E1 to E15. It will be appreciated that the microsequencing primers listed in Example 5 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in Example 5, or fragments comprising at least 8, 12, 15, 20, 25, 30, 40, or 50 consecutive nucleotides thereof, to the extent that such lengths are consistent with the primer described, and having a 3' terminus immediately upstream of the corresponding biallelic marker, for determining the identity of a nucleotide at a biallelic marker site.

3) Mismatch Detection Assays Based on Polymerases and Ligases

In one aspect the present invention provides polynucleotides and methods to determine the allele of one or more biallelic markers of the present invention in a biological sample, by mismatch detection assays based on polymerases and/or ligases. These assays are based on the specificity of polymerases and ligases. Polymerization reactions places particularly stringent requirements on correct base pairing of the 3' end of the amplification primer and the joining of two oligonucleotides hybridized to a target DNA sequence is quite sensitive to mismatches close to the ligation site, especially at the 3'end. Methods, primers and various parameters to amplify DNA fragments comprising biallelic markers of the present invention are further described above in "Amplification Of DNA Fragments Comprising Biallelic Markers".

Allele Specific Amplification Primers

Discrimination between the two alleles of a biallelic marker can also be achieved by allele specific amplification, a selective strategy, whereby one of the alleles is amplified without amplification of the other allele. For allele specific amplification, at least one member of the pair of primers is sufficiently complementary with a region of a TBC-1 gene comprising the polymorphic base of a biallelic marker of the present invention to hybridize therewith and to initiate the amplification. Such primers are able to discriminate between the two alleles of a biallelic marker.

This is accomplished by placing the polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well within the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecules. One of the oligonucleotides it biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al.(1990). In this method, PCR is used to achieve the exponential amplification of target DNA, which is then detected using OLA.

Other amplification methods which are particularly suited for the detection of single nucleotide polymorphism include LCR (ligase chain reaction), Gap LCR (GLCR) which are described above in "DNA Amplification". LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., 1989).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., 1989). Stringent conditions are sequence dependent and will be different in different circumstances. Generally, stringent conditions are selected to be about 5° C. lower than the thermal melting point (Tm) for the specific sequence at a defined ionic strength and pH. Although such hybridization can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995). In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., 1998).

The polynucleotides provided herein can be used to produce probes which can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Preferably the biallelic marker is within 4 nucleotides of the center of the polynucleotide probe. In particularly preferred probes, the biallelic marker is at the center of said polynucleotide. Preferred probes comprise a nucleotide sequence selected from the group consisting of amplicons listed in Table 1 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. Preferred probes comprise a nucleotide sequence selected from the group consisting of P1 to P7, P9 to P13, P15 to P19 and the sequences complementary thereto. In preferred embodiments the polymorphic base(s) are within 5, 4, 3, 2, 1, nucleotides of the center of the said polynucleotide, more preferably at the center of said polynucleotide.

Preferably the probes of the present invention are labeled or immobilized on a solid support. Labels and solid supports are further described in "Oligonucleotide Probes and Primers". The probes can be non-extendable as described in "Oligonucleotide Probes and Primers".

By assaying the hybridization to an allele specific probe, one can detect the presence or absence of a biallelic marker allele in a given sample. High-Throughput parallel hybridization in array format is specifically encompassed within "hybridization assays" and are described below.

5) Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in S. cerevisiae mutant strains, and in the protease gene of HIV-1 virus (Hacia et al., 1996; Shoemaker et al., 1996; Kozal et al., 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which, target sequences include a polymorphic marker. EP 785280 describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of nucleotides. Tiling strategies are further described in PCT application No. WO 95/11995. In a particular aspect, arrays are tiled for a number of specific, identified biallelic marker sequences. In particular, the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92110092 and WO 95/11995 and U.S. Pat. No. 5,424,186.

Thus, in some embodiments, the chips may comprise an array of nucleic acid sequences of fragments of about 15 nucleotides in length. In further embodiments, the chip may comprise an array including at least one of the sequences selected from the group consisting of amplicons listed in table 1 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In preferred embodiments the polymorphic base is within 5, 4, 3, 2, 1, nucleotides of the center of the said polynucleotide, more preferably at the center of said polynucleotide. In some embodiments, the chip may comprise an array of at least 2, 3, 4, 5, 6, 7, 8 or more of these polynucleotides of the invention. Solid supports and polynucleotides of the present invention attached to solid supports are further described in "Oligonucleotide Probes And Primers".

6) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts.

For genotyping biallelic markers, the microfluidic system may integrate nucleic acid amplification, microsequencing, capillary electrophoresis and a detection method such as laser-induced fluorescence detection.

Association Studies with the Biallelic Markers of the TBC-1 Gene

The identification of genes involved in suspected heterogeneous, polygenic and multifactorial traits such as cancer can be carried out through two main strategies currently used for genetic mapping: linkage analysis and association studies. Association studies examine the frequency of marker alleles in unrelated trait positive (T+) individuals compared with trait negative (T−) controls, and are generally employed in the detection of polygenic inheritance. Association studies as a method of mapping genetic traits rely on the phenomenon of linkage disequilibrium.

If two genetic loci lie on the same chromosome, then sets of alleles of these loci on the same chromosomal segment (called haplotypes) tend to be transmitted as a block from generation to generation. When not broken up by recombination, haplotypes can be tracked not only through pedigrees but also through populations. The resulting phenomenon at the population level is that the occurrence of pairs of specific alleles at different loci on the same chromosome is not random, and the deviation from random is called linkage disequilibrium (LD).

If a specific allele in a given gene is directly involved in causing a particular trait T, its frequency will be statistically increased in a trait positive population when compared to the frequency in a trait negative population. As a consequence of the existence of linkage disequilibrium, the frequency of all other alleles present in the haplotype carrying the trait-causing allele (TCA) will also be increased in trait positive individuals compared to trait negative individuals. Therefore, association between the trait and any allele in linkage disequilibrium with the trait-causing allele will suffice to suggest the presence of a trait-related gene in that particular allele's region. Linkage disequilibrium allows the relative frequencies in trait positive and trait negative populations of a limited number of genetic polymorphisms (specifically biallelic markers) to be analyzed as an alternative to screening all possible functional polymorphisms in order to find trait-causing alleles.

The general strategy to perform association studies using biallelic markers derived from a candidate region is to scan two groups of individuals (trait positive and trait negative control individuals which are characterized by a well defined phenotype as described below) in order to measure and statistically compare the allele frequencies of such biallelic markers in both groups.

If a statistically significant association with a trait is identified for at least one or more of the analyzed biallelic markers, one can assume that: either the associated allele is directly responsible for causing the trait (associated allele is the trait-causing allele), or the associated allele is in linkage disequilibrium with the trait-causing allele. If the evidence indicates that the associated allele within the candidate region is most probably not the trait-causing allele but is in linkage disequilibrium with the real trait-causing allele, then the trait-causing allele, and by consequence the gene carrying the trait-causing allele, can be found by sequencing the vicinity of the associated marker.

Collection of DNA Samples from Trait Positive (Trait+) and Trait Negative (Trait− Individuals (Inclusion Criteria)

In order to perform efficient and significant association studies such as those described herein, the trait under study should preferably follow a bimodal distribution in the population under study, presenting two clear non-overlapping phenotypes, trait positive and trait negative.

Nevertheless, even in the absence of such a bimodal distribution (as may in fact be the case for more complex genetic traits), any genetic trait may still be analyzed by the association method proposed here by carefully selecting the individuals to be included in the trait positive and trait negative phenotypic groups. The selection procedure involves to select individuals at opposite ends of the non-bimodal phenotype spectra of the trait under study, so as to include in these trait positive and trait negative populations individuals which clearly represent extreme, preferably non-overlapping phenotypes.

The definition of the inclusion criteria for the trait positive and trait negative populations is an important aspect of the present invention. The selection of drastically different but relatively uniform phenotypes enables efficient comparisons in association studies and the possible detection of marked differences at the genetic level, provided that the sample sizes of the populations under study are significant enough.

Generally, trait positive and trait negative populations to be included in association studies such as proposed in the present invention consist of phenotypically homogenous populations of individuals each representing 100% of the corresponding trait if the trait distribution is bimodal.

A first group of between 50 and 300 trait positive individuals, preferably about 100 individuals, can be recruited according to clinical inclusion criteria.

In each ease, a similar number of trait negative individuals, preferably more than 100 individuals, are included in such studies who are preferably both ethnically- and age-matched to the trait positive cases. They are checked for the absence of the clinical criteria defined above. Both trait positive and trait negative individuals should correspond to unrelated cases.

Genotyping of Trait Positive and Trait Negative Individuals

Allelic frequencies of the biallelic markers in each of the above described population can be determined using one of the methods described above under the heading "Methods of Genotyping DNA samples for biallelic markers". Analyses are preferably performed on amplified fragments obtained by genomic PCR performed on the DNA samples from each individual in similar conditions as those described above for the generation of biallelic markers.

In a preferred embodiment, amplified DNA samples are subjected to automated microsequencing reactions using fluorescent ddNTPs (specific fluorescence for each ddNTP) and the appropriate microsequencing oligonucleotides which hybridize just upstream of the polymorphic base.

Genotyping is further described in Example 5.

Associations studies can be carried out by the skilled technician using the biallelic markers of the invention defined above, with different trait positive and trait negative populations. Suitable examples of association studies using biallelic markers of the TBC-1 gene, including the biallelic markers A1 to A19, involve studies on the following populations:

a trait positive population suffering from a cancer, preferably prostate cancer and a healthy unaffected population; or a trait positive population suffering from prostate cancer treated with agents acting against prostate cancer and suffering from side-effects resulting from this treatment and an trait negative population suffering from prostate cancer treated with same agents without any substantial side-effects, or a trait positive population suffering from prostate cancer treated with agents acting against prostate cancer showing a beneficial response and a trait negative population suffering from prostate cancer treated with same agents without any beneficial response, or a trait positive population suffering from prostate cancer presenting highly aggressive prostate cancer tumors and a trait negative population suffering from prostate cancer with prostate cancer tumors devoid of aggressiveness.

It is another object of the present invention to provide a method for the identification and characterization of an association between an allele of one or more biallelic markers of a TBC-1 gene and a trait. The method comprises the steps of:

genotyping a marker or a group of biallelic markers according to the invention in trait positive;

genotyping a marker or a group of biallelic markers according to the invention in and trait negative individuals; and establishing a statistically significant association between one allele of at least one marker and the trait.

Preferably, the trait positive and trait negative individuals are selected from non-overlapping phenotypes as regards to the trait under study. In one embodiment, the biallelic marker are selected from the group consisting of the biallelic markers A1 to A19.

In a preferred embodiment, the trait is cancer, prostate cancer, an early onset of prostate cancer, a susceptibility to prostate cancer, the level of aggressiveness of prostate cancer tumors, a modified expression of the TBC-1 gene, a modified production of the TBC-1 protein, or the production of a modified TBC-1 protein.

In a further embodiment, the trait negative population can be replaced in the association studies by a random control population.

The step of testing for and detecting the presence of DNA comprising specific alleles of a biallelic marker or a group of biallelic markers of the present invention can be carried out as described further below.

Oligonucleotide Probes and Primers

The invention relates also to oligonucleotide molecules useful as probes or primers, wherein said oligonucleotide molecules hybridize specifically with a nucleotide sequence comprised in the TBC-1 gene, particularly the TBC-1 genomic sequence of SEQ ID Nos 1 and 2 or the TBC-1 cDNAs sequences of SEQ ID Nos 3 and 4. More particularly, the present invention also concerns oligonucleotides for the detection of alleles of biallelic markers of the TBC-1 gene. These oligonucleotides are useful either as primers for use in various processes such as DNA amplification and microsequencing or as probes for DNA recognition in hybridization analyses. Polynucleotides derived from the TBC-1 gene are useful in order to detect the presence of at least a copy of a nucleotide sequence of SEQ ID Nos 1–4, or a fragment, complement, or variant thereof in a test sample.

Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of a nucleotide sequence selected from the group consisting of SEQ ID Nos 1 and 2, or the complements thereof. Additionally preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least 1, 2, 3, 5, or 10 of the following nucleotide positions of SEQ ID No 1: 1–1000, 1001–2000, 2001–3000, 3001–4000, 4001–5000, 5014000, 6001–7000, 7001–8000, 8001–9000, 9001–10000, 10001–11000, 11001–12000, 12001–13000, 13001–14000, 14001–15000, 15001–16000, 16001–17000, and 17001–17590. Other preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least 1, 2, 3, 5, or 10 of the following nucleotide positions of SEQ ID No 2: 1–5000, 5001–10000, 10001–15000, 15001–20000, 20001–25000, 25001–30000, 30001–35000, 35001–40000, 40001–45000, 45001–50000, 50001–55000, 55001–60000, 60001–65000, 65001–70000, 70001–75000, 75001–80000, 80001–85000, 85001–90000, 90001–95000, and 95001–99960.

Moreover, preferred probes and primers of the invention include isolated, purified, or recombinant polynucleotides comprising a contiguous span of at least 12, 15, 18, 20, 25, 30, 35, 40, 35 50, 60, 70, 80, 90, 100, 150, 200, 500, or 1000 nucleotides of a nucleotide sequence selected from the group consisting of SEQ ID Nos 3 and 4, or the complements thereof. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, or 10 of the following nucleotide positions of SEQ ID No 3: 1–500, 501–1000, 1001–1500, 1501–2000, 2001–2500, 2501–3000, 3001–3500, and 3501–3983. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least 1, 2, 3, 5, or 10 of the following nucleotide positions of SEQ ID No 4: 1–500, 501–1000, 1001–1500, 1501–2000, 2001–2500, 2501–3000, 3001–3500, and 3501–3988.

Thus, the invention also relates to nucleic acid probes characterized in that they hybridize specifically, under the stringent hybridization conditions defined above, with a nucleic acid selected from the group consisting of the nucleotide sequences of SEQ ID Nos 1–4 or a variant thereof or a sequence complementary thereto.

In one embodiment the invention encompasses isolated, purified, and recombinant polynucleotides consisting of, or consisting essentially of a contiguous span of 8 to 50 nucleotides of any one of SEQ ID Nos 1 and 2 and the complement thereof, wherein said span includes a TBC-1-related biallelic marker in said sequence; optionally, wherein said TBC-1-related biallelic marker is selected from the group consisting of A1 to A19, and the complements thereof, or optionally the biallelic markers in linkage disequilibrium therewith; optionally, wherein said contiguous span is 18 to 35 nucleotides in length and said biallelic marker is within 4 nucleotides of the center of said polynucleotide; optionally, wherein said polynucleotide consists of said contiguous span and said contiguous span is 25 nucleotides in length and said biallelic marker is at the center of said polynucleotide; optionally, wherein the 3' end of said contiguous span is present at the 3' end of said polynucleotide; and optionally, wherein the 3' end of said contiguous span is located at the 3' end of said polynucleotide and said biallelic marker is present at the 3' end of said polynucleotide. In a preferred embodiment, said probes comprises, consists of, or consists essentially of a sequence selected from the following sequences: P1 to P7, P9 to P13, P15 to P19 and the complementary sequences thereto.

In another embodiment the invention encompasses isolated, purified and recombinant polynucleotides comprising, consisting of, or consisting essentially of a contiguous span of 8 to 50 nucleotides of SEQ ID Nos 1 and 2, or the complements thereof, wherein the 3' end of said contiguous span is located at the 3' end of said polynucleotide, and wherein the 3' end of said polynucleotide is located within 20 nucleotides upstream of a TBC-1-related biallelic marker in said sequence; optionally, wherein said TBC-1-related biallelic marker is selected from the group consisting of A1 to A19, and the complements thereof, or optionally the biallelic markers in linkage disequilibrium therewith; optionally, wherein the 3' end of said polynucleotide is located 1 nucleotide upstream of said TBC-1-related biallelic marker in said sequence; and optionally, wherein said polynucleotide consists essentially of a sequence selected from the following sequences: D1 to D19 and E1 to E19.

In a further embodiment, the invention encompasses isolated, purified, or recombinant polynucleotides comprising, consisting of, or consisting essentially of a sequence selected from the following sequences: B1 to B15 and C1 to C15.

In an additional embodiment, the invention encompasses polynucleotides for use in hybridization assays, sequencing assays, and enzyme-based mismatch detection assays for determining the identity of the nucleotide at a TBC-1-related biallelic marker in SEQ ID Nos 1 and 2, or the complements thereof, as well as polynucleotides for use in amplifying segments of nucleotides comprising a TBC-1-related biallelic marker in SEQ ID Nos 1 and 2, or the complements thereof; optionally, wherein said TBC-1-related biallelic marker is selected from the group consisting of A1 to A19, and the complements thereof, or optionally the biallelic markers in linkage disequilibrium therewith.

A probe or a primer according to the invention has between 8 and 1000 nucleotides in length, or is specified to be at least 12, 15, 18, 20, 25, 35, 40, 50, 60, 70, 80, 100, 250, 500 or 1000 nucleotides in length. More particularly, the length of these probes and primers can range from 8, 10, 15, 20, or 30 to 100 nucleotides, preferably from 10 to 50, more preferably from 15 to 30 nucleotides. Shorter probes and primers tend to lack specificity for a target nucleic acid sequence and generally require cooler temperatures to form sufficiently stable hybrid complexes with the template. Longer probes and primers are expensive to produce and can sometimes self-hybridize to form hairpin structures. The appropriate length for primers and probes under a particular set of assay conditions may be empirically determined by one of skill in the art. A preferred probe or primer consists of a nucleic acid comprising a polynucleotide selected from the group of the nucleotide sequences of P1 to P7, P9 to P13, P15 to P19 and the complementary sequence thereto, B1 to B15, C1 to C15, D1 to D19, E1 to E19, for which the respective locations in the sequence listing are provided in Tables 2, 3 and 4.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes of the invention usually ranges between 10 and 75%, preferably between 35 and 60%, and more preferably between 40 and 55%.

The primers and probes can be prepared by any suitable method, including, for example, cloning and restriction of appropriate sequences and direct chemical synthesis by a method such as the phosphodiester method of Narang et al.(1979), the phosphodiester method of Brown et al.(1979), the diethylphosphoramidite method of Beaucage et al.(1981) and the solid support method described in EP 0 707 592.

Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

Any of the polynucleotides of the present invention can be labeled, if desired, by incorporating any label known in the art to be detectable by spectroscopic, photochemical, biochemical, immunochemical, or chemical means. For example, useful labels include radioactive substances (including, $^{32}$P, $^{35}$S, $^{3}$H, $^{125}$I), fluorescent dyes (including, 5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French patent No. FR-7810975 or by Urdea et al (1988) or Sanchez-Pescador et al (1988). In addition, the probes according to the present invention may have structural characteristics such that they allow the signal amplification, such structural characteristics being, for example, branched DNA probes as those described by Urdea et al. in 1991 or in the European patent No. EP 0 225 807 (Chiron).

A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the TBC-1gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads; magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Consequently, the invention also deals with a method for detecting the presence of a nucleic acid comprising a nucleotide sequence selected from a group consisting of SEQ ID Nos 1–4, a fragment or a variant thereof and a complementary sequence thereto in a sample, said method comprising the following steps of:

a) bringing into contact a nucleic acid probe or a plurality of nucleic acid probes which can hybridize with a nucleotide sequence included in a nucleic acid selected form the group consisting of the nucleotide sequences of SEQ ID Nos 1–4, a fragment or a variant thereof and a complementary sequence thereto and the sample to be assayed; and b) detecting the hybrid complex formed between the probe and a nucleic acid in the sample.

The invention further concerns a kit for detecting the presence of a nucleic acid comprising a nucleotide sequence selected from a group consisting of SEQ ID Nos 1–4, a fragment or a variant thereof and a complementary sequence thereto in a sample, said kit comprising:

a) a nucleic acid probe or a plurality of nucleic acid probes which can hybridize with a nucleotide sequence included in a nucleic acid selected form the group consisting of the nucleotide sequences of SEQ ID Nos 1–4, a fragment thereof or a variant thereof and a complementary sequence thereto; and b) optionally, the reagents necessary for performing the hybridization reaction.

In a first preferred embodiment of this detection method and kit, said nucleic acid probe or the plurality of nucleic acid probes are labeled with a detectable molecule. In a second preferred embodiment of said method and kit, said nucleic acid probe or the plurality of nucleic acid probes has been immobilized on a substrate. In a third preferred embodiment, the nucleic acid probe or the plurality of nucleic acid probes comprise either a sequence which is selected from the group consisting of the nucleotide sequences of P1 to P7, P9 to P13, P15 to P19 and the complementary sequence thereto, B1 to B15, C1 to C15, D1 to D19, E1 to E19 or a biallelic marker selected from the group consisting of A1 to A19 and the complements thereto.

Oligonucleotide Arrays

A substrate comprising a plurality of oligonucleotide primers or probes of the invention may be used either for detecting or amplifying targeted sequences in the TBC-1 gene and may also be used for detecting mutations in the coding or in the non-coding sequences of the TBC-1 gene.

Any polynucleotide provided herein may be attached in overlapping areas or at random locations on the solid support Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092. These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854; and 5,412,087 and in PCT Publications WO 90/15070, WO 92/10692 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256.

In another embodiment of the oligonucleotide arrays of the invention, an oligonucleotide probe matrix may advantageously be used to detect mutations occurring in the TBC-1 gene and preferably in its regulatory region. For this particular purpose, probes are specifically designed to have a nucleotide sequence allowing their hybridization to the genes that carry known mutations (either by deletion, insertion or substitution of one or several nucleotides). By known mutations, it is meant, mutations on the TBC-1 gene that have been identified according, for example to the technique used by Huang et al.(1996) or Samson et al.(1996).

Another technique that is used to detect mutations in the TBC-1 gene is the use of a high-density DNA array. Each oligonucleotide probe constituting a unit element of the high density DNA array is designed to match a specific subsequence of the TBC-1 genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the TBC-1 gene. In one such design, termed 4L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. in 1996.

Consequently, the invention concerns an array of nucleic acid molecules comprising at least one polynucleotide described above as probes and primers. Preferably, the invention concerns an array of nucleic acid comprising at least two polynucleotides described above as probes and primers.

A further object of the invention consists of an array of nucleic acid sequences comprising either at least one of the sequences selected from the group consisting of P1 to P7, P9 to P13, P15 to P19, B1 to B15, C1 to C15, D1 to D19, E1 to E19, the sequences complementary thereto, a fragment thereof of at least 8, 10, 12, 15, 18, 20, 25, 30, or 40 consecutive nucleotides thereof, and at least one sequence comprising a biallelic marker selected from the group consisting of A1 to A19 and the complements thereto.

The invention also pertains to an array of nucleic acid sequences comprising either at least two of the sequences selected from the group consisting of P1 to P7, P9 to P13, P15 to P19, B1 to B15, C1 to C15, D1 to D19, E1 to E19, the sequences complementary thereto, a fragment thereof of at least 8 consecutive nucleotides thereof, and at least two sequences comprising a biallelic marker selected from the group consisting of A1 to A19 and the complements thereof.

Vectors for the Expression of a Regulatory or a Coding Polynucleotide of TBC-1

Any of the regulatory polynucleotides or the coding polynucleotides of the invention may be inserted into recombinant vectors for expression in a recombinant host cell or a recombinant host organism.

Thus, the present invention also encompasses a family of recombinant vectors that contains either a regulatory polynucleotide selected from the group consisting of any one of the regulatory polynucleotides derived from the TBC-1 genomic sequences of SEQ ID Nos 1 and 2, or a polynucleotide comprising the TBC-1 coding sequence, or both.

In a first preferred embodiment, a recombinant vector of the invention is used as an expression vector: (a) the TBC-1 regulatory sequence comprised therein drives the expression of a coding polynucleotide operably linked thereto; (b) the TBC-1 coding sequence is operably linked to regulation sequences allowing its expression in a suitable cell host and/or host organism.

In a second preferred embodiment, a recombinant vector of the invention is used to amplify the inserted polynucleotide derived from the TBC-1 genomic sequences of SEQ ID Nos 1 and 2 or TBC-1 cDNAs in a suitable cell host, this polynucleotide being amplified at every time that the recombinant vector replicates.

More particularly, the present invention relates to expression vectors which include nucleic acids encoding a TBC-1 protein, preferably the TBC-1 protein of the amino acid sequence of SEQ ID No 5 described therein, under the control of a regulatory sequence selected among the TBC-1 regulatory polynucleotides, or alternatively under the control of an exogenous regulatory sequence.

A recombinant expression vector comprising a nucleic acid selected from the group consisting of 5' and 3' regulatory regions, or biologically active fragments or variants thereof is also part of the present invention.

The invention also encompasses a recombinant expression vector comprising:

a) a nucleic acid comprising the 5' regulatory polynucleotide of the nucleotide sequence SEQ ID No 1, or a biologically active fragment or variant thereof, b) a polynucleotide encoding a polypeptide or a polynucleotide of interest operably linked with said nucleic acid.

c) optionally, a nucleic acid comprising a 3'-regulatory polynucleotide, preferably a 3'-regulatory polynucleotide of the invention, or a biologically active fragment or variant thereof.

The nucleic acid comprising the 5' regulatory polynucleotide or a biologically active fragment or variant thereof may also comprises the 5'-UTR sequence from any of the two cDNA of the invention or a biologically active fragment or variant thereof.

The invention also pertains to a recombinant expression vector useful for the expression of the TBC-1 coding sequence, wherein said vector comprises a nucleic acid selected from the group consisting of SEQ ID Nos 3 and 4 or a nucleic acid having at least 95% nucleotide identity with a polynucleotide selected from the group consisting of the nucleotide sequences of SEQ ID Nos 3 and 4.

Another recombinant expression vector of the invention consists in a recombinant vector comprising a nucleic acid comprising the nucleotide sequence beginning at the nucleotide in position 176 and ending in position 3730 of the polynucleotide of SEQ ID No 4.

Generally, a recombinant vector of the invention may comprise any of the polynucleotides described herein, including regulatory sequences, and coding sequences, as well as any TBC-1 primer or probe as defined above. More particularly, the recombinant vectors of the present invention can comprise any of the polynucleotides described in the "TBC-1 cDNA Sequences" section, the "Coding Regions" section, "Genomic sequence of TBC-1" section and the "Oligonucleotide Probes And primers" section.

Some of the elements which can be found in the vectors of the present invention are described in further detail in the following sections.

a) Vectors

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may consist of a chromosomal, non-chromosomal and synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, and (3) appropriate transcription initiation and termination sequences. Structural units intended for use in yeast or eukaryotic expression systems preferably include a leader sequence enabling extracellular secretion of translated protein by a host cell. Alternatively, where a recombinant protein is expressed without a leader or transport sequence, it may include an N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium.

The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria.

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of suitable vectors and promoters are known to those of skill in the art, and commercially available, such as bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); or eukaryotic vectors: pWLNEO, pSV2CAT, pOG44, pXT1, pSG (Stratagene); pSVK3, PBPV, pMSG, pSVL (Pharmacia); baculovirus transfer vector pVL1392/1393 (Pharmingen); pQE-30 (QIAexpress).

A suitable vector for the expression of the TBC-1 polypeptide of SEQ ID No 5 is a baculovirus vector that can be propagated in insect cells and in insect cell lines. A specific suitable host vector system is the pVL1392/1393 baculovirus transfer vector (Pharmingen) that is used to transfect the SF9 cell line (ATCC N°CRL 1711) which is derived from *Spodoptera frugiperda*.

Other suitable vectors for the expression of the TBC-1 polypeptide of SEQ ID No 5 in a baculovirus expression system include those described by Chai et al. (1993), Vlasak et al. (1983) and Lenhard et al. (1996).

Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example SV40 origin, early promoter, enhancer, splice and polyadenylation sites may be used to provide the required nontranscribed genetic elements.

b) Promoters

The suitable promoter regions used in the expression vectors according to the present invention are chosen taking into account the cell host in which the heterologous gene has to be expressed.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Preferred bacterial promoters are the LacI, LacZ, the T3 or T7 bacteriophage RNA polymerase promoters, the polyhedrin promoter, or the p10 protein promoter from baculovirus (Kit Novagen) (Smith et al., 1983; O'Reilly et al., 1992), the lambda $P_R$ promoter or also the trc promoter.

Promoter regions can be selected from any desired gene using, for example, CAT (chloramphenicol transferase) vectors and more preferably pKK232-8 and pCM7 vectors. Particularly preferred bacterial promoters include lac, lacZ, T3, T7, gpt, lambda PR, PL and trp. Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic egineering. For example, one may refer to the book of Sambrook et al. (1989) or also to the procedures described by Fuller et al. (1996).

The vector containing the appropriate DNA sequence as described above, more preferably a TBC-1 gene regulatory polynucleotide, a polynucleotide encoding the TBC-1 polypeptide of SEQ ID No 5 or both of them, can be utilized to transform an appropriate host to allow the expression of the desired polypeptide or polynucleotide.

c) Other Types of Vectors

The in vivo expression of a TBC-1 polypeptide of SEQ ID No 5 may be useful in order to correct a genetic defect related to the expression of the native gene in a host organism or to the production of a biologically inactive TBC-1 protein.

Consequently, the present invention also deals with recombinant expression vectors mainly designed for the in vivo production of the TIC-1 polypeptide of SEQ ID No 5 by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

By <<vector>> according to this specific embodiment of the invention is intended either a circular or a linear DNA molecule.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect.

In a specific embodiment, the invention provides a composition for the in vivo production of the TBC-1 protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

Compositions comprising a polynucleotide are described in PCT application N° WO 90/11092 (Vical Inc.) and also in PCT application N° WO 95/11307 (Institut Pasteur, INSERM, Université d'Ottawa) as well as in the articles of Tacson et al. (1996) and of Huygen et al. (1996).

The amount of vector to be injected to the desired host organism varies according to the site of injection. As an indicative dose, it will be injected between 0,1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired TBC-1 polypeptide or the desired fragment thereof is reintroduced into the animal body in order to deliver the recombinant protein within the body either locally or systemically.

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application N° FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host Particularly preferred retroviruses for the preparation or construction of retroviral in vitro or in vitro gene delivery vehicles of the present invention include retroviruses selected from the group consisting of Mink-Cell Focus Inducing Virus, Murine Sarcona Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR459 and VR-728). Other preferred retroviral vectors are those described in Roth et al. (Roth J A. et al., 1996), PCT Application No WO 93/25234, PCT Application No WO 94/06920, Roux et al., 1989, Julan et al., 1992 and Neda et al., 1991.

Yet another viral vector system that is contemplated by the invention consists in the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

Other compositions containing a vector of the invention advantageously comprise an oligonucleotide fragment of a nucleic sequence selected from the group consisting of SEQ ID Nos 3 or 4 as an antisense tool that inhibits the expression of the corresponding TBC-1 gene. Preferred methods using antisense polynucleotide according to the present invention are the procedures described by Sczakiel et al. (1995) or those described in PCT Application No WO 95/24223.

Host Cells

Another object of the invention consists in host cell that have been transformed or transfected with one of the polynucleotides described therein, and more precisely a polynucleotide either comprising a TBC-1 regulatory polynucleotide or the coding sequence of the TBC-1 polypeptide having the amino acid sequence of SEQ ID No 5. Are included host cells that are transformed (prokaryotic cells) or that are transfected (eukaryotic cells) with a recombinant vector such as one of those described above.

A recombinant host cell of the invention comprises any one of the polynucleotides or the recombinant vectors described therein. More particularly, the cell hosts of the present invention can comprise any of the polynucleotides described in "TBC-1 cDNA Sequences" section, the "Coding Regions" section, "Genomic sequence of TBC-1" section and the "Oligonucleotide Probes And Primers" section.

Another preferred recombinant cell host according to the present invention is characterized in that its genome or genetic background (including chromosome, plasmids) is modified by the nucleic acid coding for the TBC-1 polypeptide of SEQ ID No 5.

Preferred host cells used as recipients for the expression vectors of the invention are the following:

a) Prokaryotic host cells: *Escherichia coli* strains (I.E. DH5-α strain) or *Bacillus subtilis*.

b) Eukaryotic host cells: HeLa cells (ATCC N°CCL2; N°CCL2.1; N°CCL2.2), Cv 1 cells (ATCC N°CCL70), COS cells(ATCC N°CRL1650; N°CRL1651), Sf-9cells(ATCC N°CRL1711).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skill artisan.

Transgenic Animals

The terms "transgenic animals" or "host animals" are used herein to designate animals that have their genome genetically and artificially manipulated so as to include one of the nucleic acids according to the invention. Preferred animals are non-human mammals and include those belonging to a genus selected from *Mus* (e.g. mice), *Rattus* (e.g. rats) and *Oryctogalus* (e.g. rabbits) which have their genome artificially and genetically altered by the insertion of a nucleic acid according to the invention.

The transgenic animals of the invention all include within a plurality of their cells a cloned recombinant or synthetic DNA sequence, more specifically one of the purified or isolated nucleic acids comprising a TBC-1 coding sequence, a TBC-1 regulatory polynucleotide or a DNA sequence encoding an antisense polynucleotide such as described in the present specification.

More particularly, transgenic animals according to the invention contain in their somatic cells and/or in their germ line cells any of the polynucleotides described in "TBC-1 cDNA Sequences" section, the "Coding Regions" section, "Genomic sequence of TBC-1" section, the "Oligonucleotide Probes And Primers" section and the "Vectors for the expression of a regulatory or coding polynucleotide of TBC-1" section.

The transgenic animals of the invention thus contain specific sequences of exogenous genetic material such as the nucleotide sequences described above in detail.

In a first preferred embodiment, these transgenic animals may be good experimental models in order to study the diverse pathologies related to cell differentiation, in particular concerning the transgenic animals within the genome of which has been inserted one or several copies of a polynucleotide encoding a native TBC-1 protein, or alternatively a mutant TBC-1 protein.

In a second preferred embodiment, these transgenic animals may express a desired polypeptide of interest under the control of the regulatory polynucleotides of the TBC-1 gene, leading to good yields in the-synthesis of this protein of interest, and eventually a tissue specific expression of this protein of interest.

Since it is possible to produce transgenic animals of the invention using a variety of different sequences, a general description will be given of the production of transgenic animals by referring generally to exogenous genetic material. This general description can be adapted by those skilled in the art in order to incorporate the DNA sequences into animals. For more details regarding the production of transgenic animals, and specifically transgenic mice, it may be referred to Sandou et al. (1994) and also to U.S. Pat. No. 4,873,191, issued Oct. 10, 1989, U.S. Pat. No. 5,968,766, issued Dec. 16, 1997 and U.S. Pat. No. 5,387,742, issued Feb. 28, 1995, these documents being herein incorporated by reference to disclose methods for producing transgenic mice.

Transgenic animals of the present invention are produced by the application of procedures which result in an animal with a genome that incorporates exogenous genetic material which is integrated into the genome. The procedure involves obtaining the genetic material, or a portion thereof, which encodes either a TBC-1 coding sequence, a TBC-1 regulatory polynucleotide or a DNA sequence encoding an antisense polynucleotide such as described in the present specification.

A recombinant polynucleotide of the invention is inserted into an embryonic or ES stem cell line. The insertion is made using electroporation. The cells subjected to electroporation are screened (e.g. Southern blot analysis) to find positive cells which have integrated the exogenous recombinant polynucleotide into their genome. An illustrative positive-negative selection procedure that may be used according to the invention is described by Mansour et al. (1988). Then, the positive cells are isolated, cloned and injected into 3.5 days old blastocysts from mice. The blastocysts are then inserted into a female host animal and allowed to grow to term. The offsprings of the female host are tested to determine which animals are transgenic e.g. include the inserted exogenous DNA sequence and which are wild-type.

Screening of Agents Interacting with TBC-1

In a further embodiment, the present invention also concerns a method for the screening of new agents, or candidate substances interacting with TBC-1. These new agents could be useful against cancer.

In a preferred embodiment, the invention relates to a method for the screening of candidate substances comprising the following steps:

providing a cell line, an organ, or a mammal expressing a TBC-1 gene or a fragment thereof, preferably the regulatory region or the promoter region of the TBC-1 gene.

obtaining a candidate substance preferably a candidate substance capable of inhibiting the binding of a transcription factor to the TBC-1 regulatory region, testing the ability of the candidate substance to decrease the symptoms of prostate cancer and/or to modulate the expression levels of TDC-1.

In some embodiments, the cell line, organ or mammal expresses a heterologous protein, the coding sequence of which is operably linked to the TBC-1 regulatory or promoter sequence. In other embodiments, they express a TBC-1 gene comprising alleles of one or more TBC-1-related biallelic markers.

A candidate substance is a substance which can interact with or modulate, by binding or other intramolecular interactions, expression stability, and function of TBC-1. Such substances may be potentially interesting for patients who are not responsive to existing drugs or develop side effects to them. Screening may be effected using either in vitro methods or in vivo methods.

Such methods can be carried out in numerous ways such as on transformed cells which express the considered alleles of the TBC-1 gene, on tumors induced by said transformed cells, for example in mice, or on a TBC-1 protein encoded by the considered allelic variant of TBC-1.

Screening assays of the present invention generally involve determining the ability of a candidate substance to present a cytotoxic effect, to change the characteristics of transformed cells such as proliferative and invasive capacity, to affect the tumor growth, or to modify the expression level of TBC-1.

Typically, this method includes preparing transformed cells with different forms of TBC-1 sequences containing particular alleles of one or more biallelic markers and/or trait causing mutations described above. This is followed by testing the cells expressing the TBC-1 with a candidate substance to determine the ability of the substance to present cytotoxic effect, to affect the characteristics of transformed cells, the tumor growth, or to modify the expression level of TBC-1.

Typical examples of such drug screening assays are provided below. It is to be understood that the parameters set forth in these examples can be modified by the skilled person without undue experimentation.

Methods for Screening Substances Interacting with a TBC-1 Polypeptide

A method for the screening of a candidate substance according to the invention comprises the following steps:

a) providing a polypeptide comprising the amino acid sequence SEQ ID No 5, or a peptide fragment or a variant thereof;

b) obtaining a candidate substance;

c) bringing into contact said polypeptide with said candidate substance;

d) detecting the complexes formed between said polypeptide and said candidate substance.

For the purpose of the present invention, a ligand means a molecule, such as a protein, a peptide, an antibody or any synthetic chemical compound capable of binding to the TBC-1 protein or one of its fragments or variants or to modulate the expression of the polynucleotide coding for TBC-1 or a fragment or variant thereof.

In the ligand screening method according to the present invention, a biological sample or a defined molecule to be tested as a putative ligand of the TBC-1 protein is brought into contact with a purified TBC-1 protein, for example a purified recombinant TBC-1 protein produced by a recombinant cell host as described hereinbefore, in order to form a complex between the TBC-1 protein and the putative ligand molecule to be tested.

A. Candidate Ligands Obtained Form Random Peptide Libraries

In a particular embodiment of the screening method, the putative ligand is the expression product of a DNA insert contained in a phage vector (Parmley and Smith, 1988). Specifically, random peptide phages libraries are used. The random DNA inserts encode peptides of 8 to 20 aminoacids in length (Oldenburg K. R. et al., 1992,.; Valadon P., et al., 1996; Lucas A. H., 1994; Westerink M. A. J., 1995; Castagnoli L. et al., 1991). According to this particular embodiment, the recombinant phages expressing a protein that binds to the immobilized TBC-1 protein are retained and the complex formed between the TBC-1 protein and the recombinant phage may be subsequently immunoprecipitated by a polyclonal or a monoclonal antibody directed against the TBC-1 protein.

Once the ligand library in recombinant phages has been constructed, the phage population is brought into contact with the immobilized TBC-1 protein. Then the preparation of complexes is washed in order to remove the non-specifically bound recombinant phages. The phages that bind specifically to the TBC-1 protein are then eluted by a buffer (acid pH) or immunoprecipitated by the anti-TBC-1monoclonal antibody produced by a hybridoma, and this phage population is subsequently amplified-by an overinfection of bacteria (for example *E. coli*). The selection step may be repeated several times, preferably 2–4 times, in order to select the more specific recombinant phage clones. The last step consists in characterizing the peptide produced by the selected recombinant phage clones either by expression in infected bacteria and isolation, expressing the phage insert in another host-vector system, or sequencing the insert contained in the selected recombinant phages.

B. Candidate Ligands Obtained Through a Two-hybrid Screening Assay

The yeast two-hybrid system is designed to study protein-protein interactions in vivo (Fields and Song, 1989), and relies upon the fusion of a bait protein to the DNA binding domain of the yeast Gal4 protein. This technique is also described in U.S. Pat. Nos. 5,667,973 and 5,283,173 (Fields et al.) the technical teachings of both patents being herein incorporated by reference.

The general procedure of library screening by the two-hybrid assay may be performed as described by Harper et al. (Harper J W et al., 1993) or as described by Cho et al. (1998) or also Fromont-Racine et al. (1997).

The bait protein or polypeptide consists of a TBC-1 polypeptide or a fragment or variant thereof.

More precisely, the nucleotide sequence encoding the TBC-1 polypeptide or a fragment or variant thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "pray" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non limiting example the two different yeast strains may be the following:

Y190, the phenotype of which is (MATa, Leu2-3, 112 ura3-12, trpl-901, his3-D200, ade2-101, gal4Dgal180D URA3 GAL-LacZ, LYS GAL-HIS3, cyh$^r$);

Y187, the phenotype of which is (MATα gal4 gal80his3 trpl-901 ade2-101 ura3-52 leu2-3, -112 URA3 GAL-lacZmet$^-$), which is the opposite mating type of Y190.

Briefly, 20 μg of pAS2/TBC-1 and 20 μg of pACT-cDNA library are co-transformed into yeast strain Y190. The transformants are selected for growth on minimal media lacking histidine, leucine and tryptophan, but containing the histidine synthesis inhibitor 3-AT (50 mM). Positive colonies are screened for beta galactosidase by filter lift assay. The double positive colonies (His$^+$, beta-gal$^+$) are then grown on plates lacking histidine, leucine, but containing tryptophan and cycloheximide (10 mg/ml) to select for loss of pAS2/TBC-1 plasmids but retention of pACT-cDNA library plasmids. The resulting Y190 strains are mated with Y187 strains expressing TBC-1 or non-related control proteins; such as cyclophilin B, lamin, or SNF1, as Gal4 fusions as described by Harper et al. (1993) and by Bram et al. (1993), and screened for beta galactosidase by filter lift assay. Yeast clones that are beta gal- after mating with the control Gal4 fusions are considered false positives.

In another embodiment of the two-hybrid method according to the invention, the interaction between TBC-1 or a fragment or variant thereof with cellular proteins may be assessed using the Matchmaker Two Hybrid System 2 (Catalog No. K 1604-1, Clontech). ). As described in the manual accompanying the Matchmaker Two Hybrid System 2 (Catalog No. K1604-1, Clontech), the disclosure of which is incorporated herein by reference, nucleic acids encoding the TBC-1 protein or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into the yeast cells and the yeast cells are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay are those in which an interaction between TBC-1 and the protein or peptide encoded by the initially selected cDNA insert has taken place.

Method for Screening Ligands that Modulate the Expression of the TBC-1 Gene

Another subject of the present invention is a method for screening molecules that modulate the expression of the TBC-1 protein. Such a screening method comprises the steps of:

a) cultivating a prokaryotic or an eukaryotic cell that has been transfected with a nucleotide sequence encoding the TBC-1 protein, operably linked to a TBC-1 5'-regulatory sequence;

b) bringing into contact the cultivated cell with a molecule to be tested;

c) quantifying the expression of the TBC-1 protein.

Using DNA recombination techniques well known by the one skill in the art, the TBC-1 protein encoding DNA sequence is inserted into an expression vector, downstream from a TBC-1 5'-regulatory sequence that contains a TBC-1 promoter sequence.

The quantification of the expression of the TBC-1 protein may be realized either at the mRNA level or at the protein level. In the latter case, polyclonal or monoclonal antibodies may be used to quantify the amounts of the TBC-1 protein that have been produced, for example in an ELISA or a RIA assay.

In a preferred embodiment, the quantification of the TBC-1 mRNAs is realized by a quantitative PCR amplification of the cDNAs obtained by a reverse transcription of the total mRNA of the cultivated TBC-1-transfected host cell, using a pair of primers specific for TBC-1.

Expression levels and patterns of TBC-1 may be analyzed by solution hybridization with long probes as described in International Patent Application No. WO 97/05277, the entire contents of which are incorporated herein by reference. Briefly, the TBC-1 cDNA or the TBC-1 genomic DNA described above, or fragments thereof, is inserted at a cloning site immediately downstream of a bacteriophage (T3, T7 or SP6) RNA polymerase promoter to produce antisense RNA. Preferably, the TBC-1 insert comprises at least 100 or more consecutive nucleotides of the genomic DNA sequence or the cDNA sequences, particularly those comprising one of the nuceotide sequences of SEQ ID Nos 3, 4 and 6–8 or those encoding a mutated TBC-1. The plasmid is linearized and transcribed in the present of ribonucleotides comprising modified ribonucleotides (i.e. biotin-UTP and DIG-UTP). An excess of this doubly labeled RNA is hybridized in solution with mRNA isolated from cells or tissues of interest The hybridizations are performed under standard stringent conditions (40–50° C. for 16 hours in an 80% formamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of TBC-1 gene expression may also be performed using arrays. As used herein, the term array means a one dimensional, two dimensional, or multidimensional arrangement of a plurality of nucleic acids of sufficient length to permit specific detection of expression of mRNAs capable of hybridizing thereto. For example, the arrays may contain a plurality of nucleic acids derived from genes whose expression levels are to be assessed. The arrays may include the TBC-1 genomic DNA, the TBC-1 cDNA sequences or the sequences complementary thereto or fragments thereof, particularly those comprising at least one of the biallelic markers according the present invention. Preferably, the fragments are at least 15 nucleotides in length. In other embodiments, the fragments are at least 25 nucleotides in length In some embodiments, the fragments are at least 50 nucleotides in length More preferably, the fragments are at least 100 nucleotides in length. In another preferred embodiment, the fragments are more than 100 nucleotides in length. In some embodiments the fragments may be more than 500 nucleotides in length.

For example, quantitative analysis of TBC-1 gene expression may be performed with a complementary DNA microarray as described by Schena et al. (1995). Full length TBC-1 cDNAs or fragments thereof are amplified by PCR and arrayed from a 96well microtiter plate onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The ways are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm$^2$ microarrays under a 14×14 mm glass coverslip for 6–12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of TBC-1 gene expression may also be performed with full length TBC-1 cDNAs or fragments thereof in complementary DNA arrays as described by Pietu et al. (1996). The full length TBC-1 cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the TBC-1 genomic DNA, the TBC-1 cDNAs, or fragments thereof can be done through high density nucleotide arrays or chips as described by Lockhart et al. (1996) and Sosnowsky et al. (1997). Oligonucleotides of 15–50 nucleotides from the sequences of the TBC-1 genomic DNA, the TBC-1 cDNA sequences particularly those comprising at least one of biallelic markers according the present invention, preferably at least one of SEQ ID No 7–8 or those comprising the trait causing mutation, or the sequences complementary thereto, are synthesized directly on the chip (Lockhart et al., supra) or synthesized and then addressed to the chip (Sosnowsky et al., supra). Preferably, the oligonucleotides are about 20 nucleotides in length.

TBC-1 cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., 1997)., the dyes or labeling compounds are detected and quantified. Duplicate hybridizations are performed. Comparative analysis of the intensity of the signal originating from cDNA probes on the same target oligonucleotide in different cDNA samples indicates a differential expression of TBC-1 mRNAs.

Thus, is also part of the present invention a method for screening of a candidate substance or molecule that modulates the expression of the TBC-1 gene according to the invention, wherein this method comprises the following steps:

a) providing a recombinant cell host containing a nucleic acid, wherein said nucleic acid comprises the 5' regulatory region sequence or a biologically active fragment or variant thereof, the 5' regulatory region or its biologically active fragment or variant being operably linked to a polynucleotide encoding a detectable protein;

b) obtaining a candidate substance, and c) determining the ability of the candidate substance to modulate the expression levels of the polynucleotide encoding the detectable protein.

In a preferred embodiment of the above screening method, the nucleic acid comprising the 5' regulatory region sequence or a biologically active fragment or variant thereof also includes a 5'UTR region of one of the TBC-1 cDNAs of SEQ ID Nos 3 and 4, or one of their biologically active fragments or variants thereof.

A second method for the screening of a candidate substance or molecule that modulates the expression of the TBC-1 gene comprises the following steps:

a) providing a recombinant cell host containing a nucleic acid, wherein said nucleic acid comprises a 5'UTR sequence of one of the TBC-1 cDNAs of SEQ ID Nos 3 and 4, or one of their biologically active fragments or variants, the 5'UTR sequence or its biologically active fragment or variant being operably linked to a polynucleotide encoding a detectable protein;

b) obtaining a candidate substance, and c) determining the ability of the candidate substance to modulate the expression levels of the polynucleotide encoding the detectable protein.

In a preferred embodiment of the screening method described above, the nucleic acid that comprises a nucleotide sequence selected from the group consisting of the 5'UTR sequence of one of the TBC-1 cDNAs of SEQ ED Nos 3 and 4 or one of their biologically active fragments or variants, includes a promoter sequence, wherein said promoter sequence can be either endogenous, or in contrast exogenous with respect to the TBC-1 5'UTR sequences defined therein.

Among the preferred polynucleotides encoding a detectable protein, there may be cited polynucleotides encoding beta galactosidase, green fluorescent protein (GFP) and chloramphenicol ace transferase (CAT).

For the design of suitable recombinant vectors useful for performing the screening methods described above, it will be referred to the section of the present specification wherein the preferred recombinant vector of the invention are detailed.

Screening Using Transgenic Animals

In vivo methods can utilize transgenic animals for drug screening. Nucleic acids including at least one of the biallelic polymorphisms of interest can be used to generate genetically modified non-human animals or to generate site specific gene modifications in cell lines. The term "transgenic" is intended to encompass genetically modified animals having a deletion or other knock-out of TBC-1 gene activity, having an exogenous TBC-1 gene that is stably transmitted in the host cells, or having an,exogenous TBC-1 promoter operably linked to a reporter gene. Transgenic animals may be made through homologous recombination, where the TBC-1 locus is altered Alternatively, a nucleic acid construct is randomly integrated into the genome. Vectors for stable integration include for example plasmids, retroviruses and other animal viruses, and YACs. Of interest are transgenic mammals e.g. cows, pigs, goats, horses, and particularly rodents such as rats and mice. Transgenic animals allow to study both efficacy and toxicity of the candidate drug.

Methods for Inhibiting the Expression of a TBC-1 Gene

Other therapeutic compositions according to the present invention comprise advantageously an oligonucleotide fragment of the nucleic sequence of TBC-1 as an antisense tool that inhibits the expression of the corresponding TBC-1 gene. Preferred methods using antisense polynucleotide according to the present invention are the procedures described by Sczakiel et al. (1995).

Preferably, the antisense tools are chosen among the polynucleotides (15–200 bp long) that are complementary to the 5'end of the TBC-1 mRNA. In another embodiment, a combination of different antisense polynucleotides complementary to different parts of the desired targetted gene are used.

Preferred antisense polynucleotides according to the present invention arm complementary to a sequence of the mRNAs of TBC-1 that contains the translation initiation codon ATG.

The antisense nucleic acid molecules to be used in gene therapy may be either DNA or RNA sequences. They comprise a nucleotide sequence complementary to the targeted sequence of the PTCA-1 genomic DNA, the sequence of which can be determined using one of the detection methods of the present invention. The targeted DNA or RNA sequence preferably comprises at least one of the biallelic markers according to the present invention. The antisense nucleic acids should have a length and melting temperature sufficient to permit formation of an intracellular duplex having sufficient stability to inhibit the expression of the TBC-1 mRNA in the duplex. Strategies for designing antisense nucleic acids suitable for use in gene therapy are disclosed in Green et al., (1986) and Izant and Weintraub, (1984), the disclosures of which are incorporated herein by reference.

In some strategies, antisense molecules are obtained by reversing the orientation of the TBC-1 coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of TBC-1 antisense nucleic acids in vivo by operably linking DNA containing the antisense sequence to a promoter in a suitable expression vector.

Alternatively, suitable antisense strategies are those described by Rossi et al. (1991), in the International Applications Nos. WO 94/23026, WO 95/04141, WO 92/18522 and in the European Patent Application No. EP 0 572 287 A2

An alternative to the antisense technology that is used according to the present invention consists in using ribozymes that will bind to a target sequence via their complementary polynucleotide tail and that will cleave the corresponding RNA by hydrolyzing its target site (namely <<hammerhead ribozymes>>). Briefly, the simplified cycle of a hammerhead ribozyme consists of (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al. (1995), the specific preparation procedures being referred to in said article being herein incorporated by reference.

Throughout this application, various publications, patents and published patent applications are cited. The disclosures of these publications, patents and published patent specification referenced in this application are hereby incorporated by reference into the present disclosure to more fully describe the sate of the art to which this invention pertains.

EXAMPLES

Example 1

Analysis of the First mRNA encoding a TBC-1 Polypeptide Synthesized by the Cells TBC-1 cDNA was obtained as follows: 4 $\mu$l of ethanol suspension containing 1 mg of human prostate total RNA (Clontech laboratories, Inc., Palo Alto, USA; Catalogue N. 64038-1) was centrifuged, and the resulting pellet was air dried for 30 minutes at room temperature.

First strand cDNA synthesis was performed using the AdvantageTM RT-for-PCR kit (Clontech laboratories Inc., catalogue N. K1402-1). 1 $\mu$l of 20 mM solution of a specific oligo dT primer was added to 12.5 $\mu$l of RNA solution in water, heated at 74° C. for 2.5 min and rapidly quenched in an ice bath. 10 $\mu$l of 5×RT buffer (50 mM Tris-HCl, pH 8.3, 75 mM KCl, 3 mM MgCl$_2$), 2.5 $\mu$l of dNTP mix (10 mM each), 1.25 $\mu$l of human recombinant placental RNA inhibitor were mixed with 1 ml of MMLV reverse transcriptase (200 units). 6.5 $\mu$l of this solution were added to RNA-primer mix and incubated at 42° C. for one hour. 80 $\mu$l of water were added and the solution was incubated at 94° C. for 5 minutes.

5 $\mu$l of the resulting solution were used in a Long Range PCR reaction with hot start, in 50 $\mu$l final volume, using 2 units of rtTHXL, 20 pmol/$\mu$l of each of 5'-TGACCACCATGCCCATGCT-3' (271–289 in SEQ ID No 3) and 5'-GCATTTATTCACGTCCACGCC-3' (3929–3949 in SEQ ID No 3) primers with 35 cycles of elongation for 6 minutes at 67° C. in thermocycler.

The amplification products corresponding to both cDNA strands were partially sequenced in order to ensure the specificity of the amplification reaction.

Results of Nothern blot analysis of prostate mRNAs supported the existence of the first TBC-1 cDNA having about 4 kb in length, which is the nucleotide sequence of SEQ ID No 3.

Example 2

Detection of TBC-1 Biallelic Markers: DNA Extraction

Donors were unrelated and healthy. They presented a sufficient diversity for being representative of a French heterogeneous population. The DNA from 100 individuals was extracted and tested for the detection of the biallelic markers.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 mM Tris pH7.6; 5 mM $MgCl_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:

3 ml TE 10-2 (Tris-HCl 10 mM, EDTA 2 mM)/NaCl 0.4 M

200 µl SDS 10%

500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm.

The pellet was dried at 37° C., and resuspended in 1 ml TE 10-1 or 1 ml water. The DNA concentration was evaluated by measuring the OD at 260 nm (1 unit OD=50 µl/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 3

Detection of the Biallelic Markers: Amplification of Genomic DNA by PCR

The amplification of specific genomic sequences of the DNA samples of example 2 was carried out on the pool of DNA obtained previously. In addition, 50 individual samples were similarly amplified.

PCR assays were performed using the following protocol:

| | |
|---|---|
| Final volume | 25 µl |
| DNA | 2 ng/µl |
| $MgCl_2$ | 2 mM |
| dNPT (each) | 200 µM |
| primer (each) | 2.9 ng/µl |
| Ampli Taq Gold DNA polymerase | 0.05 unit/µl |
| PCR buffer (10× = 0.1M TrisHCl pH 8.3 0.5M KCl | 1× |

Each pair of first primers was designed using the sequence information of the TBC-1 gene disclosed herein and the OSP software (Hillier & Green, 1991). This first pair of primers was about 20 nucleotides in length and had the sequences disclosed in Table 1 in the columns labeled PU and RP.

TABLE 1

| Amplicon | Position range of the amplicon in SEQ ID 1 | | Primer name | Position range of amplification primer in SEQ ID No 1 | | Primer name | Complementary position range of amplification primer in SEQ ID No 1 | |
|---|---|---|---|---|---|---|---|---|
| 99-430 | 9391 | 9845 | B1 | 9391 | 9408 | C1 | 9828 | 9845 |

| Amplicon | Position range of the amplicon in SEQ ID 2 | | Primer name | Position range of amplification primer in SEQ ID No 2 | | Primer name | Complementary position range of amplification primer in SEQ ID No 2 | |
|---|---|---|---|---|---|---|---|---|
| 99-20508 | 988 | 1529 | B2 | 988 | 1006 | C2 | 1509 | 1529 |
| 99-20469 | 5039 | 5554 | B3 | 5039 | 5056 | C3 | 5534 | 5554 |
| 5-254 | 5997 | 6350 | B4 | 5997 | 6015 | C4 | 6332 | 6350 |
| 5-257 | 14371 | 14817 | B5 | 14371 | 14390 | C5 | 14798 | 14817 |
| 99-20511 | 18751 | 19217 | B6 | 18751 | 18771 | C6 | 19198 | 19217 |
| 99-20510 | 19605 | 20005 | B7 | 19605 | 19625 | C7 | 19986 | 20005 |
| 99-20504 | 29529 | 30061 | B8 | 29529 | 29547 | C8 | 30041 | 30061 |
| 99-20493 | 42268 | 42752 | B9 | 42268 | 42287 | C9 | 42732 | 42752 |
| 99-20499 | 69026 | 69543 | B10 | 69026 | 69046 | C10 | 69525 | 69543 |
| 99-20473 | 76323 | 76790 | B11 | 76323 | 76343 | C11 | 76771 | 76790 |
| 5-249 | 78292 | 78721 | B12 | 78292 | 78309 | C12 | 78704 | 78721 |
| 99-20485 | 81893 | 82372 | B13 | 81893 | 81912 | C13 | 82353 | 82372 |
| 99-20481 | 84392 | 84929 | B14 | 84392 | 84412 | C14 | 84909 | 84929 |
| 99-20480 | 89746 | 90198 | B15 | 89746 | 89765 | C15 | 90179 | 90198 |

Preferably, the primers contained a common oligonucleotide tail upstream of the specific bases targeted for amplification which was useful for sequencing.

Primers PU contain the following additional PU 5' sequence: TGTAAAACGACGGCCAGT (SEQ ID No 6); primers RP contain the following RP 5' sequence: CAG-GAAACAGCTATGACC (SEQ ID No 7).

The synthesis of these primers was performed following the phosphoramidite method, on a GENSET UFPS 24.1 synthesizer.

DNA amplification was performed on a Genius II thermocycler. After heating at 95° C. for 10 min, 40 cycles were performed. Each cycle comprised: 30 sec at 95° C., 54° C. for 1 min, and 30 sec at 72° C. For final elongation, 10 min at 72° C. ended the amplification. The quantities of the amplification products obtained were determined on 96well microtiter plates, using a fluorometer and Picogreen as intercalant agent (Molecular Probes).

Example 4

Detection of the Biallelic Markers: Sequencing of Amplified Genomic DNA and Identification of Polymorphisms The sequencing of the amplified DNA obtained in example 3 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis [ABI Prism DNA Sequencing Analysis software (2.1.2 version)].

The sequence data were further evaluated to detect the presence of biallelic markers among the pooled amplified fragments. The polymorphism search was based on the presence of superimposed peaks in the electrophoresis pattern resulting from different bases occurring at the same position as described previously.

15 fragments of amplification was analyzed. In this segment, 19 biallelic markers were detected. The localization of the biallelic marker is as shown in Table 2.

TABLE 3

| BM | Marker Name | Position range of probes in SEQ ID No 1 | | Probes |
|---|---|---|---|---|
| A1 | 99-430-352 | 9482 | 9506 | P1 |

| BM | Marker Name | Position range of probes in SEQ ID No 2 | | Probes |
|---|---|---|---|---|
| A2 | 99-20508-456 | 1431 | 1455 | P2 |
| A3 | 99-20469-213 | 5235 | 5259 | P3 |
| A4 | 5-254-227 | 6211 | 6235 | P4 |
| A5 | 5-257-353 | 14711 | 14735 | P5 |
| A6 | 99-20511-32 | 19174 | 19198 | P6 |
| A7 | 99-20511-221 | 18985 | 19009 | P7 |
| A9 | 99-20504-90 | 29605 | 29629 | P9 |
| A10 | 99-20493-238 | 42507 | 42531 | P10 |
| A11 | 99-20499-221 | 69312 | 69336 | P11 |
| A12 | 99-20499-364 | 69169 | 69193 | P12 |
| A13 | 99-20499-399 | 69134 | 69158 | P13 |
| A15 | 5-249-304 | 78583 | 78607 | P15 |
| A16 | 99-20485-269 | 82147 | 82171 | P16 |
| A17 | 99-20481-131 | 84510 | 84534 | P17 |
| A18 | 99-20481-419 | 84798 | 84822 | P18 |
| A19 | 99-20480-233 | 89955 | 89979 | P19 |

Example 5

Validation of the Polymorphisms Through Microsequencing

The biallelic markers identified in example 4 were further confirmed and their respective frequencies were determined through microsequencing. Microsequencing was carried out for each individual DNA sample described in Example 2.

TABLE 2

| Amplicon | BM | Marker Name | Localization in TBC-1 gene | Polymorphism Allele 1 | allele 2 | BM position in SEQ ID No 1 |
|---|---|---|---|---|---|---|
| 99-430 | A1 | 99-430-352 | Intron 1 | A | G | 9494 |

| Amplicon | BM | Marker Name | Localization in TBC-1 gene | Polymorphism allele 1 | allele 2 | BM position in SEQ ID No 1 |
|---|---|---|---|---|---|---|
| 99-20508 | A2 | 99-20508-456 | Intron upstream to Exon A | C | T | 1443 |
| 99-20469 | A3 | 99-20469-213 | Intron A | C | T | 5247 |
| 5-254 | A4 | 5-254-227 | Intron B | A | G | 6223 |
| 5-257 | A5 | 5-257-353 | Intron D | C | T | 14723 |
| 99-20511 | A6 | 99-20511-32 | Intron D | C | T | 19186 |
| 99-20511 | A7 | 99-20511-221 | Intron D | A | G | 18997 |
| 99-20510 | A8 | 99-20510-115 | Intron D | deletion of TCT | | 19891 |
| 99-20504 | A9 | 99-20504-90 | Intron D | A | G | 29617 |
| 99-20493 | A10 | 99-20493-238 | Intron D | A | C | 42519 |
| 99-20499 | A11 | 99-20499-221 | Intron G | A | G | 69324 |
| 99-20499 | A12 | 99-20499-364 | Intron G | A | T | 69181 |
| 99-20499 | A13 | 99-20499-399 | Intron G | A | G | 69146 |
| 99-20473 | A14 | 99-20473-138 | Intron H | deletion of TAACA | | 76458 |
| 5-249 | A15 | 5-249-304 | Intron I | A | G | 78595 |
| 99-20485 | A16 | 99-20485-269 | Intron I | A | G | 82159 |
| 99-20481 | A17 | 99-20481-131 | Intron I | G | C | 84522 |
| 99-20481 | A18 | 99-20481-419 | Intron I | A | T | 84810 |
| 99-20480 | A19 | 99-20480-233 | Intron J | A | G | 89967 |

BM refers to "biallelic marker". All1 and all2 refer respectively to allele 1 and allele 2 of the biallelic marker.

Amplification from genomic DNA of individuals was performed by PCR as described above for the detection of the biallelic markers with the same set of PCR primers (Table 1).

The preferred primers used in microsequencing were about 19 nucleotides in length and hybridized just upstream of tie considered polymorphic base. According to the invention, the primers used in microsequencing are detailed in Table 4.

TABLE 4

| Marker Name | Biallelic Marker | Mis. 1 | Position range of microsequencing primer mis 1 in SEQ ID No 1 | | Mis. 2 | Complementary position range of microsequencing primer mis 2 in SEQ ID No 1 | |
|---|---|---|---|---|---|---|---|
| 99-430-352 | A1 | D1 | 9475 | 9493 | E1 | 9495 | 9513 |

| Marker Name | Biallelic Marker | Mis. 1 | Position range of microsequencing primer mis 1 in SEQ ID No 2 | | Mis. 2 | Complementary position range of microsequencing primer mis 2 in SEQ ID No 2 | |
|---|---|---|---|---|---|---|---|
| 99-20508-456 | A2 | D2 | 1424 | 1442 | E2 | 1444 | 1462 |
| 99-20469-213 | A3 | D3 | 5228 | 5246 | E3 | 5248 | 5266 |
| 5-254-227 | A4 | D4 | 6204 | 6222 | E4 | 6224 | 6242 |
| 5-257-353 | A5 | D5 | 14704 | 14722 | E5 | 14724 | 14742 |
| 99-20511-32 | A6 | D6 | 19167 | 19185 | E6 | 19187 | 19205 |
| 99-20511-221 | A7 | D7 | 18978 | 18996 | E7 | 18998 | 19016 |
| 99-20510-115 | A8 | D8 | 19872 | 19890 | E8 | 19892 | 19910 |
| 99-20504-90 | A9 | D9 | 29598 | 29616 | E9 | 29618 | 29636 |
| 99-20493-238 | A10 | D10 | 42500 | 42518 | E10 | 42520 | 42538 |
| 99-20499-221 | A11 | D11 | 69305 | 69323 | E11 | 69325 | 69343 |
| 99-20499-364 | A12 | D12 | 69162 | 69180 | E12 | 69182 | 69200 |
| 99-20499-399 | A13 | D13 | 69127 | 69145 | E13 | 69147 | 69165 |
| 99-20473-138 | A14 | D14 | 76439 | 76457 | E14 | 76459 | 76477 |
| 5-249-304 | A15 | D15 | 78576 | 78594 | E15 | 78596 | 78614 |
| 99-20485-269 | A16 | D16 | 82140 | 82158 | E16 | 82160 | 82178 |
| 99-20481-131 | A17 | D17 | 84503 | 84521 | E17 | 84523 | 84541 |
| 99-20481-419 | A18 | D18 | 84791 | 84809 | E18 | 84811 | 84829 |
| 99-20480-233 | A19 | D19 | 89948 | 89966 | E19 | 89968 | 89986 |

The microsequencing reaction was performed as follows:

After purification of the amplification products, the microsequencing reaction mixture was prepared by adding, in a 20 µl final volume: 10 pmol microsequencing oligonucleotide, 1 U Thermosequenase (Amersham E79000G), 1.25 µl Thermosequenase buffer (260 mM Tris HCl pH 9.5, 65 mM $MgCl_2$), and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C., 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized classification as homozygous or heterozygous type based on the height ratio.

REFERENCES

Altschul et al., 1990, J. Mol. Biol. 215(3):403–410/ Altschul et al., 1993, Nature Genetics 3:266–272/Altschul et al., 1997, Nuc. Acids Res. 25:3389–3402/Ausubel et al. (1989)Current Protocols in Molecular Biology, Green Publishing Associates and Wiley Interscience, N.Y./Beaucage et al., *Tetrahedron Lett* 1981, 22: 1859–1862/Bram R J et al., 1993, Mol. Cell Biol., 13: 4760–4769./Brown E L, Belagaje R, Ryan M J, Khorana H G, *Methods Enzymol* 1979;68:109–151/Castagnoli L. et al. (Felici F.), 1991, J. Mol. Biol., 222:301–310/Chai H. et al., 1993, Biotechnol. Appl. Biochem., 18:259–273/Chee et al. (1996) *Science.* 274:610–614./Chen and Kwok *Nucleic Acids Research* 25:347–353 1997/Chen et al. *Proc. Natl. Acad. Sci. USA* 94/20 10756–10761, 1997/Cho R J et al., 1998, Proc. Natl. Acad. Sci. USA, 95(7): 3752–3757./Chumakov I. et al., 1995, Nature. 377(6547 Suppl): 175–297./Compton J. (1991) *Nature.* 350(6313):91–92./Dib et al., 1996, Nature, 380: III–V./Ellis N A,1997 Curr.Op.Genet.Dev., 7: 354–363/ Feldman and Steg, 1996, Medecine/Sciences, synthese, 12:47–55/Fields and Song, 1989, Nature, Vol. 340: 245–246./Fishel R & Wilson T. 1997, Curr.Op.Genet.Dev.7: 105–113/Flotte et al., 1992, Am. J. Respir. Cell Mol. Biol., 7: 349–356./Fodor et al. (1991) *Science* 251:767–777./ Fromont-Racine M. et al., 1997, Nature Genetics, 16(3): 277–282./Fuller S. A. et al., 1996, Immunology in Current Protocols in Molecular Biology, Ausubel et al. Eds, John Wiley & Sons, Inc., USA/Geysen H. Mario et al. 1984. Proc. Natl. Acad. Sci. U.S.A. 81:3998–4002/Gonnet et al., 1992, Science 256:1443–1445/Green et al., *Ann. Rev. Biochem.*

55:569–597 (1986)/Grompe, M. et al., *Proc. Natl. Acad. Sci. U.S.A.* 1989; 86:5855–5892/Grompe, M. *Nature Genetics* 1993; 5:111–117/Guatelli J C et al. *Proc. Natl. Acad. Sci. USA.* 35:273–286./Haber D & Harlow E, 1997, Nature Genet. 16:320–322./Hacia J G, Brody L C, Chee M S, Fodor S P, Collins F S, *Nat Genet* 996;14(4):441–447/Haff L. A. and Smirnov I. P. (1997) *Genome Research,* 7:378–388./Hames B. D. and Higgins S. J. (1985) *Nucleic Acid Hybridization: A Practical Approach.* Hames and Higgins Ed., IRL Press, Oxford./Harju L, et al., *Clin Chem* 1993;39(11Pt 1):2282–2287/Harper J W et al., 1993, Cell, Vol. 75: 20 805–816./Harris H et al.,1969,Nature 223:363–368./Henikoff and Henikoff, 1993, Proteins 17:49–61/Higgins et al.,1996, Methods Enzymol. 266:383–402/Hillier L. and Green P. *Methods Appl.,* 1991, 1: 124–8./Huang L. et al. (1996) *Cancer Res* 56(5):1137–1141./Huygen et al., 1996, Nature Medicine, 2(8):893–898/Izant and Weintraub, *Cell* 36:1007–1015 (1984)/Julan at al., 1992, J. Gen. Virol., 73: 3251–3255./Karlin and Altschul, 1990, Proc. Natl. Acad. Sci. USA 87:2267–2268/Koch Y., 1977, Biochem. Biophys. Res. Commun., 74:488–491/Kohler G. and Milstein C., 1975, Nature, 256: 495./Kozal M J, et al., *Nat Med* 1996;2 (7):753–759/Landegren U. et al. (1998) *Genome Research,* 8:769–776./Leger O J, et al., 1997, Hum Antibodies,8(1): 3–16/Lenhard T. et al., 1996, Gene, 169:187–190/Livak et al., *Nature Genetics,* 9:341–342, 1995/Livak K J, and Hainer J W., 1994, Hum Mutat., 3(4): 379–385./Lockhart et al. *Nature Biotechnology* 14: 1675–1680, 1996/Lucas A. H., 1994, In: Development and Clinical Uses of Haempophilus b Conjugate./Mansour S L et al., 1988, Nature, 336: 348–352./Marshall R. L. et al. (1994) *PCR Methods and Applications.* 4:80–84./Martineau P, Jones P, Winter G, 1998, J Mol Biol, 280(1):117–127/Mc Whorter W. P., et al. A screening study of prostate cancer in high risk families. J Urol 1992;148:826–828./McLaughlin et al., 1989, J. Virol., 62: 1963–1973./Muzyczka et al., 1992, Cuur. Topics in Micro. and Immunol., 158: 97–129./Narang S A, Hsiung H M, Brousseau R, *Methods Enzymol* 1979;68:90–98/Neda et al., 1991, J. Biol. Chem.,266: 14143–14146./Nickerson D. A. et al. (1990) *Proc. Natl. Acad. Sci. U.S.A.* 87:8923–8927./ Nyren P. Pettersson B. Uhlen M, *Anal Biochem* 1993;208 (1):171–175/O'Reilly et al., 1992, Baculovirus expression vectors: a Laboratory Manual. W. H. Freeman and Co., New York/Ohno et al., 1994, Sciences, 265:781–784/Oldenburg K. R. et al., 1992, Proc. Natl. Acad. Sci., 89:5393–5397./ Orita et al., *Proc. Natl. Acad. Sci. U.S.A.* 1989;86: 2776–2770/Parmley and Smith, Gene, 1988, 73:305–318./Pastinen et al., *Genome Research* 1997; 7:606–614/PCR Methods and Applications", 1991, Cold Spring Harbor Laboratory Press./Pearson and Lipman, 1988, Proc. Natl. Acad. Sci. USA 85(8):2444–2448/Pietu et al. *Genome Research* 6:492–503, 1996/Porath J et al., 1975, Nature, 258(5536): 598–599./Reimann K A, et al., 1997, AIDS Res Hum Retroviruses. 13(11): 933–943/Ridder R, et al., 1995, Biotechnology (N Y), 13(3):255–260/Rossi et al., *Pharmacol. Ther.* 50:245–254, (1991)/Roth J. A. et al., 1996, Nature Medicine, 2(9):985–991/Rougeot, C. et al., *Eur. J. Biochem.* 219 (3): 765–773, 1994/Roux et al., 1989, Proc. Natl. Acad. Sci. USA, 86: 9079–9083./Sambrook, et al. 1989. Molecular cloning: a laboratory manual. 2ed. Cold Spring Harbor Laboratory, Cold spring Harbor, New York./Samson M, et al. (1996) *Nature,* 382(6593):722–725./Samulski et al., 1989, J. Virol., 63: 3822–3828./Sanchez-Pescador R., 1988, J. Clin. Microbiol., 26(10):1934–1938/Sandou et al., 1994, Science, 265: 1875–1878./Schena et al. *Science* 270:467–470, 1995/Schwartz and Dayhoff, eds., 1978, Matrices for Detecting Distance Relationships: Atlas of Protein Sequence and Structure, Washington: National Biomedical Research Foundation/Sczakiel G. et al., 1995, Trends Microbiol., 1995, 3(6):213–217/Sheffield, V. C. et al, *Proc. Natl. Acad. Sci. U.S.A* 1991; 49:699–706/Shoemaker D D, et al., *Nat Genet* 1996;14(4):450–456/Smith et al., 1983, Mol. Cell. Biol., 3:2156–2165./Sosnowski R G, et al., *Proc Natl Acad Sci USA* 1997;94:1119–1123/Steinberg G. D., et al. Family history and the risk of prostate cancer, The prostate 1990;17,337–347./Stryer, L., *Biochemistry,* 4th edition, 1995/Syvanen A C, et al., 1994, Hum Mutat, 3(3): 172–179./Tacson et al., 1996, Nature Medicine, 2(8) :888–892./Thompson et al., 1994, Nucleic Acids Res. 22(2) :4673–4680/Tyagi et al. (1998) *Nature Biotechnology.* 16:49–53./Urdea M. S., 1988, Nucleic Acids Research, 11: 4937–4957/Urdea M S et al., 1991, Nucleic Acids Symp Ser., 24: 197–200./Valadon P., et al., 1996. J. Mol. Biol., Vol. 261:11–22./Vaughan T J, et al., 1996, Nat Biotechnol. 14(3): 309–314/Vlasak R. et al., 1983, Eur. J. Biochem., 135:123–126/Wabiko et al., 1986, DNA, 5(4):305–314./ Walker et al. (1996) *Clin. Chem.* 42:9–13./Wersterink M. A. J., 1995, Proc. Natl. Acad. Sci., 92:4021–4025./White, M. B. et al. (1992) *Genomics.* 12:301–306./White, M. B. et al. (1997) *Genomics.* 12:301–306./Wilson R. et al., 1994, Nature, 368(6466): 32–38./Zhang S D et al., 1996, Genes and development, 10: 1108–1119.

SEQUENCE LISTING FREE TEXT

The following free text appears in the accompanying Sequence Listing:

5' regulatory region
polymorphic base
complement
3' regulatory region
deletion of
or
probe
homology with Genset 5' EST in ref
sequencing oligonucleotide PrimerPU
sequencing oligonucleotide PrimerRP

What is claimed is:

1. A composition comprising: an isolated, purified, or recombinant polynucleotide which encodes a polypeptide comprising 6 amino acids of SEQ ID NO:5 or the complement thereof, provided that said polypeptide is not murine TBC-1.

2. A composition comprising an isolated, purified, or recombinant human polynucleotide which encodes a polypeptide comprising 6 amino acids of SEQ ID NO:5 or the complement thereof.

3. An isolated, purified, or recombinant polynucleotide which: a) encodes a polypeptide comprising SEQ ID NO: 5; b) comprises nucleotides 171 to 3725 of SEQ ID NO: 3; or c) the complement thereof.

4. The isolated, purified, or recombinant polynucleotide according to claim 3 attached to a solid support.

5. The isolated, purified, or recombinant polynucleotide according to claim 4, wherein said polynucleotide encodes a polypeptide comprising SEQ ID NO: 5.

6. The isolated, purified, or recombinant polynucleotide according to claim 4, wherein said polynucleotide comprises nucleotides 171 to 3725 of SEQ ID NO: 3.

7. The isolated, purified, or recombinant polynucleotide according to claim 3, wherein said polynucleotide encodes a polypeptide comprising SEQ ID NO: 5.

8. The isolated, purified, or recombinant polynucleotide according to claim 3, wherein said polynucleotide comprises nucleotides 171 to 3725 of SEQ ID NO: 3.

9. An array of polynucleotides comprising at least one isolated, purified, or recombinant polynucleotides which: a) encodes a polypeptide comprising SEQ ID NO: 5; b) comprises nucleotides 171 to 3725 of SEQ ID NO: 3; or e) the complement thereof.

10. The array according to claim 9, wherein said polynucleotide encodes a polypeptide comprising SEQ ID NO: 5.

11. The array according to claim 9, wherein said polynucleotide comprises nucleotides 171 to 3725 of SEQ ID NO: 3.

12. The array according to claim 9, wherein said array is addressable.

13. The array according to claim 10, wherein said array is addressable.

14. The array according to claim 11, wherein said array is addressable.

15. The isolated, purified, or recombinant polynucleotide according to claim 5, further comprising a label.

16. The isolated, purified, or recombinant polynucleotide according to claim 6, further comprising a label.

17. A composition comprising: a recombinant vector comprising a polynucleotide which: a) encodes a polypeptide comprising SEQ ID NO: 5; b) comprises nucleotides 171 to 3725 of SEQ ID NO: 3; or c) the complement thereof.

18. The composition according to claim 17, wherein said recombinant vector comprises a polynucleotide which encodes a polypeptide comprising SEQ ID NO: 5.

19. The composition according to claim 17, wherein said recombinant vector comprises nucleotides 171 to 3725 of SEQ ID NO: 3.

20. A composition comprising: a host cell comprising a recombinant vector comprising a polynucleotide which: a) encodes a polypeptide comprising SEQ ID NO: 5; b) comprises nucleotides 171 to 3725 of SEQ ID NO: 3; or c) the complement thereof.

21. The composition according to claim 20, wherein said recombinant vector comprises a polynucleotide which encodes a polypeptide comprising SEQ ID NO: 5.

22. The composition according to claim 20, wherein said recombinant vector comprises nucleotides 171 to 3725 of SEQ ID NO: 3.

23. A method of making a TBC-1 polypeptide comprising the steps of:
(i) obtaining a host cell comprising a recombinant vector comprising a polynucleotide which: a) encodes a polypeptide comprising SEQ ID NO: 5 or b) comprises nucleotides 171 to 3725 of SEQ ID NO: 3,
(ii) growing said cell under conditions suitable to produce said polypeptide.

24. The method according to claim 23, wherein said recombinant vector comprises a polynucleotide which encodes a polypeptide comprising SEQ ID NO: 5.

25. The method according to claim 23, wherein said recombinant vector comprises nucleotides 171 to 3725 of SEQ ID NO: 3.

26. The method according to claim 24, further comprising the step of purifying of isolating said polypeptide.

27. The method according to claim 25, further comprising the step of purifying or isolating said polypeptide.

28. A composition comprising an isolated, purified, or recombinant polynucleotide comprising a nucleotide sequence selected from the group consisting of the nucleotide sequences of SEQ ID NOs: 3 and 4, or the complements thereof.

29. A method of making a TBC-1 polypeptide comprising the steps of:
(i) obtaining a host cell comprising a recombinant vector comprising a polynucleotide comprising a nucleotide sequence selected from the group consisting of the nucleotide sequences of SEQ ID NOs: 3 and 4, or the complements thereof; and
(ii) growing said cell under conditions suitable to produce said polypeptide.

30. A composition comprising an isolated, purified, or recombinant polynucleotide consisting of the nucleotide sequences of SEQ ID NOs: 1, 2, or the complements thereof.

* * * * *

UNITED STATES PATENT AND TRADEMARK OFFICE
CERTIFICATE OF CORRECTION

PATENT NO. : 6,825,004 B1
DATED : November 30, 2004
INVENTOR(S) : Marta Blumenfeld, Lydie Bougueleret and Ilya Chumakov It is certified that error appears in the above-identified patent and that said Letters Patent is hereby corrected as shown below:

Column 8,
Lines 16-17, "Fab, in Fab'" should read -- Fab, Fab' --.

Column 10,
Line 65, "sequences ad not" should read -- sequences and not --.
Line 66, "conditions-under" should read -- conditions under --.

Column 12,
Line 60, "($CH_2CH_3$)" should read -- ($CH_2CH_2$) --.
Line 62, "CH=CH—" should read -- —CH=CH— --.

Column 14,
Line 1, "art Preferably" should read -- art. Preferably --.

Column 16,
Line 11, "murine tbc" should read -- murine *tbc1* --.
Line 14, "hematopoictic" should read -- hematopoietic --.

Column 17,
Line 32, "this fist" should read -- this first --.

Column 22,
Line 53, "SEQ ED" should read -- SEQ ID --.

Column 25,
Line 23, "401-400" should read -- 401-600 --.

Column 26,
Line 45, "polygonal" should read -- polyclonal --.

Column 29,
Line 45, "(1991)" should read -- (1997) --.

Column 31,
Line 10, "K Genotyping" should read -- B-Genotyping --.

Column 33,
Line 1, "in die art" should read -- in the art --.
Line 25, "technique/The" should read -- technique. The --.

UNITED STATES PATENT AND TRADEMARK OFFICE
CERTIFICATE OF CORRECTION

PATENT NO. : 6,825,004 B1
DATED : November 30, 2004
INVENTOR(S) : Marta Blumenfeld, Lydie Bougueleret and Liya Chumakov It is certified that error appears in the above-identified patent and that said Letters Patent is hereby corrected as shown below:

Column 34,
Line 17, "Smimov" should read -- Smirnov --
Line 58, "(Haiju et al.," should read -- (Harju et al., --.

Column 39,
Line 21, "WO 92110092" should read -- WO 92/10092 --.

Column 42,
Line 63, "5014000" should read -- 5001-6000 --.

Column 43,
Line 15, "40, 35, 50" should read -- 40, 50 --.

Column 47,
Line 56, "WO 92/10692" should read -- WO 92/10092 --.

Column 50,
Line 52, "PBPV" should read -- pBPV --.

Column 51,
Line 28, "include lac" should read -- include lacI --.

Column 52
Line 57, "VR459" should read -- VR-659 --.

Column 55,
Line 29, "TDC-1" should read -- *TBC-1* --.

Column 56,
Line 50, "amplified-by" should read -- amplified by --.

Column 59,
Line 22, "96well" should read -- 96-well --.
Line 27, "The ways are" should read -- The arrays are --.

Column 60,
Line 50, "SEQ ED" should read -- SEQ ID --.
Line 58, "ace transferase" should read -- acetyl transferase --.
Line 62, "vector" should read -- vectors --.

UNITED STATES PATENT AND TRADEMARK OFFICE
CERTIFICATE OF CORRECTION

PATENT NO. : 6,825,004 B1
DATED : November 30, 2004
INVENTOR(S) : Marta Blumenfeld, Lydie Bougueleret and Liya Chumakov It is certified that error appears in the above-identified patent and that said Letters Patent is hereby corrected as shown below:

Column 61,
Line 6, "an,exogenous" should read -- an exogenous --.
Line 32, "invention arm" should read -- invention are --.

Column 67,
Line 7, "of tie considered" should read -- of the considered --.

Column 69,
Line 6, "*Genet* 996" should read -- *Genet* 1996 --.
Lines 11-12, "75: 20 805-816" should read -- 75 : 805-816 --.

Column 199,
Line 55, "comprising 6 amino acids of SEQ ID NO:5" should read -- comprising SEQ ID NO:5 --.
Line 60, "comprising 6 amino acids of SEQ ID NO:5" should read -- comprising SEQ ID NO:5 --.

Column 200,
Line 64, "polynucleotides" should read -- polynucleotide --.
Line 66, "or e) the" should read -- or c) the --.

Column 202,
Line 16, "purifying of isolating" should read -- purifying or isolating --.

Signed and Sealed this

Fourteenth Day of June, 2005

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 17590
<212> TYPE: DNA
<213> ORGANISM: Homo sapiens
<220> FEATURE:
```

-continued

```
<221> NAME/KEY: misc_feature
<222> LOCATION: 1..2000
<223> OTHER INFORMATION: 5' regulatory region
<221> NAME/KEY: exon
<222> LOCATION: 2001..2077
<223> OTHER INFORMATION: exon 1
<221> NAME/KEY: exon
<222> LOCATION: 12292..12373
<223> OTHER INFORMATION: exon 1b
<221> NAME/KEY: exon
<222> LOCATION: 12740..13249
<223> OTHER INFORMATION: exon 2
<221> NAME/KEY: allele
<222> LOCATION: 9494
<223> OTHER INFORMATION: 99-430-352 : polymorphic base A or G
<221> NAME/KEY: primer_bind
<222> LOCATION: 9391..9408
<223> OTHER INFORMATION: 99-430.rp
<221> NAME/KEY: primer_bind
<222> LOCATION: 9828..9845
<223> OTHER INFORMATION: 99-430.pu complement
<221> NAME/KEY: primer_bind
<222> LOCATION: 9475..9493
<223> OTHER INFORMATION: 99-430-352.mis
<221> NAME/KEY: primer_bind
<222> LOCATION: 9495..9513
<223> OTHER INFORMATION: 99-430-352.mis complement
<221> NAME/KEY: primer_bind
<222> LOCATION: 9482..9506
<223> OTHER INFORMATION: 99-430-352.probe
<221> NAME/KEY: misc_feature
<222> LOCATION: 3953,4056,4167,4739,6217,6245,6860,9998..9999,10006,
      10012,10104,10477,10822,10825,11095,11256,11273,11857..11858,
      11895..11896,14057,15912..15913,16217..16218,16329..16330,17504
<223> OTHER INFORMATION: n=a, g, c or t

<400> SEQUENCE: 1
aggacagtat ctagcacaat accccaaatc gactaactcc tccgtaaaga atagctacca        60
ctattgtgag agttttaagt caagctgtga ataaaactct tgggtccact taaaaatacc       120
tcccctggat gtaagcatcc agggaaatca gggaatgcca taagacagcc ctaatctaaa       180
agcctacaag aagctcagtg ggcttcaagg aagacactgc tcttggtacg atgaggaaac       240
ctggccctct atttgcctcc tgggccacag taatattgat aatagctgct gcttttagtt       300
gaggaccatg tacgtctgtg tcactgcact ggccactttta cttacacttttt cctgctttgt    360 cctcacaaag atcctgtaag gtgtgtattg gtcccattta gcaggtaaga caatgaagac       420
cagaggtcca gcaccttgcc taaaccacac ctgctgggat ttggattcaa gtccaaccgt       480
acagctcaaa cgctcagcca cttccctaaa gtcaccccc agctacatta agtaaaaaaa        540
tccagaaaga tgccacctgg gggtctggaa ctgcctcctc cgagcacccg gctctcccct       600
ccctgcggac tcttctctgg agaggatgtg atgcttctta cttttctcag atccctctcc      660
ccaccctgcg agtgacgttg cgcctctgtg cctggtggga tagggatctg ggagcttcgc      720
ctgttttttg cacactgcca tcccctagtc ttagggagcg agctctgtcc cgcttttcac      780
atctccgcgt ctttccttgc actctacatc accgctggga atgtccccag acctgatcgg      840
ggcatgcaca ctgggtgtg cgtgtgcgtg tggtgtgtgt tcctgcgcgt gtgccgggct       900
cgcggggcag gaaaaagcgc ctaatccagg ctctgcgtca ctcccgcaat tggttagaaa      960
tggagtttcc tggtgtttaa tcccgggagg gcacttcgcc ttcgttgttt cccagagtcc     1020
ctgatttttc tgcctcgcat gccagcgccc cataggcat ccgtgcctca gttcacctct     1080
tgccatcctc caaggacggg gagaaggggt aaggcggggg agagcaaggt ggcttggtcg     1140 ccccggccc ccgcccccca tgttgtgtgc agttttccacc acgtctgttt cggagggaga    1200
agaggagggt gcagatgagg cgaggcgcct tcggagcgc ggagagcggg caggcagtgc     1260
```

-continued

```
cacctgctga gagccactca ggccgagcaa gcggcgggca gtgccacctg ctataaatag    1320
gccgccaagg acagggtgtg cgactgtaca tcccgccacg agggcctgca tcacgcgcgg    1380
ggccccgcgc ccccggctcc ccagggaaac gctgtgccca gatcctgcgc aggggtctgg    1440
atgggcggc ggcccgagta cttccccct attcccccca cagacactgg ctgaggatgg      1500
cccgcgggct tggggcggg gggtggcaag gaggggaggg aggccgcggc ggacccgcag      1560
tgcagcagct gttgctcgcg tgtgactcgc ccgtccgggc cgtgctgccc aggcacagtc    1620
acacggcgca gtggggagga ggaggacacc gagtcccct cccagctccc cggggaccga     1680
gtggggagat cccggctcct gtcttcccct cgcctccagc gcgctcgccc aggctgggag    1740
gaggaaacca gagccgcgcg cagacacctc ctccttctcc tcctcttctt cctcctcctc    1800
ctcctcctcc tcctcctctt cggctgctgc tcctggtgcc gccaccgtcc gccggtgcct    1860
gttgctgccg ccgccgcggg acctgctgtg tcctcagctg ggtggagaag aggcgggcgc    1920
cgagccgagg ggagcccct ccccgtcccc ccgcggcggg aagagcgcag ccagccgggt    1980
gcgatggact ccccgcccgc ccaggccgtc cccaggatgc ccccaagcac ctgcgcgtcc   2040
cggcccggcc ccgggctctg agcgcgccgc ggcacaggta aggcgcttcc tggggcttcg    2100
tcctggccac cctgctggct cctctcgggg cgtcgcggcc gcccctccc gcagcacgcc    2160
cctgcccgc ctggccgcgg aggggaaggc atctggccgc ccacggacgc gaggccaggg    2220
tctctcgggg gaggaagttc attgccatct cgttgccccc cttacccccc cacccccgcc    2280
gcccttggac gaaagcgaaa ccttaatgtt gctagcgacc cgagagctcc gccggcttct    2340
cccccaaccc ccgccagctc actggtccgc gcatctctcc cctccccct cccgccaatt     2400
atcctagcgt gtttgcaagg cgaccagatt ggaaagagtg tggtcagagt gaccccaagc    2460
cacgctttaa aagttcaggg tactttgcag tagtaacttt ggcagctcca ccagtgcgcg    2520
caacatttct ttctatgggt acatcctgta ccagtcattt tgaaaccctg cttcattgtt    2580
tctagccgct tcctgatggc tctgtgatta tgagaccccc ctcaaacttc accaggcatt    2640
aaggttttgt ttttgctttt ttttcagaga ggtatcattt cgtttgaaat ccacctagat    2700
gtggcttttc ctgttttgat tttacttaac atagcttatt ctctggaagt tgctttaaaa    2760
agaaattgaa agtgatggtt gttccttcca ccaaacagtt taattttcag ggtgcctcat    2820
attaatggat atgttttccc ttcatagatt tctcattgtt tcccttatga tgggatgatt    2880
tcatttatta ataaaatcag actttgaaag agcatttaaa aatgacctgg tttaaatagg    2940
tcacacccaa gaaactcagc tatctgtaca agttcaaact tctaaacttt tcaatgagc     3000
tagggtggt ggcacccacc tgtagtccca gctacttggg aggctgaggc aggaggatca     3060
cttgagccca ggagttcgag gccatagtga gctatgactg tgccacctca ctggagcctg    3120
ggtgacaaag tgagatccca tctcttaaaa aaaagagtt taggggacat tttctgaagt     3180
gaacacaagt agagcattct aacactattg agtgcaagga gacctggaag ggactaagtg    3240
gttcaaagca ggaaataaaa tcatcaggtg ataattaaaa taatttcttt cctgtggatt    3300
tgtccagcca tttgcaaacc aggagaatag gaaaaaaaat cactagtgta gttataaatt    3360
attacattac gttttcaaag gaaaattttg caaatgcgtc tccttgtcat agtctattgt    3420
tatctacccc actgagagtg ctggggcttc cccttttcac cacgacagca tttctggttg    3480
ggtggcagtc atgcagtgtt gacctggtgt cccataaggc acagtttgtc aaaacactag    3540
tgggtattag gaggaaacgt gcaactctga agcaacagag cttgcccctt cttcctcatt    3600
```

```
atccagctgg tgataatccc tgtcccccac ttccctagaa gacagctttg accaggaagg    3660
ctgcaatgac aatgagatgt acccctatgc agagccagat gtgggcgggt ggcttttttg    3720
tggtccagat cttctaggat cttctaggat gtaaccctgg caagcagtgg ggagcctgaa    3780
tcaagcagca tggctgttac ctcttctgtg ttcacagcag catcttcagt tgtcttggtg    3840
cctggagcag gcaccacagc tgcctgctct gttggccacc agctttctag agtagatggt    3900
agggaggaga gcaaggggct caagaggatt ctgtctttga acatgctttt aantttgatc    3960
tgacagaatg gcagctccct gaagtccttc ctactctctc cacagcattt ctctgtaggt    4020
ccccagtttt tgctcttttc agattcccag aggacntgaa aatgtatcac ggcccatttg    4080
gggacttcct gtatatgtgt gggtgcctca ggatcatttg ttttgccctt ttccagtcta    4140
ccgtgctgcc cttctcaagt ttaatgnacc acgttagttt caatatttta tatatttctc    4200
agcagttttc atctcttggt cattaaactt gagaagtaaa atctgctcat taaaatgact    4260
gagtccatgg ccaggcatgg tggctcatgc ctgtaatccc agcactttgg gagtccaagg    4320
cgggtggatc acttgaggtc aggagttcga gaccagcctg gccagcatgg caaaaccctg    4380
tctctacaaa aatatagatc tacaaaaact agccaggcat ggtggcatgt gcctgtagtc    4440
ccagctattt gggaggctga gacaggagaa tcgcttgaag ccaggaggcg gaggttgcag    4500
tgaaacatga tcgtgccact gagtccattc agcagcagag tagtgttggg gtttgtatcc    4560
ctgtagtgat gacgaaggat ttaggttttc agtcagaact gttaccttac aatttccttc    4620
actgactttt cttcctttcc aacaccacat tccaataaaa aatatcttta gaccagattc    4680
ttcacgaaag acatgaaggt tttcatgctt caaggttttt gactttttt tttttttna    4740 aaggagtctt gctgtgtcac ccaggctgga gtgcagtggc gtgatctcag ctcactgcaa    4800
cctccgcctc ctgggttcaa gtgattctcc tgcctcagcc tcccaagtag ctgggactac    4860
aggcgtgctc taccacggcc ggctaaattt tgtgttttta gtagaggcga ggtttcacca    4920
tcttggccag gctggtcttg aactcccgac cttgtgatcc acccgccttg gcctcccaaa    4980
gtgctgggat tacaggtgtg agccacggcg cccgaccagt ttttgacatt tctaagccaa    5040
aagttccatt tgatgaggtc ttagatgcag gggcaatgtg tccctttca gatttcagat    5100 gtttagaaaa agatgtgtca tatttgggcc aactgaaaaa ctcttgatat gtaggttttt    5160
atgaagctgt gcagaatgta ggaaatacat tttagaacca acaaagaggc atttaatttt    5220
gagtgtgcct gtctccttg agatgagcaa cagctatttt tctcttcaaa agacaatgcg    5280
tgtatttatc agcacatttt atataatcag caaatctaaa cctctgaatt aggtaagccc    5340
tataggtttg ttgccagaat tagtgaattt atacatgcaa agtgcttaga acagtgcctg    5400
gtacacagtg agcactcaat attatttatt gctattatta tgtttattta ttttatactt    5460
ttagagtata attttgatgt taggtttgga ttgctgaggc caagcaaaat ttagatagac    5520
caacccagct aatccactag aaagatattt gagggttatt cccatctaaa gatctatggg    5580
atctttggat atcatctgtg agaaacaaca gaagtttgta gataagacag atatagattc    5640
aaatgccacc ttcacaattt attagtgagg gaacccttg gtaaaatgag catgacaaaa    5700
cctacttctc agctttgtga acgtacagaa gatcatgaat gtaaaatgtc catgaagtgg    5760
taggtggtca acagatattg ctctagcaaa gtggttaaga gcaagcaaac tctggagcca    5820
aagggcctgg gttcaaatcc cgattctgcc acttcttata gtatggcctt gggcaggtga    5880
cctcactttt ctgtgccact attcaatgat aatattcctt tattgtccaa cgttttgtaa    5940
gttaaatcag ttaataaaca cactatgata atgtgttggt aactattctt tttactttta    6000
```

```
gcagaataac ttaaaggaac actgcaggta ggagggttat acataatctc tgagggccag    6060
ctaggacact cgcccatttc ccacccttt tcctgtgcaa tgaagagtat aagaagtgac    6120
agtgccattc taaaggacta gccttgagtt ggctctaatt tatatgactc gtgcctgtaa    6180
tcccagcact ttgggaggcc gaggctggca gatcacnttg aggtcaggag ttggagacca    6240
gcctnggcaa acatgacgaa atctcatctc taccaaaaat acaaagatca gccgggcatg    6300
gtagcacaca cctgtaatcc cagcttctgg ggaggctgag gcagaagaat tgtttgaacc    6360 caggggggcgg aggatgcagt gagctgagat cacgccactg cactacagcc tgggtgacag    6420
agtgagattc tgtctcaaat aataataata atttatatga gaagaagtc attcaaaagc    6480 atcattactt tacatgtcaa attagaaagg cacaccccag tactaaagca tccttgatga    6540
tgaaaacatt tagaaccact ggtttcagga gctccatgca atggtgaaac agcctctact    6600 ccaaggggttg ttgctccctg tgggattcct gggtgaggaa cacactgctc ccgttggggt    6660
ggaatcctgt ggaggaagtg gatgaagagt gtagccaagt cagtgagcct actgcatggg    6720
attagagtac ttcaggttgc agtataattc tgttcaggtg catgctcact ccatctggcg    6780
taaagaacag agaaattaaa ccattgattc acagagcaat atgagtagct gcctggggac    6840
ttcctgtcca ttctggggtn cccaacagcc aatcaatatt ggccggttcc taatctgacc    6900
tagagctaga ggccactagc accctccat tcatcctttc ttctctccct acccactccc    6960
accagcattc tgaggagtg agggctgaag ctgcagaggc tgttgtactg tcagttactg    7020
taaagtcccc atcctgctct ctgtagtttg ctgtgaagga gtggaggggg ctgggaacaa    7080
agggggttcc caataagcag cttactaata cctacccttg cttctctcac ttcctgatca    7140
ataattccca tcctttcttc atgtacctcc cccacatttt tgttctttaa gggaagaagg    7200
gagcagcttt ccatccccac acaatgttgg ggacatttgg tattatacat tatgaaaata    7260
agatttacca gattttagag atggaagaaa acttggggat gatcttgttc cattctctta    7320
taagaacaaa caatatttgg agaagctgag taacttgctt tttcaacttc acacttgaaa    7380
gtgttttcat gaggaagttg gggttctctg cagcacttgg atgggagtca gggacttgga    7440
ttgtcccaat tctgtcacta aatttggaca agccacttaa cttttccaga atctagttgc    7500
ctcatttcaa atattaggga aatttctaaa tggcttaaaa ggagcttgtt agctttaaaa    7560
ttttatgatt ctaagtgtat gctgccagag atatgtagca tagcaggaca cattaacaag    7620
attattgaaa ctgttctaat aaaggacatc tttgtgtctt gggtagctac tatgtttaaa    7680
gactgtgcta ggtgggagtt gtgcagaata cacaggtttg ctgtagaggg atagggcgtg    7740
tacacagaca actctactaa caagaacgtt actagaagct tattggaatc acagtatttc    7800
ttgctgaggg tatgaaacat aagagttctc cttggaatat gaggttctat ttggggctta    7860
aagaatggtc aaaggttgag tgcaaataac atggattgag atggctttaa aaaataatca    7920
aatggtttgt tagtattaaa ctggtgcaga ataattgca gttttttgcca ttcctttttaa    7980 tggcaaaaat tgcagttact tttaaaccaa atccctaata ttatttgcat agtttatctc    8040
tgttatggaa gtttttattg acaagtaatg tagatattca cctgatctaa gttaccctga    8100
atcttatatt agcagaatct gaattgctta taaataatta tggctatgtt ggatgtagaa    8160
cttattattt gatagtttat gaacagtgct aaggtctaat ctacttttta cagagaagct    8220
aagaacatgc tacagctggt tgaaaaacaa aaacttcagg cattgaaatg ttttgtcaat    8280
gaaatggcag gactcatttg atgactgatt attatcaact gatttaaatg actgaatttt    8340
```

```
tggtactgtg tacatctata ctctaagaag gaaattgaaa gtaattctgc tatgcttgtt    8400
gccactatat taataactgc atcatctaaa ataattgata gagctcagat ttatcctttg    8460
taataattct agtacttctt taaacatgtt ttgggattag cagctgtcaa cagttagaac    8520
atgaaacaga ttctgttaca ggagtagaag tcgatccaga catttaatgt cattttcacc    8580
tgtgagagag agaataaaga gaaagagaga tcattattta tgggattatg tgaacttcaa    8640
gtccgttttc attattagga gaagctgtgc tttaaaggac agtcagggac tttactttca    8700
tgaaatgcct gagctgtaaa taaagtattg ctttattttt tatttcttga acatttgaaa    8760 taaaaatta gctatgagtt atgttcaaat tatattataa aaatttgctc ttagcattgt    8820
gcatatatat tatacagaaa aacacagagt aaaagaata gacttcagtt cctgttcaga    8880
aaaggtttaa aatttgaata ctgattttgg aaacccaaa ccttaagaat tcaagaagct    8940
tacggtcttc ttgagggaca cctattcaaa ctcttaaata tggtgattgg gtagaaagtg    9000
cagaaaagcc tgctgataca tgccctaaaa caccttggaa aaagaggtg gtagttgctt    9060 gaggtaggac ttaagtacta gttggaaata aagacaagg atggagactg ttggtagatg    9120
actctccatg ggtccttcct gtttctacac accttgtaag cagggcattg agtgcctgtg    9180
ttccaaacta ccttttccat catgtttcta cagcaaacag tcatggaaga tagaaataga    9240
gtcttcctct ggagcaaagg gcagacacgc ttgcttcctg tacttcccac tataagatat    9300
tccggctccc taaactcagc tgcctttcct gtaacccacc atgatacaga tgtcacctga    9360
cctgtgggaa ttgggggtca gggaaccaag agaaatgctg actgtctggc tactgtgact    9420
gccctgagta ataaattgtc cttcgtctcc aacccaggag tctcatgttt tctaccagca    9480
ggataactgt ggcrggctaa cgtgttagtt tgcaagtaag gtaaaatctc agacccttg    9540 cagtttgtgg cagggattat attctgagga gagaggaacc gtatgcacca tggctcagag    9600
gcatgagaaa cggggaacca taactagttc tctatcttca gagcctttaa aaggtgcacc    9660
aaggagggca ttttagggga gaatataaag ttggagatat agacacagcc agattcctga    9720
gagaccttat atgccaggta gaagacttca gattgtatgg gggaattatt agagaatttt    9780 tagcagggt gtgatatgat aaattttgtg ttgattaagt tactccagga aatatgcgat    9840
gggtggattg aaggatgggg cacctttct ctaggacgaa aaagaaagag tagttggtga    9900
agtcagttag aggtagtaat aggatgaaga agggatctga atgaccccctt ggccattcag    9960 tgagtagtga tgctattcac ctagatacag cacatagnng ggaaangaaa tnctgggaag   10020
gagggagatg agaccgagtt agctttaaaa taactaaatt caggcctagg agcctatagg   10080
ctatccagat agaaatattt aatngccttat atggatctgg aactcaggaa ggaggcttcc   10140
gtgggagcag aacacttggg caccattagg gtgtatgtgg tagatgcatt cttgtgcagc   10200
agtcaagggg atgggattta gactcaagtg caaattgccc cccatctcct gtgataagtg   10260
actgaagctc tccgggcttc agtttcctag ttcatcatag tgggctctag cggataaatg   10320
ttacaaaggt taaatgagac aacataggca aagtgcgtgg tactcaatag aagtcagctg   10380
ctgtcatcag cagcaggatc accagaatgt ggtgcttgac accaaaagat taggtgagat   10440
tgcccaaaac agcaggtgaa atgaggggag aggatgnaag tcaaacacag gaagaaaagc   10500
ctttgaagta tgtggaaaga aacaaccaga aaggtaagat aagaaccaga agagattcaa   10560
gaaggaaggt gtggccgggc gcggtggctc aagcctgtaa tcccagcact ttgggaggcc   10620
gaggcgggcg gaacacgagg tcaggagatc gagaccatcc tggctaacac ggtgaaaccc   10680
cgtctgtact aaagatacaa aagaattagc cgggcgcggt ggcaggcgcc tgtagtccca   10740
```

```
gctactcggg aggctgacgc gggagaatgg cgcgaacccg ggaggcggag cttgcagtga    10800
gccgagatcg cgccactgca cntcnagcct gggcgacaga gcgaggagcc gtctcaaaaa    10860
aaaaagaaaa aaaaaaaaaa gtaaggaagg tgtggccaag attgagaaat tcgtcagagc    10920
aaacaaggca gtcaggggct aaatagcctc ctttaaattt tacaaccttg aggacctcgg    10980
caactttaac agaatttcag tggatcccta gggcaaacca ggccttacaa accaggaatg    11040
gatggtcaat aggaagtgga gacagtaagt gtagacctta ccttggaggg aaggnaagag    11100
aaagagccat ggccaaggga agtttgaaat caaaggaaat atcttttttt ttttttttcg    11160
attggagaga cctcagttat tcttttaaaa tacttattga gcccctcagt tattctttta    11220
aaatacgtat tgagtcccta ctttgagtca ggcacnatgg cagacacgag ggngatagca    11280
gtgaatcaga cagatgcaac gcctgccttc atggagtttc accttagcat ctgtccatat    11340
gctaggggag tggggcaggg gcagggagct ggatacagga gagactgaag atccagggag    11400
caagtgagta aagaataggg cttgagatcc cacagacaac tcagctttga acaaaagggt    11460
tttgtcatcc aataggacaa gaaggcgtta ggatacatca aacgtggttg ttgaaaacag    11520
aaaagggctg ggcactgtgg ctcatgccta taatcccagc actttgggag gccaaggtgg    11580
gcagatcact tgaggccagg agttcgagac cagcctggcc aacatggtga accccatct    11640 ctactaaaaa tacaaaaatt agccaggtgt ggtggtgcat gcctgtaatc ccagctactt    11700
ggaaggctga ggcaggagaa ttgcttgaac ccagggggtg gaggttgcag tgagccacga    11760
tcgtgccact gcactccagc ccgggcaaca gagcgagact ctgtctcaaa aaaaaaaaa    11820 ggaagaaaga acatagacag ggaaatgtag ttaaggnnag tttgggtttg ggtttggtag    11880
aagcgttttc tgttnnttgt ttgtttgttt tcagaaagag tctcactctg ttgtccagac    11940
tggagtgcag tggcacaatc ttggcttgct gcagcctctg cctcctggat tcaagcaatt    12000
ctcctgcctc agcctcctga gtagctggga ttacagacac ctaccaccac accaggctaa    12060
tttttgtatt tttagtagag acggggtttc accatgttgg ccaggctggt ctcaaactcc    12120
tgacctcagg tgatccacct atcttggcct ctcaaagtgc tgggattaca ggtgtgagcc    12180
actgcacctg gcctaacatt gatatctgtt gatgagaaga agccaggtgt tggagtgata    12240
gcttatagca catgaactga ataaaacagt gtttaagaca atgtttgcaa cataataggc    12300
actgaagaca tgttaatgga aggtggattt gtgattcaga acctctagac tacctgggcg    12360
agtcttttaa aatgtaagta atatcttaag tgatattact tgtcccagat cagttgttta    12420
aaactgaggt ttaatgctgt cagagtagca ctgtatcgtc ttctatcatg ggggcctttg    12480
ttggctttag gaggtttgtg tttcatagta gtttcccagt gggctctttg ttacctgtaa    12540
tgagtgtgac agttatgcca taaccaggtt ttatatggaa tacaattttg agaaagttct    12600
ttctaggcag agaagcttat ttgaacctct tattatattt gggtttcagg cttttgagtt    12660
cttctgaaat aatagccctt tgaaggtagc tattgctatg acttcattaa attctaatgc    12720
ctctggtttt ctcccccagg tttctgcata tgaagtgtgt aaaatagatt gcttgatcca    12780
aaacagaaaa acagtgataa ctgttttgct gagttcccag acccttccca agatggaacc    12840
aataacattc acagcaagga acatctgctt ttctaacgag gtctcggtgg attttggcct    12900
gcagctggtg ggctccctgc ctgtgcattc cctgaccacc atgcccatgc tgccctgggt    12960
tgtggctgag gtgcgaagac tcagcaggca gtccaccaga aaggaacctg taaccaagca    13020
agtccggctt tgcgtttcac cctctggact gagatgtgaa cctgagccag ggagaagtca    13080
```

```
acagtgggat cccctgatct attccagcat ctttgagtgc aagcctcagc gtgttcacaa   13140
actgattcac aacagtcatg acccaagtta ctttgcttgt ctgattaagg aagacgctgt   13200
ccaccggcag agtatctgct atgtgttcaa agccgatgat caaacaaaag taagtgagat   13260
ggagatccaa aagactaagg tgtggctggc tggttttat tgtatggggg tcaggatatt    13320
tattttaagt atactgaaat gaataaggaa ttaatgctgc agttataaat tgattactta   13380
gctgaatttt tgttttatgg tgatagttta tagttttaaa gcacatttga aaacagatac   13440
gagaaattat cagttttga gttcaaaaat tcaagagaaa tcagtctaaa actactaatt    13500
aagagcagaa gtgttaagat gtacattatt tcagatgaat gttctaaagc catgcctctc   13560
aaactgaaat gagcttgtga gtcacctggg gatcttgtta aaatgtgaat cttgattcag   13620
taggtctggg gtggaccca agactgcatt tgtaacaagc tgccaagaaa tgctgatgct    13680
gcccttttgc aggttgcact ttgagtggca agttctaaa tctccacatt tgtaatccta    13740
ttaagaaaaa tatagtcatt cgtaaactgt gtaaaatgc tactggccag tttcccaagg    13800
cataatgttc acttaggcaa aggtcattga taagaacgct ggatatgcat ctaagttttg   13860
atgcgatcag gggttctttg tgttttttc tttcgcaaac ctcaggtcag atctgattag    13920
cttgttatta tcacatgata tggctgaaaa aaaatgtgag acatggtaaa agttctgctc   13980
tttcctcgtt catttgtgct tgctttgtta ttagcattcg ttgtagctct gggcaggact   14040
catttgaaga tgcttgnccc attttatgag gattagctta gataaaattg aaaatataat   14100
gcaaatagca actttctcag ttgggctcag ggctccacag ctaaccccat ggactgtgga   14160
gtcttgccgt tgttttgggt gccaagcaag ccaagtcaca tgtgattcaa gctgtctgcc   14220
acatgtacag ggcgaggatg cgagtgtcaa tccacctgtt aactgtcagt gaagccttga   14280
aagcttctca tattttcaag gttaaaatct ggatagaaat gctaaagttt tctctctgca   14340
ctccattagg ttatttatg tactctctag ggtgtaagga cctatttag aaattaatat      14400
tcttggtatc aagtagatgc cctttgctt gttcatttgt tggttcttct agtcattcag    14460
aattgctgtt gcaggtactg ttggagatga tattagcaga ggcttgtagg aaggcaggag   14520
catcagtggg gaataggacc aggtgatcta tgtataggac ataatggaag gactgagaag   14580
ggagcctaac acacacccaa agggtagaga aggctttgtg aaataaaggc taatatggag   14640
ctcaaaacca ccatttcact cacagaatca aactctcata ttataaatca tttcatgtta   14700
ttgtccacac atctcaagtg ggcacggcag catcaggctt ggagattcag agggactaac   14760
ttcctgtact ctaatcctac ttctgcaccc ataaactggg tggcctcagg caattgagtc   14820
tgttttctta tctgttaaat ggggataatt acagtattta tccaatagag ttgctggaaa   14880
gactaaatga ggtagcactc gacctgaaac ttagtaagca tttatagcca taaaaacatt   14940
ttcattcaag aaaattttac tagaggcaga ttatatgcta atttcatttc acgtcttagg   15000
taaaagaaa catgatacct agatgagtgc cttcagcttt caaagatgag attctggtca    15060
tatttgagga acattttaaa aactacacgt ataacttaat ggctcctatt atttggacaa   15120
attccagaat gaaaatgaga ggactgaaca gcctgtacct cagtccagct ctatatagta   15180
tttggactga atttccttgg ggagagtttg tgcgtggaat cgttgttcag cattttacac   15240
atttgactct ttcccaaaat cttttacggc catctgagaa taggcttctg gccagtcatt   15300
cggatgcctg acaagagaaa gagatttata accaaattct gtaattggga cttccagtct   15360
ttccccaagt agagaattgg acttactcta tatgctaaaa acccatggtt gaaatatgaa   15420
ttagttctta agtgattttt ggcttgcata ccatttttgc aaacacaaat tgtcattact   15480
```

```
ctgctcattt aataaaagaa taatttgtag tataggtata tacctcaatc agtgattttg    15540
ttgttggaaa cagaacagta aatcacactg gccatgatgc taacagcgtg atagattttc    15600
tgttcttggg acaccaatgt cactgtatct catagcgaag gattatctgc tgtaggagca    15660
ttctcttgac tacttataac atttgctggg tgaaataatt ctccaggtta aggcctcttc    15720
taaacagatg aggtcagcac taactgcatt tgccagagaa gacatatgca tttactgcca    15780
gcatcataaa cacaaaacta cagtttgcga ggaaacccct tgaccagcat ctaattaatt    15840
cactgagtaa tgtcttggga gaagaggcat gtaaaggaac aattttataa gcatgccatg    15900
agattgtttt cnnattgtat gttccataga atatgaggaa acttcaaaac attttgtgga    15960
aaaattgaat taaaaagtaa aaaacacata tacataag ctttatttct caagataaac     16020
tttatcaagt tcaagacact tttgtaagca atgttaacag ccattgagtc ggtctctaaa    16080
gaactgaggg tcctgggaat ttaaccatgt ttatacagtc ttttatacat tattaactgg    16140
agaaaaattg gcgctctttta aagattttttt aaaattgaga agcaaaagga cgtcagaagg    16200
agccaaatta ggcctgnnaa gtggatgcct aatgatttcc catggaaact cttgcaaaat    16260
tgctcctgtt tgatgagagg aatgagcagg aacattgtca tggtggacaa ggactctggt    16320 gaagcttttnn caggcgattt tctgctaaag ctttggctaa cttctcaaa acactctcat    16380 gataaacaga tgttatcatt ctttggccct ccagaaagtc aacaaacaaa atgccttggg    16440
catcccaaaa aactattgca accatttgcc cttgaccagt ccactttcgc tttgactgga    16500
ccacttctgc tctcagtagc cattgcttaa atttgtcttg atctttagga ttgcgctggt    16560
aaaactatgt ttcatcacct gttacaattc tttgaagaaa tgcttcagga tcttgatccc    16620
acccgtttaa aatttccatt agaaactctg ctcttgtctg cagctgatct gagggcaatg    16680
gttttggcac ccatctagta aaacgtttgc tcagtgttaa ttttttcatcc aggattgtgt    16740 aagctgaacc agcagagatg tctatgatat tggctagttg gtcctcttca atgagggcat    16800
gaacaagatg aatatttttcc tcaaacaatt atctggatgg tctgctgctg caggcttcat    16860
cttcaatatt gtctcgtccc ttcttttttct tttccccccc gcttgagaca cagtcttgtt    16920
ctgttgccca ggttggagtg cagtggcccg atttcggctc actgcaacct ctgcctcccg    16980
ggctcaagcg attctcctgc ctcagcccac caagtagctg ggattacagg tacacatgat    17040
cgtgcctggc taatttttgt atttttagta gagacagggt ttcaccgtgt tggccaggct    17100
ggtctcgaac tcctgacctc aagtaatcca cctgccttgg cctcccaaag tgctgggatt    17160
ataaacatga gccaccacac ctggcctcat ccttttcttaa aatgagttat acatttgtaa    17220
gctgctgatt tcttttggaca ttgtgcctat aaacttttttg taaagcatca gtgatttcac    17280
cattcttcca cccaaaacttc accataagtt tgatgtttct tcttgctttg attttagcag    17340
gattcatgtt tctctgatag ggggtctttt caaactgatg tcttatcctt cttagagcct    17400
catcccagat cctgttcaga catgctacaa gttaatacaa gtttatttgg tgccaaaaaa    17460
tggaaatcca tgcatagttt ttaaataata tgcatttttc atgnactttt tgaagaccc     17520 ttgtatactt aaactgctcc acatggaaaa gcttccatga tcaaatgcag taaggcagca    17580
tctcaaacat                                                          17590
```

<210> SEQ ID NO 2
<211> LENGTH: 99960
<212> TYPE: DNA
<213> ORGANISM: Homo sapiens
<220> FEATURE:

```
<221> NAME/KEY: exon
<222> LOCATION: 4661..4789
<223> OTHER INFORMATION: exon A
<221> NAME/KEY: exon
<222> LOCATION: 6116..6202
<223> OTHER INFORMATION: exon B
<221> NAME/KEY: exon
<222> LOCATION: 9919..10199
<223> OTHER INFORMATION: exon C
<221> NAME/KEY: exon
<222> LOCATION: 14521..14660
<223> OTHER INFORMATION: exon D
<221> NAME/KEY: exon
<222> LOCATION: 50257..50442
<223> OTHER INFORMATION: exon E
<221> NAME/KEY: exon
<222> LOCATION: 56256..56417
<223> OTHER INFORMATION: exon F
<221> NAME/KEY: exon
<222> LOCATION: 63326..63484
<223> OTHER INFORMATION: exon G
<221> NAME/KEY: exon
<222> LOCATION: 76036..76280
<223> OTHER INFORMATION: exon H
<221> NAME/KEY: exon
<222> LOCATION: 78364..78523
<223> OTHER INFORMATION: exon I
<221> NAME/KEY: exon
<222> LOCATION: 85295..85464
<223> OTHER INFORMATION: exon J
<221> NAME/KEY: exon
<222> LOCATION: 93417..93590
<223> OTHER INFORMATION: exon K
<221> NAME/KEY: exon
<222> LOCATION: 97476..97960
<223> OTHER INFORMATION: exon L
<221> NAME/KEY: misc_feature
<222> LOCATION: 97961..99960
<223> OTHER INFORMATION: 3' regulatory region
<221> NAME/KEY: allele
<222> LOCATION: 1443
<223> OTHER INFORMATION: 99-20508-456 : polymorphic base C or T
<221> NAME/KEY: allele
<222> LOCATION: 5247
<223> OTHER INFORMATION: 99-20469-213 : polymorphic base C or T
<221> NAME/KEY: allele
<222> LOCATION: 6223
<223> OTHER INFORMATION: 5-254-227 : polymorphic base A or G
<221> NAME/KEY: allele
<222> LOCATION: 14723
<223> OTHER INFORMATION: 5-257-353 : polymorphic base C or T
<221> NAME/KEY: allele
<222> LOCATION: 19186
<223> OTHER INFORMATION: 99-20511-32 : polymorphic base C or T
<221> NAME/KEY: allele
<222> LOCATION: 18997
<223> OTHER INFORMATION: 99-20511-221 : polymorphic base A or G
<221> NAME/KEY: allele
<222> LOCATION: 19891
<223> OTHER INFORMATION: 99-20510-115 : deletion of TCT
<221> NAME/KEY: allele
<222> LOCATION: 29617
<223> OTHER INFORMATION: 99-20504-90 : polymorphic base A or G
<221> NAME/KEY: allele
<222> LOCATION: 42519
<223> OTHER INFORMATION: 99-20493-238 : polymorphic base A or C
<221> NAME/KEY: allele
<222> LOCATION: 69324
<223> OTHER INFORMATION: 99-20499-221 : polymorphic base A or G
<221> NAME/KEY: allele
<222> LOCATION: 69181
<223> OTHER INFORMATION: 99-20499-364 : polymorphic base A or T
<221> NAME/KEY: allele
<222> LOCATION: 69146
<223> OTHER INFORMATION: 99-20499-399 : polymorphic base A or G
<221> NAME/KEY: allele
<222> LOCATION: 76458
<223> OTHER INFORMATION: 99-20473-138 : deletion of TAACA
<221> NAME/KEY: allele
```

```
<222> LOCATION: 78595
<223> OTHER INFORMATION: 5-249-304 : polymorphic base A or G
<221> NAME/KEY: allele
<222> LOCATION: 82159
<223> OTHER INFORMATION: 99-20485-269 : polymorphic base A or G
<221> NAME/KEY: allele
<222> LOCATION: 84522
<223> OTHER INFORMATION: 99-20481-131 : polymorphic base G or C
<221> NAME/KEY: allele
<222> LOCATION: 84810
<223> OTHER INFORMATION: 99-20481-419 : polymorphic base A or T
<221> NAME/KEY: allele
<222> LOCATION: 89967
<223> OTHER INFORMATION: 99-20480-233 : polymorphic base A or G
<221> NAME/KEY: primer_bind
<222> LOCATION: 988..1006
<223> OTHER INFORMATION: 99-20508.pu
<221> NAME/KEY: primer_bind
<222> LOCATION: 1509..1529
<223> OTHER INFORMATION: 99-20508.rp complement
<221> NAME/KEY: primer_bind
<222> LOCATION: 5039..5056
<223> OTHER INFORMATION: 99-20469.pu
<221> NAME/KEY: primer_bind
<222> LOCATION: 5534..5554
<223> OTHER INFORMATION: 99-20469.rp complement
<221> NAME/KEY: primer_bind
<222> LOCATION: 5997..6015
<223> OTHER INFORMATION: 5-254.pu
<221> NAME/KEY: primer_bind
<222> LOCATION: 6332..6350
<223> OTHER INFORMATION: 5-254.rp complement
<221> NAME/KEY: primer_bind
<222> LOCATION: 14371..14390
<223> OTHER INFORMATION: 5-257.pu
<221> NAME/KEY: primer_bind
<222> LOCATION: 14798..14817
<223> OTHER INFORMATION: 5-257.rp complement
<221> NAME/KEY: primer_bind
<222> LOCATION: 18751..18771
<223> OTHER INFORMATION: 99-20511.rp
<221> NAME/KEY: primer_bind
<222> LOCATION: 19198..19217
<223> OTHER INFORMATION: 99-20511.pu complement
<221> NAME/KEY: primer_bind
<222> LOCATION: 19605..19625
<223> OTHER INFORMATION: 99-20510.rp
<221> NAME/KEY: primer_bind
<222> LOCATION: 19986..20005
<223> OTHER INFORMATION: 99-20510.pu complement
<221> NAME/KEY: primer_bind
<222> LOCATION: 29529..29547
<223> OTHER INFORMATION: 99-20504.pu
<221> NAME/KEY: primer_bind
<222> LOCATION: 30041..30061
<223> OTHER INFORMATION: 99-20504.rp complement
<221> NAME/KEY: primer_bind
<222> LOCATION: 42268..42287
<223> OTHER INFORMATION: 99-20493.rp
<221> NAME/KEY: primer_bind
<222> LOCATION: 42732..42752
<223> OTHER INFORMATION: 99-20493.pu complement
<221> NAME/KEY: primer_bind
<222> LOCATION: 69026..69046
<223> OTHER INFORMATION: 99-20499.rp
<221> NAME/KEY: primer_bind
<222> LOCATION: 69525..69543
<223> OTHER INFORMATION: 99-20499.pu complement
<221> NAME/KEY: primer_bind
<222> LOCATION: 76323..76343
<223> OTHER INFORMATION: 99-20473.pu
<221> NAME/KEY: primer_bind
<222> LOCATION: 76771..76790
<223> OTHER INFORMATION: 99-20473.rp complement
<221> NAME/KEY: primer_bind
<222> LOCATION: 78292..78309
<223> OTHER INFORMATION: 5-249.pu
<221> NAME/KEY: primer_bind
<222> LOCATION: 78704..78721
```

-continued

```
<223> OTHER INFORMATION: 5-249.rp complement
<221> NAME/KEY: primer_bind
<222> LOCATION: 81893..81912
<223> OTHER INFORMATION: 99-20485.pu
<221> NAME/KEY: primer_bind
<222> LOCATION: 82353..82372
<223> OTHER INFORMATION: 99-20485.rp complement
<221> NAME/KEY: primer_bind
<222> LOCATION: 84392..84412
<223> OTHER INFORMATION: 99-20481.pu
<221> NAME/KEY: primer_bind
<222> LOCATION: 84909..84929
<223> OTHER INFORMATION: 99-20481.rp complement
<221> NAME/KEY: primer_bind
<222> LOCATION: 89746..89765
<223> OTHER INFORMATION: 99-20480.rp
<221> NAME/KEY: primer_bind
<222> LOCATION: 90179..90198
<223> OTHER INFORMATION: 99-20480.pu complement
<221> NAME/KEY: primer_bind
<222> LOCATION: 9475..9493
<223> OTHER INFORMATION: 99-430-352.mis
<221> NAME/KEY: primer_bind
<222> LOCATION: 9495..9513
<223> OTHER INFORMATION: 99-430-352.mis complement
<221> NAME/KEY: primer_bind
<222> LOCATION: 1431..1455
<223> OTHER INFORMATION: 99-20508-456.probe
<221> NAME/KEY: primer_bind
<222> LOCATION: 5235..5259
<223> OTHER INFORMATION: 99-20469-213.probe
<221> NAME/KEY: primer_bind
<222> LOCATION: 6211..6235
<223> OTHER INFORMATION: 5-254-227.probe
<221> NAME/KEY: primer_bind
<222> LOCATION: 14711..14735
<223> OTHER INFORMATION: 5-257-353.probe
<221> NAME/KEY: primer_bind
<222> LOCATION: 19174..19198
<223> OTHER INFORMATION: 99-20511-32.probe
<221> NAME/KEY: primer_bind
<222> LOCATION: 18985..19009
<223> OTHER INFORMATION: 99-20511-221.probe
<221> NAME/KEY: primer_bind
<222> LOCATION: 29605..29629
<223> OTHER INFORMATION: 99-20504-90.probe
<221> NAME/KEY: primer_bind
<222> LOCATION: 42507..42531
<223> OTHER INFORMATION: 99-20493-238.probe
<221> NAME/KEY: primer_bind
<222> LOCATION: 69312..69336
<223> OTHER INFORMATION: 99-20499-221.probe
<221> NAME/KEY: primer_bind
<222> LOCATION: 69169..69193
<223> OTHER INFORMATION: 99-20499-364.probe
<221> NAME/KEY: primer_bind
<222> LOCATION: 69134..69158
<223> OTHER INFORMATION: 99-20499-399.probe
<221> NAME/KEY: primer_bind
<222> LOCATION: 78583..78607
<223> OTHER INFORMATION: 5-249-304.probe
<221> NAME/KEY: primer_bind
<222> LOCATION: 82147..82171
<223> OTHER INFORMATION: 99-20485-269.probe
<221> NAME/KEY: primer_bind
<222> LOCATION: 84510..84534
<223> OTHER INFORMATION: 99-20481-131.probe
<221> NAME/KEY: primer_bind
<222> LOCATION: 84798..84822
<223> OTHER INFORMATION: 99-20481-419.probe
<221> NAME/KEY: primer_bind
<222> LOCATION: 89955..89979
<223> OTHER INFORMATION: 99-20480-233.probe
<221> NAME/KEY: misc_feature
<222> LOCATION: 3698,12593,13035,21712,27644,27655,31143,43084,43129,
      64585,66950,67301..67302,67926,75425,98821..98822
<223> OTHER INFORMATION: n=a, g, c or t

<400> SEQUENCE: 2
```

-continued

```
ctcaagcttg aatacttgaa tccaaacttt catgcttaga gtttacccca tctgttgaag      60
gatgtgcaat ataatgactg caatagaatt cactgtggag cctccaaatt agaaattatt     120
gtctgtgagg gccaggcacg gtggctcacg cctgtaatcc tagcactttg ggaggctgag     180
atgggaggat tgtttgaggc caggagtttg agaccagctt ggtcaatata gcgagacccc     240
catctctgtt ttttttttt aaagaaatta ttgtctaaga accagtgtca tcttccaagg     300
agaaacttct agatacttgt tttaagataa ataagaaaca agtcattcct aaatgtgaat     360
tatttttaa atgcaatttt ttaaacattt tattttaatt atggcaatag acgtggaaaa     420
gactctttt tgatagtagg ggagagcaga agaaacattg aattaagtac acagagattc     480
ttcagacctg ctttaaaaac acatgcatac aaatgcactt ctgtctctta ggatctacta     540
actgatgctg cttgctttag tcttttagct aatattttct ttctttcttt ctttctttt     600
tgttggagac agagtctcgc tctgtcgcca ggctagagtg cagcggcaca atcttggctc     660
actgcaacct ccgcctcccg ggttcaagcg attctcctgc ctcagcctcc tgagtagctg     720
ggactatagg cgtgcgccac cacgcccagc taattttgt atatttagta gagacggggt     780
ttcactgtgt tggatgggat gttctccgtc tcttgtcctc gtgatccgcc tgccttggcc     840
tcctaaagtg ctgggattac aggcgtgagc cactgcgcct ggctcatatt ttctttatat     900
atcaaaacaa ttcagcttgc ttcacttta tgaaagcttt attatgagtt tgaaagcaat     960
tctgcattt cttaacattg taactggtgt tgagttgaag gcaggccct gggagccctt    1020
tgtgggcaat tcccttcact ctggaggctg cctcgagcct ggacaggcac ttacacttgg    1080
tcagtgattg cacagaaccg gttgcaacag attctgtgca cctccctgtg gcgcgtagca    1140
tttagcaggc acttggtcac tatttgctga gtgagtctgt taccttaggc gtgtatttcc    1200
cgtggacctg cctggggatc attgctcatt cactcatttt gaacaagcca atattacatg    1260
tccagggtac gctctatagt gtgaaacaca aggtaaatg atagttcccc ttctcaaagg    1320
aatttctaag gtagtagcca ttcttttgat gcatattctc attctcatag agagtccaat    1380
tatgataat tggacaaagc tgaatgtcgc tttatgaga atccattctt tctcttttat    1440
gcyttgaaaa atgtgtagca ttcattagtg aattaggatt tcattattca aagaagacat    1500
aaggtcttcg aacagcagat gactgaataa aataatacct aacagcagta gaatgagggg    1560
aggacatatt caaggaacat tttatgccca ttagattggc agaaattttt aaaaagtgac    1620
aataccgtat aaaggtgaac tttcctatac tgatactggg aacatgaatt tgtaccattc    1680
agggaagaga aacttgataa tatctggtgt agtctgaagg ggcacagtcc ctgtgaccca    1740
gtgaggacat tcctcattat ttcccttgcc aaacatttca catgagtcta aggagctc    1800
tatataagag aggtcactgc agcctccttt gtaagagcaa gaaaaaaaag caaataagtg    1860
tttaacaata ggaacataga taaattaggt tatgcagtga atatttgcac tctgactaaa    1920
gtgagtgaat caaaaaaaat ttgtcaacag gaataaatct caaaataat attgaaagaa    1980
gaaagctaat ttcagaagg atgtgtacag tatgacacca ttcatttagt ttcaactaca    2040
tatcttttat ggacacatac atataaaagc agaaaacatg aattgatagg ataaacacca    2100
aatatttctg catatggcca ggtgtgggga agtagtggtg attaagcttc aaagatgtct    2160
gcagtggttc ccattaaaag tagaaagtag gctgggcaca gtggctcacg cctgtaatcc    2220
cagcactttg ggaggccaag gcaggtggat catttaaggc caggagttcg agaacagcct    2280
ggtcaacatg gcgaaacccc atctctacaa aaaaatacac aaaattagcc agatgtggtg    2340
```

```
gcgcacactt gtagtcccag ctactcggga ggctgaggca tgagaatcac ttgagcccag   2400
gaggtagagg ttgcagtaag ccaagatcgt accactgcac tccagcctgg gtgacagagt   2460
gagactccat cccaaaaaac aagcaaacaa aaaaagctca tagagtaggt aatagtcatg   2520
atatctgatg ttttttgatt gtctggttta catttttat ttttattttt tgagacaagt   2580
ctcacgctgt cacccaagct ggagtgcggt ggtgcgatgt cagctcactg caatctctgc   2640
ctcctgggtt cgagcgattc tcctgcctca gcctcccaag tagctgggat tacaggcgtg   2700
caccaccaca cctggctaat tttatattt ttaatagaga cagggtttca ccatgttggc   2760
caggctggtc tcgaactcct gacctcaagt gattcatctg cctcagcctc ccaaagttct   2820
gggattacag gcatcagcca ctgcacctgg ccttggtata tgtgttttaa tttgtattca   2880
ttcatttaag cctcatgaca gctctgcgag gaaagttcac tatacgtctt caggctgcag   2940
gtagaggacc tgaaagggac aggaggtaac agtctggcca agaccacaga gccagggaat   3000
agcagaggaa catttcacct gggcattgca ctccagagct gggcttctca ctgttctcaa   3060
cccctggcaa atgctcactt gaacaaagcc aggtggtgat acaaaggtat tgttatatt   3120 agtctctaca cttttctgtg tgcttgaaat aactgcaaca agaatatat cagtatttag   3180 agtaatgggg gatttgcttg tgtgtgttg tatttttgag atggagtctc gctctgtcgc   3240
ccaggctgga gtgcagtagc atgatcttgg ctcactgcaa cctccggctt ctgagttcaa   3300
gcgattctcc tgcctcagcc tcctgagtaa ctgggattac aggtgtgcgc cactacaccc   3360
ggctgttttt tgtattttta gtagagacag ggtttccccg tgttggccag gctgatctca   3420
aactcccgac ctcaggtggt ccacccacct tggcctccca aagtgctgag attacaggca   3480
tgagccactg cgcctggccg ttttttttc taacaaaatt attttctaac agaaagcaat   3540
caggtgagaa tccacataag aaacaattta attcagagat ttttgttgca tattaaaaaa   3600
aaaatgtacc ttcggctggg tgtggtagct cactcctgta atcccagcac tttgggaggc   3660
tgaggcaggt agatcacttg agctcaggag tttgagnca gcctggccaa catggtgaaa   3720
ccccgtctct acaaaaacta caaaaaatta gctgtgtgta gtcccagcta ctctgggggc   3780
cgagggagaa ggattgcttg aacctgggag gtcaagactg cagtgagcca tgattgtggc   3840
cctgtactcc agcctgggca acaaagtgag accctggcac cctgtctcaa aaaaaaaaa   3900 aaagtacctc cttgtaaata agtaacacta agacttcatt tagtggttgt caagcaaact   3960
ccattgtatt tttattttca gtttttatgg ctagtagtta agggagagaa gcttggttgc   4020
agagaagaat gaaaggatga tgggaaaata aaagtaggag agaggaaaac gcaagaaagc   4080
aagagatctg tagaaaggga tgaaggaatt gtataggcag agagaatagg ttctttaatt   4140
gagaaattta tgttgtctca ccttctgaaa tgccccaaa ggtaagttat tgttttattt   4200
tgaaaagcta atgatagcta cctttctacc acgctgtgtt caatgtttta cacactttac   4260
ctgtttgagt ctcacaacac agtgttatga ttcgatcttg ccattggtct cactttactg   4320
aagaggaagt ttgaggctca gaaaagtaag aaactggccg aagaccacgg ttagtgaaga   4380
cagatctctg atccagttgc agagtctgag caataaacta cttcaactga ttggtttcaa   4440
agcacatttc gtcattttac ttggggtaat caaagcaact ctctgaggca aaattatttc   4500
ctggacttgc agccatgtca ctaaggagca gatgaggtga gatcacagac aggatcagaa   4560
tgatggcctg gtgccaaaaa gatgtgtcct agagattttt cattccttta agaagcagag   4620
aagggagcga taaatgactt ttcgtttttc acttttttag acatcgcaga tggcagcaga   4680
gaatattgga agtgaattac cacccagtgc cactcgagttt aggctagata tgctgaaaaa   4740
```

```
caaagcaaag agatctttaa cagagtcttt agaaagtatt ttgtcccggg taagtagcat      4800
aatttctcct gatttaagtt aaatcacttt ttaggagagt gtaagattga gttctatgct      4860
tttattccat caatgttcat cataaaggta aaagtataaa accttttttt atgttttctc      4920
aggcttataa cagtattatc tacattttaa attgttttta atttggccta ggtttaaaaa      4980
aaatattcct tactcttttg tattatatcc aatgggattt ttttgccgct ccaaagaata      5040
tttgttagcc agtccctata aagagcatgc attagataca ctgaagtgtg gcttctgttc      5100
tccctactat cactatgtat aacttaaaaa acagttactg tcagctgctg gtgttagcta      5160
tctaaaaggc tatatagtag gggtcagcaa actatgccca tgggccaaat tctacccacc      5220
tcctattttt gtaaataaag ttttgtygaa acaccgccac atccattcat tttccagtta      5280
tctaaggctt cttttttgca gacttcagca gttgccacaa acactatatg cctcacaaag      5340
cataagacac ttactatctg gcccttaca gaaaagttt gccaaatata gctctataga       5400
aagaacaaag tacacatgta catcaatctg ggagttcttt aagaaattat ccctccctcc      5460
catgagtgta aatagcctga tggcacgtct gagaaatcaa atctgatttt ccctcagagt      5520
ttcacacctt tctggagtgt gcagtatctt attatagttc ttttttgattt tatggcacac     5580
ttcttttgaa acatctgatt ttattttatt ttttaattaa ggaaagttaa attttatttt      5640
cttcgaagat gtttctgaga attttgcaat atcttctgag atcatgaaaa acagttgatt      5700
tacaaaacca gagttgggag gggctgcatt tgagagctcc caagggata gagtgctgtc       5760
cgagtgacat gcggctggcc gttatgatga cttgtgaccc aggggaggga gttagttgct      5820
gagtgggctt gagcacttga ttttccttat agacgaattg tcttgtcttc ctgcctatca      5880
ctcatgccaa attacttagc caccaggtgt tttggaacgt ttaggttagt gtcttattta     5940
ttttttaaaa aaatgatgga aatgttgatt attttaatgt acaaatatcc ttagtagcat      6000
ttctcagtag ataacatttt tttcctgagc ttatttaaat ggaccaatct gcttctagct      6060
gatgcctttg caaagcctc cagagtcata actcgactgc cttttcttta tgtagggtaa       6120
taaagccaga ggcctgcagg aacactccat cagtgtggat ctggatagct ccctgtctag      6180
tacattaagt aacaccagca aagtaagcac atttctcttt atrcgacacc ctgaagaaac      6240
caacaaatag gtcttgctca tctcctgtct acatacctcc aatcataaaa cgtttgctgc      6300
ttgcaaattt cttggcacag gtggaggact ggtcatgcag ttctatcata acataaaagt      6360
tttacataaa agagcagatg gggctgggtg cagtggctca acgcctgtaa tctcagcact      6420
ttgagaggcg gacgcgggcg gatcatgagg tcaggagatc gagacgctcc tggctagcac      6480
agtgaaaccc cgtctctact aaaaatacaa aaaattaaaa attagccggg cgtggtggcg      6540
ggcacccgta gtcccagcta ctcgggaggc tgaggcagga gaatggcatg aacctgggag      6600
gcggagcttg cagtgagcca agatcacgcc actgcactcc agcctgtgtg acagagagag      6660
actctgtgta aaaaaaaaa agcagtagat tttcctatta aaaaataat taatattggg         6720
aaaacatcag aaagtggatt tgtgaattta gagaagtata cagcttaaat ttttcttttt      6780
ttaagaaaat tttattttgg atttggggt acatgtgcat gtttattacc tgggtatatt       6840
gcatactggt ggggattggg cttcagtgt acccatcacc caaatagtga acattgtacc       6900
cagtaggtaa tttttcaacc ttcacacccc ctttcattct cccccacttg tggggaaatt      6960
aaatttctga aacttatcc tgtagctggc tctatgatta taatgaaaca ttactgtttt       7020
atttaaataa gcaagtatct atgtccttct tttaataact tgctttctag acatttaatc      7080
```

-continued

```
atatttaagc ctggtcagtt caactttata actcctgaaa agtgggtttg ggttttgtgc     7140
tagggaggcc agctttccct tctgctacca gaggactctc tttggcagta gtgagggagg     7200
gagtgtttgt ggaggccagc tccttaccac aggcagggtt tacagtcctc tgccatccct     7260
cctagacata tggctttcag aattttttcta acctacagta agaagcacat ttaacattgt    7320
ggcgtagttc acaaacacac atacctacac attcacacac aaaattaaaa gttcacaaaa     7380
caatatttac tgtgaacaac atacaataca tactgatatt ttgttctatt ttattttta     7440 aatgctcatg gcaaactact cagttgtacc acctactaac atgatagagg gagcagtttg     7500
agaaacactt ccttagatgg atgagtgctt ctcaaatttc aggtgctccg cctcccgggt     7560
tcaggccatt ctcttgcctc agcctcctga gtagctgaga ctggttaaag tgcagattct     7620
ggttcagtag gcaggcggg gggagccctg aaatgctgca tttctgacaa gctccaaggc      7680
aatgctgctg ctcctggtct gcagaccgcc tctggggagt gaggtcctag acagcagtct    7740
tgtaaatgtg agtttctgag ttaaaatcca ggggaacata gtgtcgtcca gcctccatct     7800
aatacacact gatcccaccc tgcaattcat tgcaagtgtg ggaaggctat ttgcttattt     7860
gttgtgtaca gatgaaccac acaccgcccc tttcatgtag gaagttacct aggaggagag     7920
agatgacaga tacagaaaca gccccagcat caagcagagt gtggtaggag cccagaagtt     7980
acaaataaga gacattggta acttcagtgt cagaagagca aggggaaggg aagttaggtt     8040
tggtcagtgg aaccagggaa aaggtgaggg gtgaggggc agtgatgctt ttggactaaa      8100
tcttggtgta ggaattgtgc ctatggaagt gaacagagaa gaaggcattc tagacagacc     8160
agtgtcaata gacataccat gaagacattc atgtcactca gtgggctttc cagtaagcct     8220
tattgcttgc ttttatttt tttccaaaag gcagatctag gaatatatac atattcattc      8280
ttcaggactc gatagttgtg aagattcttt taaaaggatt taaaagtctg tctaagattg     8340
caatttctag agtcattcta agagagatgc aacttttcag aagctgcttg tatgtattgt     8400
atatgtttaa gtgtactta catctttctt ttattcatct tgaattgaga aactactata      8460
ttctatttta tgtaattgga tcccttctaa aaaattgatc acctaggagt tgcaaagaaa     8520
ccaaatagcc ctgaaacttg acaaatgaaa atggcccttt cagttgtcca attaagctaa     8580
gggttagctc tttgatatga tttggaggga tattagtaag aatttagatc aacaggtttg     8640
catgatggag attgtgttct gtgatgtatt gtcttagaga gacttttaaa tccttaaaag     8700
aatcttcaca actgttgagt cctgaagaat gaaaaacttc agttatgaaa gtaatcaata     8760
tttcatagta tgttgggaat ttttttcctaa ttcttataca attaaatgta tgtaacttct    8820 cccctttggta aacacatttc ttttttttttt tttttcaaat taaaaccctc aatacttgtt   8880
acctaaaagg cactcaactg tgtaaatgaa caggtagaat tcagagtctc cagtccactg     8940
ttagatgcat tcattcttgt ttactctatt cctgttgatt tatttttct cttccaacaa      9000 tttcaatagg agcaagctgc tacaattcct cttttttgaat attttgaata tattaaaaat    9060
atattggcca ctagccacgt cctgggtgca gtgttaaaca tcagtttgct tgagtggtag     9120
tagttcattc ctttgaaaaa gcgtgcatcg tgaaggcata caactttaaa atattgtcat     9180
gattctcaac aaatgtttga gcactcactc catagattta ttgcatacct aataaaacaa     9240
taacttatgt ttgtgtaaca ttttacaaca taaaaagtac ttttggttgt atcatcttgc     9300
tttgttcttg aaactcagat acattttttac tttaccctct tacagaagaa attgaggtgc    9360
agaaagaaat tatttgccct gaattgcagc agtaagtgcc tacagagtga ttttccatat     9420
tctaagaata ttgatacagt tcttaatctc aaattatgaa gtcgaatctc aacagtagat     9480
```

```
cagattcgga gagagcctta aaatgtgggt ttaacatgag tgaacacatg tggcaaagat    9540
aaagaacttg gttaagcagt ggagacaagt tctccagcac tcacacccct tagaagctgc    9600
agtaaacagt cctgttttct agagagaggg cactattcat ggcgttgttc agaacgttac    9660
agattgtggc ttatgtcctt cactcctgca cttggccagt ctccccattt ctccagcaag    9720
ccagcagtgt gtccttgagg agcgggcatt tatttaatgg accttcattt tcttctgctt    9780
ttggtggtgg cttctagatg gcattataat cagaacacat acttagatac tgcaatgttt    9840
gcccgtgcag gaactagaga tttataaatc ccacatattc cccatggtgt gtctgatctg    9900
ctgtgtgttt gctcccagga gccatctgtg tgtgaaaagg aggccttgcc catctctgag    9960
agctccttta agctcctcgg ctcctcggag gacctgtcca gtgactcgga gagtcatctc   10020
ccagaagagc cagctccgct gtcgcccag caggccttca ggaggcgagc aaacaccctg   10080
agtcacttcc ccatcgaatg ccaggaacct ccacaacctg cccggggggtc cccgggggtt   10140 tcgcaaagga aacttatgag gtatcactca gtgagcacag agacgcctca tgaacgaaag   10200
taagatttgt ttaaatttgt tgcataaata gctggggcat atctgtgact agccaggtat   10260
gtgcatccca ggtatgttta ttgagtgaga gaaatgagtc aggctttact cttggtttgg   10320
agataaaact ggaagcagtg acatgttcgt tcgagctgct tgtgagtata caagcaatgg   10380
gtacttgtat tgtcaggaag caagtgaaag tgagcaaaaa tggtacctaa catgcatagt   10440
cattactcct caaacaaagt aagagacgtt gttgactgtg gaactttgct gctgtgagga   10500
agagggcaag cggatgagtc tccccatctg aagccctgga gcagggttat aatgggaggg   10560
agaggcgctg atccttacag gcagagcaag agaggtatgc tggcctcata gggtgacagg   10620
ggtgcttcag cttctggtcc tagctctgcc gtgaactaat tgtgacctgg acgaatttgc   10680
taaattctct gaataacaaa attggagtag atgttttcta aaatctctca ctgtaagaat   10740
tctagattct tctaacaaga tttattcatt gtaatagttg ggttcctgtg accagttaga   10800
atcgtctggt tatggagaag agtaatcaga agttcccccc attccttcca agtgtccctt   10860
agtgattcat ttaattctgt gtgccagaga ctataaatgg acacagttat ctttaaaaac   10920
aactttaaac aattttaaaa atctctcacc taatatgaat caaggtcaca cctgtgtaca   10980
gtcgctgcct tcttctgacc agcagccgca gaagtcccag gacctatgtg ttcgtgtagt   11040
tcatacacgg atcattgaga gtgtgagtta gtacagaagt gtttggaatg ttctgagtaa   11100
agaagtgtga gcattaacag tcctggatga tggagcagag cctcccagct tgtttttctg   11160
tcagccattg gaaagagttc ttggttctt ggaattcagc ggggtagtgg tgatcccaaa   11220
agcaggggac atgtcagaag gtactgctta ataaatacac gcttttagag acacacatcg   11280
ttgggttgta gctgtgtaag tttcttgtgt ttaacaccct gtctgcacat tacttctgtg   11340
ctgcctcacc actgcctgcc cactcctctg ttgttggcgt tttcagtgat cattgaaaca   11400
ttcctgtctg gagagtccta gttctcttgt gaagtctgct gtttctcaaa gccagagtt    11460 gataggactt agtatcagta cttttccttt ctccatgaag aatgtagctt tataatagat   11520
gatgtcacac atccgtaatg ggagggatga ggagatgcct gtctgtctgc ctctctagca   11580
tggcccattc tgctttcttt cccccttgtg agctctttc cgatttatct acaggaaata    11640
agacattgaa attcagggca ggatattgtt catttttaaag ggaaatgtat tttttaaagt   11700 tcagttttt tttgcttttg tttatacttt aattaaaaat tttttttcct gccagttcct    11760
gaaaaagaaa atagagaaag aaatattatt gttcctgggc gaagtggctc actcctgtaa   11820
```

```
tcccagagct tgggagact gaggtgggag gttgcttgag gccaagagtt caaggtcaca    11880
gtcagctgtg atcgtgctac cgcactccag cctgggtgat agagtgagac ctattaaaaa    11940
aaaaaagtat tgttgggagc ataaacacgt gggaaatggt caagaacggc cgtcaatata    12000
ctctgttttt cactgaaaac tacctttgcc agagagcgag cagagatgag gaaaaggagt    12060
ggaagaagtc ctccactctg atagtgttac tggaacaacg agacaaaagc ggtgtgctcc    12120
ttccacctgt ttgctccgtg tccctgtcgg cgcccctct cctgctaacc ccccgtgct    12180 ttctctgatt gctgtttagt gtggatcctt cacctgtggg tgagtctaag caccgcccag    12240
gtcagtcttc agctcctgct cctccacctc gtcttaaccc ctccgcctcc tcgccaaact    12300
tttttaagta cctaaaacat aattccagtg gagaacaaag tgggaatgct gtgccaaaga    12360
ggtgagcaca ctcacgtggc aagtttggtg ttgtctgttt cctggggag ttcacactga    12420 tgaggatgtg ctgaatgggg ggaatgtcca tgcaggaagc agagccactg tgtgtgtgtg    12480
tgtgtgtgtg tgtgtgtgtg tgtgtgcgcg cgcgcgcgtg tgtctttgtt tatattttgt    12540
cttattttca gctgtcattt gaaccaagtt aattttacta ttgatgactt ttnttaagat    12600
tattatgaaa acagatctta atggcagatt ggtttgtgtt tgtgtttgtt ttttttttt    12660 ttgagacagg gtctcactct gttccccagg ctggagtgca gtggcgtgat ctcggctcac    12720
tgcagcttct gccttgtggg ttcaagcagt tctcctgcct cagcctcccg agtagctggg    12780
actacaggca cacgccacca tgcccggcta atatttttat tttttttgt agagatgggg    12840 tttcaccatg ttgaccaggt tgttcttgaa ctcctaacct caagtgatcc gcctgcctca    12900
gtctcccaaa gtgctgggat tacaggtgtg agccactgca ccctgctgca aattgttttt    12960
ttatacttat tttcacattt ccttgcccta gtggacactt acatgcatgc gtatatacac    13020
acacacgcgc gcgcngtgcg cgcacacaca cacacacaca cacacacaca cacacacaca    13080
cacacaggat aacatctgtg tttgatcatg tacactgcaa tttgtgccat atcagaaact    13140
tcctgattga tttaggggaa ttattttcc cagtttgaaa ggaagagtta tttggaaaat    13200
ggatggattt tctttttaa aaaattattg atcccattca tttaaaatca aatttttattg    13260 gtgaaaatga aaattaaatc tcgttcgtga actactttta atttcttacc tagttttctt    13320
ttcttagcat tagaacaaaa atgtttcttt tattttgaag cttatatttt atactttgtg    13380
tttttatgtt tctttatcct aaactcttt ttcaaccaaa ctcttagcat ctcctactgt    13440
aatgccctgc ggaaaaaact tcattcttct tcctctgtgc caaatttct aaaatttctg    13500 gctcctgtag atgaaaataa cacctctgat tttatgaaca caaaaggta gggcttaatt    13560 tagatatatc aagcctgggt gttactaagt gttgaatatc attagatata caagggtgtt    13620
ttaattacta ttttgccatt taaaaaatca tttcagctaa atctgttgta tcttcttct    13680 tatactttt tcttactgaa tgccatttt aaaatgtgc aaccaacctg ttctctagtt    13740
ttgacgagga ttagtttaag tgttgtctta agaaaagtct ttgccaagtc tctgagacca    13800
gtgtttctgg ttagtgagca tatgtctgtt tcaaatcagg atgtctgatc tgttcaggac    13860
gtctaatctg taagttgagg ggattgctta cttacaggta cataacttgg gtataaattg    13920
gaagggcctt ctcaggttgt cctgtgaata ggagaaaaca tttatgattg tgtttatata    13980
ttgataactg tattttgtag tttaaaaaat acacacgtta aaacaattat catcatcaag    14040
tgactgcata gttattgcct tgctggttct gtgtaattaa attgcaagtt ttttcatttt    14100
ttgtgggaat ccttggagac atgggcctgt gctgagcaga tattcccatg cacagaagag    14160
ggcagaatgg ggcccttgg catcacccc tttccccctt taggcagttt ctctttatca    14220
```

```
aagtggcacc aagagaggcc caattggaac tatgatatgt ggaacatgtt tcttaatctc   14280
tgttacaatc gaaatcactt aagggcatgt aatctttctc ttttcatgaa aagaattctg   14340
taagaaagca gttctttagg aatgatgacc cactgtgagc ttgatataac ttctgtgatt   14400
gattatttgt ttatacaaag atagttgata atttagtgat ttgtttaaaa aatgttaag    14460 ctaacaaaat cccgtgaatt cctccccact agtcataaat caatcatctt ataattttag   14520
ggactttgaa tccaaagcaa accatcttgg tgattctggt gggactcctg tgaagacccg   14580
gaggcattcc tggaggcagc agatattcct ccgagtagcc accccgcaga aggcgtgcga   14640
ttcttccagc agatatgaag gtaaggccgg tacctgaaat gaaacctcaa agagagcacg   14700
ctgacagagg accctgggag ccycatcata ttggtaagaa agcagagcgc cgtcctcttc   14760
agtattggca ggtctgaggc aatcacaaag gtaactaggg agggaattta gaggttaccc   14820
tccatttctt agggaaggaa tttaaagcta atttagggta acctctccat aaacaggagc   14880
agagctctga tgtttagagt ggtcacagtg ttaaccagcg gtgaatccag acaggtctgc   14940
ggcaacctca cttcttgcct cctaggacat aaggcaaaag gagagactga ggcaagtttt   15000
agagcagcag tgaaagttta ttaaaaactt cagagcagga atgaaaggac gtcaagtaca   15060
ctttgaaggt ggtaggcggg gcaacttgag agatgaagtg tgagatttgg ccttttgacc   15120
tggggtttta tatgctgcca tacttccggg gtcttgcgtt ccttcttctc tgattcttcc   15180 cttgggtgg gctgtccgca tgtgcattgg cgtgctagca cacggggtt gtgggggagc     15240 gtgcgcaggg tgtttactgg agttgtaggc gtgctcactt gaggcgttct tccctgtcca   15300
gtctagcatt cctagaggaa cgtcatgcac caggtaaatt ccgccatgtt gcctcttaat   15360
gcgcatgctt gagcccactc gcccagctcc cgagatctta ttgggaagct gcagctcccc   15420
agttttaggt gttttctatc tactgggagc ccgcccttcc ttggtgcccg ctgtgaccaa   15480
cgatcacttt agagaaacag ttgacaactg cctgaccaac acctgatggt cgcctgacat   15540
tgctggtgca tatctggaaa gggccctctc ctgccgtcct catgtctgac gagctacccg   15600
ctgtaaccaa agcgtgggct tcggagtctg cttttcaaatc ccagcttttc cccttaggag   15660
ctgtgaacta gaataaactg tctaaagtta ccacctataa cctgggatta attatgcctg   15720
ttgccacact gatagagaca aggcagcatg atatcattac tgatacattt ttttaaagc    15780 attcaaaatt catagtactg gaaagaaaat cagtgatgcg aatgtttcca gggtaatgtc   15840
acctcccatg ctgtggaagt ccttcgggtg agcctggccc cttgcttctt ttgccccagc   15900 cttttctatgt gggggcacca tggagctgcc actcaccagc acctttttc cctcaagtag     15960 tttgtaccta taaagtattc ctgccgtggg tggcccctcg gtggagctgc tgagcctagc   16020
cagggtttga tttctcttcc tgccagtgtg agccagatgg ccacatctct cttcccctgc   16080
cccgtggaga ggtctgctta ccgcaaagaa gggctcttcc tcccaggtcc tgtagcaccc   16140
tgttagaggg tgtggagtgg agcagtggga accagagcca ccagagggag gccctggagg   16200
aggaacgaag ctgattcatg tctgaaaggg gtgccagaac ccaagtttcg gtgtttaata   16260
aagagtgcct cggtgttgcg gtggccatac ctcacagggc atggtcgctt ggaaatttct   16320
gctcggaaat gctttgtgca gtggccagga tgcgttaggg gccacagatg actgcttgct   16380
ccatcataga acagttccaa gttttcaaac gagcattcac agactgagcc gcatcctgcc   16440
tccctgtcct ctgattcctg gcttcttctc tggtctctga agccacacgg aaatgtgttt   16500
gcatctgttt cctgcccttc agatgacaga ggaccatgga agctgctgcc tcctttagct   16560
```

```
ctcttctcca gggaattgc cctcgtcact gtttgggaac ccctggtccg agtcctgtcc    16620
tccgaagagc ctctgcccct cctggagtcc tgagttgaac ttggtgttca cttggcctct    16680
ggctctggca gtgtgttgct ccttccgttg acctgccact gctctgttaa tgcagattga    16740
tcttcataat ctgtttctgc tttaagtgat taactcaaac attcttggct cttattctat    16800
cttgtccttt gggatatgaa ccattattta aatttggact ggtttcctgg cttggcacag    16860
ttgaccatgc ctgtaagctc agtgctttgg gaggccaagg caggaggatc cctggaggcc    16920
aggagttcga ggccacccett ggcaacatag tgagaccctg tctctacaaa aaaataaaaa    16980
ttagctgagc gtggtgttgt gaagctgtag tcctagctac ttgggagact gaggcaggag    17040
gattacttga gcccaggagt ttgagtttac agtgagctgt gatcacaccc ctgcactcca    17100
gcctgggcaa cagagtgaga ccttgtctcg cggggtgggg gagtcatgtc tatacttgag    17160 aagtttttt ccctcgcata gtttgtacct ataaagtatt catcagtttt gagcagtcct    17220
tttgcgattg ttttgagtct tgattctggt gaccagtaag ttgtatatat ttgcctgtca    17280
agtggacaaa catggccttt gtgcctttaa gtaatggcta aaagtaccaa acagaacagg    17340
gcctggcata gatgctgctc ctcctgttcc taggccgtaa tcacccctga ttcatcagac    17400
cccaaacaag tcagctcctc tccctcctgt gccccaccac ccaatctcct gcaggaagat    17460
gtctggagac cctgtcagc gctaggcaga gatcaccatc catgtccacc tttcctctga    17520
tgcaggctcc cactagcccc tctggcttgt gccatgccag ccatgaactc accctcatgc    17580
cccacccgag ccctggcaca ggctattccc tctgcctgga atgctcttcg tcagtatccc    17640
catggctccc tccctcccct tcccttgtat cctgactctc ccatagcagc tctctccctg    17700
taacacatgt tcacaggttc atcttcgtca cccatctccg gcagctcctg caggcttgat    17760
ggctgctaaa ggcaggcaag tcagtggctc agattcttgc aaacttagtg attagtgatt    17820
tctcaactcc ctcctcatgc ctcctctgtc tctataggca catattattt cttatctctt    17880
ctcagaacca agccgcctga atttctgaat aacattgttt aagtgttctg tgtatgcaaa    17940
agaaaaacga gaataaaagg attattaagg aagaattaat ataataatag ccacatatta    18000
tgctcttttt atactctgct aagtgcttta catgaattat ttcctttaat tagacaatct    18060
taagaacatc gacattttta tgaagcccat tttacaggtg ggtgagtgga ggctgggagt    18120
ggcttaaatc actttccccca aaccagggag ttagtgggag ccagaggcag gacctgagct    18180
cgcgggtctg agctccaaag ctcattctct gaactgtgca cagcactggg ctgcagccag    18240
agatgcagga cgctgcggga ccctctggag gtggtcctgc ctgtgcttcc ctcttcccac    18300
aggaagctcc ctataggcat ctgtgttggg cgtggactct cagtgtacct gcatgtctcc    18360
ctgttggcca gacaccaaca ctgaatggaa aacatgtttc tgggcatttt aatgtacgta    18420
cttgccttca gtcaatctcc tccgcccct tccatcctga ccgcctccct aatagttagc    18480
agtgggactg gagcttgaat ggcaactgat ttctgtctga gaggacaaat caggcatctt    18540
tgtcctctgc cactgtctgt tccccatcct taggatgcac gatgccagag ccctccactg    18600
tggtctgtga ccactttgac ccacactagc aggtctccat atgttccttc cagctgagag    18660
acatcacatc caaagacagt ttagagctct gaggtttctt tccccagagg tccctgcttt    18720
gtgcaaactg tctccagcca agcgtgcaca agactctgtt cctgatttgc ctgggcggct    18780
gagccatggg cagctgagcc tgcagccgct ggactcactg cattcccact ctgactttgg    18840
catgaaagac acacaagtgt gcttgtgaga aatagatctt aacagtacct tttaacacct    18900
atttcaggtg ctcaaaatga ctgcctgttt tacatttata ttctggcagt gcaaacttca    18960
```

```
attggacagg aaatcttaca acctctcttc caggtgraaa agcgaggcag ggatgtttat   19020
acagttccat ccatgtcatc ccacttggaa gatactagta aaacacacca acagtaatac   19080
aaaaaccatg gtgtttgcaa tagtgataat gttactagtg aaggaaaaat agaaactttc   19140
tgtaatttgg agattctaat ttttataggt gggctaaaaa aaaaayctgg agagaagggt   19200
gttaagtgag taaggagtgt gtctctaact aaatatagtg taaaaagaga agaaaataca   19260
aagtcaggca cagtggatag aggtggatag tctaatctct aatagtataa tgggcaaaat   19320
tgtctcaaac aaaattagtc tgcctcttgt ttactcaggg atgtgtgact gttttctatg   19380
cacaaaatcc ccatgaaata attaagttgc aagaatctga actttatatt ttggaaacct   19440
atctgaggta ggtaggaagt taatttatat ttagaaattt gcttgcatat gtctagtagc   19500
tccaggacaa atattcccaa atcccagact atttttttttt cttttt aaat tcaacagtga   19560
ccagttggtc tcttgtaaga attacagcct taagttagca aagtctaaga gggctggttt   19620
taatcctgaa cctcagaggg tccctgcttc tcaaatacta gtaggtcac gtgcacagca   19680
ggtactacat tgaagggaaa ttgtatgata aataggaaat cagcgatttt tacttggaga   19740
cttggcaagg caaatgtttt tgtaataaaa atagatcgtg aaatagaatc ctgaaagctg   19800
cctgtttaaa tgtaaagcaa atggcttttag tgatgcttta agtgtggcag tcacttctgg   19860
ctgccgcaga aactatagaa agtgcattct ctccttggtgc tgtgggttct tagggtgaat   19920
gccttgtgtg acgctgagta tgtggaagga ccattcattc ttggtaacta tacactaggc   19980
agagggtggc gttagcgaag ctactgcagg ttgggtgtgt ttaagatttg gatttatttt   20040
tcttttaatt tttattttta gttccagggt acatgtgcag gatgtgcagg tttgttacat   20100
ggttaaacgt gtgccatggt ggtttgctgt acctatcaac ccatcaccta ggtattaagt   20160
ccagcatgtg gttattttc gtaatgctct ccctgctccc tgccgccccc caacaggctc   20220
cagtgtttgt tgttcccttt cctatgtcca tgtgttctca tgattcagct cccatctatg   20280
agcaaaaaca tgtggtgttt ggttttctgt tcctgcgtta gtttgctgag gataatggct   20340
ttcagcttca tccatgtccc tgcaaaggac atggtctcat tcatttttat ggctgcatag   20400
tagtccatgg tgtatatgta ccacattttc tttatctagt ctatcattga tgggcatttg   20460
ggttgattcc atgtctttgc tattgtgaat agtgctgcag tgaacatatg catgcatgta   20520
tctttgtaac agagtggttt atattccttt ggttatgtac ccaggaatgg gattgctggg   20580
tcaaatggta tttctagttc tagatctttg aggaattgcc acaccatctt ctacaatgtt   20640
tgaactaatt tacattctca ccaacagtgt aaaagcattc ttacttctcc gcaacctcac   20700
tagcatctgt tgtttcttga cttttttaata atcaccgttc tgactggtgt gagacagtat   20760
ctccttgtgg ttttgatttg catttctcta atgatcagtg atgttgagct ttttttcatg   20820
tttgttggct gtatgaatat cttcttttga gaagtgtctg ttcatgagag agacatattt   20880
gctcctctga gtaaagggta aggatgctta cgtctgtgtg acagccttct ctcttttttca   20940
gaacctcact gtggatcgcc atcgttggcc tgtactgaag gtaaagcaga tagaggcagt   21000
ctcatctgtc agatgaagac ctcatacacc tgttgattaa gaggctttct tcagatcatg   21060
gtttagagcg gtgttttaca aacttgacgt gcttggagtc ttctggaaat cttgttaaaa   21120
ggcagactct gttgcagtag gtccgggtgg gttctgaagt tctaacaagc tccccagtga   21180
ggctgatgtt tcaggtccac tgtgaggagg cagggcttag aataaacaac cgtgggaaat   21240
ccagtccaga tctttgatgc atcctaggtt aggcctgtct gtcaggctgc cctgggtctc   21300
```

-continued

```
tagtgatgga ctccaggagt ctctcaagtc tcaaataagt ctgagtcatc agggatattt   21360
tttgagaaga gttgtgctgt ctgaagaagc aaagagtgag tgtgatgggg aaaatgcagt   21420
gattaaaaac atggtaaggt ttaaagaaag atttgaccat atgccaggtg aacccaaatg   21480
tatggtgctt tgcgtctttc ctgcccttg gttttccagg gaggcaaggc cttatctctt    21540
atggagcaca ggagacacag tgtgggcgtt tgttttctca gccgtgggct ctaacctaat   21600
tgtcaagcct acaaaaaaaa aatgctgaaa atcaacttct gactagatat ctggtagtac   21660
ataatctcca taattttctc tctgggtgta ttatgcaaaa gataatcctt tngttattaa   21720
gaaacaattt ttaaggcaac tcccaacttt gaaacgggga aaaatcattt tatttacctc   21780
tatgtgctag ggaacaatat taaatttagt tttatacttt tcctttaagc atttcagatt   21840
atattgtgca tttcaccaac aatagaagct ttcagacttt atatgtcttg taaaaaaaag   21900
cctaatatag ataagaataa tttattgatt tgaaacccat tgtataagaa atagtccagt   21960
gaaacttaag ttcaaagttt ttttttgtctt gtggatgtag ctatgtcaat atgcctagtt  22020
tatagtaaca ttaagtctag tggattagat attagatatc aattgagatg taagcagtaa   22080
taaacagtaa tgcctaaact gaagtatata atctgaatct ttatgatgac caatttatat   22140
tattgtgaaa aacttaggaa ctgatttgaa acatgattta catgttttac atgaaacatg   22200
atttacatgt gtcatatata gttttcaata atttacgtac cagcaggaaa ttttagtgga   22260
taagtggaat aaactgcagg tgaaactttg ctggaaaata caagcatagt gacatctgtg   22320
caccaaaagc acctggggag attttttaaa acatgggcca gacatgcctt cctggctgtc   22380
tccctcactg tcagtgagtg tggggatggg gtctgggcct gaattctttc tttttagact   22440
cctcaggatt ctgattgctg ccacgttgag agggttgacc tcaattcgga cctcagaggg   22500
tgacttgaga aactgtcacc acttggtggc agtgttgctc cccgcatctt gattgccctt   22560 gtttcttcc aatcccggaa aagtgtgctt gttttttttt ttttccctgc gtgttttgt    22620 ttttgatctt gctataatat ttatattcct tgctcatttg caacttattt gaatggagag   22680
ctactttctg aaatctagat gttttctctt ttctacaggg ttttagggca tgggcaaaac   22740
acggaagaaa aaagttgtct tcagttggca gagacgtgga tttttaagat tgttcttaat   22800
ttactttctg tataactttg ctttttctgtg gtgaacaaag accaggttca agataaaata   22860
ttgcaagcca agaatctgat tgttcatgga tttctatggt taaagatact tgatcaccc    22920 cccatccgcc ccctacccca cccaccctgc gccgccccca caccccattg tgcttcttgg   22980
cttgtcattt caaaagtcaa ggaagtcaca gtgaatggca agattttacc tcgacttgct   23040 attttttgtgc ctgttaacaa ttgtgagtta acactgactg agcttttcct agtgaacctc   23100
cggcgtttaa acagccagtc cataacactg tgtgagggct ggagctaagg ttattggtga   23160
cacaagatag cacctgagcc agtgctgctt ggtaggaggg ctgaggggaa gagggctgag   23220
ggcttggatg ctgagatgct agagtcacat cgcctggatt tgaatccctg ccctcctgtt   23280
ctgataccag ctgacccatg acgatgctac agcacctgac agcagattcc tccttagggc   23340
tggtctaact ctagagtgtg tgcctgtgtg cctgcaggag aatgtccaaa gtgggtgatc   23400
ttgatctgtt aacctttgaa ttttaaccta taccaggag ccattgaaga gtttaaagca    23460
agtgaatgac gagtagtttg aaaatatttc caggtggata gaatttgtgg acatacatga   23520
acatgagcag cctcaaaatc agggctggga ctagagtgag gccagcacgt gtccagggtg   23580
caaaatgtaa ggaggcattc actttcaggg cctggcaggt gtggaccctg aacttccagg   23640
accttgagag tgagtgtctc ctaaggatta caccctgggg gcctatttgc ctcatcctgg   23700
```

-continued

```
tccctggtcc tctgtgtacc ctattgcctg cttcagtaaa caggcagccc tgcaagggaa    23760
ggaagggttg gatcagctct gaggagggag ttttttttaga aggatagatt tgttttgttt   23820
aaaaaacagc tttattgaga tataattcac atcctataca gtttgttcat ttaaaatgta    23880
caattcaatg ttgtgaggtt attttttggt atatccacag agttgtgtga acatgaccac    23940
aatctaattt tttttatttt tttttttttg agacggagta ttgctctgtc gcccaggctg    24000
gagtgcagtg gtgcgatctc ggctcattgc aacctctgcc tcctgggttc aagtgattct    24060
catgcctcag cgacctgagt agctgggatt acaggcatgc cccaccaagc ctggctaatt    24120
tttatatgtt tactagagac ggggtttcac catgttggcc agactggtct ccaactcatg    24180
gcctcaagta tccttctgc ctcagcctcc caaagtgttg ggattacagg cgtgagcccg      24240
acccaccgca gtctaatttt gaaacatttt ttgtccccct agaaaaaaac ctgtagttgt    24300
cacttgccaa tctactgccg tccacctcta accatagaca gccctaatc tactttctgt     24360
ctctatagat ttgcctattc tgaacacttc atctaagtgc aatcatataa tatgtggtct    24420
tttgtgtctg gcttctttga tttaacatgt tttcaaaatt cattatgtca taatacatac    24480
cagtaatcca ttcttttta atgacttatt aatattccgt tgtatagaga catcacatat      24540
ggtttatcct ttaccagtcg agaggcattt ggattgtttg cacttttggc tgttacggat    24600
aataccgctg tgaacattga tgtatgtgtt tttgtgtgtt gaatgtgagc tggtgtggaa    24660
actcctcctc caggggggcc ttacctgtga ttctacccac ggggatggtt aagccagcag    24720
ggatgggaag ggtttggtcc tgctggccct aggctttcct gcaggctgcc atgtgccttt    24780
cttctgccta ggctgaaacg gaggctgccc tggtttctgg cactgccctc gtgagtgtgt    24840
gggaaggctg ggggaagcca agtctccatg gtgcctccat cagggaccct gcagctggga    24900
ggcagccaga gggccacagg ttggtagcat tcacacagag ctacatttct tttttttttt    24960
tttttgagac aatcttgctc tgtcgcccag gctggagtgc agtggtgcga tctccgctca    25020
ctgccacctc cacctcccag gttcaaggaa ttctcctgcc tcagcctccc aagtagctgg    25080
gactacaggc gtgcgctgcc atgcccggct aattttttgt gttttagta gagacggggt     25140
ttcaccacgt tgaccaggat ggtcttcatc tcccgacctc gcgattcacc tgcctcggcc    25200
tcccaaaaag tgctgggatt acaggcgtga gccaccatgc ccagcctaca tttcttttt     25260
ttttttctttt gagatggagt cttgctctgt cacccaggct ggagtgcagg ggcaccatct   25320
ctgctcactg caacctctgc ctcctgagtt caagtgattc tcctgcctca gcctccggag    25380
tagctgggat tacaggcaac tgccaccaca cctggctaat ttttttattt ttatttttta    25440
atagagacga gttttttcca tgttgaccag gctggtctcg aactcctgac ctcaagtggc    25500
ctcaagaggc caatccgcct tggcctcccc aagtgctggg attataggtg tgagccactg    25560
cacccaccca gcccgtagct acatttctgt cagctgtttg caaactgtgc cccagaatcc    25620
cctggaggac ttgtagaacc accagttact gggttacgcc cccaaatgtc tgatgctgga    25680
gatgaattat cttgggtgga gccctcaagc cgcagcagct gataagcatg gggacctcct    25740
attctgataa aaattccaaa aaagtcctga gtgattaata aacagcacat tgaaaattag    25800
aaatgagttc tatggcaggg gatgaaacag gcaacaaagc ctatttcttt tgcaatgaag    25860
cgcatcagat attaataata gccattgtaa ttatctttat catgtattaa gcattttgtg    25920
ttttcactt ttacacaatt agatgatccc cataggtatt accgcctttt ttttttttt      25980
tttttgaga cagagtcttg ctctatcccc caggctggag tgcagtggca cgatcttggc     26040
```

```
tcactgcaac ctctacctcc caggttcaag ctattctcat gcttcaccct ccttagtagc    26100
tgggattaca ggcgcctgcc accagaccca gctaattttt tgtatctttt ttagtagaga    26160
cagggtttcg ccatgttggg caggctggtc tcgaactcct gacctcaggt gatccgccca    26220
cctcggcctc ccaaagtgct gggattatag gcgtgggtca ccacaactgg acttactgcc    26280
catctttttaa gagatgagga cagaaagatt gagtgacaca gttatgtctc ctgcagctct    26340
tggttcacat agccaggatt cgtatcaatc tatttagctc taaatctagt ctcttaatca    26400
cagtaatgaa ccgttgacag ttttacgagt aaattatcaa gagttttgat aggtttgctc    26460
acttaaatta gtgcttgtac agtaatgggc tgtgttagtg tgaaggaatg tatcttatgt    26520
tggaagtact ctagaattaa atgttaactc ttgctaataa agcatacatt tggggcatta    26580
ttagcaactt tttttttttt tttttagcaa aattagaggc ttcctagttg agtggtttat    26640
gttatttata tttatttatt tgtttgtttg tgacagggtc ttgctctgtc acccaggctg    26700
gagtacagta agtagcacaa tcatagctca ctgcagcctc gacctcttgg gctcaagcag    26760
tcccctgcct cagcctccta agtgcctggg accacaggtg cgcatcacca cgccctgcta    26820
aatgtttaca gttttttgtag agacagggtc tcaccatgtt gcccaggctg gtcttgaact    26880
cttgaattaa agcaatcctc ttgcttcaga ctcccaacat gctgggatta caggttgtgc    26940
cactgcgcca ggcctccatg tatttgaatg aaagagcaga catctcctgg aggtggcaaa    27000
gctatgcatg ccccccctgg agggagctg gggctctgg ggttacagtg atggcacatt    27060
cagggagctc tccgctttgt gagatcctga gataaagcca aaggatgcat taaactgctt    27120
ctaaatgaac ttttttccaag tgaatttgtt atatcacttc tatataaatg aaaatatttg    27180
cagcatgagt actaacaaga tttttttttt cttttacccc gatggagtct cgctctgtcg    27240
cccgggctgga gtgcagtggt gcaatcttgg ctcactgcaa cctccgcctc ctgggttcaa    27300
gcgattctcc tgcctcagcc tcccgagtag ctgggattac aggtgcgcac caccacgccc    27360
agctaatttt tgtatttttta gtaaagatgg ggtttcacca tgttaaccag gatggtctct    27420
atctcttgac tttgtgatct gcccgcctcg gcctcccaaa gtgctgggat tacaggtgtg    27480
agccacgctc ccggccaaga ttttaaacat tatttaccaa agtaggaacg tggtaattat    27540
ggtcttatat aattctgaaa atgatttcta gtaccaaact atgaattta tacttgaaag    27600
aatgatgggt ttttcacaga aagttgaagt tattatggtt tgtnttcctg ttcanggtgt    27660
ttttgctgga gaatgttcga tgaacagcag ttctggtgat aagttatgga tgtacacagc    27720
tggtgtggtt tttaggattt tattttgcag cagcatcttc ctcaaacagt tgccagggga    27780
aggctttcct tcttcttact ggtaccagcc tttctcttgc agacaaggca gtatgggagg    27840
gttgggagac aaaacagaag ctgttggttt cttcagcctg gcaaggattc agattgcagg    27900
ttatagattg gaggccgtca gtggggatac cttttccggac aaagtggtgt ttctgcctgg    27960
cactgcttgc cagagaagtt tcagttcttc attctccgtc agagaaaccc atatggacca    28020
cattctgata gttttcttct gtttccctaa caccgaaggc tcagcccctg gtgcaggtcc    28080
cagtgtacag caggctgcat acagttagac cagatgttct tgtagtacga aaagtcaccg    28140
agtttccatt cacttgtggg tggcaggtat ggccctcctt acctccatg gcccaggttt    28200
ctctgtcctg ccgttttcac atttttccagg ctttcacctc caggtaccaa aattcacatc    28260
atttagagat tgtgtctgcc tgccaatacg cggatgtacc agtgagggat tgttctcgcc    28320
tgacgagagg tctggatgat gagagagcag agctggccct ggggctcagt ggtgacaccc    28380
tcgagcttgg ctgcttctgt tcttctgctt cctctgcttg gattccttcg cctttggctt    28440
```

-continued

```
ccctccagt tccaagcaga acaaaacagg agatatcaag gaggaaaggg tgaccctct      28500
atatctggag agcaaaactg tcgcggaaat ccctagtgta cttccatttg tgtctcatta      28560
tctgaaaccg agttacctgg ctggtcacgt gcagccacca gaggcaggaa ggtagtgatt      28620
ctgcctgtgt ggaatgttct agcattccct ggtagctttt gtttcttcag gcagccatga      28680
cttttgcatag atcatttcct tttgcccagg acactcctgc tcgttttctc ccctcctcac      28740
caaacccaca gtgcattaac agcgacagac ttctcctcat cctctcaggc cacttggatg      28800
tcaccatttc ttctctttac ccctcaggcg tagtcagcct ctctgtgcct gatgttttat      28860
ggctttgtgt atgcccgat ggagagcgtc ttactgtgtc ttcgggttat ttatctcaac       28920
ctcgcatctg tgctatcctg tacagtaacc aacagccaca tatcactatt taaaattaaa     28980
tacaaactaa ttatacttaa atgtaataaa aatgtagccc ctcacattag cctcatttca     29040
agagccacat gtggctaccg tattgtaagc agagctcaag aacattcagc aatattgtga    29100
gagtggctac catattgaga gcagagctct agaacattcc cttatcccag aaagttctct   29160
tggacatgct gctcaaggtg gtgaactctg agatctccag tcccccagc tccgtcactc      29220
agaaccacaa atgtggcacc atcagccttc agggtggtgc ttgtgttgta ctgtctcctg    29280
actaaagaag taaacttcag gcagtcaaga ttttctacaa cccacactgc tcctaaaact    29340
agtgttactg gatatgtaaa agctattgag cccagtgctt tcaaggaatc ctaaaagcaa    29400
gtggggactg tcatgtatcc aggttccttg ttttgcagaa gaagaaatag aggctttagg    29460
ggaaagggt ccactcaagg tcatacaggc aaggtcatac agtcagtggt agaatggact      29520
ggaatcttga ttgttcatct cactcccctt tccattaagc cataactgat tgagtatcac    29580
caacctgttt gttttccctg attatgttcc cttctcrcct gtttaatcag gtttcagctc     29640
cttgtgagag gaagttgttt tcagcttctt agcccctac ctgtaggcgg tgctctggga     29700
acgctcagga agcagatgca tgtgagcctg tctcagccaa tgattgctta gttgcaagaa    29760
acaaaaaat gactcaaact agcttaatca aaggaggct tttaaacagc aagataaggg      29820
taaggctgg gaactaggaa gttgtcagga accaaggctg tctctctgga tctctctttg    29880
aggccatgta atttttttt cctctcggtc tctttattct gcacaccagc tcacccagct   29940
tgcttgttac tatatgcagt catgccaacc cccagatctg tatgacctgt tagcctcagg   30000
ggcacccaca tagctggctg ccaatctgtg ttttcttcca ggtttcgaga gggagaaatg    30060
attggcccag ctcagggtca cttacccagg gagaggtggg ggaagtatgg aggcaccgtg    30120
gtatcaggga acccctgggc caagcttgtc caacccgcgg cctgctttct ttcattttt     30180
ctgttttttg ttttgttttg ttttgttttt ttacagctca tcagctattg ttagtgtatt    30240
ttatgtgtgg cccaagacaa ttcttcttct gctgtggctc agggaagcca aaagattggc    30300
caccctgtc ctaggccatt atctgggctg tgggaggtgt ggagcaggt cagagctgga      30360
gggggagggc atagcctcca gccaccataa gttggtgtgt tcttggtaat tatattgctt    30420
gtcaaccgaa ggcagaatca ggacaatgaa agtaatgaga atccctagct ttgtaacagt    30480
tagtggttat ctaaaagtag gtgaaattgt acatgagtga gtggcatgaa tttcttatta     30540
ctaaagtgct cagatagctg gctaactttc tgtcaaagat ccctctgcta ggatcaacat     30600
ttgattaata tatttatcct gtaataagaa tttgggattc ttaaagcaaa atagttgtca    30660
tgtggctgac tacacaacca aagatggtcc aggtgtcgct ggaagaggag agactgaaga    30720
gctgttgcca ggttcccacg tggaccttcg gcatgacccg gccatgggga ggcctcacac    30780
```

-continued

```
gctcctgcat cgcccacatc ttgccaagcc atggaaaaca cttgggattc atatctaaat    30840
cctagtttaa gcttggtgag gacagtggcc tggtgcagag tttgggtcat agatggtgct    30900
tggtttcttt tgtataaagg ggtatatgat tttggaatat ttaccaaatg tgggcatttt    30960
ttctataaaa attattgtat ctactgagat tatagtatgt aaaaaaaaca tacacatgga    31020
gaaagaatac aaagagagca ttgatattct acagaagtgg caagaagatg tggtgatagg    31080
tgatatttt gccttttgtt tcaattttgt attgtagtga cttttttggt agaaaaaact    31140
aantttctaa ttaagggaga aacatttgaa gtacatttag tctttctaga aaacctcatc    31200
ttctcataga agtttaagat ggagacatac ttccattgtg aatcatgatg ctaaccagta    31260
ttcagatttg ttggaaatgg actcagtttt aaaattgctt ctctcttgtg ggctggaact    31320
gcaaatgatt gtttggggat ttttcccctt ttcttctatg gagttattca acttggcatg    31380
accagtgatt tgagctgaga acatggaacc cttgatttgc agaaatcaag cccccaaagg    31440
tacagataca gtggtcattg tctgaagggt ttcttttgtt cttggccctc ctgtccctgc    31500
tcttactgtg gcagctgcag ctgcaggtgc ctctgaagcc ttgccatcca tggtcacttc    31560
ctgcctgctc cccacccacc cctgggaaag agccccaag tgtccaaaag cactgtgttg    31620
cctaatgctt gttgagagtc tacatttctc tagatctagc agaagtaaaa tttcagtttg    31680
ttatatttat agtttcagga atagtttggg aatggattta ataaaaaatt taaaagccca    31740
tcatttttat atctctttt cgatatttga tggtttaaaa gacatcaaag ttatcttctc    31800
ccattactca tcctatacaa ttaaaacctg ttttttgaag ttgtaatagg taagttagcc    31860
ttaggtcacc ccatatttat gtaaactcca gcccactgcc acagctactt tgattgtgat    31920
ctgtcattgt gttacccact gtagggcaga aatggttcct gcctcatgcc gttgctgctt    31980
tactcttcct gaagtggtgt ggttctgtct ctgtagtcct tggcacactg taggttctca    32040
gatggcaggg tgaaaagttc ttctgtttgc ttaaatctct cataatacc tgagtctgtg     32100
gagctcaata aattctactt ggtattattg atagattatt tggagccttt tatgttagaa    32160
aagggattct taatccaatg ctccgtttta cagatgagaa gactgaggct caaagaccat    32220
acccccagga gccatgattt gcactgtatt taggaatagt gtctagggtc agcacctggt    32280
gttggccgac tgcagagcag cctggttagg agccctgggg ttgggcgggt ctgggctgct    32340
ggtgccacag cagtctccct cccctgggac tttgggcctg ctacccaccc ctgttccttc    32400
ctttgtgaga tagggctagc agtaactgtc ttgtttcatc agaggcagta ttgcataatg    32460
aatgagagct ggggcctaaa ttaggcacaa gtgcaagccc tcagaaaact atgtacacct    32520
agagagagag agagacacac gtctgtatga cagagaggca gggtttggga atgttctgat    32580
ttcatgtttt gaattggtgt gaccctttgggg aggatatcct tggaatcgca gagcttcgtt   32640
tacatcatga ctttcctgcc cacccacatt ttctgagaag ccagagtttt aaatgtggac    32700
cccgtgagct tttctctgtt gcctcatttt ggcctgtggc ctttgttttt cttggtatgt    32760
catgaggcaa aataaaatga aactcagtgc tggttaataa ctcccatcat aatgtatatt    32820
tctgtgaatg gcttttttagc catttgagag gaaaagggt catgtaaatt tcagaaaggc     32880
ctgattggct ggagagtcag tgtagtgtca cagttaagag tatagattta aaaaaatt      32940
tttattgtgg taaaaacat aaacataata ctaccatcta aaccatattt aagtataaag     33000
ttcagtagtg ttaagtatat tcacattgtt gtgcaatgga tctgcagaat ttttcatctt    33060
gttaaactga aactctatgc ccaataaaca actcctattc cccctctccc agcccctggc    33120
aaccaccatt ctactttctg tttctctgag tttgactact gtagataact catttaagta    33180
```

```
gagtcatatg gtatttgtct tcttatttct ggtttatttc gcttagcata atgtcctcaa    33240
ggttcattca cgttgtagca tatgacagga tttctctctt ttttttccgc cttttttttg    33300
agttatattc tgttgtatgt atatttaaca ttttcttcat tcatctgttg acattcatct    33360
gcttccacct tccaccttt ggctattgtg aagactgcag ctatgaacat gggtgtgcaa     33420
atgtctcttc aagatcctgc tttcagttct ttcggatatg tacccagaag tgggtttgct    33480
ggatcgatca tagtgtagtt ctgtgagtaa ccctcatact gttttctgca gctgctgtac    33540
cattttacat tcccaccaac agtgcccaag ggctccagtt cctctacacc ctcacccaca    33600
cttgtaatct tctggattgc agattttctg gatcaatctt ctggattaca cttgattttc    33660
tgtgttgggc ctgatgtttt agaacagtat ccctcctttg gagtggtaaa tatgtaagtt    33720
tttattataa aataatggcc atcctagtga gcgtgaggta atatctcatt gtggttttga    33780
tttccttcat agttaatgtg gttgggcatc atttcatgtc ctggtcggcc atttatgttt    33840
catatttggg gaaatgtctt ttcaagtctc aagtcctttg cccatttttt aattgagtta    33900
tttgattttc tactgttgag tatggattat taaatcagac tggcctgaac ttaaatcatg    33960
gcccttccat ttttgaccaa aagcagctgt gtgtcccatt tgtgccttgg cttcttcggt    34020
gtaatgccgg cataatgata gccccacctt gtagttaaga gtgttgggg agtcagtgag    34080
gaagcactca ctccacagga gcttgttacg taaggagaag gcagccggtc cattcctaat    34140
aggggtctga aggaaggaag aagggctgaa ggaagtaaaa agagcctcct ccatgaatgg    34200
cagccattct tgaaatccac cttggctgcc ttcattttta atgtcagtgg acttttaaga    34260
caaccaaaag gatgttcttg gatgaccaga gactgtggca gagggaggat ggtcacattg    34320
ccaaggatct ctctcaacct cttggatagt gtgctgctgg tagtttgcac aattgcttca    34380
gcttttggc aaagtacatg taaaatcctg aagtcactgc cagaggaaac ctggttcctg    34440
agatagcagc ttgatgctcc tgccccatcc caggtgcaca cctcactggg cagctctggc    34500
tctgaattga gggacagcaa aaacctctaa ccaaccatac tgaaaagcag gcattggggg    34560
ctttagggga aggttctttt caaaactcat gatggggaga gaccaaagac tgggaatcat    34620
tgtaaagaag ttagtcatag atgcttcact ctttacaatc atcccaacac aaggttaaac    34680
aacatgcagt tttcacgatg tcccagaaag cgacgagtgc agtgaggtga aacgtggcca    34740
tctgagcaca caatgaccag gcttggaagg atcgatttcc cctgtgctgg ccctcagaat    34800
ttaaggcaca acttttaagc tgagtgtgca gcactcgatt ttctatgttg ggcctggatg    34860
tttagaaaag tatctctcct tcagagtggt aaatatgcaa attttttact gaattacttc    34920
atttaatcaa agcagccgac ttctcctgcc tcccctgttt ctgtcttggg gttgaatatt    34980
tggtcccatg taacaactct tgattcttaa tgatgccaca tggaagctgt gtgtgctggg    35040
atttgccata ttcagttatg gtcagtagag actttcttag tctctctctc ttttttttt     35100
tttttgagac aaattcttgc tctgtcaccc aggctggagt gcagtggccc aatcttggct    35160
cgctgcaacc tctgcctccg ggttcaaatg attctcctgc ctcagcctcc cgagtagctg    35220
ggattgcagg cacgcgccac catacttggc taatttttgt attttttagta gagacagggt    35280
tttgccatgt tgtccagact agtccttgaac tcctgacctc gtcatccgcc tgccttggtc    35340
tcccaaagtg ctgggattac aggcgtgagc caccgcgcct ggccacagtc agtagagact    35400
tttgaaagga aatattacct ctttaatgat gtttttagtc caagtaaatt gtggtaatgt    35460
ttaagaaatt tgcttaccac aaaaacagtt ttcaaggagc atttgaactt gtccacttta    35520
```

```
agtcataaaa tggattaaag tgtttgaaat ctattgggat tgtaaattta tgtcagtgta    35580
ctgactttca agagatcttg atgatcatgt cgtctgtttt cattttctac tacatgagaa    35640
cattgaagcc tgaaacttaa cacaaacccg agttccccac ttgcctaaga gtcatggata    35700
cctaaaaagt atgctacttc ccaagttgat ttctttcagg atatgggccc ttcaaaggaa    35760
agcagtgagg ctggggtttt ccaggtggaa aggtcacatt tccacatata actcagcgaa    35820
cattgtgttg ggttgggaga agaattggtt cactatttta aacttttttgt ttcatcttga    35880 ggacttcccc atcccctctc ctccgcaaag cacaaaagta tttcctaatt tttaagtcat    35940
gggcttcctt taatggattc tgaactcaga tcacgtccag ataagcattg tgtaatggga    36000
tgggtggggt tagatatttt agtcacagat gcatgagagg agggagggtg gaggacagca    36060
aagtttataa ctggagccta tagtagttta tctcttgtca tcggccaggt cacagagtct    36120
cacttcagga cagctgtgca agcagaaccc ccatcacggt tttcttgatg cctttgacag    36180
tcacctgtac atgcctctgg gacctttcct cctcctttct cttttttgttt ttttccctt    36240 ggtcacatgt ttcattctac taaatgtcta accagctctt ctctgtaaat tacagagctg    36300
tgatggcacc ttgcttgttg attatttctg gttgaatagt ttccaatggg acttctctgg    36360
agataagtcc tgtattagtc cgttctcaca ctgctaataa aaacataacct gagactgggt    36420 aatttataaa ggaaagaggt tgactcacag ttcagcatgg ctggggagac ctcaggaaac    36480
ttacaatcgt ggtggaaggg gaagcaaaca tgtccttcac atggcagcag gagagagaag    36540
tgccgagcaa aaggggggaa agcccttttat aaaaccatca gatctcatga gaactaactc    36600
actatcatga gaacaggatg ggggaaactg ccccccatgat taaattatct ctgcctgttc    36660
cctcccatga catggggatt atgagaacta caattcaaga tgagaattgg tggtgacata    36720
gccaaaccac attaaatccc aagtgcgcat gtctggccct gatcccttta tgtgagactg    36780
gggtcatgat cctcccgcac ccgtcttctg agccctattc ctacttgggc atgcttaggc    36840
acttcagcat ctgcatccca ttgatgtctt aagggtggtt ccagaccttg gaggtacaca    36900
cgacacactg ctgatgaaaa cctagaatat agaatggaag ttacatttat tcatagagtg    36960
aaaatccaaa aatagaccag agagaagata tgaaaatatc aagaatgctt atcttaggga    37020
ggtaggatta taggtaactt tttttttcct tagataaata tatagataga tatattagtg    37080
tttacagttt ctctgccacc aaccaaaata tttttttcag gaggaaaaaa aaccccagcc    37140
agccaacata cctaaaaacc atctcctggg cccgagaggg aaaaattggg ctccttttct    37200
tgaaattgcc atttgtgcca ctgttgtatt attttaccag taactccaga ttccaggctc    37260
ctgtatctga gttctctctc cttccacagt ggagctcata ccttcctgtt tcctggctgc    37320
cactcagatt taggctccgt ttttcagacc tcagtggctg taatagctgt tccttctacc    37380
tcttaggatg gttctttctg taatagcctt tgtcatcaca tcatcagagg atgatagctc    37440
ttaatgagga tctaaaattt gcaggtaaga tatccctgcc tctgacatga gatagatgta    37500
ttgcatgcta tttaacatac aactatactg agtgtgcagt tgtatgtaaa agcattgttc    37560
taggtattgg gttgaaagtg gatcaaatgc tagacaaagg agcgtacaag tcttgtaagg    37620
aagacagctg ccaagagaga agaaaggatg gggaaatgct gcgtctacta agttcaaggt    37680
tctgaattgg aaagctgcag ctattgagga gaagagtctt ttaaaattcc taagggtttt    37740
ttgttatctt ttattgatgc aaatgctatt ttgtggcata aaccttaata attttggggt    37800
tgaaactctt atcaggataa aatgatcctt ttctatccca agcttaataa atattgttta    37860
agtacaaatt aaatatatga aatctgccca tctatattat aaatgtcata tggcagaaat    37920
```

-continued

```
tataccttga cttttggttc tttcacaaaa ccttaattt tttttttttt ttttgccttc    37980
aatgaatttt gtctgatttt acattaaaag cctgtaattt ctcaagtctt gagtctgggg    38040
agccgtcgtc atccttttt cccctctccc ttgtcttctg gatgttcaag cgattttaat    38100
tagatgttgg gcttttatgt caagtgctgg cattgcactc catgataatc cagggactcg    38160
gaagcacatg ttatgcgtca ccctgggttg gtgcagtgga actggggtgg gttgaagta    38220 gtattctaaa tctgcttcct gcgatggggt aggtcaggtt gtcctgtgtt gacaaggaag    38280
aagtctgggt gaggaagcgg gatgaaagca gaccagacgc tagagtccac tttcaagtcc    38340
gatcccagga cctggcttaa agttaaagaa cagcaaagat gaaaggtgcc gcacagcagc    38400
acaggtcggt ggccacgtta atgacataga agcaagtgc tgtgaattca aagaaagga    38460 cagctctgag ccagagtact tggtgacttt gctcaaacaa atccctttct ggcaccccca    38520
ggccttccct cccgcttcaa aaaaattctg aattgtgcca atccattgag gctcagctca    38580
aggccatccc atgcctttcc atcgtaataa agccttgttt cctgggcttt aaacatattc    38640 ctttttctt aggtacagat tgaacttttt taaaagggaa gttgtcagag gctctgtaaa    38700
acgttaaatc aaacctgctt tgttttaggg atggggtagc ttggaatcag atttgctcct    38760
gctatggact gaacatttgt gtccccccaa aattcctatg ttgaagccct aatgcacagt    38820
gttatggtgt ttgaagggag gcccttggga ggtgattaag tttagatgag attgtgtgag    38880
tgaagccctc atgaatggga ttactgtcat cccaaaaaga ggtagagacc ccagagcttc    38940
ctctctcttc accctgtgag gatacagcaa gaaggaagct ctctgcaagt caggaagaga    39000
gagggctctc actagaatac acttgtactg ccaccctgat cttggacttc ccctccagaa    39060
ctgtgagaaa caaatgtgtg ttgtttaagc cacccagtcc ctatgatttt attagagcag    39120
cccgagctcc attctccact ccctggcttc ctgcatggac tttgcaacca gagcttcacg    39180
gggtatagtt taatagctgt ttctctgtaa cgtagccact tttctctttc caggtctagt    39240 tttgacccctc ataacacttt gttaggggag atttgagggt gaggaagttg gcttgctttt    39300
cttttcacca tgtctcagta gaaacagaag cagaaaggcc ctgagatact gagcccacct    39360
ttctcagcag ggtgtgacag cccggagtac cctgggctga ggaggccagg gctggagggg    39420
aggctcccac ggtggagggg ttgaaagctg ggttgtaatg agctgctttt ctgtagatgc    39480
ctaaatgatg tgggttgaga aatcgtgatc ttagctttta gtagtatatt tttctgttta    39540
tgttaggtga gtcatcagtc tgtctctgac tatgttcaga tctggaagtt ttctggaagg    39600
aaatttgtta ttgctgtaat agtgtaggtt gttgatctgg attagcaggg agcggcccct    39660
taatacattc ttaagaaaat ggtatttagt tcagtctttg gctttgaact ttgcctttga    39720
caaagatgaa agtgcgactt gactggtgtt tgaaaaacat ggtgatatgg ccaggtgtgg    39780
tggctcatgc ctgtatccca gcacgttggg aggccgaggc gggcagatca cctgagatca    39840
ggagttcgac acctgacttg gtcaacgtgg tgaaacctca tctctactta aaatacaaaa    39900
aaattagcca ggtgtggtgg tgtgcaccca taattgcagc tacttgggag gctgaggcaa    39960
gggaatcact tgaaccctgg aaggcggagg ttgcaatgag ccaagattgt gccattgcag    40020
tccagcctgg gcaacaagag cgagactcca tctcaaaaaa aaaaagcaag ttatattaca    40080
ttttaaaact ctatttaatg gtcaggtcat ccatccataa tgggtagagt cattgcttaa    40140
ttaatttaaa acaatgtatt taaaggtac ctttgttccc tagtgtcaca taacgtgaaa    40200
tatccaatta aggtaactgt aatgtaaagt aagtggctaa aaaagtgctg aacgccaaag    40260
```

```
gccagagatt caacctttg tgtgcattag aatttcccaa ttgttcaaat ccaggttgct    40320
ggatctaccc cagagttttt gatccagtag gtttggggtg ggaccaagaa tttgcatttc    40380
taacaagctc ccaggtggtg ttgaggctga agctcgtgtg gggaccacat tttgagaact    40440
tctcccgtag actgaactca tggtctaggt tctgtcagct gtgacccctg tgctgctgga    40500
gggagtggtc agatgtcctg acctctgtgc ccacagtgag gtccaagctg agtaggtttg    40560
accagcagct gtaatcacag agtgaacaat gtaaacgacc aatgttgggt ggtctgacat    40620
cttttaaaaa aaatccacgt ggatgagatc acagggttaa gtgtgggcag cagtcagggt    40680
aactccatgt ggttactgcc catgcactct ctgctgtttt tcacctcttc ttcagagtgt    40740
ggtcaggatg gtggccttgc ccagcacagg aggcccttt ccttctgacc acctgacctg    40800
acccacctct tagcatctgc aggcactccc tgtcccttcg ctgggccccg tggggaacta    40860
cttgcagtca tcaaattcat catgctgctt tcttttaatt cccacacttg ccaaggtggg    40920
actgccccgc atctccttcc cagtcgtgtg tcagaactca gcactggacc tttccccttt    40980
ccccactccc accccctcctc accccgacga acgtctcact tgggatcatc tcttctgagg    41040
ttggacctgc acagccgccc tctgcactct cgccaccta tgggctgccc ttgacccctt    41100
ggcacacaga cctggaagtt ggcctgctca gctgtctcct tagggggtgga gcttggtttt    41160 cttcatcac tgttctgcga tgaattgaat gcatgattgg tcacaggaag gtaggggagg    41220
gataaacacc ttatgatatg tttcttataa ggttttatat gtagaaagtt atatgaaagt    41280
gtcagatatc tatatatgaa gtatatgtga agttttatga tagttttgca taatttaaga    41340
ataaactctt taaaggagct gagtcccaat cccttgggtc gagagttgcg tggctcccgg    41400
ggcctgcttg tttccttcca ctctgcgtgt tcgttgctgg cccctcatag gctgtcccag    41460
acctctttga cttctctcct ttctgcccag tcttccctga gacgctccag gctccctggc    41520
ctcctgcttc tcggagcttc tcttgtgttt gttttctgtg ctcagggcgc catggtgcta    41580
taggccacag aggaggcgtc tggggtccct cggggcaggt gcagcaggag gaagccgtct    41640
ccgagggcat gaccttggaa ctgagcattg acagaggaga gtcagccaga caaagaaagg    41700
ccaaaacccc accctctcc caccctattt ctacgtgacc atgggccctg acacagcaa    41760 gacggtgacc ccgggcctcc tattgttgcg aggagcccct gggaaaatgt tggcattttc    41820
ttcatagaac aggtttctct tctccagtat tcttcagtaa atcaactttc ttttttatcc    41880
ccaaccccag tctgattgcg aagaagtcta agcaacagaa agattttgcc aaatagatta    41940 tctttttag aacaaaatag atcatgatat taataggaat tcagcactta ctcttgtcta    42000
agtactgttt ttaagtgctc tcaaggattt tcatttaat ccccacaaca aagctgtggg    42060
gggtggatgc tattattatc ggtgatttat gaatgaggaa actgacacag agggggtggtc    42120 gaggagcttg cccattcct ggtagttagt accagggctg gcatcatcag ttgcctgctc    42180
cttttcctct ttgcttttgt gtccattacc ccaaggcatt aggatgagcc agccaagttc    42240
tagtcctgga ttcaccacct aattagctct gtgtcccatg tcttgccgtg agggataaa    42300 accaattcct agcttatccg ttggtggtga agatgaaatc agtggggtac ttgtaaagca    42360
cactgcccag cacatagtaa gtgcccagaa aatgtgacgt cggacctctt taagcttcag    42420
tttccacatc tgggaagaga gggggagttg agctaagtca ttttccagtg tccctttcag    42480
ctccatgttc ctgtgagcac tgacagtttc cccacaatmc tgaagaaaga aggaaaataa    42540
gggcggggtg gcgaaggtcg ccactgtgac gtggctgctg gtgggaagtc cctggggagg    42600
caaggcccag cttcccagac acagccctca ggtgctcatc ctggtggcac tgaccagggg    42660
```

```
ccatggtggg cttttccacc ccaccatgtc tcataaaatt acaagaacca cagttgaaaa   42720
tcagtgttac agaaatggta ataggatagg gcaaactgtt acaaagatca gcacttaaga   42780
ttctggctga ggcggaatat ttgtttctct ttagttttgt tgtctttaat caagaactga   42840
gagccctgac tttcagctcc tcaaaaaata cagcttcctt ccccttgcag atgcaaaaac   42900
aaacgccact tctttccaag cataattttc tcccatgcgt tatctcctgt ctacagcttt   42960
ttcttgatcc ttctccagct cctgtagacc tcccatttag agccaccagc cgcccatcac   43020
tggggctgcg cagagctctt ggtgctctgt gccctgggct cgcccaccca ggcctgttct   43080
ctgngcctct tcctggttct cttccctgga cttcccactg ccgtgtggnc ttcagtgctc   43140
ctctgagctg ttgtcatgac ctctaaccag actgagtcag gactttttc ttcctcatct   43200 ctaagtcatc cttacacagc cttggaagtt taccctaaat ggctattttg ggagggagtg   43260
gggataaaga tctgcaggcc tcttgctcct ggtccttgtt tctgcttatc ttggcttctg   43320
tttttaagtg tgtgtgcacc tctttcctca tcacaccctt ccccctccgta tggctcccat   43380 ctcaggcaga gttaggtgct ctgttctgtg tccatagctc tttttcgagc ccttcttctc   43440
actgtttggt agtggccttt catgtgtgtc tgatccacta ggctgtgcac tccctgcctg   43500
ccaggatatg gttaaagtgc taaagaatgt atatatgaga tcacttttgc ttaaaaaacc   43560
cccaatcttc tggaattccc aatttctaac caattaatat gtggattgac tagaccttaa   43620
gcaaccaaga gtcagccagc cttgtcttct atattcaggc gcatactatc tggtcgttag   43680
acaaaatggg tcattatcag tgatgagtta ataattacct gcacatcttg tttatgctgg   43740
ttctttacct aaagtggctc ccatcaatta aacctgtatg gatttacct gttcttccag   43800 aaccacccca ctttccacaa aaactgacaa caatgatggg aagaagaatg gtagttgaca   43860
ttttattaaa tgtttactgt gtgcaggctt gttttttttcc acacatttac ctacttaatg   43920
ctcacaataa tccatatgaac tagtcagttt tatgcagatt tcgcagatta ggaaactaag   43980
gtggcaagtg atcagataac ctgtttgagg ttgagtagct agatcatggt agagccaggt   44040
tcaatcccag atacctggct ccagggccca tgctcttgac cttataaacg gctgaaattc   44100 atctttttt gctgaacttc cagaacactt tctttgtatt tccttattt tggtagtctt   44160 gtacttctct gctaccctga ttcatacttg gatttctagc agcatgcctg gcatgaggca   44220
acaacttaac agtatttctt tataccaaat gaatgttgtc tttttttttt tttttttct   44280 tgagacagag tctcgctctg tcgcccaggc tagagtgcag tggcactatc ttggctcact   44340
gcaagctccg cctcccgggt tcatgccatt ctcctgcctc agcctcccaa gtagctggga   44400
ctataggcgc ctgccatggc gcccggctaa ttttttgtat tagtagagac ggggtttcac   44460
cgtgttagcc aggatggtct cgatctcctg acctcatgat ctgcccgcct cggcctccca   44520
aagtgctggg attacaggtg tgagccacca tgcccggcca tgaatgttgt ctttaaaaaa   44580
ttctgttttc ctctagctag actgtcatat aatgcaactg taggaaataa tcaggttctc   44640
tttggagtat tttccataaa agatccacag aagtcatggc agggttgaga gtggacttgg   44700
gcaaatgaat ctgttcattc attgaatatt ccatgcatat ctgctgtttc ccaggcatgg   44760
gatatggcag ggaacacaga aatctctgcc tcctgggctc tgctttctgt tgtagtagag   44820
gtaaagctgc tcatactttg taaacaatat gacaacatta agtctacatg gtcattttac   44880 tttgttttt tctaagaaat tttgagctgt tcgtaacaac agacgctgca gatgttaatc   44940
ccgttgttgt taacttttct ccagagattt aatgttcaat tttctccttt ccagaatcga   45000
```

-continued

```
tttatgttgt tcaaacagag gtttgagaat aactggaatt ttttttaactt cttttttttt    45060 tttcgcatgg agttcagaat tttcaagagg gatgaagaga gttataaaat gctctatggt    45120
gggtaacaca cagaaaaagc cagaaaattg gagaataagg atctgtctac tcgtttcctt    45180
ctagagctcc tctttcttac agggcactta acatgtgatt taatgtcgtg tctttaaaag    45240
gaggagaact gcagttcaga acttaatgtc agtgctttgt gaaagtgcaa gaaagaagcc    45300
ctgtattctg cacttgagag agccagatac tgggcagata ggaggtggtg tgcacgttgc    45360
tttttgtctt tctcgatcat ggcattgatt ctgttcataa caatgatgca atgtcatcct    45420
cttccccaca catttgtgtg cagatagaaa gaatgcaaca gcacagagtt gttggggaat    45480
aatttggcat ctaaaatatc gacataccag catagatcat atttatgact ctgttgggag    45540
tgtcacagca atgatttaat aggaggcagt tgtctccaag gcctcctgaa ttatgactgg    45600
ttttaaaatt cttagaaccc attggaggct attgtttctg aaaggctaca taatttaagt    45660
gctccacatc cgtcattata ggagatgtca gaatagtaaa atctaatcct ggactaagtt    45720
gttatcgcag ccctttggtt tggtggcttt gccgacttta taaatatgcc tgtcagtgcc    45780
tgtggtctct acagttgggc agtcggcggt gaatatcatt tctcacattt tacactgggg    45840
gactggaacc cagaaggcat atgttttccc aagaggcacc aacacagttg gcccatgagg    45900
tagagcagcc cctccttcgg ctcagcctcc gctgcactga gccaagccaa gcttcctaca    45960
ctggcctctg tgcagctgtc tctcagcaag aatgcaagtc ggggagagaa gccggatccc    46020
tgggattgtt ctagagagta gaaacctcag agtagccctc cttagaccac ctaacgcatt    46080
gcatcgctgc atacatgtaa gggactcaat gctggtagga ttggcttagg aatgatgcaa    46140
gtgaaaacag tgccccggtt tatcattaga acaaggttct tagctgacag ttgcctcaga    46200 cttttgatttt gttctccttg acctgccact ccactcgagt ccacatctct caagactgca    46260
cacgcctgaa ggaggactga ttacaaacca aagccttgtg cccagtctgg atcttttgc     46320 attgttgaga aagcagctta ctttctttgg actgattcag caggccaaat ttagaacaaa    46380
gatttttaac tatctcccett tataaattac tgagctattt tgtagccagg ctactcttaa    46440
tatgaacaaa aaatattata caaatttgtt gttaatcgta aactataaaa aaatcagtaa    46500
ttgttaccac gtgaaatgaa tttggataaa agagatacgt ttttgccect tcccagggtt    46560 taggagagac gaaatggtga gattttagct ctgaatcaga ggttcttatt agaggtggtt    46620
ttgttcctcc tgacccctag gggatatttta gcaatgccta gaggcattga tggtgggcag    46680
atgctactat gccctctgct aaacattcta cagtgtataa aactgttcct cctgacaaag    46740
aatcatccag ccccaaaatg tcagtagtgc tgaggttgag aaaccctcct ttaaactctt    46800
gggtttattt gctgacctt acagtggatc agctttatt tagttcatgt agaggtgaaa     46860
ttaatactag tgctcaaata tgtctttgta ttctggactt ggcctggatc ccccgaccaa    46920
atttgggaca agtcctgcc atgtgttgag gacctgaatt caggcagcta acaacagtat     46980
ttgaactgtg ttttcagtgg tgggagtgaa ggagatgagc cgacgtgcta gcaagcgcat    47040
agggttgcat gaggaaatag agagtaaagc tgcagcgtgg agccctgcta ttcagagtgt    47100
gcttggagaa acagcagtgg aggcattact ggggagcttg atggaaatgc tcccctcaga    47160
cttgctgaat caaaatcttt aatttagcaa gatccccagt gaggcttgtg catgtagaag    47220
ttagagaagc acgggtaaa ctcttctttt ttttactttg gaggaaaata caccttttt     47280 cttattatgg ctctgaccct tactagctgt gtgaccttgg ccaagttata aaaccctcact   47340 gcaccttatt tgttttagct ggaaaatgga gatcataata tcacctgtcc tatgagattg    47400
```

-continued

```
ttgtaagaat caaacaagct tatttatgcc aagaacccat atggtaaaag ctcaacaaac    47460
tgtcactagt gataataaga aaaagatcac aaaagtagaa acattaggg agacagctta    47520 ggtcttaaat ctcacagttg tcgtccccaa acaatacttg tattttttgca gatccagttt    47580 ctctgaatac taaaataaaa ccggagtttc ataaacttct atagacagtg gtccttgtca    47640
gtagcccaag tggcagagag tacatggatc tggggacaaa cagcctctac tgttaggaat    47700
gttccatcct cctggcctga gttacacctg ctcattgtga ttccgaattt gaaaggaaca    47760
cagtaggaat tttcaagacc ctgggaagag aaggctgtg gtaaacagga aggatgagat    47820
tagaagaagg agtttaggtg aggtgagccc ttgtttttact agtagggttt aagaatatcc    47880
aagtcagctg gacatggtgg ctcacacctg taattctagc actttgggag gccgaggtgg    47940
gcagatcacc tgaggtcagg agttcgagac cagtctggcc aacatggtga aaccccgtct    48000
caactgaaaa tacagaaatt agcagggcat ggtggcgcat gcctgtaatt ccaactactc    48060
actcgggagt tgaggcagg agaatcgctt gaacttggga ggtagaggtt gcagtgagcc    48120
aagattgggc caccacactc ccacctgggc aacagaatga gattccgtct ccaaaaaaaa    48180 aaaaaaaga aaaaaaaaaa aagaatatcc aggtcaaccc cacctaaccc tcagcggggc    48240
tcccttctgt tgcctgggtg ggtcctgggt tctcttgacg cacacgagat tgtgagagtg    48300
tatgaaaaca ctgccctcgc tatcaggaca gcgcctgcca tgccagccag aacacatcat    48360
aggaattgca aaactctttt gcaaaccagt gagagatatg cttccaatgt gaggtaaagc    48420
agaactttaa tcacagctgc agtgttccac agaattccaa gagccaagat ggtaaaagaa    48480
taaaaaaaaa gaaaggaaag ggctcaaatt aaagacttca agctgcagaa taagattaaa    48540
taaaaggatt caattgaact gcatcatatt cagtaatgac taatcctaag tatacagggt    48600
ttgggggtga aaggatttgt aagtgttttg caggaaaata ttttttccat cttttcatttt    48660 aattagaata gatttgcatt attttttctt agtttttatt tttaaaatat ttattgccac    48720
aaatttagaa aatacaggga aaacataaat aacagtacat gtaaaccaat attttgtccc    48780
ttcttttgtt caacagctat ttctcaggca cctgctgggt gtcagcagct gtgctcagtg    48840
tggtgaccaa aaccccttgtc aacaaggcag caaggttcta acctggttag ggcttacagt    48900
tgagtagctg aaattttgat ttcttttctg tgcccctagt aaagatatga tagcaaacaa    48960
taagagctat ttttttttatt gtgttcttac tctgtgttgg gccctgttct cagtggttta    49020
tagcctatta actcagtctc tttaccacca ctctgagggg aggctctgtc atacccactt    49080
gacagatcgg gaagtggaag catcaggagg ttaagcaact tgttaaagat cacaaaatca    49140
ataatgacag agttttgatt agaatcccag cagcctgtct ccagaacctg ccctattaag    49200
tgcagtgcaa ctgtactgcc tttcataata tgtatcaaat tgagatgata ctttataatt    49260
tcaattcttg cttttctatt gaacagtaca cagtaacatc ctcctataat gcatataaac    49320
ccccaaaaga tgtagaattt taatttattc atttgtctga taggctcata atgaaataag    49380
actctataaa gctgtgtaat ttagatatag gaaacatttg gattatagtg gtatgtagtg    49440
ggaacaaatg gtcttctgaa tcaggaagac atgagttaga gtatgccggt gtacctcctt    49500
actcactgta tgaccttggg caagtttctg aactttagtt tcctttccag gctaatatct    49560
gccttctgga cttgtcatca ggattaaatg agtctaccta tataaaatgc ccagcgcagt    49620
gcccagcacg tggtagaagg tctgctagtg gttactgtta ctgctggcta ttaaatacat    49680
tttaatcttc cttcagaata cctggccaga tagcacagtg gttaagaatg cacatgaaag    49740
```

```
ccagactgtt gggttccagt cctggctcga ctccttccta gctatgtgac attaggcaac    49800
ttacataaac tccttgttcc tcagtttgca tttcttaaaa actgcatagt tatcataccc    49860
atgtcttaga gttttgtgag tgtaaattat tgtatataaa gctctgagaa cagtttggta    49920
cacagtaggc actgtatgaa catttttctgt aattatcaat aatataatta ttaaataaca   49980
ttttcagaag gagataaaaa tattacacct taaaaagcag gtatctttaa attcttcctc    50040
agctactgaa gttttgctta ctatttgaca tatcatttgt ttcacgtttg tggctcagac    50100
gtggcttatg ccaatgcata ttaacacagg aatttttaaat ttggtgatat tattatattt   50160
tatctgaatg aacagaattt gctgatttga cactgtgttt gaatgtgcat ttttttgttga   50220
aaaatgacaa ttctggaatg ccgtctccct ttccagatta ttcagagctg ggagagcttc    50280
ccccacgatc tccttttagaa ccagtttgtg aagatgggcc ctttggcccc ccaccagagg   50340
aaaagaaaag gacatctcgt gagctccgag agctgtggca aaaggctatt cttcaacaga    50400
tactgctgct tagaatggag aaggaaaatc agaagctcca aggttggttt gccatcttga    50460
tattgaacag gcctggtctt atcttggctc tgaagttaat cacatcagac ataagcatgc    50520
tgtcttaaaa atacagcagc acgatagtct aatgtataca tctatctata tctgtttact    50580
ttttcagagt aatattaaca ctgtttactt tctggtgatc taatgatagt ttcaccaaca    50640
atattcatta ttcctctatg gtcactgtta gtacagtgtt tagaacttct gagatccaag    50700
ctttaaatct aagctctaac acgctgaaag gtgcttttca ttttgttttg ttttcccctc    50760
tgtctctctc tctctctcta ctttatcctc agccatggtc tgtgcctgtg tgttaggtat    50820
gaactttttct tgtgtaagtc attaacatac gtaacttcac tctgtgtgct ttttcagtga   50880
tttgcaagta atctgaaaaa aaagaattag ctgagttcta cctgtactga tatcaatagt    50940
gtcaaaatat gacatgaact ttgaaagttt agattttgtt catttcctgt ttccatgctg    51000
acactggaac caattaatgt tatcttcaaa gtagcttaag atgcaaagtt tacatactct    51060
ttggaaagag catgagtctt agggtatcta gagaactgcc cggtgataaa gtagtgaaga    51120
ttttgagcag gaagtctgca taatctcttt caaagggaag atgtagcaga tggttcagtc    51180
accctgccat tgccccagaa caattttgga attacagtac atttcattca gcatcattct    51240
tgattgcaaa ttttgatctt ttaaaatgac cttgatgctt gtatagagct aaaaagtcat    51300
taagacacca actctgagga ataagctcct gagaatgtgt tgcatctgtg agtttcagtt    51360
gcatagctag tgtcatagcg agtggataga cgttctctgt gcatgtccct acaatgcttg    51420
tgagttatga caacactgtg tacgagcaac atagtttctg cagttgaaaa gtacgaattc    51480
atagaatgta aagagatagt gtctatatct tttgactgaa aacagaaaat gagatataaa    51540
ggaataagac ctttcgacat gaaagtaacc ccacagttgg aataggctag taagcttttc    51600
aacatgcagt tttgaagctg agaaagacgg gtcctctcat cagggtgctg tggaagatga    51660
tagcacactg ggggcgttt agagcaggtg agtgctgttt tcttccaacc cagttttttct   51720
gccactttct tatgttttttg tgaaggtaat tttaaaagca gatgtctaaa agatgtttgg   51780
tagtgatggc attactgcat gtgtcatcag ttaaatgaca gctcgggagc acagcagtta    51840
tgttcgtgtg tatcttggga ttttttgttga agaggaaaaa ggcagttatg ttcatcatgt   51900
aggtcaaact ttaatgccaa tactggccaa tattcttgca aatgacagcc atgtaaaatc    51960
agggcatagc tataaaatgg gaacggtgct cacagctggc ttctttgtgg tgaggacagc    52020
tataattggt gaggcaaaac cagtgtgcca caaaagcaga atacattctg ctgtgcaagc    52080
aatgaccaga cagactagaa tgaaaaggca agagtttcct aaggttacct ggaaccccctt   52140
```

-continued

```
gccaggtgtt gcattaagtt tactggccct tgccaacatt cttctaatgc ttcctcattt    52200
catctggctt cttggcagtg ttcagttttt gtggtctttt attttttactg tttgacttca    52260
tttctcttct tagctctgta aagttccaca tgtgtttatc tttgtggtga aaacacaata    52320
aacttgctta atataatgtt ggaagtatta atccattgta ttagtgtgta caggacctgg    52380
attgctgata aaaaataaac tagcaataac agcctgattg cttaaaaata tttagtaagt    52440
tttgtcgggg tggattgggg cagggcagaa cttttacatt aaatatagat gcaagatttg    52500
ataagaatca gccagagtgt acagtaagta ttcacttaat gttgccaata ggttcatgga    52560
aactgcgaat ttaagcaaaa tgatgtataa tgaaacaaat tttactaagg gtttattgat    52620
aaaaacaaga gttaagttcc tatggcatat ttctgggcac aaaaacatca ccaaacttct    52680
aaataaagac ccaagacact tctaatatta aatattgatg taaacgtgag atatgcaaac    52740
atttaagcaa gattaataca aatatgataa ttattggctt ggcacagtgg ctcactcctg    52800
taatcccagc actttgggag gctgagacag ggagatcacc tgaggtcagg ggttcgagac    52860
cagcctggcc aatgtggtga aaccctgtct ctactataat tacaaaaaaa aattagccag    52920
gtgtggttgt gcacacctgt aatcccagct acttggaaga gtgaggcagg agaatcgctt    52980
gaacccagga gacgaaggtt gcagtgagcc aagatggtgc cactgcactc cagcctgggc    53040
aacacagtga gactccatct taaaaaaaaa aaaaaaaga aagaagtaat tattttttcca    53100
cttattccac ttcagggtct caggggggcca gaacctatcc ctacagcttg ggatgcaagg    53160
caggaaccag ccctggaccg aatgccattc catcttgggg tgactcacac acacactcag    53220
actgggacca tgtagacata ctgattaacc taatgtgcac atctttgaga tgtgggagga    53280
aactggagca cttggagaaa acccacacag acatgaagag aacacaaact ccacacagat    53340
aatggccccg ggctaagaat ccatttttt cttgtcaaca ttataagaaa gcgacattga     53400
gcataaagac attatttgag gacctgctgt actatgtact tagagagata ggcattctat    53460
cttgagttcc ttttttttct cccttcttga aggaaggtta aattgcatct gagatggctc    53520
ttgaaattga tcagggggttc aagctgactt gcatactctt tgggaaagaa tttagaagga   53580
tgtgtatgag gaagttctta tggttaagcc tgtttcctga cttgaataga tgaatcaaat    53640
attttttact attctggaag catcgcattc tggaaagaac catactatgt catctcagtc    53700
tacctcactc cattgtaggc acttggaagc tgaagttgtg atttctccaa aattagatag    53760
ctaattttca ttggtgttag aacaaaaagc gctgcctctc tttgaagaca ccagtcctcc    53820
accgtcctcc tctgcaaggc cgtttttcccc cccctttttt tttttttga gacagagttt    53880
tgctcttgtt gcttaggcta cagtacagtg gcacaatctc ggctcactgc aacctccgcc    53940
tcctgggttc aagcgattct cctgtcttag cctccagagt agattacagg cacccaccac    54000
cacacccggc taattttat tattagtagt agtagtagta gtagagatgg ggtttcacca    54060
tgttggccag aatggtctcg aactcctgac ctcaggtaat cctcccacct tggcctccca    54120
aagttctggg attacaggca tgagccactg tgtccagcca atttttctgt attttttaaat   54180
gaagatgtga gcagcctaat gtaagatcac aacatgtgat tcaatacagc cgtggcttgg    54240
tgttgacatg ttattaccag ttgagctaat ccatgtaact cagcatttta tgctttacta    54300
agattaaaat gatgtgataa cattaaattt tgaattacag ttgatgtttt ttatttaaaa    54360
aacattttc ttagttaaat aatacatgat ggtttaaaaa tcaaatattc agtgcaattc     54420
ttctaaaatc tctgcaagtg tgggggtcat ttaattgctg agcctcccag cctattagct    54480
```

```
ttccattctg agctttcaag agatggtggc agctggcaag gcagttttgt ctgggaaagc    54540
cattgttaac agagcagaat tggggatgga gcagccatag cccacccacc agagtaggca    54600
caaatcagac ctgaacgtta tcacaaagtc caagttggct cagacatttg tgttaaatca    54660
taataaatat tttagagaac ttggttgcaa atttacatttt gatctcagtc agtcctcttc    54720
ccctatctct acaagcttac aaaccgcatg ggtgtgtggg ggtcttatttt aatattgcga    54780
acagctggtt cctgtatctg aagttcttgc cctggagcct gggtgtttgt tgtagttctg    54840
caccatctgc cttggttgat aaggcatttt ggaggccact gatttttaggc agcagtgttg    54900
ttaggatacg gaaacagcag gatgtttgtg gattgagcct tttcagctga atcttctggc    54960
cagttctttc tggctgtgtg aagttgtgtc gactacagag caggatgctc atgttgcctg    55020
ctgggctctg ttagggtggc cagacgtgct tgtagcagcc ttactgccag ggaacgtac     55080
gttggcatcc agagtccagt gctgccgcca gttgcagtgc agcaaggcta gccccaaacc    55140
tgatttgctg caaggattag ctcaactcta gtgacatttta ttgtgttttc tcatagccca    55200
aatcacagcc aaaaaaaaaa aaaaaaaat ctaggggttga cattttttaaa aattttttta     55260
aaaaacattt ttcttggtta aataatacat gatggtttaa aaatcaaata ttcattgcag    55320
ttctaaaatc tctgcaagtg tgggggtcat ttaattgctg agcctcccag cctcttagct    55380
aaaaaatcta gggttgacat ttttaaaaat gtattcaaca gagtacgagg gaaaagatta    55440
aagatggtgg atggaaaacc ataaaagctg agaggaaggc agcactgggc ttagagtcac    55500
ttggcttccc tctagctagt aaataaccag caccaaatca cctgatcctc ctgaacttca    55560
gtttctgtgg ccatgaaata agaggttggg tccaggaatc aatgtaaatt gtcaatttaa    55620
catttccctt tattgatatt actccccccct gggcttgata atttagttat aattcttcat    55680
gcagctttag gttgagtaag tttggtggga aacagtagct ctcttcatat atttgagaga    55740
tgtcatttga aaggggtaga tttattcagt ttaactccaa gaagcagaaa tgggacccat    55800
ggtagaagct accaaatgga ggtttggctc taaataagaa aacgatcttt ggagtgcctc    55860
tcctagtttta gatgaaaaaa attgcatcaa gttgtaacca tgctagtcat tgggaatttt    55920
attaacaaca cgtagctcct gtcctgggga ggctcatagt ttgatagggg taagatggaa    55980
agaattgggc agatgtggat tatgtcttag cagtagagcc aacagagtat gttgggggtg    56040
aagggggtaag agaaatcaca tacctcctag gttttttagca ttttccaaaa tgaggaaaat    56100
gggtagaggc atggacagtg acttatattt agacgcgtta agccagttgt aactgcttga    56160
cgtctcagcg ggataacaag taggcagcca tgttgtgtaa tggaaattcc atagctgtag    56220
cctttactaa tgcgctctgg aatggtctat tccagcctct gaaatgatt tgctgaacaa     56280
gcgcctgaag ctcgattatg aagaaattac tccctgtctt aaagaagtaa ctacagtgtg    56340
ggaaaagatg cttagcactc caggaagatc aaaaattaag tttgacatgg aaaaaatgca    56400
ctcggctgtt gggcaaggta agcttcattg ggaagcatct agtcaacctc acccctcatt    56460
ggtgattggg gagaagtgtg gaattaaaaa aaagtcaagt ctaattttag tggccatctc    56520
ccttcttttc atcacatctt aatctatttc catataccctt acttaataga catgagtttc    56580
accacctttc atgattcctc ttaattaaaa ttcccagaag gccgggaaat aggaagaaga    56640
cagaaaaacc caagggtttt gttgcctata aactagataa tgatttgatg atatactttg    56700
aattaaatta taaactagaa actaattgta tggcttgtct ctgggtactc tagggagaca    56760
acatagtgtg gggagcacag acttcagaca ggtggtcttg ggcttaaatc tcaggcctgc    56820
cacttacttt gcagtgtgat cttagacaaa tgcctcaccc tctctgagct ccagtttcta    56880
```

-continued

```
caagtgtaag atgtgggtgc tgacagtgga tgttgtgagg agcacacagc atgtgtctgc    56940
tatactgtaa ggccttagag agcgggcagg attcactgtt ttttcagtga gatctgccag    57000
cccaaactgt tactggtcca agaagagata agtacagaac ttgaaactaa gcttttggaa    57060
atgtttccag caatgtgaca cagtgatcct aattaaaaat gtggacttat attttgtcca    57120 tctgttttt tttaaatttt gttttctac taatttattt ttactgtatc gtataaaaat       57180
atcagcctgt agtagattgg aaaattttta aaagaaaaa aaattgatgc ttcacagata      57240
gtttgagaac cgctattttg aagcttacct tcagtcatta ttagtgttct agtcaaacaa    57300
tgatttcttt aaaaatatat gttaatgtct tctggcaaga gtaaaagcct gagtctaatc    57360
tgattctatg ctactgagtt ctggttgagc tcatcatgaa taaccaggtg ttctgaataa    57420
gggtttcaag tatgtataga atgggttttt cctgagttta tcagttgtgc agtgggaaaa    57480
cgttgtatat gcactttttc tttttgaga tgtagtttca ctcttgttgc ccaggctgga     57540
gtgcaatggc gcgatctcag ctcactgcaa ccctgcctc ccaggtttaa gctattctcc     57600
tgcctcagcc tcctgactag ctgggattac aggcgcccgg caccatgcct ggctaatttt    57660
ttgtgggttt ttttttttt ttttaagaca gagtcttgct ctgtcgccca ggctggaatg      57720
cagtggcgtg atctcagctc actgcaagct ctgcctcccg ggttcacacc attctcctgc    57780
ctcagcctcc tgagtagctg ggactacagg tgcccgccac catgcccggg taaattttt     57840 ttgtatttt agtagagatg gggtttcact atgttagcca ggatggtctc gatctcctga     57900
cctcatgatc cacccacctt ggcctcccaa agtgctggga ttacaggtgt gagccaccgt    57960
gcccggccaa tttttgtgt tttactaga gacgggtttt cactgtgttg gcaaggctgg       58020
tcttgaactc tggacctcag gtgatctgcc tgcctcggcc tcccaaagtg ctgggattac    58080
agatgtgagc cactgcaccc ggcctgcata tgcattttc atctctagga gcataaatgg    58140
aacaaagcag tgttttttac tatagttttt taggcatttt taacctttc tgaatttga     58200 catcaatttt agtaatcatg ggaagttatt gtttgttacg catttttccct ttctatggat   58260 aaggaaactt gggcttagag cagttgaata gtggcttagg gccacagagc tgggttcaca    58320
ccaccgtact gcactgcctc ctgttgaaca ggatctccag gtgcttatct cagaacacgt    58380
atgcagtggt gaagaccgaa gttctggatg gacaccagct ttcagtgtga ctttagcagg    58440
taccctcttt ctgggctctt gcccccttac tgatagaagg agagacttgc actgagtaga    58500
ggatcttgga gctgtcttgg agttctaata ttccttgcac ctgtactttt tcttgaggtt    58560
tacctttaca ccaaatgacc ccaaattgct gttttgaaaa gggagaaagc agagaaaaga    58620
atgagtctgt tcttcccca ttcacagttg cctagatgat caccttcagg tgtcttttgct    58680 tctgcgaaag gcaaattgca tgggtctgtg acagctattc caaatatttg agcttcttag    58740
aagcctggca cctggatatt tgttttcac tgggcatatt ttgtgggggc taatagaaat     58800
actctaggaa tctggaccct gggtagtgaa agttgggcac agatgattga gcattctgta    58860
tactggagtg agctaaggct gacctggaat ttccttatgt gttgcctgac tttgccacat    58920 cacttttac tgcagaagct ctaaccataa agggggcttt gtcagtcagg tggttttaac     58980
acattaagat ttaacaactc caaacaaatg agggcggtct attttgtggt tcagaataaa    59040
aatgtgaatc aaaaaatttg agcctaaatt tgaatcatat ctttgacctt tgaagtagag    59100
gccaactcac ctcagagacc ttgtaagaga ggacagttgt gtggattaag aggcccttcc    59160
tcatagtgac ataaaagacc ctgaagtgat ggaaataaag gaatttataa aattttccca    59220
```

```
gttaaaatta gatgaggggc caggattagg gtatcaattt aggagaagat aacataatcc    59280
tatgacatta tagataattc agtttagtac acatcaaaat gatttctcta aagatatcta    59340
gatagaacct tataagctgg aatgtctttt ttaggaatgg gattgcagag gggctgcctg    59400
ggctgctgac agtaggggcc agatgcaaac tctgcttgcc tttgacccgg caatgccatt    59460
tataaaaact tactctagaa actaatcagc caaaaatgta ctgcagtaag aatgcttatt    59520
gtgacattgt ttaatagtca aaacaaaaca aaaacccaa catgtgacta tcccatgtca     59580
tattccttga aaatgacacc ataagtagag ctgtatttac tgacgtaaaa gatgtctaag    59640
ttgttaaatg aaaagagtac agcatggtct cctgtactgt tgatatttcc atgtgcgtat    59700
acatggaaaa acacccacga tgcagatgtc caggttatag acaggatgac catagggccc    59760
aacctggcat agccctggtt tatgactcct gtcctggcaa aattattaat agccttcctc    59820
ctcttcactg tcaaaagctt cctgctttgg atggtaaata tatgcttatt ctagttatgg    59880 gtggttttc actttcttct ttatacctct tgcatttcag aggttttttt gcaccacttt     59940
taaacagtga gtgtatatta tttttttaagt gagtaagaag ctatttacat ggggatgga   60000 ggaatggcct cctgccctcc cagacccgtc ctgcaagccg taggtgggct ccactgccag    60060
gtttctcttg ggttaggagt gaaggcagca ccatggtggg gaagggcatt ccaggccatt    60120
cttagcaaaa acattgggtc caacctgcat gatcctgtgc tttaaatcac agaatctaag    60180
cttactcctg aataccacaa tatctggtac tgtccagtga cacagccaat attcttttct    60240
ttcaaaaaat aaaggtctga taagacaatg ggaatgattt agtaatagga aattggacat    60300
ttcataactt gggaaaattt cccagtttga gaaaagtat tttgtgaaaa aagccccac     60360 tataaatcac ttatcatgct gactgttttc tagcccacat ttacttctca tcagcatttg    60420
aagtatttgt ggggagggtg tgcgtgtgtg tgtatgtacc caggatatat ctatgagctg    60480
gaatagcaga gggagacaag aaatagaata atagtagaaa gcagagatca gggtatattt    60540
gcttcctgtt gctaccataa caagttacta caaaaatagt gactaaagca acagaaattc    60600
ttctctcagt gttctggagg ccatagctcc aaaaccatgc cgttagcttg tctgtacttg    60660
gcctcttcca gcttctggtg tctgtcagct tcctagactt gtggtcacgg cactccagcc    60720
tctgcctcct tggtcacatt gattcccctt ctcatctcct cctctgtatg tctattataa    60780
gaatgcttgt cactggatat agggcccatc tggataatcc aggatgctct cctcctccca    60840
aagtccttac ttaattatat ctgcaaagaa ggtaacattc acaagctcca gggattagga    60900
agtgaacaca tctcttttga ggggacacca ttcaactcac tctacagggt cattatatta    60960
atgctgagat aaaattacag aaggtatagg atgtggtcat ggtttacagg ggccctgtat   61020
ttcttctaca ggccaactta aaaaaaatga tacgtgaaag ggaaagaaga aagtacttac    61080
tacacagtaa gtatttccaa gaggtggccc agtgagactt ttgaatctgt taataaaatg    61140
attactattt ggttcaaatc cacagatggt tattttatca ttaattgcaa gataggaaca    61200
caaaatattt tttctctagt ccccatttga gtagcagcct tgtttgacat ttctgacatg    61260
gaggacacca agagaaaatg gcagtcagca tccctgggct gtcactcacc ggcctaatga    61320
cctagggcaa gggacctgtt ctcactgcct ctcttttctt taccatgagg ataatcatgt    61380
ttcccttaga gggttatgag tatggtatgg gccaatacac ataacgtgca tggaatggcg    61440
atggtgcata gtggcctcgc aatcagtgct atctgctgct gctacctgcc agagcagaaa    61500
cttttcccaa aggtggccag agacagaaac cagagaaacc atccttctgg acaggctgtc    61560
tgagtggcag ggcagggtac aaagcggcca ctttttttcc cggatggaaa gaaagatcaa    61620
```

-continued

```
tgcctaactt ggaggcttcc tttctcccaa aagacaagaa agacttggca tcttattctt    61680
cagtcttctt gctctccccc tttccacctt tttggccttg taatagctga gtaatgagct    61740
aaagaatttt ggttcaaaac tgtcaccttt taaaattagg tttgccctaa ataacatcct    61800
tgactttaag agaattttct taagttttag acatttttaa tcactgtgag tattcaaatt    61860
aatcacatgc aaagcattag ttagaggctc ttggacattt tctgttttta gagctttgtt    61920
ggatgctcac atggcaatgt ctgtgcagtc agttcctacc cagcctctgg gctcttcttg    61980
cagcttatct tgcagaaaga agcctcatca gaattccaga atctcagcta tgattagctt    62040
actccacctc agctcagaaa catgcatgat tccctggagc taccaaacgt ggggcaggtt    62100
tcttgccgtc aattttgcct ctcacaataa cccttccagc cttcttgcca gctgctctct    62160
tccacatgca cccttgtgcc tgaggcaaac tgaatcactc tcggttccct ctctcttgta    62220
cttttctctt cctttccct catccttaag gctcggctca aatgaaggat tctgtggaac    62280
cttgattgct cagttagaaa tgagcaaact gtcgcaagga cagaaaacca acatcgcat    62340
gttctcactc ataggtggga attgaacaat gagaacactt ggacacagga agggaacat     62400
caaacactgg ggcctatcgt ggggtggggg gagcggggag ggatagcatt aggagatata    62460
cctaatgtta aatgacgagt taatgggtgc agcacaccaa catggcacac ttatacatat    62520
gtaacaaacc tgcacgttgt gcacatgtac cctaaaattt aaagtataat aataataata    62580
ataaaaagaa atgagccagc ttctctttca tctgagctct acttccttt gattctctct     62640
gctttctgag atcacatctt acatgacaat ttttcatact tggctttatt tccctagaat    62700
gttgttaatt ggcaccaggt tggagctcag gtcgtatact ttattccttg cagagtctga    62760
cagggtcaga acatgataac acatttgaga agtgagaaga agggaggaag gggccaggga    62820
agtgagggga gaatagggg tggaagtagg ggaagaagca aataggggcaa ggttttagtt    62880
gcctcccttc tgttcttatg ctgttaatta ataatggaac cagtggccag gcatgatggc    62940
tcatccctgt aatcccagga ctttggaggc tgaggcagga gtatcgcttg agcccaggag    63000
tttgagacaa gcctggacag catagtgaga ccctgtctct acaaaaataa aaaaaaaatt    63060
agccaggcat ggtggtgggc acctataatt tcagctactt gggaggccga ggtgggagga    63120
tcattggagc ccacaaggtt gaggctgcag tgagatgtga ttgtgcctct gcactgcagc    63180
tcgggtgaca aagccagact ctgtctcaaa aaaaaaaaa aaggaacaag aattttggata    63240
aatggaacat gaaacacaat tcatttttat tattaagttg tattctgtgc ataaattatt    63300
tccatgtctt ctctcccttt taaaggtgtg ccacgtcatc accgaggtga aatctggaaa    63360
tttctagctg agcaattcca ccttaaacac cagtttccca gcaaacagca gccaaaggat    63420
gtgccataca aagaactctt aaagcagctg acttcccagc agcatgcgat tcttattgac    63480
cttggtaagt ctgtgccatc gattggagat gacaatggaa gtttcactca catgaaaaat    63540
ctgaagagac tgtccaagtt atgtattgac ctgcctttag gtttagcaat caaaatttac    63600
tactgagact tttaatttaa aaagccctag ggtaatcaca aatgtcatct tcaagcatat    63660
aaaaatctct gtattttcac tggggagctt gttaactttg cttggcatgg agggagggtg    63720
ttcattaagg ctgcagtcat aattgtggtt cagtccagta actcaaatat tgataggagg    63780
tttttacagt caaccgaagg aacatcctgg aaaacgtata gatgttcaga accgaggctt    63840
ggtttaatta caggagccac tccctcgttt ttactgctca caaacagaat tcatcagaaa    63900
aattgtagaa agcagtttgt gtgtgtgcct tgaatgattt tattttggaa actgggtggc    63960
```

-continued

| | |
|---|---|
| accttgtctc ttgaatagtt tttaaaataa gaagatggga acaatataca gtcagccctc | 64020 |
| catatctatg ggttctgaat ttggggactc aaccaacctc agatggaaag tatttgggaa | 64080 |
| gaaaaatcaa tgaaaactaa acaataatat agattttaaa atatagtaac tatctatgta | 64140 |
| gaatttacat tgtattaggt gttataggta atctagagat gatttaaggt gtgtgggagg | 64200 |
| atgtggccgg gcacagtggc tcacgcctgt aatctcagca ctttgggagg ccaaggctgg | 64260 |
| tggatcatga agtcaggaga tcgagaccat cctggctgac acggtgaaac cctgtctcta | 64320 |
| ctaaaaatac aaaaaaatta gccaggcatg gtggtgggcg cctatagtcc cagctactca | 64380 |
| ggaggccgag gcaggagaat ggcgtgaacc caggaggcgg agcttgcagt gagccaagat | 64440 |
| catgccacta cgctccagcc tgggtgacag aatgagactc tgtctcaaaa aaaaaaaaaa | 64500 |
| aaagtgtatg ggaggatgtg tgtaggttat gtgcaaacat agcaccatct tatagaaggg | 64560 |
| ccttgagcac cgtggatttt ggtgntctgt ggggactcct gcaacctatc ccccgaggat | 64620 |
| gccaagggat gactgtattg gatagatttg cagttgccac tgtgaaggac ttgttgaact | 64680 |
| ggggtgtgat tatgatgcac agagggccct cctgacttgt cagtggccat gcacagggcc | 64740 |
| aggtggcaat gcactcccgt ttgcctgccg cctatcaccc aagctgctgt ctctactggt | 64800 |
| ggtgagctgg ctcgatgtgg taggagatgg gccctgctgc ttttagagca tgtggccctg | 64860 |
| cttccagaat acctgttctg gttgcagctg ctgctgctga aggctccaca gaacacacag | 64920 |
| tgctttgggg ccctgcggtg gcccggttct ctgattgttc ctgcagccac gacagaggat | 64980 |
| gcagtgtgag ccgcatcagg cagtatgaag tcctttcctc tcaagccacg tagctagcct | 65040 |
| taaaggttaa tttcataacc cttaaggtta ttttttttt ttaattttt tttttgagac | 65100 |
| ggtgtctcgc tctgtcgccc aggctagagt gcagtggtgt gatctcagct cactgcaagc | 65160 |
| tccgtctcct gggttcacag cattctcctg cctcagtctc ccaagtagct gggactacag | 65220 |
| gtgcccgcca ccatgcctag ctaatttttt gtatttttag tagagacggg gtttcaccgt | 65280 |
| gttagccagg atggtctcaa tctcctgacc tcgtgatccg cccgccttgg cctctcaaag | 65340 |
| tgctgggatt acaggcgtga ccaccacac ccggccccac ttaaggttat tctttagctt | 65400 |
| gaacatcatc tctgagaaac tttccctgac tgtggtctcc tctcccacct caagactgga | 65460 |
| tgaggtgtct tgctaagccc cctgtagcac cccacactct ccccatggtg cgtatcacat | 65520 |
| ttctcatcat caccgttatc tgcttattat catcactgct gctgcctaac ttcaccttgg | 65580 |
| gccaaatgtt gtgcaaaggg acttaaactc cttctttaa tccttacaac atgatcaggt | 65640 |
| agatgttgtt ctgtttctct ttagagttga gaaaatagaa acagacaggt tacgtaactt | 65700 |
| gctgaaagtg acacagccga tttgccgcta atcagtgtga cttcggaagc tgcacttttt | 65760 |
| tttcaacttt tattttagat tccaggattg cgtatgcagg tttcttacaa aggtgtattg | 65820 |
| tgtgatgctg aggattggag tgtgattgaa cttgtcaccc aggaaccaag catggtaccc | 65880 |
| aataggtagt ttttcaaccc ttgccttcct ccctccctct ccaccccca ggagtccctg | 65940 |
| gtgtctgttc tcatctttat gtccatgtgt acccagtgtt cagctctcat ttctaagtga | 66000 |
| gaacatgtga tgcttggttt ctgtttctga attagtttac ttagggtaat gacctgcagc | 66060 |
| tgcatccatg ttgctgcaaa ggacatgatt ttgtcccttt ctatggctgc agagtattgc | 66120 |
| atggtgtcca tatatcacat tttctttatc cggttcactg ttactgggca cctgggttgg | 66180 |
| ttccatgtct ttgcaattgt gaatagtgct gtgatgaacg tgtgagtaca tgtgtctttt | 66240 |
| tggtaggatg atttattttg ttttgagtat atactcagta atgggattgc agggtcgaat | 66300 |
| ggtaattcag ctcttagcag aacctgtatt tcttactcca cctccccgc ctgtccttag | 66360 |

```
tatacagcag tggctctttta ttgccttttt cccttatagg atacagccct ctgcggactg    66420
ggctggggct gtttggccat tataccctcg gcttctagga cagtggctgt gacacagcag    66480
atgctcaaag aatatcttta agattcagag tgtgagacac tgcactagca ccgccatctc    66540
atgggccctc acaacagccc tgggaaggtg gcctgcaccc tctctaagaa atgaagaaac    66600
tgaggtcaca tgttgaccat ggtcacaaag tcacctgagg ggaggtgaca ggaactgaac    66660
ccactgtcac tctgtgtttc cctgggaccc tctgagcgca ggaggcccgt gttgctgtgc    66720
agtggcaggc caaggcaatg ccttggtgga gctggggccc atttggccca ctgacctgag    66780
gaaagcagtt ttgtgaattg gcagtagctg catttgctga catggtgagt tacaggaaat    66840
gccatcatgt tcctatcatg tgaaacaaag tgagaaatag gttcagggtg ggaggctgaa    66900
agggaggaat gcagacagcc ccgctcccca cacttgctcc aaggctgggn aggaggaacg    66960
ggaaggtgtc tcccctcctg gattcagtca ccttcttctc ttcattcccc tgcagtatcc    67020
cctcattctt ccacggacac gatcagcccc tgcttcttgt tgctcagatg tcatcacttt    67080
tctgcagagg gaaagaaga gaccagatca gaacaagggc ctcggcgtgg ctgtgcactc    67140
cgaaggcact gtgtgtgcct gagccccacc acggcctccc ctgcagggct caggcagcct    67200
tccttgagct ggcatgaggt ctgtgggagc ccggtccact ggcagggctg gctgcattca    67260
agtcctctcc atccctgcct ctccccaccc tctccctctg nngccccctt ctctgacagt    67320
gctgaccccc ctctctcttc cccactcttt cccatcctcg cctggcctcc ggtttggatg    67380
ctgtccacac acttcccgag ggcctgagag gacctccgtg tgaggcaatg catttcccag    67440
gtcacctctg tgtctctctc caggcttttt ccagggactc cccggggtca gtctcctctc    67500
cccactggaa cggggaaact gggattggcc tagacccggc agtggagtcc caggtgccct    67560
gcctgcccgg ctgactccgc ccagggaggc ctcccacaga agctcctcca gactccacct    67620
gttacctccc ccactcctct cacccaaggc tgtgctgtgg ccaagtcagt tgtttagtct    67680
acactttctg tttagtctac accatggcta cctcaaggcc cagtgaaggt gtgtagtata    67740
aagcaaaatc aaatccatat ttcagttttc cttaaaaagt gaccttcata ttctggccag    67800
aagaacagaa tggttggttg gatatatttt gagttttcat gggttttgt tttcctgcct    67860 cttgttatac tttctgaaat tggcttttag tctaaacagg tttttttttt tttttttttt    67920
tttttnggca atgtgttttc ctccaaagag taagaataat aggcctcatg gctgggtcgt    67980
gttctacagt ttgtgaatat tttctcaacc tttgtcaaat ttcatcttta cacatcctgt    68040
gtgaaattgg gcacgtgccg ttatttccaa cttagagggg atgaatgagc ccttaagagc    68100
ttgagttctc tgcccacatt gcgagttact cagtgccaga aggagttctg gaacccaggt    68160
ctcctcagtc tccataccac atcccttcta gggcaccatg ttgcttctgt gtttcttggc    68220
tctgcccact ccatgccagc acaactctcc ccacccctgc tttggtggaa tcatgttcct    68280
ttggggtaga tcacaccagc cagaggcaac tgctctcagc ttagcagatg gtactcatca    68340
cattattctt gaagccttgg gtcaggagcc tgcccaccc atctgcatcc atttgtccag    68400
ccctcagaca attgccactg ttttcatgtc tattctttga ctctctatcc tgggtagaca    68460
acatggactg cccagcatcc tgtcttctgt ctggggctcc cactgtcgtc ctgaccacgc    68520
tgggggctgc cagtgacact gggaaactcc cgagggaccc ccttcaggct tcacatcatc    68580
tgctccctcc ctagcatccc agcctagaac actttccagc catcagctgc attcccagt    68640 gaggcgtgca gcctctccca tgataggagg gcttcagccg aaagaacact tcaacaggcc    68700
```

```
cagaaaccca ggagcaccat tagatcagaa agcagaagca agaatgcatc taatctcccc    68760
cacatcaatt gctatagttt tattaatctg catattatag gtcagtaagg ggatggcaca    68820
gtttataatc cctgcaagag tctgatgatc ttttggtgac cagaagtgcc atttttgat    68880 gggcttctag agatcctcca tcagggatac cagacatgtt tggcatgcct gtgctgccgc    68940
gagacgctaa gcgtgtgtcc agactacacg tgtgggtcat gggtccagca gcagagctgt    69000
catattgatt gtttgcttct actaaatgta taaagcctgc ctggtgtcca agaaaaga     69060 aactataatc caattttta gaatccataa aaggtaagaa gtaggagaac atttagaatc    69120
cacaaaagat gagaagtagg agaacrgttg gattttttag aatccataaa agatgagaag    69180
waggagaacc tccaaaagga aggaatcagc tgagagtatt gaagatgacc aagtacaaac    69240
aggcagaggg gagcgcttcc ccttctcctc tcccaggcgg tgggctgcct cgctcggcca    69300
ggacacacag agcagcatcg tgcrctttga ggggcaggtg gagctgctca tcactagcag    69360
gggtgctggc ggggaccaca gtgttctctt ccatctttga gttgaagtcc tgtgtgagaa    69420
atgagaaacc ttcatggcaa aagacagaaa gggacctaga atgtaacatt cagcagtctt    69480
gttatctcac gcacctgtct gtccagttgg ggacgttgct gtatggaggt cagttgaaca    69540
atcacagttg aggagcctaa tgaattcttg caccaccagc cacacacatt attctgaaga    69600
gtgagccatt gtctctgatc ttatcaggat cacatcgtgg gatcatattt atttggtcat    69660
tctgaatata ccctttaagt ccaaagtgaa ataactaaat gtcgttgata aaggaaaga    69720 ataaagtggg gtatgatttc cttcacaga ggtctggaat cttcctgcct ttttcaagtc    69780
agtcggtggt gctggcaaat gtttaataac cagctcctct caccctcag aggaagccct    69840 tggtgttcag tgtttgcaga tttccattgt gcaactagtc ctcccacacc ccattttaaa    69900
ctacccactt gatgtcactg gtcatggagt tgggctcaca gagccagtgg gagtcaactg    69960
gagcagccac tggactcatt caagtgtttc ccaaaacaat ctgctcctag aaggactctc    70020
ccttaatctc ctaaccctgc cattcaggat gattccctgc actctgggaa gcacacgttc    70080
tagtgggaag actgatactg ggcaactgat aaccaagtga cttaaacttc tgagggttac    70140
aaagggtgtt tgtatcctca gtgtctcatt tcagattctg ctcagagcta aatgcaacaa    70200
tgtgagaaga tgttagtatc ccagatcttc atccaggaag gaatcttaga gatcattagg    70260
ttgtagggtt tctcttctgc agaggagata gagggtcggt gtcagattgc tggtttgcca    70320
gtaccactcc ctggagaaaa gagcaaaaga aagaaacttg ttagtcaact gtgcagagcc    70380
accgtgagac tgaatagctt tgtgggtggc cccgtgtttg ctgcaagaga cctctggcct    70440
cttgtagcag ctgccacatg gtaaacagag ccgagatatc aggagtctcg ctgaaaatgc    70500
agtcagatgg gctctgaata gaggaaggca ggacactctt gagatgggat ggggtttctc    70560
acagcaccgt acagggacca cctgcaagat ctcttgaggg gcttgtgaaa aacacatccc    70620
tgaggtcacc attcttgacc tgctgcttat tgagtttctg atgcctggga tgtgcaggtt    70680
taacaagccc ccagatgatc ctaataggat tcctgcctga aaattgctgg gtgaaggctc    70740
ttccccctcc aagtgataaa gaaggaaaag attgatcctg gaagaacatc cgttagatga    70800
gcaaaatttt gtggagcact tcatgaagag gaattactag gtcatttaga aatatgtttg    70860
aattgtggat catcttgtag gcctttctgg catatttctc cacttagatc cacaagacac    70920
atcgaatgtc tttttataaa ggggtttttt aatgcccatg tttgacccctc tccacttaac    70980 agtcccattc tcattttata tgtgaaggta atctgcttta cagaaaaatg taaaggacct    71040
gcacttctct gctttgtggt aagttgtaaa atgcagttta aagaggcagg cctcatatcc    71100
```

-continued

```
tgatagattt gtaggaagga ttgcacagtt ttacccagct tccctcgagt ttggcagaaa       71160
ttagctttcc ctgagctggt gtcttcccga gctagcatgc ttctcctatg gggtgtgtgg       71220
ccttctctcc tgtcttttg aggcagagct tcaatctaga atctgttcac aaactgaaca       71280
aatgcaacaa acagtaaaca gtcttttgct catagttaag gtgccttgag ttgggtgtga       71340
ggggctgagt gtgttctcag gggtgctctg cccacggctc cggccaactg ctgcaggtgc       71400
gcatcatatg ggtggtcttt gtggaatgcc atcagcacta gcttagtacc tcctaaatgg       71460
gagctggagg gctacagtgc tcaacactgg attatacgaa tgtggattgt ccaggaaatg       71520
cttttaatcc ccctcatcca ctctctaccc acgtgacctg cctctccctc tttacttggt       71580
gtttactcag gaatgtgggt gagttgtcgt gttagcctag aacagccatt cccaaacttt       71640
gatggaagga tgccattcac tttgaaaatt atcgagtagc ccaaagagct tctgtttcca       71700
tggataattc ctatcaatat ttactatatt accaattaat taaaactgag attagtattt       71760
atttgattcg tatttatttt tacatagcta taataaactc atacatataa aaaattatta       71820
aaaaatgact gttttccaaa ataaaattag ttagaaatgt gacattgttt ctacattgaa       71880
aaaatctctt taatgtctga tttaatagaa tccgctgaat tttatttgct tcattcattc       71940
tgttttgctt gttatttgaa gcatataaag caaaagctga ccttgcacag atctatagta       72000
ggaaaagcag ggggagggcc tcatggaccc ctaaaaggat ctcagcgacc tccagggggtc      72060
ctcaggctga ccaaacattg agaactattg acctggaaga atgtaaaata ggaaaacagt       72120
gtctccccca atagaatttc gtgtaaaacg tggactgtgt tacaaagtca gatgggtgca       72180
gttgtcctgc ttaaccgcta atcaggagct gaaggccaga gactcacagc tgttccccag       72240
cctggtagtg aacccagagg cctgtcttgc tgtgcagtgg gacaggaagt tgcatttggg       72300
agtctcatag aacacactgg aagatgtgtt ttagcttggc caggttcatg caggacagat       72360
tttctgcata aagaaaatca atgacagttt ctgaaactgc atcctggaag ccttgaccag       72420
tttgggtaat aacaagagat ttgaaagtgt ggggtgtaca ggtgttttgc tgaatctagg       72480
tggtggtggt gattattatt atttggaatt cagcttttcag ttctacctgc ttgtgagttc      72540
caaactttgt gaaaattagt tgcttggacg aaacttttct ttgcctctgg aaggctgtca       72600
gaaagcgaga tttcccagct tatgtgcagt gttatagtta atagagtaat ggctctgcaa       72660
agttgttcct ttactttaaa tgtaatttat tttgcatttg tgctacagaa cggtcataag       72720
tgtgccctt tgtcctcttg tttggaaact gggttttat aatgtgtgtg gtctatccga        72780
agattattgc ccattattga acaccattca tagcaaccat ttgcattagg cattgtacgt       72840
gtactctcca ctctgcaaac tatgtgttct gtccctttt aaaaagagga agctaaggtt        72900
cagagaagct aggtagtcca ttctgagctt cacgtgccag aggccatttt gtacttactt       72960
caaatgccat tgaaataaat gcacatcaga gaattgttct tagcataagg ggcgctacat       73020
gtaactttt attagtgaaa tggatgatgt tcaagggctg tggttgatta gaaaggcgtc        73080
cagaccctgg ctccagggac tatggagcag aactcgaggc cagtgcctgt cgagcgggtc       73140
cccacactcc atctgtgtga cctgactgtg gatggcctgg ctctgccgtt agattgccac       73200
ggtgccctcc tctggttgaa ccttctcga gaagtgcttg ttggaggctt gagtgcagag        73260
cctgtgagaa gctctatgtg gttcctattg cctgtcagct tgctgataaa ggtcattggt       73320
ttggcaaaat ttggcccaag gtttgccttc tcataacata ccactcggta gcaaggctgg       73380
gaggaaggtg gctatagcta tttctggaag ctgcttaggg ggctgcctcc ccctaaattg       73440
```

```
gtacataatt tgcagggcct attgcaagat gaaaatgcag aacccttcct tgaaagatta    73500
ttaggaattt caagacagag acaacagagc atgaagcctt gtgcaaggtc cttctaagca    73560
cagagccagt gtgaccgcac agaacacaca cccgtgaagc cagctctgcc cccaccatct    73620
gaccactctt gagtggccaa ttagcatagg tcactcccca ccctgctagg cccaccctct    73680
taggaatgtt gtgaggctta aataagaaat agccactcta caagcggtgt caattagcat    73740
gggctctggt ttctgtgtga ggtagtttgc taacatgaga gggtatctga ttagctaaaa    73800
cgataacact gacagattaa attcagaata actaaacctt ccctgtgttc ctttatgcca    73860
catgactcct gcatattctg ctaccagcac ctgtttgata ccagacggag gggtccattt    73920
gggatgggac aggagcatca gcagaaatgc agaagtgggg aagtgctcca tcttcttgga    73980
agctgagctg gcaagggtaa tggaatgaaa gagattgtga atattttga gactatgagg      74040 aaaccagtac actggtgttg cccagtacag aagccacatg tggctgttaa gcacttgaga    74100
tgtggctact ccaaattgag gcgtgctgtc agtataaaga acacactgga tttcaaagac    74160
ttggcatgaa aaagaatgc ctaatgtctc agtattttta tattgattat gttgaagtga      74220
tagtattttg tgtatgttgg gtgtaacaaa atatctaatt aaaattaact tcacctgtta    74280
ttttctaatg tgggtgctag aaactgttac atcctgcatg ggggtcacat tccagttcag    74340
ttgcatgtgc tgctacccat tgttctacac acacacacac acacacag ctgcacacaa      74400 cctagagggg tcagagaccc caggagcccc tgcttctggt gcccaggcta agcgctggag    74460
tggaagataa agctgggagg gtgggtaagg aggtgagtgc acggagctcc aggctaacag    74520
agtggataat ttgttctttg agcactgggg agctatggat tgcttactag cagcaaggtg    74580
acttgtgcag ggtatatctg ggggaggttt actgggggaa gagatagagg aggcaagaag    74640
tgaatacaga acgagaaatc aggacagtgg ttaggagacc gtagctttcc tcttgagtca    74700
agttcagata acacatctgg actgatgaaa ttcttttca ggaagctgag gaagagccca    74760
tgaaaatatg ttcctcctg tgctgagacc gaataattgc agtgaacaat taacgtgtgg      74820
cctagatcca ccttttgcct tcgctgatcc aagcaggttc ataattcttg cctgggccca    74880
agcttggccc tggctgccag ctgcctggct ccagatgttt cttaatcgtt tcaagtactt    74940
ctctgctccc tggaaacagg cactcccatc agtcacattc cagaggagga ggaagaggaa    75000
cttgacaagt atcagctaca aaagcctcct gaacaaaaga aatcctttaa gcctatttga    75060
ataacagttt tttgtgaaaa taatcaggat gttgagagct tttttttttt tcttttaaac    75120 tcttttttgga aggtaacttt tgtgaaaaga aaacacctgc tgctcctcag gctgttttcaa   75180 aacactgcct atagtttgaa agtacgaga tatgcatgtg gtatgaagca tttgcaggca      75240
taatatgtgt agtctgggaa aagcagatcc agagagtgct tgtagtaagg cgaggccttt    75300
tagctgcatt tagatgatgc tgggattggg gtgggtgcag ggtgcagcag tggggaggaa    75360
gaactgtgtg tgttcctctt gagaataggg gttatgtcta gaggattaac agttttcttt    75420
tttcnttttt tttttttttt ttggagttgg agttttcct ttgtctccca ggctggagtg      75480
cagtggcatg atctcagctc actgccatct ctgcctccca ggttcaagca attctcctgc    75540
ctcagcctcc cgagtagctg ggattacagg cacctgccac cacgcctgac taatttttc     75600 tattcttagt agcgatgggg tttcgccatg ttgggcaggc tggtctcgaa ctcctgacct    75660
caggcgatcc tcccgcctag gcctctgaaa gtgctgggat tacaggcatg agccaccaca    75720
cctggccaac agttttcttt tttcgattga agttcagcta tttgcaggac cgaaggtagt    75780
tctgattact ttcacctgta cttccaccaa aaaataaata aaacaaccat gagtaattgc    75840
```

-continued

```
tgatttttaa ttgaaagcat tattccagga ataactggtg gacttcgttt gcagaggaag    75900
tggcaaagac tgattgatat tatgatccag cttctaaaga ttttgctgct taatctgaag    75960
cacattggat ttctggttca ataggctttc ttttttttgtt tttattatta caactaatat    76020
gtattctttt cacagggcga acctttccta cacacccata cttctctgcc cagcttggag    76080
caggacagct atcgctttac aacattttga aggcctactc acttctagac caggaagtgg    76140
gatattgcca aggtctcagc tttgtagcag gcattttgct tcttcatatg agtgaggaag    76200
aggcgtttaa aatgctcaag tttctgatgt ttgacatggg gctgcggaaa cagtatcggc    76260
cagacatgat tattttacag gtatagagtg ttccttatgt ctttaataca acaaaatgct    76320
aagaatgttt cttatccctc tccagatgtg cctcaggagc tttttcaccg tcaggtaaca    76380
ttgtaatagc tgtcactgct gataaaggac tctgtgctag gcattattcc aagcgcttca    76440
tctgcacttc cctctaataa caggaagaca ctgttcatcg tctcaatttg tagattggaa    76500
aactgagtct ccaagagatt ataaattggg cccagtcaca cagctagcaa gtgtcagagc    76560
tggactggaa acccaggcct ctctgactct agggccttcc ctcttgcccc catcagccat    76620
cagatgatct cagacctacc tcccagcctc tgcatctgct cttcctctgc ctcacccca    76680 cccttgtcat ctcaggttca gctcaaatat cacatcctgg gagaagctca ttctgactac    76740
cctgatgttg tgttccccac ttccaccttg ggcacactgc gtcacgttat cctggctgat    76800
ttcttttgca caacacagcc actgccagaa atgatcttgt ttccataatc atctccctgt    76860
ctattttctg attttcata gcctgtgaac tttaggagag ggaagggatc ttacgggtct    76920
tggagccgag ttcctagttt ctgaaacagt gcgtgggttg aagtaggcac cccataagta    76980
tttgttgaat gaacaattct gtcagagaaa accaaacaca gtagcgtatt gcaaatacca    77040
cgtgctgctc ttgctgcctg tcagagggaa aactctggat cctgcttcag gaatattcct    77100 aaaatgttgca gcacatgttg atatgttcat ttactaccag taagatacta tgccttcaga    77160
gctctagaga gtatcctggg agggaataca ttagagccaa ggacttgctt tgagagcacc    77220 aaaattatgtg attcaaaatc ttttcacctt gacctgtgaa catggaccac gtgaatgcaa    77280
atatcataga aggaactcat tcactgaaag attttgacca cataacactt tccacatgta    77340
ctgtgaggtt cttcctacat tcccttatt aactttaaag acagtggtca ccaggcagtg    77400 gaattttttga gttttctata atttatgtaa cacacaactc ttttggggtg gtgcctttgg    77460
ttgattagac agtcttcgat atgggagagc cacagctggt gcttatggga ttatattatc    77520
tgagcctctg aaaacggttt tgttttcttt ctctcagttt agataggaca tatccaactt    77580
ggtggatctc agcggattct gaccctctgt aggttgttgt ttctttaggc tcaggccgtg    77640
gcactgctca gatctgggct ggctctcggg cctctgtgag cctgtaactc ttggtggcac    77700
tactaggaac tggcatgaga tttctgccag aatcatgtca ttctgtgaag ttggagttcc    77760
actttagttg gaaaaagttt ttatttcatc ttaagatgca cacttgtctt cttgttttaa    77820
cttgccaggt atctggatat tccatatatt atacaccaaa agaaattatg cttctcctgc    77880
ctattgagta atttcagggg tccagaggga acttgctgag tgaacatgta caatggattc    77940
ctatggaatc ataagatgcc cctaattcag tcttagtaaa gagactggct tcttatttct    78000
aattcctcca ggcttgagtt gtgcaaagag tatgtatttg taagagaatt tatgaaatgt    78060
ttgcacaaga cagatttta gatcttctta gtggaggaat acaagggaac aataaaaagg    78120
aagtggcagt agaagaccca gcgttagcgt cctgggccta cacccagcca gtgcctggca    78180
```

```
ccagcaggca cttgggaagc acttgttgga tgaattagta gctgagctca gtggatcgca    78240
agccaaatcg aatgtttaaa gttctagtaa gtcttctctt acacccaccc tgtgagcagt    78300
aggcataact ttattgctgt ggcagatccc taattctcag cccttgtggc tgtcttcctg    78360
cagatccaga tgtaccagct ctcgaggttg cttcatgatt accacagaga cctctacaat    78420
cacctggagg agcacgagat cggccccagc ctctacgctg cccctggtt cctcaccatg      78480
tttgcctcac agttcccgct gggattcgta gccagagtct ttggtgagca ttagtaaatc    78540
tgtttgccag aaccagcctt ctcttattag aggggaaaca tttcctgtct ctccrtggtg    78600
attcttattt ttatacctgt agctcttacc agaacagggt attgtttgat agtctaagat    78660
tagtcagggg tgggttttgt gactttggag tcctccttaa cttctgataa tcacggggct    78720
tcccttagat gccttcatct tgtgggatgt ggatccgatc cgtgtagatc cgatcgctca    78780
ccatgagggt ctccctagag cagacatttg gaggacttgg ctgaggagcc acaggtgtat    78840
gtttctcatg aattgccttc ctcagccact ctgggttgtg agtattgact gatgctgact    78900
gtgggcctct gggcccttc tagattccct tggcatctct tcctcccctt tctcttcttg      78960
ccctgccctt ggctctacac tttctcccaa gtcactgtct tggagaccag tgtcaggacc    79020
ttgagtaaca cctccgtgtg gatggctcgc tctccccgct cagccttgac acttcatgaa    79080
ggcctcttgc ccctgagccc acatgtcaca gccactgcca ctcccgtgcc ccgctgtta     79140
accttgggtg gttcacatgt aaaacctgcc tttatattct tgatttactt tttgagaaca    79200
ttgtcaaagt taggtgagtg ttcatacaca aagccttcaa cctgccttca tatgcaggga    79260
tagggctgtc cacgtgcgca tcaggaaccg agtggaatgt tgtgagcatg gtcagttcgg    79320
gcacagtttg ttttccctac tgcagaataa aagtgatatt tttgacaatt caggttcttt    79380
tttttattgt aaaggaggag gctactaaaa aaatgatagt tattatatat caaatgtttt    79440
taagcatcac ttgacagctt aaaaacatgt gatctttaaa aaatttgttt ttatgattag     79500
agagcatctt aagggaaatg ttcaaagaca ttgatactac ttcagacatg ctttgggtaa    79560
acatcttaaa tatccaaatt ctagaaatcc taaaatttgc tttttaatat aagtgagcat    79620
ttacccttct tctctctttt cctttccccc caaatactag attttattta ttcactttta    79680
tctacaagaa cctttaaaga gtttcccatt ttgctttact ataagaattc atattccttc    79740
ttttctgtcc ctgaaaaaat aaaatcacta aattaaaata gatacaaaaa gctatctcct    79800
ggttgagcat atctttagtg agagttcatg aaggtttata ccatggttaa aaaaaaaaa      79860
agattaacta aaagcctcaa aattgtgtgc ttagtttatt aacaaaagag ttacagaaac    79920
taaaatctca agctctaggc tttaagcttt cttgccaata acttctatgt ttttgacttc    79980
tctaacactg gaaattaaaa gaaaattatt aatctacctt ccttacattt tctccacatt    80040
ttagctatga ttttcataca gggtcatgaa gaggagtgag gatggaaatg gggaggaggg    80100
agcgctgttt gttaatggtt tgtaaacagc tcaggcatta aattacttgg ttagtgaaga    80160
aaattctacc aaggcaacca ggctgaccac agactggagg gctgagggt catcactgag      80220
tcatctctgc cctggggccc caggcactgg agctgctgct tgcagaaagt tctgggctc      80280
tggaagagaa atttttcctt cggctcataa atgggtaaaa agacgttaac aaacaagcag    80340
actccacttt ggaaatgata gcccttctat tgcagagtaa tttgaagctc tctgaagctc    80400
actctaatga cttcataaat caaagctgca gcttgtaaag gtaagatatt tttctgtaga    80460
cttttgtaggc agtggtgaga ctcggagttt cataaacatt atgcatagag atgccagtgt    80520
ctacatcatt cctggatccc acagactcct gctgtgctaa gtgggtcgtt gtccagctgg    80580
```

```
ccaagggctc ctgggattag aggcgggaag tgggatctca aggccgcact ggcttgtgat    80640
gtcactttgc aagaactgct ttttttttcca cagtccatcc catctttcag tacttaaaaa    80700
cagaaaagat aggtttttac aaaccatttc tattttttagc actgatgact tagagaatgg   80760
tgatggagat agcttagttt tatatttcaa agcctgccat tcagtcacta tagtctttttt   80820 tggcctaggg cccatttcat tataagcctt taagtctgga taaactctaa aaacatgtag   80880
aactttgttg actaagtaaa atatttcagt ttgcaccacc ttagctcata tattagttaa   80940
taggttacct ggcattaagt atgtatctgc tccttggagg ggcggctgcc agtgatgtgt   81000
gcgccttaac cttcacatga tactcacacc ttgctgaatg gcagttcttc tacctggtgt   81060
cacataatgt caatagcccc ttcctgtatt tttctagctt gagtacagca gggcctggg    81120 agagacgctt gctctgttca ctttctcatc acatctacct ttgggggaaa aaaaatctaa   81180
aaaacaggac ctggcttgct cctgatggag gaggaggctg cagtgttcag cctctgatgt   81240
ttttctatag gacatgctgc caaatagatg agggaggagg aggagtataa aaactaaggg   81300
tttggcaaaa aacacagaag ccacctgcaa tatagtgaag gcttcagaga gactttagga   81360
tgaaaataga ctgaaaacaa gattgtttct gtggccagga aaatctccag ctattcaggt   81420
gacatgatgc cgcgtgatga tgagtgtgtc cagtctgtct gtgctgttgt tctgcacagc   81480
actgtcatca gccttcagcg tcccctttac ccgttactca tagaatgtag cggagccacg   81540
actggaggac cgcagccttc cagaagaaag ttgagaaggc tcagccttga caaagacaaa   81600
ggtggctgga aaaagagatg cagtgcaatc tcacatagga agattgcact ttgagatcat   81660
gaagtttagt ttcaaataga gttccaatac acagtaacgc aataagaggg ttgctgaaat   81720
gtcctcaaag aaaagcagtt cctttgtgtt gttcccagcg aatacagtgc aaagtaatag   81780
agtcagctga atttaagatt cctatttcct gccggataaa acgtcttgcc tgtttctagg   81840
tggcttgaaa aaggagagga gagaaggaag aggcaggaga aaagtcccac tgaaaggacg   81900
tgggctacag tgtagtgagc taggctactg cctcactgcg ctgggcggct ccaacagttc   81960
actgtctcct agggaggttt tcaaatgcag gacatttgct cacttttcca aggagagtta   82020 ttgtttttttt gttttgtttt gttttgtttt gttttaaaaa attccagaat gtaaatgtat   82080
aagataccgg aagacaggca aaataaaaat aattggtttg gggcagtggg tttataggta   82140 acattttttct ttactattrt tttaaaatta gatgtgattt aaaaaaattt ccaaagccaa   82200
aaaacggtac aaatgcttta aaggatgaag atgttgtccc caagtgtcat cagacaaatt   82260
taggaggccc ttcctcccaa gcaaagcttc ctgcagtcct tccttcaact ctgaattcaa   82320
gcacattcct gcattgtgca cccaaatgat ctcccgattt aagacccct gtgtctcaca    82380 gaagcttctg gggctgaact ttctccggcc ttggagggtt ggacgctttg aatgggagga   82440
gtggtggtga gtggagcatc tctggcagca ggcatttggg agtctctggc aggaatcaat   82500
cagcgtagtc tccaaaggtg gcctttctct gacactaact agcccttgca ggggtcatac   82560
ccataacctg catctcatta acatcatctc cttaccagtg cactgaccta gtgagaaaag   82620
gaacaacaag cattcagcga ctcctgcggt gctccagggg aagttagaat tgcttggctg   82680
gggcagaggc cctggtgat ctggacctgc gtgcccccat ttgcccacct tctgccctgc    82740
acaaccagtg cccctgcctt gccagccaga ctgttttttca ggctcctgca cacctccctg   82800
tattgacacc ctatttttcct tttattcaga gtattaatcc tgaggtctga cctaggaaat   82860
tttcattggt tcttcaagca gtcacctttc tgtgggcctt ttctttcctc tttgttctcg   82920
```

```
taacaccctg ggcataactc taccgaacca gaactccttg gtgtctctgc agcgtgttct    82980
ttgtgttttg ctcatggctt aatctccaga gcctaataca gtgcctgatg tgtattagat    83040
gctcaataga tgctcattaa gttaaagtag aagacacctc tcagcagagt tctcttaagg    83100
tgttgtgaat agcattggga aagaacattt attttttaat tacattaaat acaaacagat    83160
ataataaaat aaatcatatg cccagtgcta tgtcttaatt ttttaacata tcaataaaga    83220
gactttaaaa cacataacac caccctctcc cctccaaatt tcctttccgg gaaagtctcc    83280
ttttggaatc ataggaagca cttactaagt tgatttattg taaaaaaacc aagatcctaa    83340
taaatctcag aagatctcct gttaacctaa agagaccact gatgtggatt ctgtatttgg    83400
ttgtgctgac aaaagtttcc cagtaattgt ttatttttaat tggcgtagat gtggtactgt    83460
acctaattta aggcacttgt ccctctgaga gtagagacca agctatagaa aatcactggt    83520
gttgtaggga aagcctttcc ccaggatccc tgcaaaaaag gtcttgattt ttattctgaa    83580
agatgccctc attttttgtt cagctataaa agttcatata ttgaaaggag gtctaggaag    83640
tctcactgtg taaaccactg aaacttcaaa tttactttag agttttgttt ctggaaatgt    83700
catttctgtt taaaaataca tctttgttat agtattattt tagatctttt tattttctgt    83760
agtggggaat tatacaggta gactacattt tataaaccag atatttcaga ggaatattct    83820
tcaattggcc tgccttggtg tatgtaacac ttaccctgaa aagctctgat ttcaaagaca    83880
cagttagttc tctagtatat cttcccagcc tcaacaacca gacttaagaa ggaagtgaag    83940
gattcatctt tcccactttc ctgcggccac cctgagccat cagtagttgt gatgtttgtg    84000
gaaagagtgt ggaccctgag ctgggtggga aagcaggct gatctcagcg ctggcatggc    84060
ttagggctgc acccatctca gctcacatgg ttaattaagg gttttgtggt ggttacagag    84120
gatctcgagg gctatcccag ccagcgggct cctgggtctg tcatccctgc ctgtgctttg    84180
ttcagaaact acagggattc agtttcccat ttgcacagca gcacccagtc tttgcttttc    84240
tgtttcttcg tggcttttaa atgttatcat attaaccatc tagagaggca ccctgcaagg    84300
ttattcctct cacctgcttt tgctttcctt gatttgatga aatttacagc ttctttctct    84360
cttccattat ctttcagcca aaagaaacag agaaaagaaa tactgacact tgcctccaat    84420
tatatttcta ctctgatttt taaaattgtt tttttcttat attattattc tagttattag    84480
gtaacctgcc tcagtttagt caaccaataa ttagttatcg tsgctctgct ttaaccccag    84540
gacatcagac tcttttttttc cccagcagct tcaactctat gaggaaggtg agacagggct    84600
ggggttgctg ctcggccgct tgccttggcc ggtgccctcc ctcttattct gcagtctgta    84660
tagaagttgc atccatttgc cagccactct aagaacaaaa tatggccaga actaggaagt    84720
aaccttgaca gagttcttga actcctcaga gggaaaaatg ttctttattc cattatcatg    84780
ttaaaaatca gtaaacttgt atttaacaaw gtacttctgc agttgtacag ctgttgtaca    84840 gttttttaaag atctttgaat tctattcctt gtttcaaaac agaggaaaca gagacacttt    84900
ttcacttact ctatcttaat ttctgatgct ttatctataa aaatctttta gtgtgaccca    84960
taaaaacatg ttttagtatc tcctttaaaa cccaggagca ttcctggaaa aatagactaa    85020
taaaaccttt ttcccttttcc cagtttaact tttgaagcat gtttgaattt tattttcaga    85080
gtaaaacata atttttaatg tttatgtact ttatttgca atactgtctt gacaacactg    85140
tctgagatat caggctctta aaaatgaaat aaagtttgca atgtggggct atgtctccca    85200
cactcctgct ctgtgatgtg tggaaaaggc aatggaatgg tattgcgtga gaaactggtc    85260
tggtttaact ttctgcattt ctgtgttttc tcagatatga tttttcttca gggaacagag    85320
```

-continued

| | |
|---|---|
| gtcatattta aagtggcttt aagtctgttg ggaagccata agcccttgat tctgcagcat | 85380 |
| gaaaacctag aaaccatagt tgactttata aaaagcacgc tacccaacct tggcttggta | 85440 |
| cagatggaaa agaccatcaa tcaggtatga gtcagtccaa accttgcaaa tgcttaagcc | 85500 |
| atcctagata tgtagaaact taaatctctc ttgagcagga actgtttcct accactttgt | 85560 |
| gttctgaacg gcattctgca tgatgcctgg catggaggag gcatatcaca aacgtgtgga | 85620 |
| atgatcgtga gtgtgtgtgt tgtgagcgtc atggtgaaat gccacatgga aacatggtgg | 85680 |
| caatgtttag ctgtagaaac cagcacaggt tattagtagt ttcttacatt taagagactt | 85740 |
| cagctctagt agcttgttct tctgaaacat atatatattt atgcaatgat gcaatgtagg | 85800 |
| gttttgtaca ttgagtgctt tgatttgtgt gtgtgtatgt tgaatggttt taattggaat | 85860 |
| tttctccaaa taattctttg ataacaaagt tatgataggg aacatatatt ctatgaattt | 85920 |
| gtttcatgat gtgtgtgtgt ggtttttttt taactgaatt cagttcaata tctgtggctt | 85980 |
| cattacctct ggtttcagta tacaatagaa ccattatcct ctgaagtgtt agaggctgag | 86040 |
| aggtgagttt tactgggaat tacaactaaa ctagatggtg aatgccctgg gttgggcatg | 86100 |
| ggagcagatt ttgatcctgt acagtttaag gaagaacctg ccagtaatgg ctgctgatga | 86160 |
| tggaggacta tgctccttag tagagaaagg ggcatcattg gaagtgtcta gaggctgggt | 86220 |
| agctacgaaa gcactggaag ggatttcatc attgagtcac tgcagagtca gcagtcaagc | 86280 |
| ctctcataag cctagaatct gctccagata gtcatgtgtc acttaataat agcaatacgt | 86340 |
| tttgagaact gcatcattag gtgatttcat cattgtgcaa acttcataaa gtgtacttaa | 86400 |
| acccaagtgg tatagcctac tacacaccta cacatgttgt tcctaggccc tacaaatctg | 86460 |
| tatgacatgt gactatactg aatactgttg gtagttgtaa cacaaggtgg agtatttgtg | 86520 |
| tatctaaaca taactaaaca tagaaaaggt acaataaaaa tatggtattc taatcttatg | 86580 |
| ggaccaccat catatatgca gttcgccatt gaccaaaatg ttgtaatgca acacacaact | 86640 |
| gtgtaacgaa agcatagagc aatcaggcaa aaacaaatgg tgaaataaag ctattttga | 86700 |
| aaaatcctta ctctggagat ttctgtagtc caaaaggaat ccatgattcc agtggattgc | 86760 |
| atccacatgc agtgtttgtg attttcattt gcagccacac cttaggtgtt aagcacagaa | 86820 |
| aaagatgcaa atttggcctg caaaagaaag aggtttcata ccagttgtta actttagatt | 86880 |
| tctgtttgca cattgcatat gcccttatga agaacagtt cttgtctgtt ctgcactcat | 86940 |
| ctttaattga gagcctctcc atctcttttc cttccctgga acactcttct tgatgtggat | 87000 |
| agctttggct tgttggggcc ttgcttttg ccaggttggg tgggcatcga aatatacgca | 87060 |
| tgatcccatt cagtgcaggc cgcactcctg agaggatata aagtggttca ctgactgacc | 87120 |
| cacactcact ctgctgcaaa gtggaaaggt aggggttcaa actcaagtcc ctcccacctc | 87180 |
| aaagtgcttt agcagctctc ctacactgcc aagagcctct ggaggtcatt taatttagag | 87240 |
| tttttcccta ttttaccagg attctaatac tgacttctcc acccttttga ttctttgatt | 87300 |
| tctggcattt tcattcattc tttcttcat tcattctctt cttacagctt ttgttgcatg | 87360 |
| tacttactta catttacagc ttctagggca gaccccgag agccttggtt acctagactg | 87420 |
| agggctatat ccactacctg acatgtcacc ttgctcctgt ccctcaggcc atcccagctg | 87480 |
| acattgttta cctcctaagt attgagcctc agaaaaaaat cccattgtct cctatttct | 87540 |
| gtaaaaaaca aaaataaaa cgtattgaga atacttagga tacatcaggt gctgtttcag | 87600 |
| tgctggaaga gtggaaatgg acacagcatg ggaagaaaat agctgtgcgt gtacctggtt | 87660 |

```
tgtttcaagc cgctatctgg ctatttggaa gttgccattc attttccac tgactttttt    87720
tttttttttt tttttgagac agagtcttgc tctgctaccc aggctggaat gcggtggtgt    87780
gatcttggct cactgcaacc tccaccttct gggctcaagc attctcgtgc ctcagcttcc    87840
tgagtacctg ggactatagg catgtgccac cacgctcagc taattttgt attttagta    87900
gaggtggggt ttcgccatgt tggccaggct ggtcttgaac tcctggcctc aagtgatcca    87960
cctgcctcat cctcccaaag tgctgggatt acatgcatga ccactgtgc ccgacctcca    88020
ctgacttaat aactctagga cataggtatt ataattccta tttttataga tgaagctgag    88080
cagagagtaa catgcccggc cccctgtaga aaggcagggt ctgtgggagc cagggctgtg    88140
aggttggagc tgaggtgttt gagtccagct ggacttaaaa gatgacctaa gatcggctgg    88200
cagacatttt ccaagaagg ccaggcagta tatattttag gcttcacggg tcataacgtc     88260
acaactactc acctctgcga cagctactca cctcagcctt gcagcacaa acaatccatg     88320
acagcatgta aggggatgat gggtcatgtt gcaaaaaact ttattttaaa aactgtgcag    88380
cgtgatgggc ttggtccaca ggtggtggtt tgctgatccc tgaactaaag gatcacagca    88440
tgtgagaagg tacaggaatg agagcagaga gcaattctca gaacctgagg tgttcaacat    88500
tttgggggta tcgggagcac aaaaatttgc atttagggcc cgggtttta tcagtggtcc     88560
ttatagaaag tagatctacc cgcatctctc ccctctttcc ctctggtgtt tctatctgaa    88620
cttgacatct gagtgttctc tgtcaggctt tctgctttcc cactgccccc tcccatccag    88680
agggtgctgt agtcttaagt tctacacaga aagcagacat ggggtccagc atgattcctc    88740
tgcagcctta gagatccccc aggcccaaat cttgggggtc ttcagagtag atgtaatgga    88800
tgcttccatt gcagatggtg gagcatactg ccctgtgtac agatgggtg gggcaggaag    88860
tgagggcatc tgggtggtcc tctgtgatag ctgtggttcc atttcattaa atgccctccc    88920
tgtatagata gtctcagcct gagcaactgg gacacagctg gatcctgggt ggaagaggtg    88980
gccaaggaca gggctctgga gctctggctc aatgtggaca ggctgaaagc agccagagag    89040
ggcaattcca aaggtgacag agcccaggac agaagaccaa gggtgtctga agcctttgtg    89100
gcagtgtact taccaaagga cctgtccatt gaataaacca tctacatctt ctgacccaag    89160
aagaatggaa actttgggaa taattagtaa caaaggaaag gaggtcagtg ttgtattctt    89220
gtcacagtgg gtgctctgtg gctgtgaagt ctcagctcag tttaaggaag aaaaaagga    89280
aggtggctg tgggaggcag ggcaaatagc ctatttcag catcctttag gctccactca    89340
gagcatggcc tcagcccagc attgtcatca tatcatgtca gagcttgtta gaaactcagc    89400
atctggggcc acacccgaga cctgctgaat cagaatctgc atttcagtga gatcaccagg    89460
ggattcacat acacacaaac agctgagaaa ccctgctgtg gcaactctg ttagaaacac     89520
aatgaacaaa ggagcccctg ttccagttga gcttgtaggt tagaaaccag ggttcctgta    89580
ttcagaagac acacctcaaa tcagggcaa aggtgcctct tctgcctgtg ggggagccgt     89640
cacttcttgg gcagtttgca ccgtggaaaa ggagtagttt tgtacgagga caactggtgc    89700
cataccagga gggtggggcg tggcgggag aagtggttta ccactggcgt tgttgaaaat     89760
tgctcacatg cagtggtaat aacaagcaga gggacttta gtgggtttga tgttttttgt     89820
aattcactac agatagtgtg tgccccttg ttgctgatac caggccgact gttcccactc     89880
tccagcccttt ggtatgacaa tgggaccagc agattggagg gcagggggtt aggaaggcgg    89940
aagctctgtg gcgagttctg caaaccrtca gggttcatga ctttattaat cagtgtccat    90000
ggactgtgaa gagaaatgct gagtctacaa tagcaaatga gccaagaaca taaacagaca    90060
```

-continued

```
attcaccgaa gaggagatat ctagtaaaca aatatctggg aaagtatttg gcttcatgtg    90120
taatttaaac ttatgtaaca tataatgctt tactctacta gataatagaa agacatttct    90180
tgatgccagt acccagcacc aagggtatac tgtatgcaga acattagcat gttgctgatg    90240
gcagtgcaca ttgattagtg gctgttggga gacaatttgg cgaaacatat cccaagccag    90300
taaaatattc atacccttg actcagtcat cccgtttctt ggaatgtatc ctcaggaaat    90360
aatccaaaat atgagggaag ccatatgtat aaggatattc tcctagactt gtcacttata    90420
ataacagaaa cttggaacta gatgtctaac acttgatgac tggattaata tgatgatggt    90480
aggttgagct ggtagaatat catgaagcca gttatatata gcgacatgaa aaagctctta    90540
tttgatacaa tgttaagtaa aggaaaagtg ggataggaaa ttttatgttg gttatgttta    90600
gaactagaaa aacatgcttt taggaaatag gaaatatagc tagatataaa agttgtattt    90660
ggtgattttt cttttatttt tcaagcttcc aataatgtag ctctattgct tcagtaactt    90720
aaaatagttt tatcttttcg gcaaaacatc gaaagtatgg aaatagtcat tcctactttg    90780
gcaaacagaa gagaaatttt cttcagtacc aaaattctgg aacttgactg aaaactatga    90840
agaacctaag agccaggatg acaggaaggc tctagatccc cagtaattac aactctagtg    90900
gaattgctct gagatgggcc agcaagaaag aagatgagag ccagtccccc ttgcagaggg    90960
gccaggtacc ttgcagcttt gtgtagtgac cagtgctcag gaacggctt aggcaagacc    91020 ctggggagg tgggcactgc acttgtccag cctcaggagt gactcagacc agaaatgaaa    91080
acaccttaaa gtgtatatat cttgttttcc tatcaacacc tagttttaa tattcgtctg    91140 ttttattcat ctgagacaac ataccaaagg attgggtttt taatgttagg ccttcctgct    91200 cttctctgg ctgagaactg ctcctggcag tggatcactt gtgctgtcta agtgtgcaag    91260
gacaggcgcc cctcccaatt ctttctttc cccaagtaat tagcccaagg gctgaagccc    91320
tcgtccagtg accagggttc tccttgacc accagcctca tattgccatg gtttggggta    91380
aattcagggg cataactgca gaatgaaggg cctaggagtc ttggcagtca ggagatcatc    91440
aggcaattaa gcagagatga ttgtgaccca gggtggttcc tagggattaa tggaggcctg    91500
gaagagttta tggctttggg tactgctgag agccattaac ttaacacaga acatcaatcc    91560
gtaggaaaag ccagaggttt tgttcccagg cttccaggt taggagatca cttaaatctt    91620
tgtgaaagaa aaaagtaat agtgtacatg acatttattc agcaccatat ttataattat    91680
acatgagtgc caaacaatct cagttttaac atttgtggtt tttactgttc agactattca    91740
gaagttccat gacgtggcat ccattgatga tggttttgct gaggttgaaa tgtgagggtt    91800
ttgtggcagt tgtgtggaag cagatcccctt agctaagaga gcgcctgctc aacctgccag    91860
gcgtgtgctg ggaacttcca ggagttgcct cgtttaattc tcacagccat cctgggaggt    91920
aggcgctgtc tgccccaggt gggaggccag gaactgtggc tgagagaggt taagtaccga    91980
gctcaagtca ttcatagagt cgccagtgga gccgcaattt taaggctgac tcaaagcctc    92040
tgagccagtt acctcggctg tcaaatggag ataataatcc ctgctgacct cacggtcgct    92100
ctgaaggaca aaagagaatc agttcaatcc agtaaacaat tctctctctc cctcttactc    92160
ccctcgcaca catgcacaca caccccacag atataatgga ttttagtttt taggcatcaa    92220
atgacttttg tgccttatta atattatcca ctgaatcaaa aacagcaagc tgaaaaattc    92280
atctcaagga agagaaaata agattgttgg gaatggtgag aaaggaaaca tggttttga    92340 aaattgattc cagggaagat aggctagttt gaatgccagt agggagccat cagaagaagt    92400
```

```
agttttacac tgattttttaa caatattgga gttgcttaag gcaatgcaat agagaggcag    92460
tttctgccct tttaaagcct gacttcactt tctgaatgtg tgttctgatc tagcagggtt    92520
tttttttttt ttcttttaag atggtcccag cttgactgca ttctcagatc catcagataa    92580
acgttagggc ttcactgctg tgctgagagg ccccagcccc tggggttctc tcatagaaac    92640
aactggaaag aaaggaaatg ccttgggcag cagcagcagc agctgtcttc tgattctgct    92700
ttccgccctg ccttccttac caagagaaag tacagacacg gacggcttga gtcacttagg    92760
cacttaggag ttgttttttca cacgtgtggt gttttcgtca ccattactat tgtgggaaag    92820
aagacaactc aggcatcgtt tcgtattcac tcatctgtgt gggtgacatg tgggttttgg    92880
ctcatttctg catatttgtg tgcaaaggag agttttttag taaacagtcc cattacttag    92940
ctgttcttgt aactctgaaa acccaactga actataatta aactttgact tggtgactct    93000
gcaaacaggc tatgattctt ttgtttcttt tctccttta  acccatagtt gatgtatcta    93060
acctaacaga atttcagag  aaagaagtg  aaataagaac taaaaataaa tttttatgtc    93120
tttaaaaatg agaggttttt tttttttttt tggcttttgg aaggtgagta tcaaaaacct    93180
gtacttaatg ttaccttgga attatttcta gatgtttctt atatccttt  gtcccaagta    93240
aaattattac cttctcagtg cgtagttttt cttatttatt acttctagta ccaagtgtag    93300
agctaagcgt agaggagacg cttcacaggt gcgcattgtc gtgattgcag acgcctgcct    93360
gtacttgtgg ggttttttctc agttttagta cgtgatgact tttctttcta taacaggtat    93420
ttgaaatgga catcgctaaa cagttacaag cttatgaagt tgagtaccac gtccttcaag    93480
aagaacttat cgattcctct cctctcagtg acaaccaaag aatggataaa ttagagaaaa    93540
ccaacagcag cttacgcaaa cagaaccttg acctccttga acagttgcag gtagagcata    93600
tttataaagc agcttcctga atcacaaata tatggtagtt cattaactca ccaaaggcaa    93660
cagcaggctg ggctttccca tgaccagagg acctttccca ccctgatctg tttatagttg    93720
ggatcaaagg tatcccggga gaatgggtcc ttttttattat ggagcagaca gattgtcctt    93780
tgctaaggtc aggcagtccc agagcttcct gagaggctgt ttctgcactt aactcttta   93840
ggggacaggc ccagagatga acttggattc aggatgccgt ggcctgttag ctgaatgcca    93900
gccgttgtca ttactcaaag agaatctaag agcttttaac ttctatgagc aaaaccagct    93960
aggtccacag agggatggta aaggaggaaa gtaacacaga aataaatata acaaaccaga    94020
agagatgata attctttgtg agtccttggt gcatatacaa agatttgatt aatgaaggtc    94080
tcagttctcc cctctagaaa cttccatttc aacacggata tactcaggtg aggacataca    94140
gaagaaagac cagttgagac tgtgcacgca ggagggtgtg cagagcaagc actgaggtgc    94200
agcacggaga ccagagctgg ccaggtccag catcaccccc accccacat  cacccaggca    94260
cactgcccaa agaacacct  aactgcggag tgcagctctt ttgtcaatct gatggcatga    94320
agcaaccata tgttctactt ttttctactt tttttaatgt cacaagtgtg tagcagtgct    94380
gtccctgtta aggagttgtt ttgagggtgt ttttaaagt  tgtttttgag tggctgtgga    94440
taaaaataca tattttttgcc gaaatttta  tggtgttcct gggctgtcct gagaataagt    94500
tccattctga tctaagcctc tgattttttct tcatagaaag atgagctttg cagacacaag    94560
cttggcagca aggtgagaaa ggccagccta gtgagtcaag ctatctgaaa tgcattcctc    94620
ccagcgggca ttccatccca gcatacccta tcagatatgt gaaagagagg aaccaagacc    94680
gaatgctatt cctgcccagc cctaataacc actcacattc tgaaatttaa cttcttttt    94740
tccctaaga  tagagatgtc ctaactgaaa atatgcctgt atacaattta ccctggaagt    94800
```

```
ctcagccatc actcaaggga agtctccaga gggtgaagag cctgtctggc ctgtaggggt    94860
acacagtgta ggtggtcatt ttaaatggct tccaagccaa tgataggtcc ctgaaatata    94920
acatggtgga aacttctaat aaagctcaca tttgcattga agtgtttagc ttgttaagat    94980
aggcagttct caaataaaag gtttgtttta ttgggtaaat gaccttgtag ttttttggtg    95040
acagagcata gaaagtaatt tcatgctgct cctgtgctat tgttttttgtg aagacaggga   95100 gctgtgaaaa actgcttagc tacctacatt cctcaataaa ggcatcagac agtaattggt    95160
gattacagat gttctccctg gaatggtcgt tctcttgacc aagtagtcct acacttctgg    95220
aaggatcatt cagaactgtg gtctatgcca acccaccagt agttcctgag tccctgcagt    95280
gctgagtgct gggggccacc aagttgagta agacactgca gctctcaaag agttggatct    95340
aggattgtat tgtatcgatt tgtggtgttt ggatatagtt tttccatgat cccctacgaa    95400
aatatgcctc tcatatgtaa gaatcatgcc tcctccgtgt cacttttca gacactgaca     95460 aggaagggtg ttcaatacag tactgaattt tcatatagct tttctggggg ggccaaaata    95520
ccaaaatcaa cccatttcct accttattc tgtccataaa attgttagaa atatcaaaat     95580
cccatttcat tccctgttaa atacatgtga acgttgtcta gacgctggag agcaaattct    95640
accacctctt ttgttcagca gtacatcaga cgattgcata gacgtgccag atggaaccaa    95700
ataataatgc acatggattt gtcataatcc gtacaagtca ttgacgccca cactgagcca    95760
ggtgctgtgg gagacaggac catgtgtgaa agagaagaca tgcttgcttc tataaaagca    95820
tcggtgttat tgaggagacc tgacattaat gcagaatagc aaatgaccat gcaaattaat    95880
tcactactaa ctaagctgca ggttgcacct cggaatgcag aggggcttca aagtgatgag    95940
ggtaggccct gagccaggcc ctgatgatgg gtggattttg aggatcagag agtacagctt    96000
agagagatac cccaagtggg accacccctt gcccagtagg ctgacaaact aaggctcttg    96060 gtccctttt catattttgg gtgttctagt ggcccagcca gagctagact tcgagtcatg    96120
aattttctgg cacaagtgtt gtcacattca aaaagtatt ttctttgttt gaaaaatgaa     96180
aaatatatat atatgtgtgt gtgtatatat atatgtgtgt gtgtgtgtat atatgtgtgt    96240
gtgtatatat acgtgtgtgt gtatatgtgt gtgtgtgtgt gtgtgtgtgt gtgtatatat    96300
gtgtatatat ataccatttt tcccacctaa aatggagcat ggcaaatctg gactggatta    96360
gtgagataga ccaagtcaca gagcactcca ggatgcagct gtgagctggg aacaggtca    96420 gaaaggcctc agggacatca gcatacatgt tggagtttct gcagttttct tagggaaccc    96480
tttaatgtca ctagagctaa cacacttgtc acctgggaag caagcctgcc agagcaaatt    96540
agagagacga gggacagttg ctagaaagac acacctggaa gttctatta actagcatta    96600 attatgtgct aggtgctgag gatgtagact gagtgagatc ctcattcctc ctctgtaggg    96660
tggaagagag gatattgctt gtctccatgg ctcgtagtga acagtcagtg agaccaggca    96720
cataaacctc ttagcagaac acttggcctt tctaaggact ccatatgtgt tccggggtaa    96780
atgcctgtgt ttcttgacgt agtgatgtct tgttcctcta gacatcacta actttacaca    96840
gtagctttag atggcgtgga cgtgaataaa tgcaacttag gttttcttgt tggtttcttt    96900
ttgagtatca ttgtgtttgt aaagaatttc agattagagg attgttacca cgtgggcctt    96960
caggaggaaa ctgttttgag tttttgtcag cccgaaatcg atttgtgcgt ttaagtatat    97020
gtgctcatca aaacaggcca ggctctgctg cagtaacaaa cttacaagtc tccgaggctt    97080
ggcacaacgg aagtctttgt gtcactgacg cccacttcag ctttgtgttg ctgaagcatt    97140
```

-continued

```
ctttggccct atccgagctg tccctctggt ggtggtgcct gggggtttgg gttccctctg    97200
tgttgtgatc caccatctca gcatcggctt ccacagcagc catagcagga gaagaaaatg    97260 ctggggctc tcagggtgct tttaagggcc tggccaccga cctgcaaggg gtgcgagttg     97320
ccttcctgtg tggccagaac tgatgataaa ctgtagactc atccctgctg aaactcggct    97380
ccagagtgct cccaaggctg gacagcgtgt gggcactgga tcccacctgt gttagcactg    97440
gcaattgtat tctcatttct tcttttattc tccaggtggc aaatggtagg atccaaagcc    97500
ttgaggccac cattgagaag ctcctgagca gtgagagcaa gctgaagcag gccatgctta    97560
ccttagaact ggagcggtcg gccctgctgc agacggtgga ggagctgcgg cggcggagcg    97620
cagagcccag cgaccgggag cctgagtgca cgcagcccga gcccacgggc gactgacagc    97680
tctgcaggag agattgcaac accatcccac actgtccagg ccttaactga gagggacaga    97740
agacgctgga aggagagaag gaagcgggaa gtgtgcttct cagggaggaa accggcttgc    97800
cagcaagtag attcttacga actccaactt gcaattcagg gggcatgtcc cagtgttttt    97860
tttgttgttt ttagatacta aatcgtccct tctccagtcc tgattactgt acacagtagc    97920
tttagatggc gtggacgtga ataaatgcaa cttatgtttt cttgttggtt ccttttttgag   97980 tgtcactgtg tttgtaaaga gcattcacaa tacggtggaa tttcaaaagc tggaagagct    98040
cgagatcatg cctcaggcaa aggcgtgggt ccatcgttct tccgagaggg tttgtgtggc    98100
gactacaccc tcagcgtccc tggcaaggtg cagttggctc tcgcccattc ttgttatgga    98160
aacctaagat gatcattggg aagatcagtg atcttgggtc attgatccct ggctcagagg    98220
atagcggttt ccatcataaa ccaagatgat gagttcagcc tttatccctc gtggttccac    98280
tagatgtaac ttaaaggagt taacatttga ggactttgtt ctacatcaga ttttactatt    98340
tgaatgttta agatcacttt attgaatttg aagatcatca aattaaataa aatgatttat    98400
ttaatttgga tatcctgatc actgtcaagt gaaatggatc tctctctttg gtatttaagg    98460
aagtttgtct ttaaaaaaaa aatagagtgt tttcatacat ttttgcttat cccataagta    98520
cagttgatca aagtcatagt aggtaaatgc tttatgggac agctgacacc ttttagaccc    98580
taccaggtat tgctagcatg tgagctgcag ttgtggggtc tgagatattt ctttgtggta    98640
gtttcatacc catactatag agtcatgtat ttatttttgc ctgttgtgtg atgtaatgca    98700
atcatgttcc tttgagtctc catcccttgg aaatctgact tcttgcagaa ggagtaggca    98760
catcaagata ttcagggtg ccccaagagt ctgggacttt caaaaaaaaa agatcaggct     98820
nnaactgcag tcagatttat gacagctgac agttttttcag aggtcgcaca cagtgactct   98880
cctctctcag gatgacgagg acctgtgcct tcaacaagca aaatgctgct cacggttgtc    98940
ctgcttgcag ccagtcactg tgtaaagcct ctctgatgtg cacttaagag tgggttgctt    99000
tctcacaaag atggggttct gtgcagtcac aggtcacttc cttgacaaca caatcatttc    99060
tgatctttat cactgtaacc acgtcttcta ttccatagga gtttcttttg attctctcag    99120
ttgcgggggg catctcttaa tcctgggta aaggagaga ttgccatact tagactcact      99180
gtgagtctcc ccggccattt cacgaggaga ccacagtgct gccaccagtg cctaaacagg    99240
tggctggcat tcgagacttc ctcctgttcc ctgggtcaga ggatagcggt ttccatcata    99300
aaccaagatg atgagttcag cctttatccc tcgtggttcc gctagatgta acttatagga    99360
gttaacattt gaggactttg ttctgcatca gatcttacta tttgaatgtt tactgttgga    99420
ttttgggcat cttattactg ttactcaaaa acattgactc tgcatcaaga aagaaacaag    99480
aaagcaataa aacaagaaat aattcatgct cacatttta tggtggtttt ttttttttt     99540
```

-continued

```
ttaactttgg attttttgctt ttcagcccag gagtaaagga atgccttatg aacacctgtg    99600
gcctacgtgt ggtcatgacc caaccatcag tgagattatt tgagatattg gtgtctgcat    99660
ccagtgttgt tatctgagtg tttattacgt aagttgtaac acctctacac agggtgtgag    99720
tttagcactg atgagaccag ctccatcatt gtatgtggca gtgagtcctg ttacgagatt    99780
gggttgggca gaaaggactg ttgacatgag cctgtggatg taggttggac agtctcagcc    99840
tgtgactgac taggcaagga gcggagaggc aactgtgtga ggattctcag agccaaattt    99900
ttaagccatg ttttgggtta tatttccccc aacactcatt tgtgcacttg gtggtgtcaa    99960
```

<210> SEQ ID NO 3
<211> LENGTH: 3983
<212> TYPE: DNA
<213> ORGANISM: Homo sapiens
<220> FEATURE:
<221> NAME/KEY: CDS
<222> LOCATION: 171..3725
<221> NAME/KEY: polyA_signal
<222> LOCATION: 3942..3947
<223> OTHER INFORMATION: AATAAA
<221> NAME/KEY: misc_feature
<222> LOCATION: 36
<223> OTHER INFORMATION: n=a, g, c or t

<400> SEQUENCE: 3

```
ccaggccgtc cccaggatgc ccccaagcac ctgcgntgtcc cggcccggcc ccgggctctg    60
agcgcgccgc ggcacaggtt tctgcatatg aagtgtgtaa aatagattgc ttgatccaaa    120
acagaaaaac agtgataact gttttgctga gttcccagac ccttcccaag atg gaa      176
                                                          Met Glu
                                                          1 cca ata aca ttc aca gca agg aaa cat ctg ctt cct aac gag gtc tcg    224
Pro Ile Thr Phe Thr Ala Arg Lys His Leu Leu Pro Asn Glu Val Ser
      5                  10                  15 gtg gat ttt ggc ctg cag ctg gtg ggc tcc ctg cct gtg cat tcc ctg    272
Val Asp Phe Gly Leu Gln Leu Val Gly Ser Leu Pro Val His Ser Leu
 20                  25                  30 acc acc atg ccc atg ctg ccc tgg gtt gtg gct gag gtg cga aga ctc    320
Thr Thr Met Pro Met Leu Pro Trp Val Val Ala Glu Val Arg Arg Leu
35                  40                  45                  50 agc agg cag tcc acc aga aag gaa cct gta acc aag caa gtc cgg ctt    368
Ser Arg Gln Ser Thr Arg Lys Glu Pro Val Thr Lys Gln Val Arg Leu
                 55                  60                  65 tgc gtt tca ccc tct gga ctg aga tgt gaa cct gag cca ggg aga agt    416
Cys Val Ser Pro Ser Gly Leu Arg Cys Glu Pro Glu Pro Gly Arg Ser
             70                  75                  80 caa cag tgg gat ccc ctg atc tat tcc agc atc ttt gag tgc aag cct    464
Gln Gln Trp Asp Pro Leu Ile Tyr Ser Ser Ile Phe Glu Cys Lys Pro
         85                  90                  95 cag cgt gtt cac aaa ctg att cac aac agt cat gac cca agt tac ttt    512
Gln Arg Val His Lys Leu Ile His Asn Ser His Asp Pro Ser Tyr Phe
     100                 105                 110 gct tgt ctg att aag gaa gac gct gtc cac cgg cag agt atc tgc tat    560
Ala Cys Leu Ile Lys Glu Asp Ala Val His Arg Gln Ser Ile Cys Tyr
115                 120                 125                 130 gtg ttc aaa gcc gat gat caa aca aaa gtg cct gag atc atc agc tcc    608
Val Phe Lys Ala Asp Asp Gln Thr Lys Val Pro Glu Ile Ile Ser Ser
                 135                 140                 145 atc cgt cag gcg ggg aag atc gcc cgg cag gag gag ctg cac tgc ccg    656
Ile Arg Gln Ala Gly Lys Ile Ala Arg Gln Glu Glu Leu His Cys Pro
             150                 155                 160
```

-continued

```
tcc gag ttc gac gac acg ttt tcc aag aag ttc gag gtg ctc ttc tgc      704
Ser Glu Phe Asp Asp Thr Phe Ser Lys Lys Phe Glu Val Leu Phe Cys
        165                 170                 175 ggc cgc gtg acg gtg gcg cac aag aag gct ccg ccg gcc ctg atc gac      752
Gly Arg Val Thr Val Ala His Lys Lys Ala Pro Pro Ala Leu Ile Asp
180                 185                 190 gag tgc atc gag aag ttc aat cac gtc agc ggc agc cgg ggg tcc gag      800
Glu Cys Ile Glu Lys Phe Asn His Val Ser Gly Ser Arg Gly Ser Glu
195                 200                 205                 210 agc ccc cgc ccc aac ccg ccc cat gcc gcg ccc aca ggg agc cag gag      848
Ser Pro Arg Pro Asn Pro Pro His Ala Ala Pro Thr Gly Ser Gln Glu
            215                 220                 225 cct gtg cgc agg ccc atg cgc aag tcc ttc tcc cag ccc ggc ctg cgc      896
Pro Val Arg Arg Pro Met Arg Lys Ser Phe Ser Gln Pro Gly Leu Arg
        230                 235                 240 tcg ctg gcc ttt agg aag gag ctg cag gat ggg ggc ctc cga agc agc      944
Ser Leu Ala Phe Arg Lys Glu Leu Gln Asp Gly Gly Leu Arg Ser Ser
        245                 250                 255 ggc ttc ttc agc tcc ttc gag gag agc gac att gag aac cac ctc att      992
Gly Phe Phe Ser Ser Phe Glu Glu Ser Asp Ile Glu Asn His Leu Ile
260                 265                 270 agc gga cac aat att gtg cag ccc aca gat atc gag gaa aat cga act     1040
Ser Gly His Asn Ile Val Gln Pro Thr Asp Ile Glu Glu Asn Arg Thr
275                 280                 285                 290 atg ctc ttc acg att ggc cag tct gaa gtt tac ctc atc agt cct gac     1088
Met Leu Phe Thr Ile Gly Gln Ser Glu Val Tyr Leu Ile Ser Pro Asp
                295                 300                 305 acc aaa aaa ata gca ttg gag aaa aat ttt aag gag ata tcc ttt tgc     1136
Thr Lys Lys Ile Ala Leu Glu Lys Asn Phe Lys Glu Ile Ser Phe Cys
            310                 315                 320 tct cag ggc atc aga cac gtg gac cac ttt ggg ttt atc tgt cgg gag     1184
Ser Gln Gly Ile Arg His Val Asp His Phe Gly Phe Ile Cys Arg Glu
        325                 330                 335 tct tcc gga ggt ggc ggc ttt cat ttt gtc tgt tac gtg ttt cag tgc     1232
Ser Ser Gly Gly Gly Gly Phe His Phe Val Cys Tyr Val Phe Gln Cys
340                 345                 350 aca aat gag gct ctg gtt gat gaa att atg atg acc ctg aaa cag gcc     1280
Thr Asn Glu Ala Leu Val Asp Glu Ile Met Met Thr Leu Lys Gln Ala
355                 360                 365                 370 ttc acg gtg gcc gca gtg cag cag aca gct aag gcg cca gcc cag ctg     1328
Phe Thr Val Ala Ala Val Gln Gln Thr Ala Lys Ala Pro Ala Gln Leu
                375                 380                 385 tgt gag ggc tgc ccc ctg caa agc ctg cac aag ctc tgt gag agg ata     1376
Cys Glu Gly Cys Pro Leu Gln Ser Leu His Lys Leu Cys Glu Arg Ile
            390                 395                 400 gag gga atg aat tct tcc aaa aca aaa cta gaa ctg caa aag cac ctg     1424
Glu Gly Met Asn Ser Ser Lys Thr Lys Leu Glu Leu Gln Lys His Leu
        405                 410                 415 acg aca tta acc aat cag gag cag gcg act att ttt gaa gag gtt cag     1472
Thr Thr Leu Thr Asn Gln Glu Gln Ala Thr Ile Phe Glu Glu Val Gln
        420                 425                 430 aaa ttg aga ccg aga aat gag cag cga gag aat gaa ttg att att tct     1520
Lys Leu Arg Pro Arg Asn Glu Gln Arg Glu Asn Glu Leu Ile Ile Ser
435                 440                 445                 450 ttt ctg aga tgt tta tat gaa gag aaa cag aaa gaa cac atc cat att     1568
Phe Leu Arg Cys Leu Tyr Glu Glu Lys Gln Lys Glu His Ile His Ile
                455                 460                 465 ggg gag atg aag cag aca tcg cag atg gca gca gag aat att gga agt     1616
Gly Glu Met Lys Gln Thr Ser Gln Met Ala Ala Glu Asn Ile Gly Ser
```

-continued

```
                470                 475                 480
gaa tta cca ccc agt gcc act cga ttt agg cta gat atg ctg aaa aac    1664
Glu Leu Pro Pro Ser Ala Thr Arg Phe Arg Leu Asp Met Leu Lys Asn
            485                 490                 495 aaa gca aag aga tct tta aca gag tct tta gaa agt att ttg tcc cgg    1712
Lys Ala Lys Arg Ser Leu Thr Glu Ser Leu Glu Ser Ile Leu Ser Arg
500                 505                 510 ggt aat aaa gcc aga ggc ctg cag gaa cac tcc atc agt gtg gat ctg    1760
Gly Asn Lys Ala Arg Gly Leu Gln Glu His Ser Ile Ser Val Asp Leu
515                 520                 525                 530 gat agc tcc ctg tct agt aca tta agt aac acc agc aaa gag cca tct    1808
Asp Ser Ser Leu Ser Ser Thr Leu Ser Asn Thr Ser Lys Glu Pro Ser
            535                 540                 545 gtg tgt gaa aag gag gcc ttg ccc atc tct gag agc tcc ttt aag ctc    1856
Val Cys Glu Lys Glu Ala Leu Pro Ile Ser Glu Ser Ser Phe Lys Leu
            550                 555                 560 ctc ggc tcc tcg gag gac ctg tcc agt gac tcg gag agt cat ctc cca    1904
Leu Gly Ser Ser Glu Asp Leu Ser Ser Asp Ser Glu Ser His Leu Pro
            565                 570                 575 gaa gag cca gct ccg ctg tcg ccc cag cag gcc ttc agg agg cga gca    1952
Glu Glu Pro Ala Pro Leu Ser Pro Gln Gln Ala Phe Arg Arg Arg Ala
            580                 585                 590 aac acc ctg agt cac ttc ccc atc gaa tgc cag gaa cct cca caa cct    2000
Asn Thr Leu Ser His Phe Pro Ile Glu Cys Gln Glu Pro Pro Gln Pro
595                 600                 605                 610 gcc cgg ggg tcc ccg ggg gtt tcg caa agg aaa ctt atg agg tat cac    2048
Ala Arg Gly Ser Pro Gly Val Ser Gln Arg Lys Leu Met Arg Tyr His
            615                 620                 625 tca gtg agc aca gag acg cct cat gaa cga aag gac ttt gaa tcc aaa    2096
Ser Val Ser Thr Glu Thr Pro His Glu Arg Lys Asp Phe Glu Ser Lys
            630                 635                 640 gca aac cat ctt ggt gat tct ggt ggg act cct gtg aag acc cgg agg    2144
Ala Asn His Leu Gly Asp Ser Gly Gly Thr Pro Val Lys Thr Arg Arg
            645                 650                 655 cat tcc tgg agg cag cag ata ttc ctc cga gta gcc acc ccg cag aag    2192
His Ser Trp Arg Gln Gln Ile Phe Leu Arg Val Ala Thr Pro Gln Lys
            660                 665                 670 gcg tgc gat tct tcc agc aga tat gaa gat tat tca gag ctg gga gag    2240
Ala Cys Asp Ser Ser Ser Arg Tyr Glu Asp Tyr Ser Glu Leu Gly Glu
675                 680                 685                 690 ctt ccc cca cga tct cct tta gaa cca gtt tgt gaa gat ggg ccc ttt    2288
Leu Pro Pro Arg Ser Pro Leu Glu Pro Val Cys Glu Asp Gly Pro Phe
            695                 700                 705 ggc ccc cca cca gag gaa aag aaa agg aca tct cgt gag ctc cga gag    2336
Gly Pro Pro Pro Glu Glu Lys Lys Arg Thr Ser Arg Glu Leu Arg Glu
            710                 715                 720 ctg tgg caa aag gct att ctt caa cag ata ctg ctg ctt aga atg gag    2384
Leu Trp Gln Lys Ala Ile Leu Gln Gln Ile Leu Leu Leu Arg Met Glu
            725                 730                 735 aag gaa aat cag aag ctc caa gcc tct gaa aat gat ttg ctg aac aag    2432
Lys Glu Asn Gln Lys Leu Gln Ala Ser Glu Asn Asp Leu Leu Asn Lys
            740                 745                 750 cgc ctg aag ctc gat tat gaa gaa att act ccc tgt ctt aaa gaa gta    2480
Arg Leu Lys Leu Asp Tyr Glu Glu Ile Thr Pro Cys Leu Lys Glu Val
755                 760                 765                 770 act aca gtg tgg gaa aag atg ctt agc act cca gga aga tca aaa att    2528
Thr Thr Val Trp Glu Lys Met Leu Ser Thr Pro Gly Arg Ser Lys Ile
            775                 780                 785 aag ttt gac atg gaa aaa atg cac tcg gct gtt ggg caa ggt gtg cca    2576
```

-continued

```
                 Lys Phe Asp Met Glu Lys Met His Ser Ala Val Gly Gln Gly Val Pro
                                 790                 795                 800 cgt cat cac cga ggt gaa atc tgg aaa ttt cta gct gag caa ttc cac           2624
Arg His His Arg Gly Glu Ile Trp Lys Phe Leu Ala Glu Gln Phe His
            805                 810                 815 ctt aaa cac cag ttt ccc agc aaa cag cag cca aag gat gtg cca tac           2672
Leu Lys His Gln Phe Pro Ser Lys Gln Gln Pro Lys Asp Val Pro Tyr
    820                 825                 830 aaa gaa ctc tta aag cag ctg act tcc cag cag cat gcg att ctt att           2720
Lys Glu Leu Leu Lys Gln Leu Thr Ser Gln Gln His Ala Ile Leu Ile
835                 840                 845                 850 gac ctt ggg cga acc ttt cct aca cac cca tac ttc tct gcc cag ctt           2768
Asp Leu Gly Arg Thr Phe Pro Thr His Pro Tyr Phe Ser Ala Gln Leu
                855                 860                 865 gga gca gga cag cta tcg ctt tac aac att ttg aag gcc tac tca ctt           2816
Gly Ala Gly Gln Leu Ser Leu Tyr Asn Ile Leu Lys Ala Tyr Ser Leu
            870                 875                 880 cta gac cag gaa gtg gga tat tgc caa ggt ctc agc ttt gta gca ggc           2864
Leu Asp Gln Glu Val Gly Tyr Cys Gln Gly Leu Ser Phe Val Ala Gly
    885                 890                 895 att ttg ctt ctt cat atg agt gag gaa gag gcg ttt aaa atg ctc aag           2912
Ile Leu Leu Leu His Met Ser Glu Glu Glu Ala Phe Lys Met Leu Lys
900                 905                 910 ttt ctg atg ttt gac atg ggg ctg cgg aaa cag tat cgg cca gac atg           2960
Phe Leu Met Phe Asp Met Gly Leu Arg Lys Gln Tyr Arg Pro Asp Met
915                 920                 925                 930 att att tta cag atc cag atg tac cag ctc tcg agg ttg ctt cat gat           3008
Ile Ile Leu Gln Ile Gln Met Tyr Gln Leu Ser Arg Leu Leu His Asp
                935                 940                 945 tac cac aga gac ctc tac aat cac ctg gag gag cac gag atc ggc ccc           3056
Tyr His Arg Asp Leu Tyr Asn His Leu Glu Glu His Glu Ile Gly Pro
            950                 955                 960 agc ctc tac gct gcc ccc tgg ttc ctc acc atg ttt gcc tca cag ttc           3104
Ser Leu Tyr Ala Ala Pro Trp Phe Leu Thr Met Phe Ala Ser Gln Phe
    965                 970                 975 ccg ctg gga ttc gta gcc aga gtc ttt gat atg att ttt ctt cag gga           3152
Pro Leu Gly Phe Val Ala Arg Val Phe Asp Met Ile Phe Leu Gln Gly
980                 985                 990 aca gag gtc ata ttt aaa gtg gct tta agt ctg ttg gga agc cat aag           3200
Thr Glu Val Ile Phe Lys Val Ala Leu Ser Leu Leu Gly Ser His Lys
995                 1000                1005                1010 ccc ttg att ctg cag cat gaa aac cta gaa acc ata gtt gac ttt ata           3248
Pro Leu Ile Leu Gln His Glu Asn Leu Glu Thr Ile Val Asp Phe Ile
                1015                1020                1025 aaa agc acg cta ccc aac ctt ggc ttg gta cag atg gaa aag acc atc           3296
Lys Ser Thr Leu Pro Asn Leu Gly Leu Val Gln Met Glu Lys Thr Ile
            1030                1035                1040 aat cag gta ttt gaa atg gac atc gct aaa cag tta caa gct tat gaa           3344
Asn Gln Val Phe Glu Met Asp Ile Ala Lys Gln Leu Gln Ala Tyr Glu
    1045                1050                1055 gtt gag tac cac gtc ctt caa gaa gaa ctt atc gat tcc tct cct ctc           3392
Val Glu Tyr His Val Leu Gln Glu Glu Leu Ile Asp Ser Ser Pro Leu
1060                1065                1070 agt gac aac caa aga atg gat aaa tta gag aaa acc aac agc agc tta           3440
Ser Asp Asn Gln Arg Met Asp Lys Leu Glu Lys Thr Asn Ser Ser Leu
1075                1080                1085                1090 cgc aaa cag aac ctt gac ctc ctt gaa cag ttg cag gtg gca aat ggt           3488
Arg Lys Gln Asn Leu Asp Leu Leu Glu Gln Leu Gln Val Ala Asn Gly
                1095                1100                1105
```

-continued

| | |
|---|---|
| agg atc caa agc ctt gag gcc acc att gag aag ctc ctg agc agt gag<br>Arg Ile Gln Ser Leu Glu Ala Thr Ile Glu Lys Leu Leu Ser Ser Glu<br>        1110                    1115                   1120 | 3536 |
| agc aag ctg aag cag gcc atg ctt acc tta gaa ctg gag cgg tcg gcc<br>Ser Lys Leu Lys Gln Ala Met Leu Thr Leu Glu Leu Glu Arg Ser Ala<br>   1125                    1130                    1135 | 3584 |
| ctg ctg cag acg gtg gag gag ctg cgg cgg cgg agc gca gag ccc agc<br>Leu Leu Gln Thr Val Glu Glu Leu Arg Arg Arg Ser Ala Glu Pro Ser<br>1140                    1145                    1150 | 3632 |
| gac cgg gag cct gag tgc acg cag ccc gag ccc acg ggc gac tga<br>Asp Arg Glu Pro Glu Cys Thr Gln Pro Glu Pro Thr Gly Asp *<br>1155                  1160                  1165 | 3677 |
| cagctctgca ggagagattg caacaccatc ccacactgtc caggccttaa ctgagaggga | 3737 |
| cagaagacgc tggaaggaga gaaggaagcg ggaagtgtgc ttctcaggga ggaaaccggc | 3797 |
| ttgccagcaa gtagattctt acgaactcca acttgcaatt caggggggcat gtcccagtgt | 3857 |
| ttttttttgtt gttttttagat actaaatcgt cccttctcca gtcctgatta ctgtacacag | 3917 |
| tagctttaga tggcgtggac gtgaataaat gcaacttatg ttttaaaaaaa aaaaaaaaaa | 3977 |
| aaaaaa | 3983 |

```
<210> SEQ ID NO 4
<211> LENGTH: 3988
<212> TYPE: DNA
<213> ORGANISM: Homo sapiens
<220> FEATURE:
<221> NAME/KEY: CDS
<222> LOCATION: 176..3730
<221> NAME/KEY: polyA_signal
<222> LOCATION: 3947..3952
<223> OTHER INFORMATION: AATAAA
<221> NAME/KEY: misc_feature
<222> LOCATION: 1..458
<223> OTHER INFORMATION: homology with Genset 5' EST in ref : A35235

<400> SEQUENCE: 4
```

| | |
|---|---|
| ataataggca ctgaagacat gttaatgaa ggtggatttg tgattcagaa cctctagact | 60 |
| acctgggcga gtcttttaaa atgtttctgc atatgaagtg tgtaaaatag attgcttgat | 120 |
| ccaaaacaga aaaacagtga taactgtttt gctgagttcc cagaccttc ccaag atg<br>                                                                                    Met<br>                                                                                     1 | 178 |
| gaa cca ata aca ttc aca gca agg aaa cat ctg ctt cct aac gag gtc<br>Glu Pro Ile Thr Phe Thr Ala Arg Lys His Leu Leu Pro Asn Glu Val<br>             5                        10                    15 | 226 |
| tcg gtg gat ttt ggc ctg cag ctg gtg ggc tcc ctg cct gtg cat tcc<br>Ser Val Asp Phe Gly Leu Gln Leu Val Gly Ser Leu Pro Val His Ser<br>            20                      25                      30 | 274 |
| ctg acc acc atg ccc atg ctg ccc tgg gtt gtg gct gag gtg cga aga<br>Leu Thr Thr Met Pro Met Leu Pro Trp Val Val Ala Glu Val Arg Arg<br>35                  40                      45 | 322 |
| ctc agc agg cag tcc acc aga aag gaa cct gta acc aag caa gtc cgg<br>Leu Ser Arg Gln Ser Thr Arg Lys Glu Pro Val Thr Lys Gln Val Arg<br>50                  55                    60                      65 | 370 |
| ctt tgc gtt tca ccc tct gga ctg aga tgt gaa cct gag cca ggg aga<br>Leu Cys Val Ser Pro Ser Gly Leu Arg Cys Glu Pro Glu Pro Gly Arg<br>                  70                      75                      80 | 418 |
| agt caa cag tgg gat ccc ctg atc tat tcc agc atc ttt gag tgc aag<br>Ser Gln Gln Trp Asp Pro Leu Ile Tyr Ser Ser Ile Phe Glu Cys Lys<br>                  85                      90                    95 | 466 |
| cct cag cgt gtt cac aaa ctg att cac aac agt cat gac cca agt tac<br>Pro Gln Arg Val His Lys Leu Ile His Asn Ser His Asp Pro Ser Tyr | 514 |

-continued

```
              100                 105                 110
ttt gct tgt ctg att aag gaa gac gct gtc cac cgg cag agt atc tgc      562
Phe Ala Cys Leu Ile Lys Glu Asp Ala Val His Arg Gln Ser Ile Cys
115                 120                 125 tat gtg ttc aaa gcc gat gat caa aca aaa gtg cct gag atc atc agc      610
Tyr Val Phe Lys Ala Asp Asp Gln Thr Lys Val Pro Glu Ile Ile Ser
130                 135                 140                 145 tcc atc cgt cag gcg ggg aag atc gcc cgg cag gag gag ctg cac tgc      658
Ser Ile Arg Gln Ala Gly Lys Ile Ala Arg Gln Glu Glu Leu His Cys
                150                 155                 160 ccg tcc gag ttc gac gac acg ttt tcc aag aag ttc gag gtg ctc ttc      706
Pro Ser Glu Phe Asp Asp Thr Phe Ser Lys Lys Phe Glu Val Leu Phe
            165                 170                 175 tgc ggc cgc gtg acg gtg gcg cac aag aag gct ccg ccg gcc ctg atc      754
Cys Gly Arg Val Thr Val Ala His Lys Lys Ala Pro Pro Ala Leu Ile
        180                 185                 190 gac gag tgc atc gag aag ttc aat cac gtc agc ggc agc cgg ggg tcc      802
Asp Glu Cys Ile Glu Lys Phe Asn His Val Ser Gly Ser Arg Gly Ser
195                 200                 205 gag agc ccc cgc ccc aac ccg ccc cat gcc gcg ccc aca ggg agc cag      850
Glu Ser Pro Arg Pro Asn Pro Pro His Ala Ala Pro Thr Gly Ser Gln
210                 215                 220                 225 gag cct gtg cgc agg ccc atg cgc aag tcc ttc tcc cag ccc ggc ctg      898
Glu Pro Val Arg Arg Pro Met Arg Lys Ser Phe Ser Gln Pro Gly Leu
                230                 235                 240 cgc tcg ctg gcc ttt agg aag gag ctg cag gat ggg ggc ctc cga agc      946
Arg Ser Leu Ala Phe Arg Lys Glu Leu Gln Asp Gly Gly Leu Arg Ser
            245                 250                 255 agc ggc ttc ttc agc tcc ttc gag gag agc gac att gag aac cac ctc      994
Ser Gly Phe Phe Ser Ser Phe Glu Glu Ser Asp Ile Glu Asn His Leu
        260                 265                 270 att agc gga cac aat att gtg cag ccc aca gat atc gag gaa aat cga     1042
Ile Ser Gly His Asn Ile Val Gln Pro Thr Asp Ile Glu Glu Asn Arg
275                 280                 285 act atg ctc ttc acg att ggc cag tct gaa gtt tac ctc atc agt cct     1090
Thr Met Leu Phe Thr Ile Gly Gln Ser Glu Val Tyr Leu Ile Ser Pro
290                 295                 300                 305 gac acc aaa aaa ata gca ttg gag aaa aat ttt aag gag ata tcc ttt     1138
Asp Thr Lys Lys Ile Ala Leu Glu Lys Asn Phe Lys Glu Ile Ser Phe
                310                 315                 320 tgc tct cag ggc atc aga cac gtg gac cac ttt ggg ttt atc tgt cgg     1186
Cys Ser Gln Gly Ile Arg His Val Asp His Phe Gly Phe Ile Cys Arg
            325                 330                 335 gag tct tcc gga ggt ggc ggc ttt cat ttt gtc tgt tac gtg ttt cag     1234
Glu Ser Ser Gly Gly Gly Gly Phe His Phe Val Cys Tyr Val Phe Gln
        340                 345                 350 tgc aca aat gag gct ctg gtt gat gaa att atg atg acc ctg aaa cag     1282
Cys Thr Asn Glu Ala Leu Val Asp Glu Ile Met Met Thr Leu Lys Gln
355                 360                 365 gcc ttc acg gtg gcc gca gtg cag cag aca gct aag gcg cca gcc cag     1330
Ala Phe Thr Val Ala Ala Val Gln Gln Thr Ala Lys Ala Pro Ala Gln
370                 375                 380                 385 ctg tgt gag ggc tgc ccc ctg caa agc ctg cac aag ctc tgt gag agg     1378
Leu Cys Glu Gly Cys Pro Leu Gln Ser Leu His Lys Leu Cys Glu Arg
                390                 395                 400 ata gag gga atg aat tct tcc aaa aca aaa cta gaa ctg caa aag cac     1426
Ile Glu Gly Met Asn Ser Ser Lys Thr Lys Leu Glu Leu Gln Lys His
            405                 410                 415 ctg acg aca tta acc aat cag gag cag gcg act att ttt gaa gag gtt     1474
```

```
                                                                       -continued Leu Thr Thr Leu Thr Asn Gln Glu Gln Ala Thr Ile Phe Glu Glu Val
            420                 425                 430 cag aaa ttg aga ccg aga aat gag cag cga gag aat gaa ttg att att       1522
Gln Lys Leu Arg Pro Arg Asn Glu Gln Arg Glu Asn Glu Leu Ile Ile
435                 440                 445 tct ttt ctg aga tgt tta tat gaa gag aaa cag aaa gaa cac atc cat       1570
Ser Phe Leu Arg Cys Leu Tyr Glu Glu Lys Gln Lys Glu His Ile His
450                 455                 460                 465 att ggg gag atg aag cag aca tcg cag atg gca gca gag aat att gga       1618
Ile Gly Glu Met Lys Gln Thr Ser Gln Met Ala Ala Glu Asn Ile Gly
            470                 475                 480 agt gaa tta cca ccc agt gcc act cga ttt agg cta gat atg ctg aaa       1666
Ser Glu Leu Pro Pro Ser Ala Thr Arg Phe Arg Leu Asp Met Leu Lys
            485                 490                 495 aac aaa gca aag aga tct tta aca gag tct tta gaa agt att ttg tcc       1714
Asn Lys Ala Lys Arg Ser Leu Thr Glu Ser Leu Glu Ser Ile Leu Ser
            500                 505                 510 cgg ggt aat aaa gcc aga ggc ctg cag gaa cac tcc atc agt gtg gat       1762
Arg Gly Asn Lys Ala Arg Gly Leu Gln Glu His Ser Ile Ser Val Asp
515                 520                 525 ctg gat agc tcc ctg tct agt aca tta agt aac acc agc aaa gag cca       1810
Leu Asp Ser Ser Leu Ser Ser Thr Leu Ser Asn Thr Ser Lys Glu Pro
530                 535                 540                 545 tct gtg tgt gaa aag gag gcc ttg ccc atc tct gag agc tcc ttt aag       1858
Ser Val Cys Glu Lys Glu Ala Leu Pro Ile Ser Glu Ser Ser Phe Lys
            550                 555                 560 ctc ctc ggc tcc tcg gag gac ctg tcc agt gac tcg gag agt cat ctc       1906
Leu Leu Gly Ser Ser Glu Asp Leu Ser Ser Asp Ser Glu Ser His Leu
            565                 570                 575 cca gaa gag cca gct ccg ctg tcg ccc cag cag gcc ttc agg agg cga       1954
Pro Glu Glu Pro Ala Pro Leu Ser Pro Gln Gln Ala Phe Arg Arg Arg
            580                 585                 590 gca aac acc ctg agt cac ttc ccc atc gaa tgc cag gaa cct cca caa       2002
Ala Asn Thr Leu Ser His Phe Pro Ile Glu Cys Gln Glu Pro Pro Gln
595                 600                 605 cct gcc cgg ggg tcc ccg ggg gtt tcg caa agg aaa ctt atg agg tat       2050
Pro Ala Arg Gly Ser Pro Gly Val Ser Gln Arg Lys Leu Met Arg Tyr
610                 615                 620                 625 cac tca gtg agc aca gag acg cct cat gaa cga aag gac ttt gaa tcc       2098
His Ser Val Ser Thr Glu Thr Pro His Glu Arg Lys Asp Phe Glu Ser
            630                 635                 640 aaa gca aac cat ctt ggt gat tct ggt ggg act cct gtg aag acc cgg       2146
Lys Ala Asn His Leu Gly Asp Ser Gly Gly Thr Pro Val Lys Thr Arg
            645                 650                 655 agg cat tcc tgg agg cag cag ata ttc ctc cga gta gcc acc ccg cag       2194
Arg His Ser Trp Arg Gln Gln Ile Phe Leu Arg Val Ala Thr Pro Gln
            660                 665                 670 aag gcg tgc gat tct tcc agc aga tat gaa gat tat tca gag ctg gga       2242
Lys Ala Cys Asp Ser Ser Ser Arg Tyr Glu Asp Tyr Ser Glu Leu Gly
675                 680                 685 gag ctt ccc cca cga tct cct tta gaa cca gtt tgt gaa gat ggg ccc       2290
Glu Leu Pro Pro Arg Ser Pro Leu Glu Pro Val Cys Glu Asp Gly Pro
690                 695                 700                 705 ttt ggc ccc cca cca gag gaa aag aaa agg aca tct cgt gag ctc cga       2338
Phe Gly Pro Pro Pro Glu Glu Lys Lys Arg Thr Ser Arg Glu Leu Arg
            710                 715                 720 gag ctg tgg caa aag gct att ctt caa cag ata ctg ctg ctt aga atg       2386
Glu Leu Trp Gln Lys Ala Ile Leu Gln Gln Ile Leu Leu Leu Arg Met
            725                 730                 735
```

-continued

| | |
|---|---|
| gag aag gaa aat cag aag ctc caa gcc tct gaa aat gat ttg ctg aac<br>Glu Lys Glu Asn Gln Lys Leu Gln Ala Ser Glu Asn Asp Leu Leu Asn<br>     740                       745                     750 | 2434 |
| aag cgc ctg aag ctc gat tat gaa gaa att act ccc tgt ctt aaa gaa<br>Lys Arg Leu Lys Leu Asp Tyr Glu Glu Ile Thr Pro Cys Leu Lys Glu<br>755                       760                     765 | 2482 |
| gta act aca gtg tgg gaa aag atg ctt agc act cca gga aga tca aaa<br>Val Thr Thr Val Trp Glu Lys Met Leu Ser Thr Pro Gly Arg Ser Lys<br>770                       775                     780                     785 | 2530 |
| att aag ttt gac atg gaa aaa atg cac tcg gct gtt ggg caa ggt gtg<br>Ile Lys Phe Asp Met Glu Lys Met His Ser Ala Val Gly Gln Gly Val<br>     790                       795                     800 | 2578 |
| cca cgt cat cac cga ggt gaa atc tgg aaa ttt cta gct gag caa ttc<br>Pro Arg His His Arg Gly Glu Ile Trp Lys Phe Leu Ala Glu Gln Phe<br>805                       810                     815 | 2626 |
| cac ctt aaa cac cag ttt ccc agc aaa cag cag cca aag gat gtg cca<br>His Leu Lys His Gln Phe Pro Ser Lys Gln Gln Pro Lys Asp Val Pro<br>     820                       825                     830 | 2674 |
| tac aaa gaa ctc tta aag cag ctg act tcc cag cag cat gcg att ctt<br>Tyr Lys Glu Leu Leu Lys Gln Leu Thr Ser Gln Gln His Ala Ile Leu<br>835                       840                     845 | 2722 |
| att gac ctt ggg cga acc ttt cct aca cac cca tac ttc tct gcc cag<br>Ile Asp Leu Gly Arg Thr Phe Pro Thr His Pro Tyr Phe Ser Ala Gln<br>850                       855                     860                     865 | 2770 |
| ctt gga gca gga cag cta tcg ctt tac aac att ttg aag gcc tac tca<br>Leu Gly Ala Gly Gln Leu Ser Leu Tyr Asn Ile Leu Lys Ala Tyr Ser<br>               870                     875                     880 | 2818 |
| ctt cta gac cag gaa gtg gga tat tgc caa ggt ctc agc ttt gta gca<br>Leu Leu Asp Gln Glu Val Gly Tyr Cys Gln Gly Leu Ser Phe Val Ala<br>885                       890                     895 | 2866 |
| ggc att ttg ctt ctt cat atg agt gag gaa gag gcg ttt aaa atg ctc<br>Gly Ile Leu Leu Leu His Met Ser Glu Glu Glu Ala Phe Lys Met Leu<br>     900                       905                     910 | 2914 |
| aag ttt ctg atg ttt gac atg ggg ctg cgg aaa cag tat cgg cca gac<br>Lys Phe Leu Met Phe Asp Met Gly Leu Arg Lys Gln Tyr Arg Pro Asp<br>915                       920                     925 | 2962 |
| atg att att tta cag atc cag atg tac cag ctc tcg agg ttg ctt cat<br>Met Ile Ile Leu Gln Ile Gln Met Tyr Gln Leu Ser Arg Leu Leu His<br>930                       935                     940                     945 | 3010 |
| gat tac cac aga gac ctc tac aat cac ctg gag gag cac gag atc ggc<br>Asp Tyr His Arg Asp Leu Tyr Asn His Leu Glu Glu His Glu Ile Gly<br>     950                       955                     960 | 3058 |
| ccc agc ctc tac gct gcc ccc tgg ttc ctc acc atg ttt gcc tca cag<br>Pro Ser Leu Tyr Ala Ala Pro Trp Phe Leu Thr Met Phe Ala Ser Gln<br>965                       970                     975 | 3106 |
| ttc ccg ctg gga ttc gta gcc aga gtc ttt gat atg att ttt ctt cag<br>Phe Pro Leu Gly Phe Val Ala Arg Val Phe Asp Met Ile Phe Leu Gln<br>     980                       985                     990 | 3154 |
| gga aca gag gtc ata ttt aaa gtg gct tta agt ctg ttg gga agc cat<br>Gly Thr Glu Val Ile Phe Lys Val Ala Leu Ser Leu Leu Gly Ser His<br>995                       1000                  1005 | 3202 |
| aag ccc ttg att ctg cag cat gaa aac cta gaa acc ata gtt gac ttt<br>Lys Pro Leu Ile Leu Gln His Glu Asn Leu Glu Thr Ile Val Asp Phe<br>1010                  1015                  1020                  1025 | 3250 |
| ata aaa agc acg cta ccc aac ctt ggc ttg gta cag atg gaa aag acc<br>Ile Lys Ser Thr Leu Pro Asn Leu Gly Leu Val Gln Met Glu Lys Thr<br>        1030                  1035                  1040 | 3298 |
| atc aat cag gta ttt gaa atg gac atc gct aaa cag tta caa gct tat<br>Ile Asn Gln Val Phe Glu Met Asp Ile Ala Lys Gln Leu Gln Ala Tyr<br>1045                  1050                  1055 | 3346 |

-continued

```
gaa gtt gag tac cac gtc ctt caa gaa gaa ctt atc gat tcc tct cct    3394
Glu Val Glu Tyr His Val Leu Gln Glu Glu Leu Ile Asp Ser Ser Pro
    1060                1065                1070 ctc agt gac aac caa aga atg gat aaa tta gag aaa acc aac agc agc    3442
Leu Ser Asp Asn Gln Arg Met Asp Lys Leu Glu Lys Thr Asn Ser Ser
1075                1080                1085 tta cgc aaa cag aac ctt gac ctc ctt gaa cag ttg cag gtg gca aat    3490
Leu Arg Lys Gln Asn Leu Asp Leu Leu Glu Gln Leu Gln Val Ala Asn
1090                1095                1100                1105 ggt agg atc caa agc ctt gag gcc acc att gag aag ctc ctg agc agt    3538
Gly Arg Ile Gln Ser Leu Glu Ala Thr Ile Glu Lys Leu Leu Ser Ser
            1110                1115                1120 gag agc aag ctg aag cag gcc atg ctt acc tta gaa ctg gag cgg tcg    3586
Glu Ser Lys Leu Lys Gln Ala Met Leu Thr Leu Glu Leu Glu Arg Ser
    1125                1130                1135 gcc ctg ctg cag acg gtg gag gag ctg cgg cgg cgg agc gca gag ccc    3634
Ala Leu Leu Gln Thr Val Glu Glu Leu Arg Arg Arg Ser Ala Glu Pro
        1140                1145                1150 agc gac cgg gag cct gag tgc acg cag ccc gag ccc acg ggc gac tga    3682
Ser Asp Arg Glu Pro Glu Cys Thr Gln Pro Glu Pro Thr Gly Asp  *
    1155                1160                1165 cagctctgca ggagagattg caacaccatc ccacactgtc caggccttaa ctgagaggga    3742
cagaagacgc tggaaggaga gaaggaagcg ggaagtgtgc ttctcaggga ggaaaccggc    3802
ttgccagcaa gtagattctt acgaactcca acttgcaatt caggggggcat gtcccagtgt    3862 ttttttttgtt gttttttagat actaaatcgt cccttctcca gtcctgatta ctgtacacag    3922
tagctttaga tggcgtggac gtgaataaat gcaacttatg ttttaaaaaa aaaaaaaaaa    3982
aaaaaa                                                                3988
```

<210> SEQ ID NO 5
<211> LENGTH: 1168
<212> TYPE: PRT
<213> ORGANISM: Homo sapiens

<400> SEQUENCE: 5

```
Met Glu Pro Ile Thr Phe Thr Ala Arg Lys His Leu Leu Pro Asn Glu
1               5                   10                  15

Val Ser Val Asp Phe Gly Leu Gln Leu Val Gly Ser Leu Pro Val His
                20                  25                  30

Ser Leu Thr Thr Met Pro Met Leu Pro Trp Val Ala Glu Val Arg
            35                  40                  45

Arg Leu Ser Arg Gln Ser Thr Arg Lys Glu Pro Val Thr Lys Gln Val
        50                  55                  60

Arg Leu Cys Val Ser Pro Ser Gly Leu Arg Cys Glu Pro Glu Pro Gly
65                  70                  75                  80

Arg Ser Gln Gln Trp Asp Pro Leu Ile Tyr Ser Ile Phe Glu Cys
                85                  90                  95

Lys Pro Gln Arg Val His Lys Leu Ile His Asn Ser His Asp Pro Ser
                100                 105                 110

Tyr Phe Ala Cys Leu Ile Lys Glu Asp Ala Val His Arg Gln Ser Ile
            115                 120                 125

Cys Tyr Val Phe Lys Ala Asp Asp Gln Thr Lys Val Pro Glu Ile Ile
        130                 135                 140

Ser Ser Ile Arg Gln Ala Gly Lys Ile Ala Arg Gln Glu Glu Leu His
145                 150                 155                 160
```

-continued

```
Cys Pro Ser Glu Phe Asp Asp Thr Phe Ser Lys Lys Phe Glu Val Leu
            165                 170                 175

Phe Cys Gly Arg Val Thr Val Ala His Lys Lys Ala Pro Pro Ala Leu
            180                 185                 190

Ile Asp Glu Cys Ile Glu Lys Phe Asn His Val Ser Gly Ser Arg Gly
            195                 200                 205

Ser Glu Ser Pro Arg Pro Asn Pro Pro His Ala Ala Pro Thr Gly Ser
            210                 215                 220

Gln Glu Pro Val Arg Arg Pro Met Arg Lys Ser Phe Ser Gln Pro Gly
225                 230                 235                 240

Leu Arg Ser Leu Ala Phe Arg Lys Glu Leu Gln Asp Gly Gly Leu Arg
                245                 250                 255

Ser Ser Gly Phe Phe Ser Ser Phe Glu Glu Ser Asp Ile Glu Asn His
            260                 265                 270

Leu Ile Ser Gly His Asn Ile Val Gln Pro Thr Asp Ile Glu Glu Asn
            275                 280                 285

Arg Thr Met Leu Phe Thr Ile Gly Gln Ser Glu Val Tyr Leu Ile Ser
            290                 295                 300

Pro Asp Thr Lys Lys Ile Ala Leu Glu Lys Asn Phe Lys Glu Ile Ser
305                 310                 315                 320

Phe Cys Ser Gln Gly Ile Arg His Val Asp His Phe Gly Phe Ile Cys
                325                 330                 335

Arg Glu Ser Ser Gly Gly Gly Phe His Phe Val Cys Tyr Val Phe
            340                 345                 350

Gln Cys Thr Asn Glu Ala Leu Val Asp Glu Ile Met Met Thr Leu Lys
            355                 360                 365

Gln Ala Phe Thr Val Ala Ala Val Gln Gln Thr Ala Lys Ala Pro Ala
            370                 375                 380

Gln Leu Cys Glu Gly Cys Pro Leu Gln Ser Leu His Lys Leu Cys Glu
385                 390                 395                 400

Arg Ile Glu Gly Met Asn Ser Ser Lys Thr Lys Leu Glu Leu Gln Lys
            405                 410                 415

His Leu Thr Thr Leu Thr Asn Gln Glu Gln Ala Thr Ile Phe Glu Glu
            420                 425                 430

Val Gln Lys Leu Arg Pro Arg Asn Glu Gln Arg Glu Asn Glu Leu Ile
            435                 440                 445

Ile Ser Phe Leu Arg Cys Leu Tyr Glu Glu Lys Gln Lys Glu His Ile
450                 455                 460

His Ile Gly Glu Met Lys Gln Thr Ser Gln Met Ala Ala Glu Asn Ile
465                 470                 475                 480

Gly Ser Glu Leu Pro Pro Ser Ala Thr Arg Phe Arg Leu Asp Met Leu
            485                 490                 495

Lys Asn Lys Ala Lys Arg Ser Leu Thr Glu Ser Leu Glu Ser Ile Leu
            500                 505                 510

Ser Arg Gly Asn Lys Ala Arg Gly Leu Gln Glu His Ser Ile Ser Val
            515                 520                 525

Asp Leu Asp Ser Ser Leu Ser Ser Thr Leu Ser Asn Thr Ser Lys Glu
            530                 535                 540

Pro Ser Val Cys Glu Lys Glu Ala Leu Pro Ile Ser Glu Ser Ser Phe
545                 550                 555                 560

Lys Leu Leu Gly Ser Ser Glu Asp Leu Ser Ser Asp Ser Glu Ser His
                565                 570                 575

Leu Pro Glu Glu Pro Ala Pro Leu Ser Pro Gln Gln Ala Phe Arg Arg
```

-continued

```
            580                 585                 590
Arg Ala Asn Thr Leu Ser His Phe Pro Ile Glu Cys Gln Glu Pro Pro
            595                 600                 605
Gln Pro Ala Arg Gly Ser Pro Gly Val Ser Gln Arg Lys Leu Met Arg
        610                 615                 620
Tyr His Ser Val Ser Thr Glu Thr Pro His Glu Arg Lys Asp Phe Glu
625                 630                 635                 640
Ser Lys Ala Asn His Leu Gly Asp Ser Gly Gly Thr Pro Val Lys Thr
                645                 650                 655
Arg Arg His Ser Trp Arg Gln Gln Ile Phe Leu Arg Val Ala Thr Pro
            660                 665                 670
Gln Lys Ala Cys Asp Ser Ser Arg Tyr Glu Asp Tyr Ser Glu Leu
            675                 680                 685
Gly Glu Leu Pro Pro Arg Ser Pro Leu Glu Pro Val Cys Glu Asp Gly
            690                 695                 700
Pro Phe Gly Pro Pro Glu Glu Lys Lys Arg Thr Ser Arg Glu Leu
705                 710                 715                 720
Arg Glu Leu Trp Gln Lys Ala Ile Leu Gln Gln Ile Leu Leu Leu Arg
                725                 730                 735
Met Glu Lys Glu Asn Gln Lys Leu Gln Ala Ser Glu Asn Asp Leu Leu
            740                 745                 750
Asn Lys Arg Leu Lys Leu Asp Tyr Glu Glu Ile Thr Pro Cys Leu Lys
            755                 760                 765
Glu Val Thr Thr Val Trp Glu Lys Met Leu Ser Thr Pro Gly Arg Ser
770                 775                 780
Lys Ile Lys Phe Asp Met Glu Lys Met His Ser Ala Val Gly Gln Gly
785                 790                 795                 800
Val Pro Arg His His Arg Gly Glu Ile Trp Lys Phe Leu Ala Glu Gln
            805                 810                 815
Phe His Leu Lys His Gln Phe Pro Ser Lys Gln Pro Lys Asp Val
                820                 825                 830
Pro Tyr Lys Glu Leu Leu Lys Gln Leu Thr Ser Gln His Ala Ile
        835                 840                 845
Leu Ile Asp Leu Gly Arg Thr Phe Pro Thr His Pro Tyr Phe Ser Ala
850                 855                 860
Gln Leu Gly Ala Gly Gln Leu Ser Leu Tyr Asn Ile Leu Lys Ala Tyr
865                 870                 875                 880
Ser Leu Leu Asp Gln Glu Val Gly Tyr Cys Gln Gly Leu Ser Phe Val
                885                 890                 895
Ala Gly Ile Leu Leu Leu His Met Ser Glu Glu Ala Phe Lys Met
            900                 905                 910
Leu Lys Phe Leu Met Phe Asp Met Gly Leu Arg Lys Gln Tyr Arg Pro
        915                 920                 925
Asp Met Ile Ile Leu Gln Ile Gln Met Tyr Gln Leu Ser Arg Leu Leu
        930                 935                 940
His Asp Tyr His Arg Asp Leu Tyr Asn His Leu Glu Glu His Glu Ile
945                 950                 955                 960
Gly Pro Ser Leu Tyr Ala Ala Pro Trp Phe Leu Thr Met Phe Ala Ser
                965                 970                 975
Gln Phe Pro Leu Gly Phe Val Ala Arg Val Phe Asp Met Ile Phe Leu
            980                 985                 990
Gln Gly Thr Glu Val Ile Phe Lys Val Ala Leu Ser Leu Leu Gly Ser
            995                 1000                1005
```

```
His Lys Pro Leu Ile Leu Gln His Glu Asn Leu Glu Thr Ile Val Asp
    1010                1015                1020

Phe Ile Lys Ser Thr Leu Pro Asn Leu Gly Leu Val Gln Met Glu Lys
1025            1030                1035                1040

Thr Ile Asn Gln Val Phe Glu Met Asp Ile Ala Lys Gln Leu Gln Ala
                1045                1050                1055

Tyr Glu Val Glu Tyr His Val Leu Gln Glu Glu Leu Ile Asp Ser Ser
                1060                1065                1070

Pro Leu Ser Asp Asn Gln Arg Met Asp Lys Leu Glu Lys Thr Asn Ser
            1075                1080                1085

Ser Leu Arg Lys Gln Asn Leu Asp Leu Leu Glu Gln Leu Gln Val Ala
        1090                1095                1100

Asn Gly Arg Ile Gln Ser Leu Glu Ala Thr Ile Glu Lys Leu Leu Ser
1105            1110                1115                1120

Ser Glu Ser Lys Leu Lys Gln Ala Met Leu Thr Leu Glu Leu Glu Arg
                1125                1130                1135

Ser Ala Leu Leu Gln Thr Val Glu Glu Leu Arg Arg Arg Ser Ala Glu
                1140                1145                1150

Pro Ser Asp Arg Glu Pro Glu Cys Thr Gln Pro Glu Pro Thr Gly Asp
            1155                1160                1165

<210> SEQ ID NO 6
<211> LENGTH: 18
<212> TYPE: DNA
<213> ORGANISM: Artificial Sequence
<220> FEATURE:
<221> NAME/KEY: misc_binding
<222> LOCATION: 1..18
<223> OTHER INFORMATION: sequencing oligonucleotide PrimerPU

<400> SEQUENCE: 6
tgtaaaacga cggccagt                                                18

<210> SEQ ID NO 7
<211> LENGTH: 18
<212> TYPE: DNA
<213> ORGANISM: Artificial Sequence
<220> FEATURE:
<221> NAME/KEY: misc_binding
<222> LOCATION: 1..18
<223> OTHER INFORMATION: sequencing oligonucleotide PrimerRP

<400> SEQUENCE: 7
caggaaacag ctatgacc                                                18
```